(12) United States Patent
Qiu et al.

(10) Patent No.: US 11,267,885 B2
(45) Date of Patent: Mar. 8, 2022

(54) CD47 ANTIGEN BINDING UNIT AND USES THEREOF

(71) Applicant: ZLIP HOLDING LIMITED, Grand Cayman (KY)

(72) Inventors: Yangsheng Qiu, Shanghai (CN); Jing Li, Shanghai (CN); Honghai Gao, Shanghai (CN); Fenglan Wu, Shanghai (CN); Xu Fang, Shanghai (CN); Shou Li, Shanghai (CN); Hongtao Lu, Shanghai (CN); James S. Yan, Shanghai (CN); Lei Shi, Shanghai (CN)

(73) Assignee: ZLIP HOLDING LIMITED, Grand Cayman (KY)

( * ) Notice: Subject to any disclaimer, the term of this patent is extended or adjusted under 35 U.S.C. 154(b) by 201 days.

(21) Appl. No.: 16/481,048

(22) PCT Filed: Jan. 26, 2018

(86) PCT No.: PCT/CN2018/074318
§ 371 (c)(1),
(2) Date: Jul. 25, 2019

(87) PCT Pub. No.: WO2018/137705
PCT Pub. Date: Aug. 2, 2018

(65) Prior Publication Data
US 2020/0247886 A1    Aug. 6, 2020

(30) Foreign Application Priority Data

Jan. 26, 2017   (WO) ................ PCT/CN2017/072738

(51) Int. Cl.
| | | |
|---|---|---|
| A61K 39/00 | (2006.01) | |
| A61K 39/395 | (2006.01) | |
| C07K 16/00 | (2006.01) | |
| C07K 16/46 | (2006.01) | |
| C07H 21/04 | (2006.01) | |
| C12P 21/06 | (2006.01) | |
| C12N 5/02 | (2006.01) | |
| C12N 5/20 | (2006.01) | |
| C07K 16/28 | (2006.01) | |
| A61P 35/00 | (2006.01) | |

(52) U.S. Cl.
CPC .......... *C07K 16/2803* (2013.01); *A61P 35/00* (2018.01); *A61K 2039/505* (2013.01); *C07K 2317/24* (2013.01); *C07K 2317/33* (2013.01); *C07K 2317/55* (2013.01); *C07K 2317/565* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 5,270,202 A | 12/1993 | Raychaudhuri |
| 5,405,783 A | 4/1995 | Pirrung et al. |
| 5,412,087 A | 5/1995 | McGall et al. |
| 5,445,934 A | 8/1995 | Fodor et al. |
| 5,624,659 A | 4/1997 | Bigner et al. |
| 5,695,937 A | 12/1997 | Kinzler et al. |
| 5,861,510 A | 1/1999 | Piscopio et al. |
| 5,863,949 A | 1/1999 | Robinson et al. |
| 5,969,108 A | 10/1999 | McCafferty et al. |
| 6,147,203 A | 11/2000 | Pastan et al. |
| 6,150,584 A | 11/2000 | Kucherlapati et al. |
| 6,162,963 A | 12/2000 | Kucherlapati et al. |
| 6,174,708 B1 | 1/2001 | Sodoyer et al. |
| 6,187,287 B1 | 2/2001 | Leung et al. |
| 6,511,993 B1 | 1/2003 | Dack et al. |
| 6,833,441 B2 | 12/2004 | Wang et al. |
| 7,030,242 B2 | 4/2006 | Noe et al. |
| 9,045,541 B2 * | 6/2015 | Eckelman .......... C07K 16/2803 |
| 9,382,320 B2 | 7/2016 | Liu et al. |

(Continued)

FOREIGN PATENT DOCUMENTS

| | | |
|---|---|---|
| EP | 0606046 B1 | 10/1997 |
| EP | 0818442 A2 | 1/1998 |
| EP | 0780386 B1 | 10/2002 |

(Continued)

OTHER PUBLICATIONS

Petrova et al. Lack of CD47 membrane mobility contributes to the poor erythrocyte binding of SIRPαFc, a novel CD47-blocking cancer immunotherapeutic. AACR, 106th Annual Meeting 2015; Abstract 4271, Apr. 18-22, 2015. (Year: 2015).*

(Continued)

*Primary Examiner* — Maher M Haddad
(74) *Attorney, Agent, or Firm* — McDermott Will & Emery LLP; Judy M. Mohr; Brett A. Schweers

(57) ABSTRACT

Disclosed herein are antigen binding units that specifically bind to CD47. Further disclosed herein are polynucleic acids encoding said antigen binding units, vectors comprising said polynucleic acids, and hybridomas and host cells comprising said vectors. Further provided herein are methods for inducing phagocytosis of CD47-expressing cells.

21 Claims, 29 Drawing Sheets

Specification includes a Sequence Listing.

(56) References Cited

U.S. PATENT DOCUMENTS

| | | | | |
|---|---|---|---|---|
| 2016/0251435 A1* | 9/2016 | Eckelman | ............... | A61K 45/06 424/133.1 |
| 2017/0369572 A1* | 12/2017 | Sato | ....................... | A61K 45/06 |

FOREIGN PATENT DOCUMENTS

| | | | |
|---|---|---|---|
| EP | | 0931788 B1 | 11/2002 |
| EP | | 1004578 B1 | 2/2004 |
| EP | | 0699755 B1 | 4/2004 |
| WO | WO-9005719 | A1 | 5/1990 |
| WO | WO-9201047 | A1 | 1/1992 |
| WO | WO-9627583 | A1 | 9/1996 |
| WO | WO-9633172 | A1 | 10/1996 |
| WO | WO-9803516 | A1 | 1/1998 |
| WO | WO-9807697 | A1 | 2/1998 |
| WO | WO-9830566 | A1 | 7/1998 |
| WO | WO-9833768 | A1 | 8/1998 |
| WO | WO-9834915 | A1 | 8/1998 |
| WO | WO-9834918 | A1 | 8/1998 |
| WO | WO-9907675 | A1 | 2/1999 |
| WO | WO-9929667 | A1 | 6/1999 |
| WO | WO-9952889 | A1 | 10/1999 |
| WO | WO-9952910 | A1 | 10/1999 |
| WO | WO-2005044857 | A1 | 5/2005 |
| WO | WO-2013119714 | A1 | 8/2013 |
| WO | WO-2014093678 | A2 | 6/2014 |
| WO | WO-2014123580 | A1 | 8/2014 |
| WO | WO-2016109415 | A1 | 7/2016 |
| WO | WO-2016141328 | A2 | 9/2016 |
| WO | WO-2018137705 | A1 | 8/2018 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*

Lloyd et al., Modelling the human immune response: performance of a 1011 human antibody repertoire against a broad panel of therapeutically relevant antigens. Protein Eng Des Sel. Mar. 2009;22(3):159-68. (Year: 2009).*

Goel et al., Plasticity within the antigen-combining site may manifest as molecular mimicry in the humoral immune response. J Immunol. Dec. 15, 2004; 173(12):7358-67. (Year: 2004).*

Kanyavuz et al., Breaking the law: unconventional strategies for antibody diversification. Nat Rev Immunol. Jun. 2019; 19(6):355-368. (Year: 2019).*

Aalberse, et al. IgG4 breaking the rules. Immunology. Jan. 2002; 105(1): 9-19. doi: 10.1046/j.0019-2805.2001.01341.x.

GenBank Accession No. ADQ12919.1. Version No. ADQ12919.1. integrin-associated protein [Mus musculus]. May 4, 2012. 1 page. Retrieved May 22, 2020 at URL: www.ncbi.nlm.nih.gov/protein/ADQ12919.1.

GenBank Accession No. BAA25401.1. Version No. BAA25401.1. CD47 [Mus musculus]. Feb. 5, 1999. 1 page. Retrieved May 22, 2020 at URL: www.ncbi.nlm.nih.gov/protein/BAA25401.1.

GenBank Accession No. CAA80977.1. Version No. CAA80977.1 integrin associated protein (macronuclear) [Homo sapiens]. Sep. 9, 2004. 2 pages. Retrieved May 22, 2020 at URL: www.ncbi.nlm.nih.gov/protein/CAA80977.1.

GenBank Accession No. CEJ95640. Version No. CEJ95640.1. CD47 [Homo sapiens]. Dec. 3, 2014. 1 page. Retrieved May 22, 2020 at URL: www.ncbi.nlm.nih.gov/protein/CEJ95640.

Gherardi, et al. A Single-Step Procedure for Cloning and Selection of Antibody-Secreting Hybridomas. J Immunol Methods. Jan. 24, 1990;126(1):61-68. doi: 10.1016/0022-1759(90)90012-k.

Glaser, et al. Dissection of the Combining Site in a Humanized anti-Tac Antibody. J Immunol. Oct. 15, 1992;149(8):2607-2614.

International search report with written opinion dated Apr. 28, 2018 for PCT/CN2018/074318.

Larrick, et al. Rapid Cloning of Rearranged Immunoglobulin Genes From Human Hybridoma Cells Using Mixed Primers and the Polymerase Chain Reaction. Biochem Biophys Res Commun. May 15, 1989;160(3):1250-1256. doi: 10.1016/s0006-291x(89)80138-x.

Levitt M. Molecular Dynamics of Native Protein. I. Computer Simulation of Trajectories. J Mol Biol. Aug. 15, 1983;168(3):595-617. DOI: 10.1016/s0022-2836(83)80304-0.

Miltenyi, et al. High gradient magnetic cell separation with MACS. Cytometry. 1990;11(2):231-238. DOI: 10.1002/cyto.990110203.

Olsnes, et al. Chimeric Toxins. Pharmacol Ther. 1981;15(3):355-381. doi: 10.1016/0163-7258(81)90050-4.

Orlandi, et al. Cloning immunoglobulin variable domains for expression by the polymerase chain reaction. Proc Natl Acad Sci USA. May 1989;86(10):3833-3837. doi: 10.1073/pnas.86.10.3833.

Sastry, et al. Cloning of the Immunological Repertoire in *Escherichia coli* for Generation of Monoclonal Catalytic Antibodies: Construction of a Heavy Chain Variable Region-Specific cDNA Library. Proc Natl Acad Sci USA. Aug. 1989;86(15):5728-5732. doi: 10.1073/pnas.86.15.5728.

Shalaby, et al. Development of humanized bispecific antibodies reactive with cytotoxic lymphocytes and tumor cells overexpressing the HER2 protooncogene. J Exp Med. Jan. 1, 1992;175(1):217-25.

Tempest, et al. Reshaping a Human Monoclonal Antibody to Inhibit Human Respiratory Syncytial Virus Infection in Vivo. Biotechnology (NY). Mar. 1991;9(3):266-271. doi: 10.1038/nbt0391-266.

Vitetta, et al. Redesigning nature's poisons to create anti-tumor reagents. Science. Nov. 20, 1987:vol. 238. Issue 4830. pp. 1098-1104. DOI: 10.1126/science.3317828.

Winter, et al. Man-made antibodies. Nature. Jan. 24, 1991;349(6307):293-299. doi: 10.1038/349293a0.

European search report and opinion dated Oct. 28, 2020 for EP Application No. 18743968.2.

Foote et al. Antibody Framework Residues Affecting the Conformation of the Hypervariable Loops. J. Mol. Biol. 224(2):487-99 (1992).

Chao et al. Anti-CD47 antibody synergizes with rituximab to promote phagocytosis and eradicate non-Hodgkin lymphoma. Cell 142:699-713 (2010).

European partial supplementary search report dated Jul. 17, 2020 for EP Application No. 18743968.2.

Pietsch et al. Abstract 2470: Anti-leukemic activity and tolerability of antihuman CD47 monoclonal antibodies. Cancer Research. AACR 106th Annual Meeting 2015. Aug. 1, 2015. Retrieved from the Internet: URL: http://cancerres.aacrjournals.org/content/75/15_supplement/2470 [retrieved on Feb. 21, 2017] Abstract.

Rudikoff, et al. Single amino acid substitution altering antigen-binding specificity. Proc Natl Acad Sci U S A. Mar. 1982;79(6):1979-83.

* cited by examiner

Positive control 1

ABU 2

ABU 4

Isotype IgG
(negative control)

ABU 6

Positive control 2

CD47 ANTIGEN BINDING UNIT AND USES THEREOF

CROSS-REFERENCE

The present application is a 371 of International Application No. PCT/CN2018/074318, filed Jan. 26, 2018, which claims priority to International Application No. PCT/CN2017/072738 filed Jan. 26, 2017, the contents of which are hereby incorporated by reference in their entirety.

SEQUENCE LISTING

The instant application contains a Sequence Listing which has been filed electronically in ASCII format and is hereby incorporated by reference in its entirety. Said ASCII copy, created on Jan. 29, 2020, is named 51750-701_831_SL.txt and is 258,486 bytes in size.

BACKGROUND OF THE DISCLOSURE

CD47 is a key molecule that governs macrophage phagocytosis which acts by sending inhibitory signals through SIRPα, a transmembrane receptor that is expressed on macrophages and other myeloid cells. CD47 is ubiquitously expressed and serves as a "marker of self" to prevent macrophage phagocytosis. The same mechanism is employed by cancer cells to evade immunological eradication. In fact, CD47 expression is elevated in several human cancers including solid tumors such as breast, colon, liver, bladder, brain, ovarian, renal, prostate carcinomas, melanoma, and blood cancers such as AML, ALL, CLL, CML, DLBL, FL, MCL, MM and others. CD47 interacts with SIRPα, an inhibitory transmembrane receptor on myeloid cells, such as macrophages. The CD47/SIRPα interaction leads to bidirectional signaling, resulting in different cell-to-cell responses including inhibition of phagocytosis by the macrophages. Therefore, disruption of this interaction can remove this inhibition, thereby inducing phagocytosis. Existing agents that disrupt such interaction suffers from a number of drawbacks. Amongst them are relative lower affinity and/or selectivity towards CD47, as well as high propensity to induce undesired hemagglutination.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE DISCLOSURE

There exists a considerable need for alternative CD47-binding agents. The present invention addresses this need and provides related advantages.

Disclosed herein are antigen binding units comprising a light chain CDR and a heavy chain CDR, wherein the antigen binding unit (a) specifically binds to CD47; (b) induces phagocytosis of cells expressing CD47 upon binding to CD47; and (c) lacks the ability to induce substantial hemagglutination when mixed with red blood cells at a concentration range of 1.5 ng/ml to 30 ug/ml of said antigen binding unit. In some aspects, binding of the antigen binding unit to CD47 prevents binding of CD47 to SIRPα that is expressed on a macrophage cell. In some aspects, the antigen binding unit induces phagocytosis of cells expressing CD47 to a greater extent as compared to an antigen binding unit having the amino acid sequences of SEQ ID NO:240-241. In some aspects, the antigen binding unit induces phagocytosis of cells expressing CD47 to a greater extent as compared to an antigen binding unit having the amino acid sequences of SEQ ID NO:242-243. In some aspects, the antigen binding unit induces phagocytosis of cells expressing CD47 to a greater extent as compared to an antigen binding unit having the amino acid sequences of SEQ ID NO:244-245. In some aspects, the antigen binding unit exhibits a higher binding affinity to CD47 as compared to an antigen binding unit having the amino acid sequences of SEQ ID NO:240-241, when assayed in an in vitro binding assay utilizing cells expressing CD47. In some aspects, the antigen binding unit exhibits a higher binding affinity to CD47 as compared to an antigen binding unit having the amino acid sequences of SEQ ID NO:242-243, when assayed in an in vitro binding assay utilizing cells expressing CD47. In some aspects, the antigen binding unit exhibits a higher binding affinity to CD47 as compared to an antigen binding unit having the amino acid sequences of SEQ ID NO:244-245, when assayed in an in vitro binding assay utilizing cells expressing CD47. In some aspects, hemagglutination induced upon contacting the red blood cells with the antigen binding unit is at least 1 fold less as compared to that induced by an antigen binding unit having the amino acid sequences of SEQ ID NO:240-241. In some aspects, hemagglutination induced upon contacting the red blood cells with the antigen binding unit is at least 1 fold less as compared to that induced by an antigen binding unit having the amino acid sequences of SEQ ID NO:242-243. In some aspects, hemagglutination induced upon contacting the red blood cells with the antigen binding unit is at least 1 fold less as compared to that induced by an antigen binding unit having the amino acid sequences of SEQ ID NO:244-245. In some aspects, the light chain CDR comprises LC-CDR1, LC-CDR2, and LC-CDR3; and the heavy chain CDR comprises HC-CDR1, HC-CDR2, and HC-CDR3; wherein said LC-CDR1, LC-CDR2, and LC-CDR3 each have a sequence selected from the group consisting of SEQ ID NO: 1-22 and 162-190; and wherein said HC-CDR1, HC-CDR2, HC-CDR3 each have a sequence selected from the group consisting of SEQ ID NO: 23-44 and 191-237. In some aspects, said light chain CDR comprises amino acid sequences selected from among the following combinations of LC-CDR sequences: a) SEQ ID NO:4, SEQ ID NO:8, and SEQ ID NO:21; b) SEQ ID NO:5, SEQ ID NO:10, and SEQ ID NO:16; c) SEQ ID NO:6, SEQ ID NO:9, and SEQ ID NO:17; d) SEQ ID NO:2, SEQ ID NO:12, and SEQ ID NO:20; e) SEQ ID NO:7, SEQ ID NO:11, and SEQ ID NO:15; f) SEQ ID NO:1, SEQ ID NO:13, and SEQ ID NO:22; g) SEQ ID NO:3, SEQ ID NO:14, and SEQ ID NO:19; h) SEQ ID NO:169, SEQ ID NO:173, and SEQ ID NO:180; i) SEQ ID NO:168, SEQ ID NO:173, and SEQ ID NO:181; k) SEQ ID NO:165, SEQ ID NO:177, and SEQ ID NO:182; l) SEQ ID NO:163, SEQ ID NO:178, and SEQ ID NO:183; m) SEQ ID NO:163, SEQ ID NO:172, and SEQ ID NO:184; n) SEQ ID NO:163, SEQ ID NO:178, and SEQ ID NO:185; o) SEQ ID NO:163, SEQ ID NO:178, and SEQ ID NO:186; p) SEQ ID NO:163, SEQ ID NO:170, and SEQ ID NO:187; q) SEQ ID NO:163, SEQ ID NO:174, and SEQ ID NO:187; r) SEQ ID NO:164, SEQ ID NO:175, and SEQ ID NO:187; s) SEQ ID NO:162, SEQ ID NO:178, and SEQ ID NO:187; t) SEQ ID NO:163, SEQ ID NO:178, and SEQ ID NO:187; u) SEQ ID NO:164, SEQ ID NO:178, and SEQ ID NO:187; v) SEQ ID NO:163, SEQ ID NO:179, and SEQ ID NO:187; w) SEQ ID NO:166, SEQ ID NO:176, and SEQ ID NO:188; x) SEQ ID NO:167, SEQ ID NO:171, and SEQ ID NO:189; and y) SEQ ID NO:167, SEQ ID NO:171, and SEQ ID NO:190. In some aspects, said heavy chain CDR comprises amino acid sequences selected from among the following combinations of HC-CDR sequences: a) SEQ ID NO:25, SEQ ID NO:32, and SEQ ID NO:38; b) SEQ ID NO:28, SEQ ID NO:35, and SEQ ID NO:39; c) SEQ ID NO:24, SEQ ID NO:34, and SEQ ID NO:40; d) SEQ ID NO:29, SEQ ID NO:33, and SEQ ID NO:43; e) SEQ ID NO:27, SEQ ID NO:30, and SEQ ID NO:42; f) SEQ ID NO:23, SEQ ID NO:36, and SEQ ID NO:41; g) SEQ ID NO:26, SEQ ID NO:31, and SEQ ID NO:44; h) SEQ ID NO:191, SEQ ID NO:207, and SEQ ID NO:226; i) SEQ ID NO:192, SEQ ID NO:222, and SEQ ID NO:237; j) SEQ ID NO:193, SEQ ID NO:219, and SEQ ID NO:233; k) SEQ ID NO:194, SEQ ID NO:220, and SEQ ID NO:228; l) SEQ ID NO:195, SEQ ID NO:221, and SEQ ID NO:229; m) SEQ ID NO:196, SEQ ID NO:214, and SEQ ID NO:225; n) SEQ ID NO:197, SEQ ID NO:212, and SEQ ID NO:232; o) SEQ ID NO:197, SEQ ID NO:213, and SEQ ID NO:232; p) SEQ ID NO:198, SEQ ID NO:210, and SEQ ID NO:224; q) SEQ ID NO:198, SEQ ID NO:208, and SEQ ID NO:234; r) SEQ ID NO:198, SEQ ID NO:210, and SEQ ID NO:234; s) SEQ ID NO:199, SEQ ID NO:210, and SEQ ID NO:224; t) SEQ ID NO:200, SEQ ID NO:222, and SEQ ID NO:230; u) SEQ ID NO:201, SEQ ID NO:210, and SEQ ID NO:224; v) SEQ ID NO:201, SEQ ID NO:216, and SEQ ID NO:224; w) SEQ ID NO:202, SEQ ID NO:210, and SEQ ID NO:234; x) SEQ ID NO:203, SEQ ID NO:218, and SEQ ID NO:227; y) SEQ ID NO:204, SEQ ID NO:211, and SEQ ID NO:224; z) SEQ ID NO:204, SEQ ID NO:217, and SEQ ID NO:224; aa) SEQ ID NO:204, SEQ ID NO:214, and SEQ ID NO:225; bb) SEQ ID NO:204, SEQ ID NO:215, and SEQ ID NO:235; cc) SEQ ID NO:204, SEQ ID NO:214, and SEQ ID NO:236; dd) SEQ ID NO:205, SEQ ID NO:209, and SEQ ID NO:224; ee) SEQ ID NO:205, SEQ ID NO:210, and SEQ ID NO:224; ff) SEQ ID NO:205, SEQ ID NO:223, and SEQ ID NO:231; and gg) SEQ ID NO:206, SEQ ID NO:210, and SEQ ID NO:224. In some aspects, the antigen binding unit is a monoclonal antibody, humanized antibody, or chimeric antibody. In some aspects, the antigen binding unit of is sFc, Fv, Fab, or (Fab)2. In some aspects, the antigen binding unit of claim competes for binding to an epitope recognized by an antigen binding unit having the amino acid sequences of 1) SEQ ID NO:240-241, 2) SEQ ID NO:242-243, or 3) SEQ ID NO:244-245.

Disclosed herein are antigen binding units comprising a light chain CDR and a heavy chain CDR, wherein the antigen binding unit (a) specifically binds to CD47 with a binding affinity higher than that of a reference antigen binding unit and prevents binding of CD47 to SIRPα; and (b) lacks the ability to induce substantial hemagglutination when mixed with red blood cells at a concentration range of 1.5 ng/ml to 30 ug/ml of antigen binding unit, wherein the reference antigen binding have the amino acid sequences of 1) SEQ ID NO:240-241, 2) SEQ ID NO:242-243, or 3) SEQ ID NO:244-245. In some aspects, the light chain CDR comprises LC-CDR1, LC-CDR2, and LC-CDR3; and the heavy chain CDR comprises HC-CDR1, HC-CDR2, and HC-CDR3; wherein said LC-CDR1, LC-CDR2, and LC-CDR3 each have a sequence selected from the group consisting SEQ ID NOs: 1-22, and 162-190; and wherein said HC-CDR1, HC-CDR2, HC-CDR3 each have a sequence selected from the group consisting of SEQ ID NOs: 23-44 and 191-237. In some aspects, said light chain CDR comprises amino acid sequences selected from among the following combinations of LC-CDR sequences: a) SEQ ID NO:4, SEQ ID NO:8, and SEQ ID NO:21; b) SEQ ID NO:5, SEQ ID NO:10, and SEQ ID NO:16; c) SEQ ID NO:6, SEQ ID NO:9, and SEQ ID NO:17; d) SEQ ID NO:2, SEQ ID NO:12, and SEQ ID NO:20; e) SEQ ID NO:7, SEQ ID NO:11, and SEQ ID NO:15; f) SEQ ID NO:1, SEQ ID NO:13, and SEQ ID NO:22; g) SEQ ID NO:3, SEQ ID NO:14, and SEQ ID NO:19; h) SEQ ID NO:169, SEQ ID NO:173, and SEQ ID NO:180; i) SEQ ID NO:168, SEQ ID NO:173, and SEQ ID NO:181; k) SEQ ID NO:165, SEQ ID NO:177, and SEQ ID NO:182; l) SEQ ID NO:163, SEQ ID NO:178, and SEQ ID NO:183; m) SEQ ID NO:163, SEQ ID NO:172, and SEQ ID NO:184; n) SEQ ID NO:163, SEQ ID NO:178, and SEQ ID NO:185; o) SEQ ID NO:163, SEQ ID NO:178, and SEQ ID NO:186; p) SEQ ID NO:163, SEQ ID NO:170, and SEQ ID NO:187; q) SEQ ID NO:163, SEQ ID NO:174, and SEQ ID NO:187; r) SEQ ID NO:164, SEQ ID NO:175, and SEQ ID NO:187; s) SEQ ID NO:162, SEQ ID NO:178, and SEQ ID NO:187; t) SEQ ID NO:163, SEQ ID NO:178, and SEQ ID NO:187; u) SEQ ID NO:164, SEQ ID NO:178, and SEQ ID NO:187; v) SEQ ID NO:163, SEQ ID NO:179, and SEQ ID NO:187; w) SEQ ID NO:166, SEQ ID NO:176, and SEQ ID NO:188; x) SEQ ID NO:167, SEQ ID NO:171, and SEQ ID NO:189; and y) SEQ ID NO:167, SEQ ID NO:171, and SEQ ID NO:190. In some aspects, said heavy chain CDR comprises amino acid sequences selected from among the following combinations of HC-CDR sequences: a) SEQ ID NO:25, SEQ ID NO:32, and SEQ ID NO:38; b) SEQ ID NO:28, SEQ ID NO:35, and SEQ ID NO:39; c) SEQ ID NO:24, SEQ ID NO:34, and SEQ ID NO:40; d) SEQ ID NO:29, SEQ ID NO:33, and SEQ ID NO:43; e) SEQ ID NO:27, SEQ ID NO:30, and SEQ ID NO:42; f) SEQ ID NO:23, SEQ ID NO:36, and SEQ ID NO:41; g) SEQ ID NO:26, SEQ ID NO:31, and SEQ ID NO:44; h) SEQ ID NO:191, SEQ ID NO:207, and SEQ ID NO:226; i) SEQ ID NO:192, SEQ ID NO:222, and SEQ ID NO:237; j) SEQ ID NO:193, SEQ ID NO:219, and SEQ ID NO:233; k) SEQ ID NO:194, SEQ ID NO:220, and SEQ ID NO:228; l) SEQ ID NO:195, SEQ ID NO:221, and SEQ ID NO:229; m) SEQ ID NO:196, SEQ ID NO:214, and SEQ ID NO:225; n) SEQ ID NO:197, SEQ ID NO:212, and SEQ ID NO:232; o) SEQ ID NO:197, SEQ ID NO:213, and SEQ ID NO:232; p) SEQ ID NO:198, SEQ ID NO:210, and SEQ ID NO:224; q) SEQ ID NO:198, SEQ ID NO:208, and SEQ ID NO:234; r) SEQ ID NO:198, SEQ ID NO:210, and SEQ ID NO:234; s) SEQ ID NO:199, SEQ ID NO:210, and SEQ ID NO:224; t) SEQ ID NO:200, SEQ ID NO:222, and SEQ ID NO:230; u) SEQ ID NO:201, SEQ ID NO:210, and SEQ ID NO:224; v) SEQ ID NO:201, SEQ ID NO:216, and SEQ ID NO:224; w) SEQ ID NO:202, SEQ ID NO:210, and SEQ ID NO:234; x) SEQ ID NO:203, SEQ ID NO:218, and SEQ ID NO:227; y) SEQ ID NO:204, SEQ ID NO:211, and SEQ ID NO:224; z) SEQ ID NO:204, SEQ ID NO:217, and SEQ ID NO:224; aa) SEQ ID NO:204, SEQ ID NO:214, and SEQ ID NO:225; bb) SEQ ID NO:204, SEQ ID NO:215, and SEQ ID NO:235; cc) SEQ ID NO:204, SEQ ID NO:214, and SEQ ID NO:236; dd) SEQ ID NO:205, SEQ ID NO:209, and SEQ ID NO:224; ee) SEQ ID NO:205, SEQ ID NO:210, and SEQ ID NO:224; ff) SEQ ID NO:205, SEQ ID NO:223, and SEQ ID NO:231; and gg) SEQ ID NO:206, SEQ ID NO:210, and SEQ ID NO:224. In some aspects, the antigen binding unit is a monoclonal antibody, humanized antibody, chimeric antibody, or bispecific antibody. In some aspects, the antigen binding unit of is sFc, Fv, Fab, or (Fab)2.

Disclosed herein are antigen binding units comprising a light chain CDR and a heavy chain CDR, wherein the antigen binding unit (a) specifically binds to CD47; and (b)

induces phagocytosis of cells expressing CD47 upon binding to CD47 to a greater extent as compared to a reference antigen binding unit, wherein the reference antigen binding unit have the amino acid sequences of 1) SEQ ID NO:240-241, 2) SEQ ID NO:242-243, or 3) SEQ ID NO:244-245. In some aspects, the antigen binding unit induces phagocytosis of cells expressing CD47 to a greater extent as compared to an antigen binding unit having the amino acid sequences of SEQ ID NO:240-241. In some aspects, the antigen binding unit induces phagocytosis of cells expressing CD47 to a greater extent as compared to an antigen binding unit having the amino acid sequences of SEQ ID NO:242-243. In some aspects, the antigen binding unit induces phagocytosis of cells expressing CD47 to a greater extent as compared to an antigen binding unit having the amino acid sequences of SEQ ID NO:244-245. In some aspects, the light chain CDR comprises LC-CDR1, LC-CDR2, and LC-CDR3; and the heavy chain CDR comprises heavy chain HC-CDR1, HC-CDR2, and HC-CDR3; wherein said LC-CDR1, LC-CDR2, and LC-CDR3 each have a sequence selected from the group consisting of SEQ ID NOs: 1-22, and 162-190; and wherein said HC-CDR1, HC-CDR2, HC-CDR3 each have a sequence selected from the group consisting of SEQ ID NOs: 23-44 and 191-237. In some aspects, said light chain CDR comprises amino acid sequences selected from among the following combinations of LC-CDR sequences: a) SEQ ID NO:4, SEQ ID NO:8, and SEQ ID NO:21; b) SEQ ID NO:5, SEQ ID NO:10, and SEQ ID NO:16; c) SEQ ID NO:6, SEQ ID NO:9, and SEQ ID NO:17; d) SEQ ID NO:2, SEQ ID NO:12, and SEQ ID NO:20; e) SEQ ID NO:7, SEQ ID NO:11, and SEQ ID NO:15; f) SEQ ID NO:1, SEQ ID NO:13, and SEQ ID NO:22; g) SEQ ID NO:3, SEQ ID NO:14, and SEQ ID NO:19; h) SEQ ID NO:169, SEQ ID NO:173, and SEQ ID NO:180; i) SEQ ID NO:168, SEQ ID NO:173, and SEQ ID NO:181; k) SEQ ID NO:165, SEQ ID NO:177, and SEQ ID NO:182; l) SEQ ID NO:163, SEQ ID NO:178, and SEQ ID NO:183; m) SEQ ID NO:163, SEQ ID NO:172, and SEQ ID NO:184; n) SEQ ID NO:163, SEQ ID NO:178, and SEQ ID NO:185; o) SEQ ID NO:163, SEQ ID NO:178, and SEQ ID NO:186; p) SEQ ID NO:163, SEQ ID NO:170, and SEQ ID NO:187; q) SEQ ID NO:163, SEQ ID NO:174, and SEQ ID NO:187; r) SEQ ID NO:164, SEQ ID NO:175, and SEQ ID NO:187; s) SEQ ID NO:162, SEQ ID NO:178, and SEQ ID NO:187; t) SEQ ID NO:163, SEQ ID NO:178, and SEQ ID NO:187; u) SEQ ID NO:164, SEQ ID NO:178, and SEQ ID NO:187; v) SEQ ID NO:163, SEQ ID NO:179, and SEQ ID NO:187; w) SEQ ID NO:166, SEQ ID NO:176, and SEQ ID NO:188; x) SEQ ID NO:167, SEQ ID NO:171, and SEQ ID NO:189; and y) SEQ ID NO:167, SEQ ID NO:171, and SEQ ID NO:190. In some aspects, said heavy chain CDR comprises amino acid sequences selected from among the following combinations of HC-CDR sequences: a) SEQ ID NO:25, SEQ ID NO:32, and SEQ ID NO:38; b) SEQ ID NO:28, SEQ ID NO:35, and SEQ ID NO:39; c) SEQ ID NO:24, SEQ ID NO:34, and SEQ ID NO:40; d) SEQ ID NO:29, SEQ ID NO:33, and SEQ ID NO:43; e) SEQ ID NO:27, SEQ ID NO:30, and SEQ ID NO:42; f) SEQ ID NO:23, SEQ ID NO:36, and SEQ ID NO:41; g) SEQ ID NO:26, SEQ ID NO:31, and SEQ ID NO:44; h) SEQ ID NO:191, SEQ ID NO:207, and SEQ ID NO:226; i) SEQ ID NO:192, SEQ ID NO:222, and SEQ ID NO:237; j) SEQ ID NO:193, SEQ ID NO:219, and SEQ ID NO:233; k) SEQ ID NO:194, SEQ ID NO:220, and SEQ ID NO:228; l) SEQ ID NO:195, SEQ ID NO:221, and SEQ ID NO:229; m) SEQ ID NO:196, SEQ ID NO:214, and SEQ ID NO:225; n) SEQ ID NO:197, SEQ ID NO:212, and SEQ ID NO:232; o) SEQ ID NO:197, SEQ ID NO:213, and SEQ ID NO:232; p) SEQ ID NO:198, SEQ ID NO:210, and SEQ ID NO:224; q) SEQ ID NO:198, SEQ ID NO:208, and SEQ ID NO:234; r) SEQ ID NO:198, SEQ ID NO:210, and SEQ ID NO:234; s) SEQ ID NO:199, SEQ ID NO:210, and SEQ ID NO:224; t) SEQ ID NO:200, SEQ ID NO:222, and SEQ ID NO:230; u) SEQ ID NO:201, SEQ ID NO:210, and SEQ ID NO:224; v) SEQ ID NO:201, SEQ ID NO:216, and SEQ ID NO:224; w) SEQ ID NO:202, SEQ ID NO:210, and SEQ ID NO:234; x) SEQ ID NO:203, SEQ ID NO:218, and SEQ ID NO:227; y) SEQ ID NO:204, SEQ ID NO:211, and SEQ ID NO:224; z) SEQ ID NO:204, SEQ ID NO:217, and SEQ ID NO:224; aa) SEQ ID NO:204, SEQ ID NO:214, and SEQ ID NO:225; bb) SEQ ID NO:204, SEQ ID NO:215, and SEQ ID NO:235; cc) SEQ ID NO:204, SEQ ID NO:214, and SEQ ID NO:236; dd) SEQ ID NO:205, SEQ ID NO:209, and SEQ ID NO:224; ee) SEQ ID NO:205, SEQ ID NO:210, and SEQ ID NO:224; ff) SEQ ID NO:205, SEQ ID NO:223, and SEQ ID NO:231; and gg) SEQ ID NO:206, SEQ ID NO:210, and SEQ ID NO:224. In some aspects, the antigen binding unit is a monoclonal antibody, humanized antibody, chimeric antibody, or bispecific antibody. In some aspects, the antigen binding unit of is sFc, Fv, Fab, or (Fab)2.

Disclosed herein are antigen binding units comprising a light chain CDR and a heavy chain CDR, wherein the light chain CDR comprises LC-CDR1, LC-CDR2, and LC-CDR3; and the heavy chain CDR comprises HC-CDR1, HC-CDR2, and HC-CDR3, wherein said LC-CDR1, LC-CDR2, and LC-CDR3 each comprises a sequence sharing at least 80% sequence homology to a sequence selected from the group consisting of SEQ ID NOs: 1-22, and 162-190, and wherein said HC-CDR1, HC-CDR2, and HC-CDR3 each comprises a sequence having least 80% sequence homology to a sequence selected from the group consisting of SEQ ID NOs: 23-44 and 191-237. In some aspects, said light chain CDR and said heavy chain CDR comprise, respectively, the LC-CDR and the HC-CDR selected from the group consisting of: a) SEQ ID NO:54 and SEQ ID NO:55; b) SEQ ID NO:65 and SEQ ID NO:63; c) SEQ ID NO:58 and SEQ ID NO:64; d) SEQ ID NO:68 and SEQ ID NO:60; e) SEQ ID NO:66 and SEQ ID NO:61; f) SEQ ID NO:57 and SEQ ID NO:62; g) SEQ ID NO:56 and SEQ ID NO:59; h) SEQ ID NO:85 and SEQ ID NO:86; i) SEQ ID NO:87 and SEQ ID NO:88; j) SEQ ID NO:89 and SEQ ID NO:90; k) SEQ ID NO:91 and SEQ ID NO:92; l) SEQ ID NO:93 and SEQ ID NO:94; m) SEQ ID NO:95 and SEQ ID NO:96; n) SEQ ID NO:97 and SEQ ID NO:98; o) SEQ ID NO:99 and SEQ ID NO:100; p) SEQ ID NO:101 and SEQ ID NO:102; q) SEQ ID NO:103 and SEQ ID NO:104; r) SEQ ID NO:105 and SEQ ID NO:106; s) SEQ ID NO:107 and SEQ ID NO:108; t) SEQ ID NO:109 and SEQ ID NO:110; u) SEQ ID NO:111 and SEQ ID NO:112; v) SEQ ID NO:113 and SEQ ID NO:114; w) SEQ ID NO:115 and SEQ ID NO:116; x) SEQ ID NO:117 and SEQ ID NO:118; y) SEQ ID NO:119 and SEQ ID NO:120; z) SEQ ID NO:121 and SEQ ID NO:122; aa) SEQ ID NO:123 and SEQ ID NO:124; bb) SEQ ID NO:125 and SEQ ID NO:126; cc) SEQ ID NO:127 and SEQ ID NO:128; dd) SEQ ID NO:129 and SEQ ID NO:130; ee) SEQ ID NO:131 and SEQ ID NO:132; ff) SEQ ID NO:133 and SEQ ID NO:134; gg) SEQ ID NO:135 and SEQ ID NO:136; hh) SEQ ID NO:137 and SEQ ID NO:138; ii) SEQ ID NO:139 and SEQ ID NO:140; jj) SEQ ID NO:141 and SEQ ID NO:142; kk) SEQ ID NO:143 and SEQ ID NO:144; ll) SEQ ID NO:145 and SEQ ID NO:146; mm) SEQ ID NO:147 and SEQ ID NO:148; nn) SEQ ID NO:238 and SEQ ID NO:239 oo) SEQ ID NO:47 and SEQ ID NO:70; pp) SEQ ID NO:49 and SEQ ID NO:73; qq) SEQ ID NO:71 and SEQ ID NO:51; rr) SEQ ID NO:50 and SEQ ID NO:74; ss) SEQ ID NO:45 and SEQ ID NO:53; tt) SEQ ID NO:67 and SEQ ID NO:72; uu) SEQ ID NO:69 and SEQ ID NO:52; vv) SEQ ID NO:46 and SEQ ID NO:77; ww) SEQ ID NO:46 and SEQ ID NO:78; xx) SEQ ID NO:46 and SEQ ID NO:79; yy) SEQ ID NO:48 and SEQ ID NO:75; zz) SEQ ID NO:48 and SEQ ID NO:76; —aaa) SEQ ID NO:48 and SEQ ID NO:80, and bbb) any sequence pair listed in Table 1. In some aspects, the antigen binding unit is a monoclonal antibody, humanized antibody, chimeric antibody, or bispecific antibody. In some aspects, the antigen binding unit of is sFc, Fv, or Fab.

Disclosed herein are pharmaceutical compositions comprising any one of the antigen binding units disclosed herein, and a pharmaceutically acceptable excipient.

Disclosed herein are isolated nucleic acids encoding any one of the antigen binding units disclosed herein.

Disclosed herein are vectors comprising a nucleic acid sequence encoding any one of the antigen binding units disclosed herein.

Disclosed herein are host cells expressing any one of the antigen binding units disclosed herein.

Disclosed herein are host cells comprising a nucleic acid encoding any one of the antigen binding units disclosed herein.

Disclosed herein are methods of producing any one of the antigen binding units disclosed herein, comprising: culturing any of the host cells disclosed herein under conditions suitable for expressing the antigen binding unit; and isolating said antigen binding unit expressed by the host cell.

Disclosed herein are methods of inducing phagocytosis of cells expressing CD47, said method comprising contacting the cell with any one of the antigen binding units disclosed herein. In some aspects, phagocytosis of cells expressing CD47 occurs with at least 5% efficiency. In some aspects, the antigen binding unit does not cause significant hemagglutination. In some aspects, the cell is a cancer cell. In some aspects, the cell is a non-lymphoma and non-leukemia cancer cell.

Disclosed herein are methods of inducing phagocytosis of cells expressing CD47 in a human subject, said method comprising administering to the human subject any one of the pharmaceutical compositions disclosed herein. In some aspects, phagocytosis of cells expressing CD47 occurs with at least 5% efficiency. In some aspects, the antigen binding unit does not cause significant hemagglutination. In some aspects, the cell is a cancer cell. In some aspects, the cell is a non-lymphoma and non-leukemia cancer cell. In some aspects, the cell is a hematological cancer cell or a solid tumor cell.

Disclosed herein are methods of treating a cancer in a subject in need thereof, said method comprising administering to the subject an effective amount of any one of the antigen binding units disclosed herein. In some aspects, the method further comprises administering a therapeutic antibody. In some aspects, the therapeutic antibody is an anti-CD20 antibody. In some aspects, treating the cancer comprises reducing tumor volume. In some aspects, the tumor volume is reduced to a greater extent as compared to an antigen binding unit having the amino acid sequences of SEQ ID NO:240 and 241, or SEQ ID NO: 242 and 243, or SEQ ID NO: 244 and 245.

Disclosed herein are methods of treating a cancer in a subject in need thereof, said method comprising administering to the subject an effective amount of any one of the pharmaceutical compositions disclosed herein. In some aspects, the cancer is a hematological cancer or a solid tumor. In some aspects, the method further comprises administering a therapeutic antibody. In some aspects, the therapeutic antibody is an anti-CD20 antibody. In some aspects, treating the cancer comprises reducing tumor volume. In some aspects, the tumor volume is reduced to a greater extent as compared to an antigen binding unit having the amino acid sequences of SEQ ID NO:240 and 241, or SEQ ID NO: 242 and 243, or SEQ ID NO: 244 and 245.

DETAILED DESCRIPTION OF THE DISCLOSURE

Figure 1:
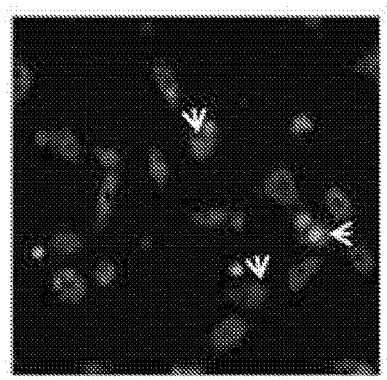
FIG. 1 depicts data from an example phagocytosis experiment.
Figure 1:
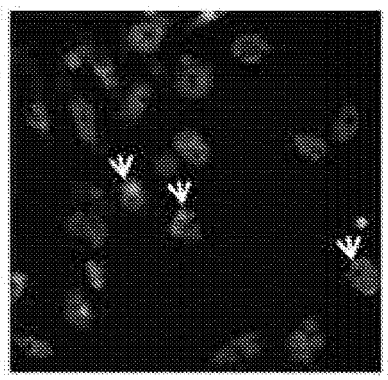
Figure 1:
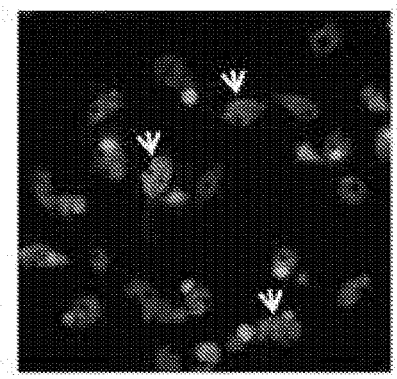
Figure 1:
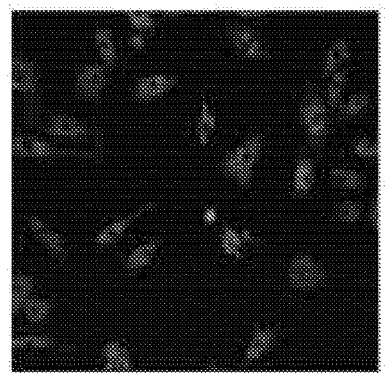
Figure 1:
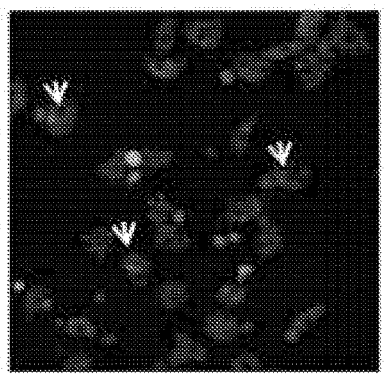
Figure 1:
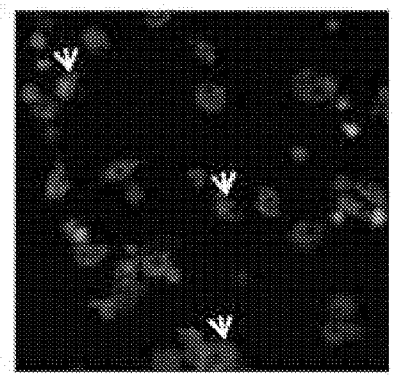

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

The terms "polypeptide", "peptide", and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics. A polypeptide or amino acid sequence "derived from" a designated protein refers to the origin of the polypeptide. Preferably, the polypeptide has an amino acid sequence that is essentially identical to that of a polypeptide encoded in the sequence, or a portion thereof wherein the portion consists of at least 10-20 amino acids, or at least 20-30 amino acids, or at least 30-50 amino acids, or which is immunologically identifiable with a polypeptide encoded in the sequence. This terminology also includes a polypeptide expressed from a designated nucleic acid sequence.

The term "antigen binding unit" as used herein refers to an immunoglobulin molecule and immunologically active portions of immunoglobulin molecule, i.e., a molecule that contains an antigen-binding site which specifically binds ("immunoreacts with") an antigen. Also encompassed within the term "antigen binding unit" are immunoglobulin molecules of a variety of species origins including invertebrates and vertebrates. Structurally, the simplest naturally occurring antibody (e.g., IgG) comprises four polypeptide chains, two heavy (H) chains and two light (L) chains inter-connected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Also encompassed within the term "antigen binding unit" is any polypeptide chain-containing molecular structure that has a specific shape which fits to and recognizes an epitope, where one or more non-covalent binding interactions stabilize the complex between the molecular structure and the epitope.

An antigen binding unit "specifically binds to" or "immunoreactive with" an antigen if it binds with greater affinity or avidity than it binds to other reference antigens including polypeptides or other substances.

"Antigen" as used herein means a substance that is recognized and bound specifically by an antigen binding unit. Antigens can include peptides, proteins, glycoproteins, polysaccharides, and lipids; portions thereof and combinations thereof. Non-limiting exemplary antigen included CD47 from human, murine, and other homologues thereof. Another example antigen is SIRPα from human, murine, and other homologues thereof.

A "chimeric" protein contains at least one fusion polypeptide comprising regions in a different position in the sequence than what occurs in nature. The regions may normally exist in separate proteins and are brought together in the fusion polypeptide; or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship.

"Domain" refers to a portion of a protein that is physically or functionally distinguished from other portions of the protein or peptide. Physically-defined domains include those amino acid sequences that are exceptionally hydrophobic or hydrophilic, such as those sequences that are membrane-associated or cytoplasm-associated. Domains may also be defined by internal homologies that arise, for example, from gene duplication. Functionally-defined domains have a distinct biological function(s). The ligand-binding domain of a receptor, for example, is that domain that binds ligand. An antigen-binding domain refers to the part of an antigen-binding unit or an antibody that binds to the antigen. Functionally-defined domains need not be encoded by contiguous amino acid sequences. Functionally-defined domains may contain one or more physically-defined domain. Receptors, for example, are generally divided into the extracellular ligand-binding domain, a transmembrane domain, and an intracellular effector domain.

A "host cell" includes an individual cell or cell culture which can be or has been a recipient for the subject vectors. Host cells include progeny of a single host cell. The progeny may not necessarily be completely identical (in morphology or in genomic of total DNA complement) to the original parent cell due to natural, accidental, or deliberate mutation. A host cell includes cells transfected in vivo with a vector of this invention. A "host cell" can refer to a prokaryotic cell, a eukaryotic cell, or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

A "cell line" or "cell culture" denotes bacterial, plant, insect or higher eukaryotic cells grown or maintained in vitro. The descendants of a cell may not be completely identical (either morphologically, genotypically, or phenotypically) to the parent cell.

As used herein, the term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

"Linked" and "fused" or "fusion" are used interchangeably herein. These terms refer to the joining together of two more chemical elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence (e.g. "flexon").

In the context of polypeptides, a "sequence" is an order of amino acids in a polypeptide in an amino to carboxyl terminus direction in which residues that neighbor each other in the sequence are contiguous in the primary structure of the polypeptide. A sequence can also be a linear sequence of part of a polypeptide which is known to comprise additional residues in one or both directions.

"Heterologous" means derived from a genotypically distinct entity from the rest of the entity to which it is being compared. For example, a promoter removed from its native coding sequence and operatively linked to a coding sequence other than the native sequence is a heterologous promoter. The term "heterologous" as applied to a polynucleotide, a polypeptide, means that the polynucleotide or polypeptide is derived from a genotypically distinct entity from that of the rest of the entity to which it is being compared. For instance, a heterologous polynucleotide or antigen may be derived from a different species origin, different cell type, and the same type of cell of distinct individuals.

The terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, primers, oligonucleotides, or synthesized DNA. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

"Recombinant" as applied to a polynucleotide means that the polynucleotide is the product of various combinations of cloning, restriction and/or ligation steps, and other procedures that result in a construct that is distinct from a polynucleotide found in nature.

The terms "gene" or "gene fragment" are used interchangeably herein. They refer to a polynucleotide containing at least one open reading frame that is capable of encoding a particular protein after being transcribed and translated. A gene or gene fragment may be genomic, cDNA, or synthesized, as long as the polynucleotide contains at least one open reading frame, which may cover the entire coding region or a segment thereof.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

A "fusion gene" is a gene composed of at least two heterologous polynucleotides that are linked together.

A gene "database" denotes a set of stored data which represent a collection of sequences including nucleotide and peptide sequences, which in turn represent a collection of biological reference materials.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectively referred to as gene product. If the polynucleotide is derived from genomic DNA, expression may include splicing of the mRNA in a eukaryotic cell.

A "vector" is a nucleic acid molecule, preferably self-replicating, which transfers an inserted nucleic acid molecule into and/or between host cells. The term includes vectors that function primarily for insertion of DNA or RNA into a cell, replication of vectors that function primarily for the replication of DNA or RNA, and expression vectors that function for transcription and/or translation of the DNA or RNA. Also included are vectors that provide more than one of the above functions. An "expression vector" is a polynucleotide which, when introduced into an appropriate host cell, can be transcribed and translated into a polypeptide(s). An "expression system" usually connotes a suitable host cell comprised of an expression vector that can function to yield a desired expression product.

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, e.g. mouse, rat, rabbit, pig, primate, including humans and other apes, particularly a human, and includes: (a) preventing the disease or symptom from occurring in a subject which may be predisposed to the disease or symptom but has not yet been diagnosed as having it; (b) inhibiting the disease symptom; (c) arresting development of the disease; (d) relieving the disease symptom; (e) causing regression of the disease or symptom; or any combination thereof.

The terms "recipient", "individual", "subject", "host", and "patient", can be used interchangeably herein and refer to any mammalian subject for whom diagnosis, treatment, or therapy is desired, particularly humans.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.).

Phagocytic cells or phagocytes are interchangeable terms and refer to a cell that is capable of phagocytosis. Non-limiting categories of phagocytes include macrophages, mononuclear cells (e.g., histiocytes and monocytes), polymorphonuclear leukocytes (e.g., neutrophils), and dendritic cells.

Compositions

In one embodiment, the present disclosure provides an antigen binding unit comprising a light chain CDR and a heavy chain CDR, wherein the antigen binding unit (a) specifically binds to CD47; (b) induces phagocytosis of cells expressing CD47 upon binding to CD47; and (c) lacks the ability to induce substantial hemagglutination when mixed with red blood cells at a concentration ranging from about 1.5 ng/ml to about 30 ug/ml of the antigen binding unit disclosed herein.

In another embodiment, the present disclosure provides an antigen binding unit comprising a light chain CDR and a heavy chain CDR, wherein the antigen binding unit (a) specifically binds to CD47 with a binding affinity higher than that of a reference antigen binding unit and prevents binding of CD47 to SIRPα; and (b) lacks the ability to induce substantial hemagglutination when mixed with red blood cells at a concentration range of about 1.5 ng/ml to about 30 ug/ml of said antigen binding unit, wherein the reference antigen binding unit has the amino acid sequences shown in 1) SEQ ID NO: 240-241, 2) SEQ ID NO:242-243, or 3) SEQ ID NO:244-245.

In yet another embodiment, the present disclosure provides an antigen binding unit comprising a light chain CDR and a heavy chain CDR, wherein the antigen binding unit (a) specifically binds to CD47; and (b) induces phagocytosis of cells expressing CD47 upon binding to CD47 to a greater extent as compared to a reference antigen binding unit, wherein the reference antigen binding unit has the amino acid sequences shown in 1) SEQ ID NO: 240-241, 2) SEQ ID NO:242-243, or 3) SEQ ID NO:244-245.

In still yet another embodiment, the present disclosure provides an antigen binding unit comprising a light chain CDR and a heavy chain CDR, wherein the light chain CDR comprises LC-CDR1, LC-CDR2, and LC-CDR3; and the heavy chain CDR comprises HC-CDR1, HC-CDR2, and HC-CDR3, wherein said LC-CDR1, LC-CDR2, and LC-CDR3 each comprises a sequence sharing at least 80% sequence homology to a sequence selected from the group consisting of SEQ ID NOs: 1-22, and 162-190, and wherein said HC-CDR1, HC-CDR2, and HC-CDR3 each comprises a sequence having least 80% sequence homology to a sequence selected from the group consisting of SEQ ID NOs: 23-44 and 191-237.

In some aspects, an antigen binding unit can compete for binding to an epitope recognized by a reference antigen binding unit. For example, an antigen binding unit can compete for binding to an epitope recognized by a reference antigen binding wherein having the amino acid sequences shown in 1) SEQ ID NO: 240-241, 2) SEQ ID NO:242-243, or 3) SEQ ID NO:244-245. Epitope binning of select antibodies was conducted using CD47-expressing CHO cells with a commercialized anti-CD47 blocking antibodies. Briefly, seven neutralizing CD47 antibodies and two reference antibodies (positive 1 and positive 2) were analyzed and grouped according to their competitive binding to CHO cell expressing CD47 using flow cytometry. A biotinylated antibody was first used to calculate the concentration for 90% binding, then the 9 CD47 antibodies were serially diluted and mixed with one of the biotinylated antibodies at the pre-determined 90% binding concentration. SA-APC was used to detect the binding of biotinylated antibody binding. All antibodies were compared against each other and the controls. Antibodies that showed no change in the binding were classified as the same group. Antibodies that showed a change in cell surface binding were categorized into separate groups. Three binding profiles on the CHO expressing CD47 were identified and the six hits subjected to three groups as below. One group consisted of ABU1, ABU6, and positive 1. A second group consisted of ABU4, ABU5, and positive 1. A third group consisted of ABU2, ABU3, positive 1, and positive 2.

In some aspects of any of the embodiments disclosed herein, an antigen binding unit comprises a light chain CDR. A light chain CDR can be a complementarity determining region of a light chain of an antigen binding unit. A light chain CDR can comprise a continuous sequence of amino acid residues, or two or more contiguous sequences of amino acid residues separated by, and optionally flanked by, non-complementarity determining regions, such as framework regions. In some examples, a light chain CDR comprises two or more light chain CDRs, which can be referred to as light chain CDR-1, CDR-2, and so on. In advantageous examples, a light chain CDR comprises three light chain CDRs, which can be referred to as light chain CDR-1, light chain CDR-2, and light chain CDR-3 respectively. In some examples, a group of CDRs present on a common light chain can collectively be referred to as light chain CDRs.

In some aspects of any of the embodiments disclosed herein, an antigen binding unit comprises a heavy chain CDR. A heavy chain CDR can be a complementarity determining region of a heavy chain of an antigen binding unit. A heavy chain CDR can comprise a continuous sequence of amino acid residues, or two or more contiguous sequences of amino acid residues separated by, and optionally flanked by, non-complementarity determining regions, such as framework regions. In some examples, a heavy chain CDR comprises two or more heavy chain CDRs, which can be referred to as heavy chain CDR-1, CDR-2, and so on. In advantageous examples, a heavy chain CDR comprises three heavy chain CDRs, which can be referred to as heavy chain CDR-1, heavy chain CDR-2, and heavy chain CDR-3 respectively. In some examples, a group of CDRs present on a common heavy chain can collectively be referred to as heavy chain CDRs.

In some aspects of any of the embodiments disclosed herein, a subject antigen binding unit specifically binds to CD47. CD47 as used herein can also refer to orthologues, homologues, codon-optimized forms, truncated forms, fragmented forms, mutated forms, or any other known derivative form of a known CD47 sequence. For example, CD47 can be human CD47, which is represented by GenBank accession number CEJ95640 and comprises the sequence of SEQ ID NO:81. CD47 can be murine CD47, which is represented by GenBank accession number BAA25401.1 and comprises the sequence of SEQ ID NO:82. In some contexts, CD47 is referred to as Integrin-Associated Protein (IAP). Human IAP is represented by GenBank accession number CAA80977.1, and comprises the sequence of SEQ ID NO:83. Murine IAP is represented by GenBank accession number ADQ12919.1, and comprises the sequence of SEQ ID NO:84. Additionally, CD47 can comprise a sequence sharing at least 50% identity to any one of SEQ ID NO: 81-84. CD47 can be comprise a sequence sharing at least 50%, 55%, 60%, 65%, 70%, 75%, 80%, 85%, 90%, 95%, 99%, or greater than 99% identity to any one of SEQ ID NO: 81-84.

Binding specificity can be determined by complementarity determining regions, or CDRs, such as light chain CDRs or heavy chain CDRs. In many cases, binding specificity is determined by light chain CDRs and heavy chain CDRs. A given combination of heavy chain CDRs and light chain CDRs provides a given binding pocket that confers greater affinity and/or specificity towards CD47 as compared to other reference antigens.

In some aspects of an embodiment disclosed herein, an antigen binding unit specifically binds to CD47 with a binding affinity higher than that of a reference antigen binding unit. Such reference antigen binding units include, but are not limited to, an antigen binding unit having the amino acid sequences shown in 1) SEQ ID NO: 240-241, 2) SEQ ID NO:242-243, or 3) SEQ ID NO:244-245.

Binding of an antigen binding unit to CD47 can be characterized or expressed by any method known in the art. For example, binding can be characterized by binding affinity, which can be the strength of the interaction between the antigen binding unit and the antigen. Binding affinity can be determined by any method known in the art, such as in vitro binding assays. For example, binding affinity of antigen binding units disclosed herein can be determined when assayed in an in vitro binding assay utilizing cells expressing CD47. Binding affinity of subject antigen binding unit can be expressed in term of Kd, which is the equilibrium dissociation constant between an antibody and its respective antigen. In some cases, antigen binding units as disclosed herein specifically bind to CD47 with a Kd within a range of about 10 μM to about 1 fM. For example, an antigen binding unit can specifically bind to CD47 with a Kd of less than about 10 μM, 1 μM, 0.1 μM, 10 nM, 1 nM, 0.1 nM, 10 pM, 1 pM, 0.1 pM, 10 fM, 1 fM, 0.1 fM, or less than 0.1 fM. In some examples, a subject antigen binding unit exhibits a higher binding affinity to CD47 as compared to a reference antigen binding unit having the amino acid sequences shown in 1) SEQ ID NO: 240-241, 2) SEQ ID NO:242-243, or 3) SEQ ID NO:244-245.

In some aspects of an embodiment disclosed herein, an antigen binding unit reduces or even prevents binding of CD47 to SIRPα, and thereby induces phagocytosis by a macrophage cell that expresses SIRPα. Typically, such phagocytosis is induced upon binding of the antigen binding unit to CD47.

In some aspects, a subject antigen binding unit induces phagocytosis of a cell expressing CD47 to a greater extent than that of a reference antigen binding unit. Such reference antigen binding unit can have the amino acid sequences shown in 1) SEQ ID NO: 240-241, 2) SEQ ID NO:242-243, or 3) SEQ ID NO:244-245. Phagocytosis can be accessed qualitatively by any method known in the art. In some cases, the extent of phagocytosis is determined by the number of macrophages that have performed phagocytosis (referred to as phagocytes) among a population of macrophages. For example, the number of phagocytes per 100 macrophages can be determined so that the extent of phagocytosis can be expressed as a percentage or phagocytic index.

Inducing phagocytosis of cells expressing CD47 can by evidenced by an increase in the level of phagocytosis of these cells in the presence of an antigen binding unit disclosed herein. In some examples, the level of phagocytosis of such cells is increased by at least 1%, 5%, 10%, 15%, 20%, 25%, 30%, 35%, 40%, 45%, 50%, 55%, 60%, 65%, 70%, 75%, 80%, 85%, 90%, 95%, 100%, 200%, 500%, 1000%, or greater than 1000% as compared to the level of phagocytosis observed in the absence of the composition.

In some aspects of any of the embodiments disclosed herein, an antigen binding unit lacks the ability to induce substantial hemagglutination. In some cases, an antigen binding unit lacks the ability to induce substantial hemagglutination when mixed with red blood cells at a concentration range between about 1.5 ng/ml to about 30 μg/ml of said antigen binding unit. For example, a subject antigen binding unit can lack the ability to induce substantial hemagglutination when mixed with red blood cells, when the antigen binding unit is at a concentration of about 0.1 ng/mL, 1 ng/mL, 5 ng/mL, 10 ng/mL, 15 ng/mL, 20 ng/mL, 25 ng/mL, 30 ng/mL, 35 ng/mL, 40 ng/mL, 45 ng/mL, 50 ng/mL, 55 ng/mL, 60 ng/mL, 65 ng/mL, 70 ng/mL, 75 ng/mL, 80 ng/mL, 85 ng/mL, 90 ng/mL, 100 ng/mL, 150 ng/mL, 200 ng/mL, 250 ng/mL, 300 ng/mL, 350 ng/mL, 400 ng/mL, 450 ng/mL, 500 ng/mL, 550 ng/mL, 600 ng/mL, 650 ng/mL, 700 ng/mL, 750 ng/mL, 800 ng/mL, 850 ng/mL, 900 ng/mL, 950 ng/mL, 1 μg/ml, 1.5 μg/ml, 2 μg/ml, 3 μg/ml, 4 μg/ml, 5 μg/ml, 10 μg/ml, 15 μg/ml, 20 μg/ml, 25 μg/ml, 30 μg/ml or more of said antigen binding unit. In other examples the antigen binding unit concentration can be less than 1.5 ng/mL. In other examples, the antigen binding unit concentration can be greater than 30 µg/ml.

In some cases, hemagglutination induced upon contacting the red blood cells with a subject antigen binding unit is at least 1 fold less as compared to that induced by a reference antigen binding unit having the amino acid sequences shown in 1) SEQ ID NO: 240-241, 2) SEQ ID NO:242-243, or 3) SEQ ID NO:244-245. In some cases, hemagglutination induced upon contacting the red blood cells with a subject antigen binding unit is at least 1 fold less, at least 2 fold less, at least 3 fold less, at least 4 fold less, at least 5 fold less, at least 6 fold less, at least 7 fold less, at least 8 fold less, at least 9 fold less, or at least 10 fold less as compared to that induced by a reference antigen binding unit having the amino acid sequences shown in 1) SEQ ID NO: 240-241, 2) SEQ ID NO:242-243, or 3) SEQ ID NO:244-245. In some cases, hemagglutination induced upon contacting the red blood cells with a subject antigen binding unit is greater than at least 10 fold less as compared to that induced by a reference antigen binding unit having the amino acid sequences shown in 1) SEQ ID NO: 240-241, 2) SEQ ID NO:242-243, or 3) SEQ ID NO:244-245.

In some cases, evidence of hemagglutination is demonstrated by the presence of non-settlement of RBCs. Where a punctate red dot appears instead of a haze indicates a lack of substantial hemagglutination.

In some aspects, hemagglutination can be quantified and expressed as a hemagglutination index. Hemagglutination index can be quantified by the area of a red blood cell pellet in the presence or absence of subject antigen binding units. For example, the diameter of a red blood cell pellet can be determined either manually or using computer software, such as Image J. When using computer software, the area of a red blood cell pellet can be determined by counting the number of pixels making up the pellet. The area can then be calculated manually or by using software such as Excel. In some cases, the area can then be normalized to a control data set and expressed as a percent of maximum hemagglutination index. In such examples, subject antigen binding units can induce about 0%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150% or greater of the maximum hemagglutination index. In some examples, subject antigen binding units induce less than 100% of the maximum hemagglutination index. For example, subject antigen binding units can induce less than about 100%, 95%, 90%, 85%, 80%, 75%, 70%, 65%, 60%, 55%, 50%, 45%, 40%, 35%, 30%, 25%, 20%, 15%, 10%, 5%, or less of the maximum hemagglutination index.

In some aspects, a subject antigen binding unit lacks the ability to induce substantial hemagglutination when the antigen binding unit is added to a solution of red blood cells (RBC), in which the RBCs constitute more than about 1%, 2%, 3%, 4%, 5%, 6%, 7%, 8%, 9%, 10%, 11%, 12%, 13%, 14%, 15%, 16%, 17%, 18%, 19%, or 20% RBCs in a suitable buffer, such as PBS. In some examples, the solution is greater than 20% RBCs in a suitable buffer, such as PBS.

In some aspects, a subject antigen binding unit lacks the ability to induce substantial hemagglutination of RBCs in a solution containing RBCs, where the antigen binding unit is present at a concentration from about 100 µg/mL to about 1 pg/mL. For example, a lack of the substantial hemagglutination is observed when the antigen binding unit concentration is at least about, 0.1 ng/mL, 0.2 ng/mL, 0.3 ng/mL, 0.4 ng/mL, 0.5 ng/mL, 0.6 ng/mL, 0.7 ng/mL, 0.8 ng/mL, 0.9 ng/mL, 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 20 ng/mL, 30 ng/mL, 40 ng/mL, 50 ng/mL, 60 ng/mL, 70 ng/mL, 80 ng/mL, 90 ng/mL, 100 ng/mL, 0.1 µg/mL, 0.2 µg/mL, 0.3 µg/mL, 0.4 µg/mL, 0.5 µg/mL, 0.6 µg/mL, 0.7 µg/mL, 0.8 µg/mL, 0.9 µg/mL, 1 µg/mL, 2 µg/mL, 3 µg/mL, 4 µg/mL, 5 µg/mL, 6 µg/mL, 7 µg/mL, 8 µg/mL, 9 µg/mL, 10 µg/mL, 20 µg/mL, 30 µg/mL, 40 µg/mL, 50 µg/mL, 60 µg/mL, 70 µg/mL, 80 µg/mL, 90 µg/mL, 100 µg/mL, or higher.

In some aspects of any of the embodiments disclosed herein, an antigen binding unit lacks the ability to induce substantial hemagglutination after the antigen binding unit is added to red blood cells and incubated for about 10 minutes to about 10 hours. For example, substantial hemagglutination is not observed after about 10 min, 15 min, 30 min, 45 min, 1 hr, 1.5 hr, 2 hr, 2.5 hr, 3 hr, 3.5 hr, 4 hr, 4.5 hr, 5 hr, 5.5 hr, 6 hr, 6.5 hr, 7 hr, 7.5 hr, 8 hr, 8.5 hr, 9 hr, 9.5 hr, 10 hr, or greater than 10 hr of incubation time.

In some aspects of any of the embodiments disclosed herein, an antigen binding unit comprises a light chain CDR and a heavy chain CDR. Subject antigen binding units can comprise any LC-CDR or HC-CDR listed in Table 1. Additionally or alternatively, a subject antigen binding unit can comprise a LC-CDR or a HC-CDR with at least 60% identity to any of the LC-CDR or HC-CDR listed in Table 1. In some aspects, a subject LC-CDR or HC-CDR can exhibit at least 65%, 70%, 75%, 80%, 85%, 90%, 95%, 99%, or greater sequence identity to any of the SEQ ID NOs listed in Table 1.

TABLE 1

| Antigen binding unit | LC-CDR | HC-CDR |
|---|---|---|
| ABU1 | SEQ ID NO: 54 | SEQ ID NO: 55 |
| ABU2 | SEQ ID NO: 65 | SEQ ID NO: 63 |
| ABU3 | SEQ ID NO: 58 | SEQ ID NO: 64 |
| ABU4 | SEQ ID NO: 68 | SEQ ID NO: 60 |
| ABU5 | SEQ ID NO: 66 | SEQ ID NO: 61 |
| ABU6 | SEQ ID NO: 57 | SEQ ID NO: 62 |
| ABU7 | SEQ ID NO: 56 | SEQ ID NO: 59 |
| ABU8 | SEQ ID NO: 85 | SEQ ID NO: 86 |
| ABU9 | SEQ ID NO: 87 | SEQ ID NO: 88 |
| ABU10 | SEQ ID NO: 89 | SEQ ID NO: 90 |
| ABU11 | SEQ ID NO: 91 | SEQ ID NO: 92 |
| ABU12 | SEQ ID NO: 93 | SEQ ID NO: 94 |
| ABU13 | SEQ ID NO: 95 | SEQ ID NO: 96 |
| ABU14 | SEQ ID NO: 97 | SEQ ID NO: 98 |
| ABU15 | SEQ ID NO: 99 | SEQ ID NO: 100 |
| ABU16 | SEQ ID NO: 101 | SEQ ID NO: 102 |
| ABU17 | SEQ ID NO: 103 | SEQ ID NO: 104 |
| ABU18 | SEQ ID NO: 105 | SEQ ID NO: 106 |
| ABU19 | SEQ ID NO: 107 | SEQ ID NO: 108 |
| ABU20 | SEQ ID NO: 109 | SEQ ID NO: 110 |
| ABU21 | SEQ ID NO: 111 | SEQ ID NO: 112 |
| ABU22 | SEQ ID NO: 113 | SEQ ID NO: 114 |
| ABU23 | SEQ ID NO: 115 | SEQ ID NO: 116 |
| ABU24 | SEQ ID NO: 117 | SEQ ID NO: 118 |
| ABU25 | SEQ ID NO: 119 | SEQ ID NO: 120 |
| ABU26 | SEQ ID NO: 121 | SEQ ID NO: 122 |
| ABU27 | SEQ ID NO: 123 | SEQ ID NO: 124 |
| ABU28 | SEQ ID NO: 125 | SEQ ID NO: 126 |
| ABU29 | SEQ ID NO: 127 | SEQ ID NO: 128 |
| ABU30 | SEQ ID NO: 129 | SEQ ID NO: 130 |
| ABU31 | SEQ ID NO: 131 | SEQ ID NO: 132 |
| ABU32 | SEQ ID NO: 133 | SEQ ID NO: 134 |
| ABU33 | SEQ ID NO: 135 | SEQ ID NO: 136 |
| ABU34 | SEQ ID NO: 137 | SEQ ID NO: 138 |
| ABU35 | SEQ ID NO: 139 | SEQ ID NO: 140 |
| ABU36 | SEQ ID NO: 141 | SEQ ID NO: 142 |
| ABU37 | SEQ ID NO: 143 | SEQ ID NO: 144 |
| ABU38 | SEQ ID NO: 145 | SEQ ID NO: 146 |
| ABU39 | SEQ ID NO: 147 | SEQ ID NO: 148 |
| ABU40 | SEQ ID NO: 238 | SEQ ID NO: 239 |
| C-ABU1 | SEQ ID NO: 47 | SEQ ID NO: 70 |
| C-ABU2 | SEQ ID NO: 49 | SEQ ID NO: 73 |
| C-ABU3 | SEQ ID NO: 71 | SEQ ID NO: 51 |

TABLE 1-continued

| Antigen binding unit | LC-CDR | HC-CDR |
|---|---|---|
| C-ABU4 | SEQ ID NO: 50 | SEQ ID NO: 74 |
| C-ABU4 | SEQ ID NO: 309 | SEQ ID NO: 310 |
| C-ABU5 | SEQ ID NO: 45 | SEQ ID NO: 53 |
| C-ABU6 | SEQ ID NO: 67 | SEQ ID NO: 72 |
| C-ABU7 | SEQ ID NO: 69 | SEQ ID NO: 52 |
| C-ABU8 | SEQ ID NO: 311 | SEQ ID NO: 312 |
| H-ABU1a | SEQ ID NO: 46 | SEQ ID NO: 77 |
| H-ABU1b | SEQ ID NO: 46 | SEQ ID NO: 78 |
| H-ABU1c | SEQ ID NO: 46 | SEQ ID NO: 79 |
| H-ABU2a | SEQ ID NO: 48 | SEQ ID NO: 75 |
| H-ABU2b | SEQ ID NO: 48 | SEQ ID NO: 76 |
| H-ABU2c | SEQ ID NO: 48 | SEQ ID NO: 80 |
| H-ABU 3 | SEQ ID NO: 265 | SEQ ID NO: 246 |
| H-ABU 4 | SEQ ID NO: 266 | SEQ ID NO: 247 |
| H-ABU 5 | SEQ ID NO: 267 | SEQ ID NO: 248 |
| H-ABU 6 | SEQ ID NO: 268 | SEQ ID NO: 249 |
| H-ABU 7 | SEQ ID NO: 269 | SEQ ID NO: 250 |
| H-ABU 8 | SEQ ID NO: 270 | SEQ ID NO: 251 |
| H-ABU 9 | SEQ ID NO: 270 | SEQ ID NO: 252 |
| H-ABU 10 | SEQ ID NO: 271 | SEQ ID NO: 253 |
| H-ABU 11 | SEQ ID NO: 272 | SEQ ID NO: 249 |
| H-ABU 12 | SEQ ID NO: 287 | SEQ ID NO: 292 |
| H-ABU 13 | SEQ ID NO: 288 | SEQ ID NO: 292 |
| H-ABU 14 | SEQ ID NO: 289 | SEQ ID NO: 292 |
| H-ABU 15 | SEQ ID NO: 290 | SEQ ID NO: 292 |
| H-ABU 16 | SEQ ID NO: 291 | SEQ ID NO: 292 |
| H-ABU 17 | SEQ ID NO: 287 | SEQ ID NO: 293 |
| H-ABU 18 | SEQ ID NO: 288 | SEQ ID NO: 293 |
| H-ABU 19 | SEQ ID NO: 289 | SEQ ID NO: 293 |
| H-ABU 20 | SEQ ID NO: 290 | SEQ ID NO: 293 |
| H-ABU 21 | SEQ ID NO: 291 | SEQ ID NO: 293 |
| H-ABU 22 | SEQ ID NO: 287 | SEQ ID NO: 294 |
| H-ABU 23 | SEQ ID NO: 288 | SEQ ID NO: 294 |
| H-ABU 24 | SEQ ID NO: 289 | SEQ ID NO: 294 |
| H-ABU 25 | SEQ ID NO: 290 | SEQ ID NO: 294 |
| H-ABU 26 | SEQ ID NO: 291 | SEQ ID NO: 294 |
| H-ABU 27 | SEQ ID NO: 287 | SEQ ID NO: 295 |
| H-ABU 28 | SEQ ID NO: 288 | SEQ ID NO: 295 |
| H-ABU 29 | SEQ ID NO: 289 | SEQ ID NO: 295 |
| H-ABU 30 | SEQ ID NO: 290 | SEQ ID NO: 295 |
| H-ABU 31 | SEQ ID NO: 291 | SEQ ID NO: 295 |
| H-ABU 32 | SEQ ID NO: 287 | SEQ ID NO: 296 |
| H-ABU 33 | SEQ ID NO: 288 | SEQ ID NO: 296 |
| H-ABU 34 | SEQ ID NO: 289 | SEQ ID NO: 296 |
| H-ABU 35 | SEQ ID NO: 290 | SEQ ID NO: 296 |
| H-ABU 36 | SEQ ID NO: 291 | SEQ ID NO: 296 |
| H-ABU 37 | SEQ ID NO: 291 | SEQ ID NO: 292 |
| H-ABU 38 | SEQ ID NO: 291 | SEQ ID NO: 294 |
| H-ABU 39 | SEQ ID NO: 291 | SEQ ID NO: 295 |
| H-ABU 40 | SEQ ID NO: 288 | SEQ ID NO: 296 |
| H-ABU 41 | SEQ ID NO: 291 | SEQ ID NO: 296 |
| H-ABU 42 | SEQ ID NO: 290 | SEQ ID NO: 292 |
| H-ABU 43 | SEQ ID NO: 291 | SEQ ID NO: 293 |
| H-ABU 44 | SEQ ID NO: 298 | SEQ ID NO: 302 |
| H-ABU 45 | SEQ ID NO: 273 | SEQ ID NO: 254 |
| H-ABU 46 | SEQ ID NO: 274 | SEQ ID NO: 255 |
| H-ABU 47 | SEQ ID NO: 275 | SEQ ID NO: 256 |
| H-ABU 48 | SEQ ID NO: 276 | SEQ ID NO: 257 |
| H-ABU 49 | SEQ ID NO: 277 | SEQ ID NO: 258 |
| H-ABU 50 | SEQ ID NO: 265 | SEQ ID NO: 259 |
| H-ABU 51 | SEQ ID NO: 278 | SEQ ID NO: 260 |
| H-ABU 52 | SEQ ID NO: 279 | SEQ ID NO: 261 |
| H-ABU 53 | SEQ ID NO: 280 | SEQ ID NO: 262 |
| H-ABU 54 | SEQ ID NO: 281 | SEQ ID NO: 263 |
| H-ABU 55 | SEQ ID NO: 282 | SEQ ID NO: 246 |
| H-ABU 56 | SEQ ID NO: 283 | SEQ ID NO: 264 |
| H-ABU 57 | SEQ ID NO: 284 | SEQ ID NO: 249 |
| H-ABU 58 | SEQ ID NO: 268 | SEQ ID NO: 249 |
| H-ABU 59 | SEQ ID NO: 268 | SEQ ID NO: 249 |
| H-ABU 60 | SEQ ID NO: 272 | SEQ ID NO: 249 |
| H-ABU 61 | SEQ ID NO: 268 | SEQ ID NO: 249 |
| H-ABU 62 | SEQ ID NO: 285 | SEQ ID NO: 249 |
| H-ABU 63 | SEQ ID NO: 268 | SEQ ID NO: 249 |
| H-ABU 64 | SEQ ID NO: 272 | SEQ ID NO: 249 |
| H-ABU 65 | SEQ ID NO: 272 | SEQ ID NO: 249 |
| H-ABU 66 | SEQ ID NO: 268 | SEQ ID NO: 249 |
| H-ABU 67 | SEQ ID NO: 286 | SEQ ID NO: 249 |
| H-ABU 68 | SEQ ID NO: 268 | SEQ ID NO: 249 |

TABLE 1-continued

| Antigen binding unit | LC-CDR | HC-CDR |
|---|---|---|
| H-ABU 69 | SEQ ID NO: 268 | SEQ ID NO: 249 |
| H-ABU 70 | SEQ ID NO: 268 | SEQ ID NO: 249 |
| H-ABU 71 | SEQ ID NO: 297 | SEQ ID NO: 300 |
| H-ABU 72 | SEQ ID NO: 298 | SEQ ID NO: 300 |
| H-ABU 73 | SEQ ID NO: 299 | SEQ ID NO: 300 |
| H-ABU 74 | SEQ ID NO: 297 | SEQ ID NO: 301 |
| H-ABU 75 | SEQ ID NO: 298 | SEQ ID NO: 301 |
| H-ABU 76 | SEQ ID NO: 299 | SEQ ID NO: 301 |
| H-ABU 77 | SEQ ID NO: 297 | SEQ ID NO: 302 |
| H-ABU 78 | SEQ ID NO: 299 | SEQ ID NO: 302 |
| H-ABU 79 | SEQ ID NO: 297 | SEQ ID NO: 303 |
| H-ABU 80 | SEQ ID NO: 298 | SEQ ID NO: 303 |
| H-ABU 81 | SEQ ID NO: 299 | SEQ ID NO: 303 |
| H-ABU 82 | SEQ ID NO: 297 | SEQ ID NO: 304 |
| H-ABU 83 | SEQ ID NO: 298 | SEQ ID NO: 304 |
| H-ABU 84 | SEQ ID NO: 299 | SEQ ID NO: 304 |

In some cases, the light chain (LC) CDR comprises light LC-CDR1, LC-CDR2, and LC-CDR3; and the heavy chain (HC) CDR comprises HC-CDR1, HC-CDR2, and HC-CDR3. In some examples, said LC-CDR1, LC-CDR2, and LC-CDR3 each have a sequence selected from the group consisting of SEQ ID NOs: 1-22, and 162-190. In some examples, said HC-CDR1, HC-CDR2, HC-CDR3 each have a sequence selected from the group consisting of SEQ ID NO: 23-44 and 191-237. In some examples, said LC-CDR1, LC-CDR2, and LC-CDR3 each have a sequence selected from the group consisting of SEQ ID NO: 1-22 and 162-190 and said HC-CDR1, HC-CDR2, HC-CDR3 each have a sequence selected from the group consisting of SEQ ID NO: 23-44 and 191-237.

In some aspects of any of the embodiments disclosed herein, an antigen binding unit comprises a light chain CDR wherein said light chain (LC) CDR comprises a combination of three LC-CDRs, namely LC-CDR1, LC-CDR2, and LC-CDR3. A combination of three LC-CDRs can comprise any combination listed in Table 2.

TABLE 2

| Example LC-CDR | LC-CDR1 | LC-CDR2 | LC-CDR3 |
|---|---|---|---|
| Example 1 | SEQ ID NO: 4 | SEQ ID NO: 8 | SEQ ID NO: 21 |
| Example 2 | SEQ ID NO: 5 | SEQ ID NO: 10 | SEQ ID NO: 16 |
| Example 3 | SEQ ID NO: 6 | SEQ ID NO: 9 | SEQ ID NO: 17 |
| Example 4 | SEQ ID NO: 2 | SEQ ID NO: 12 | SEQ ID NO: 20 |
| Example 5 | SEQ ID NO: 7 | SEQ ID NO: 11 | SEQ ID NO: 15 |
| Example 6 | SEQ ID NO: 1 | SEQ ID NO: 13 | SEQ ID NO: 22 |
| Example 7 | SEQ ID NO: 3 | SEQ ID NO: 14 | SEQ ID NO: 19 |
| Example 8 | SEQ ID NO: 169 | SEQ ID NO: 173 | SEQ ID NO: 180 |
| Example 9 | SEQ ID NO: 168 | SEQ ID NO: 173 | SEQ ID NO: 181 |
| Example 10 | SEQ ID NO: 165 | SEQ ID NO: 177 | SEQ ID NO: 182 |
| Example 11 | SEQ ID NO: 163 | SEQ ID NO: 178 | SEQ ID NO: 183 |
| Example 12 | SEQ ID NO: 163 | SEQ ID NO: 172 | SEQ ID NO: 184 |
| Example 13 | SEQ ID NO: 163 | SEQ ID NO: 178 | SEQ ID NO: 185 |
| Example 14 | SEQ ID NO: 163 | SEQ ID NO: 178 | SEQ ID NO: 186 |
| Example 15 | SEQ ID NO: 163 | SEQ ID NO: 170 | SEQ ID NO: 187 |
| Example 16 | SEQ ID NO: 163 | SEQ ID NO: 174 | SEQ ID NO: 187 |
| Example 17 | SEQ ID NO: 164 | SEQ ID NO: 175 | SEQ ID NO: 187 |
| Example 18 | SEQ ID NO: 162 | SEQ ID NO: 178 | SEQ ID NO: 187 |
| Example 19 | SEQ ID NO: 163 | SEQ ID NO: 178 | SEQ ID NO: 187 |
| Example 20 | SEQ ID NO: 164 | SEQ ID NO: 178 | SEQ ID NO: 187 |
| Example 21 | SEQ ID NO: 163 | SEQ ID NO: 179 | SEQ ID NO: 187 |
| Example 22 | SEQ ID NO: 166 | SEQ ID NO: 176 | SEQ ID NO: 188 |
| Example 23 | SEQ ID NO: 167 | SEQ ID NO: 171 | SEQ ID NO: 189 |
| Example 24 | SEQ ID NO: 167 | SEQ ID NO: 171 | SEQ ID NO: 190 |

In some aspects of any of the embodiments disclosed herein, an antigen binding unit comprises a heavy chain CDR wherein said heavy chain (HC) CDR comprises a combination of three HC-CDRs, namely HC-CDR1, HC-CDR2, and HC-CDR3. A combination of three HC-CDRs can comprise any combination listed in Table 3.

TABLE 3

| Example HC-CDR | HC-CDR1 | HC-CDR2 | HC-CDR3 |
|---|---|---|---|
| Example 1 | SEQ ID NO: 25 | SEQ ID NO: 32 | SEQ ID NO: 38 |
| Example 2 | SEQ ID NO: 28 | SEQ ID NO: 35 | SEQ ID NO: 39 |
| Example 3 | SEQ ID NO: 24 | SEQ ID NO: 34 | SEQ ID NO: 40 |
| Example 4 | SEQ ID NO: 29 | SEQ ID NO: 33 | SEQ ID NO: 43 |
| Example 5 | SEQ ID NO: 27 | SEQ ID NO: 30 | SEQ ID NO: 42 |
| Example 6 | SEQ ID NO: 23 | SEQ ID NO: 36 | SEQ ID NO: 41 |
| Example 7 | SEQ ID NO: 26 | SEQ ID NO: 31 | SEQ ID NO: 44 |
| Example 8 | SEQ ID NO: 191 | SEQ ID NO: 207 | SEQ ID NO: 226 |
| Example 9 | SEQ ID NO: 192 | SEQ ID NO: 222 | SEQ ID NO: 237 |
| Example 10 | SEQ ID NO: 193 | SEQ ID NO: 219 | SEQ ID NO: 233 |
| Example 11 | SEQ ID NO: 194 | SEQ ID NO: 220 | SEQ ID NO: 228 |
| Example 12 | SEQ ID NO: 195 | SEQ ID NO: 221 | SEQ ID NO: 229 |
| Example 13 | SEQ ID NO: 196 | SEQ ID NO: 214 | SEQ ID NO: 225 |
| Example 14 | SEQ ID NO: 197 | SEQ ID NO: 212 | SEQ ID NO: 232 |
| Example 15 | SEQ ID NO: 197 | SEQ ID NO: 213 | SEQ ID NO: 232 |
| Example 16 | SEQ ID NO: 198 | SEQ ID NO: 210 | SEQ ID NO: 224 |
| Example 17 | SEQ ID NO: 198 | SEQ ID NO: 208 | SEQ ID NO: 234 |
| Example 18 | SEQ ID NO: 198 | SEQ ID NO: 210 | SEQ ID NO: 234 |
| Example 19 | SEQ ID NO: 199 | SEQ ID NO: 210 | SEQ ID NO: 224 |
| Example 20 | SEQ ID NO: 200 | SEQ ID NO: 222 | SEQ ID NO: 230 |
| Example 21 | SEQ ID NO: 201 | SEQ ID NO: 210 | SEQ ID NO: 224 |
| Example 22 | SEQ ID NO: 201 | SEQ ID NO: 216 | SEQ ID NO: 224 |
| Example 23 | SEQ ID NO: 202 | SEQ ID NO: 210 | SEQ ID NO: 234 |
| Example 24 | SEQ ID NO: 203 | SEQ ID NO: 218 | SEQ ID NO: 227 |
| Example 25 | SEQ ID NO: 204 | SEQ ID NO: 211 | SEQ ID NO: 224 |
| Example 26 | SEQ ID NO: 204 | SEQ ID NO: 217 | SEQ ID NO: 224 |
| Example 27 | SEQ ID NO: 204 | SEQ ID NO: 214 | SEQ ID NO: 225 |
| Example 28 | SEQ ID NO: 204 | SEQ ID NO: 215 | SEQ ID NO: 235 |
| Example 29 | SEQ ID NO: 204 | SEQ ID NO: 214 | SEQ ID NO: 236 |
| Example 30 | SEQ ID NO: 205 | SEQ ID NO: 209 | SEQ ID NO: 224 |
| Example 31 | SEQ ID NO: 205 | SEQ ID NO: 210 | SEQ ID NO: 224 |
| Example 32 | SEQ ID NO: 205 | SEQ ID NO: 223 | SEQ ID NO: 231 |
| Example 33 | SEQ ID NO: 206 | SEQ ID NO: 210 | SEQ ID NO: 224 |

In some aspects of any of the embodiments disclosed herein, an antigen binding unit comprises a light chain CDR and a heavy chain CDR, wherein said light chain CDR and said heavy chain CDR comprise, respectively, the LC-CDR and the HC-CDR selected from the group consisting of any combination of LC-CDRs listed in Table 2 and any combination of HC-CDRs listed in Table 3.

In some aspects, a subject antigen binding unit is a monoclonal antigen binding unit, a polyclonal antigen binding unit, a humanized antigen binding unit, a chimeric antigen binding unit, a monovalent antigen binding unit, a multivalent antigen binding unit, a bispecific antigen binding unit, or any combination thereof. The antigen binding units can adopt a variety of formats, including but not limited to sFC, Fv, ccFv, Fab', F(ab')2, and Fd. Such antibody binding units can be generated from whole immunoglobulins by ricin, pepsin, papain, or other protease cleavage.

In addition, antigen binding units can be designed utilizing recombinant immunoglobulin techniques. For instance "Fv" immunoglobulins for use in the present invention may be produced by linking a variable light chain region to a variable heavy chain region via a peptide linker. For example, a peptide linker can be poly-glycine or another sequence which does not form an alpha helix or beta sheet motif. Fvs can also be made which comprise stabilizing disulfide bonds between the $V_H$ and $V_L$ regions, as described in U.S. Pat. No. 6,147,203, incorporated fully herein by reference. Any of these antigen binding unites can be utilized in the present invention. In some aspects, an antigen binding unit can be a whole immunoglobulin having two light chains paired with two heavy chains.

Antigen-binding units can be heteromultimers comprising a light-chain polypeptide and a heavy-chain polypeptide. Examples of an antigen binding unit include but are not limited to (i) a ccFv fragment stabilized by the heterodimerization sequences disclosed U.S. Pat. No. 6,833,441, incorporated herein in its entirety; (ii) any other monovalent and multivalent molecules comprising at least one ccFv fragment as described herein; (iii) a Fab fragment consisting of the VL, VH, CL and CH1 domains; (iv) an Fd fragment consisting of the VH and CH1 domains; (v) an Fv fragment consisting of the VL and VH domains of a single arm of an antibody; (vi) an F(ab')2 fragment, a bivalent fragment comprising two Fab fragments linked by a disulfide bridge at the hinge region; and (vii) a diabody.

Polyclonal antibodies can be raised by a standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.). When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH.

Polyclonal or monoclonal antigen binding units or antibodies can be produced from animals which have been genetically altered to produce human immunoglobulins. A transgenic animal can be produced by initially producing a "knock-out" animal which does not produce the animal's natural antibodies, and stably transforming the animal with a human antibody locus (e.g., by the use of a human artificial chromosome). In such cases, only human antibodies are then made by the animal. Techniques for generating such animals, and deriving antibodies therefrom, are described in U.S. Pat. Nos. 6,162,963 and 6,150,584, incorporated fully herein by reference. Such antibodies can be referred to as human xenogenic antibodies.

Alternatively, antigen binding units can be produced from phage libraries containing human variable regions. See U.S. Pat. No. 6,174,708, incorporated fully herein by reference.

In some aspects of any of the embodiments disclosed herein, an antigen binding unit is produced by a hybridoma. For example, an antigen binding unit disclosed herein can be produced by a hybridoma selected form the group consisting of hybridomas expressing one of the antigen binding units listed in Table 1. For example, the hybridoma can be any hybridoma as deposited on [date] with reference number [insert reference number].

For monoclonal antigen binding units or monoclonal antibodies, hybridomas may be formed by isolating the stimulated immune cells, such as those from the spleen of the inoculated animal. These cells can then be fused to immortalized cells, such as myeloma cells or transformed cells, which are capable of replicating indefinitely in cell culture, thereby producing an immortal, immunoglobulinsecreting cell line. The immortal cell line utilized can be selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterinthymidine medium (HAT).

In addition, the antigen binding unit may be produced by genetic engineering. Humanized, chimeric, or xenogeneic human antigen binding units, which produce less of an immune response when administered to humans, are of use in the present invention.

Antigen binding units disclosed herein can have a reduced propensity to induce an undesired immune response in humans, for example, anaphylactic shock, and can also exhibit a reduced propensity for priming an immune response which would prevent repeated dosage with the antibody therapeutic or imaging agent (e.g., the human-anti-murine-antibody "HAMA" response). Such antigen binding units include, but are not limited to, humanized, chimeric, or xenogenic human antigen binding units.

Chimeric antigen binding units or chimeric antibodies can be made, for example, by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference).

The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In some examples, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

Humanized antibodies can be engineered to contain human-like immunoglobulin domains, and incorporate only the complementarity-determining regions of the animal-derived antibody. This can be accomplished by carefully examining the sequence of the hyper-variable loops of the variable regions of a monoclonal antigen binding unit or monoclonal antibody, and fitting them to the structure of a human antigen binding unit or human antibody chains. See, e.g., U.S. Pat. No. 6,187,287, incorporated fully herein by reference.

Methods for humanizing non-human antibodies are well known in the art. "Humanized" antibodies are antibodies in which at least part of the sequence has been altered from its initial form to render it more like human immunoglobulins. In some versions, the heavy (H) chain and light (L) chain constant (C) regions are replaced with human sequence. This can be a fusion polypeptide comprising a variable (V) region and a heterologous immunoglobulin C region. In some versions, the complementarity determining regions (CDRs) comprise non-human antibody sequences, while the V framework regions have also been converted to human sequences. See, for example, EP 0329400. In some versions, V regions are humanized by designing consensus sequences of human and mouse V regions, and converting residues outside the CDRs that are different between the consensus sequences.

In principle, a framework sequence from a humanized antibody can serve as the template for CDR grafting; however, it has been demonstrated that straight CDR replacement into such a framework can lead to significant loss of binding affinity to the antigen. Glaser et al. (1992) *J. Immunol.* 149:2606; Tempest et al. (1992) *Biotechnology* 9:266; and Shalaby et al. (1992) *J. Exp. Med.* 17:217. The more homologous a human antibody (HuAb) is to the original murine antibody (muAb), the less likely that the human framework will introduce distortions into the murine CDRs that could reduce affinity. Based on a sequence homology search against an antibody sequence database, the HuAb IC4 provides good framework homology to muM4TS.22, although other highly homologous HuAbs would be suitable as well, especially kappa L chains from human subgroup I or H chains from human subgroup III. Kabat et al. (1987). Various computer programs such as ENCAD (Levitt et al. (1983) *J. Mol. Biol.* 168:595) are available to predict the ideal sequence for the V region. The invention thus encompasses HuAbs with different variable (V) regions. It is within the skill of one in the art to determine suitable V region sequences and to optimize these sequences. Methods for obtaining antibodies with reduced immunogenicity are also described in U.S. Pat. No. 5,270,202 and EP 699,755.

Humanized antibodies can be prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved.

A process for humanization of subject antigen binding units can be as follows. The best-fit germline acceptor heavy and light chain variable regions is selected based on homology, canonical structure and physical properties of the human antibody germlines for grafting. Computer modeling of mVH/VL versus grafted hVH/VL is performed and prototype humanized antibody sequence is generated. If modeling indicated a need for framework back-mutations, second variant with indicated FW changes is generated. DNA fragments encoding the selected germline frameworks and murine CDRs are synthesized. The synthesized DNA fragments are subcloned into IgG expression vectors and sequences are confirmed by DNA sequencing. The humanized antibodies are expressed in cells, such as 293F and the proteins are tested, for example in MDM phagocytosis assays and antigen binding assays. The humanized antigen binding units are compared with parental antigen binding units in antigen binding affinity, for example, by FACS on cells expressing the target antigen. If the affinity is greater than 2-fold lower than parental antigen binding unit, a second round of humanized variants can be generated and tested as described above.

As noted above, an antigen binding units can be either "monovalent" or "multivalent." Whereas the former has one binding site per antigen-binding unit, the latter contains multiple binding sites capable of binding to more than one antigen of the same or different kind. Depending on the number of binding sites, antigen binding units may be bivalent (having two antigen-binding sites), trivalent (having three antigen-binding sites), tetravalent (having four antigen-binding sites), and so on.

Multivalent antigen binding units can be further classified on the basis of their binding specificities. A "monospecific" antigen binding unit is a molecule capable of binding to one or more antigens of the same kind. A "multispecific" antigen binding unit is a molecule having binding specificities for at least two different antigens. While such molecules normally will only bind two distinct antigens (i.e. bispecific antigen binding units), antibodies with additional specificities such as trispecific antibodies are encompassed by this expression when used herein. This disclosure further provides multispecific antigen binding units. Multispecific antigen binding units are multivalent molecules capable of binding to at least two distinct antigens. Preferred multispecific antigen binding units are bispecific and trispecific molecules exhibiting binding specificities to two and three distinct antigens, respectively.

In some aspects of an embodiment disclosed herein, an antigen binding unit is a bispecific antigen binding unit, wherein the antigen binding unit specifically binds to CD47 and a second antigen. In some examples, the second antigen is not CD47. In some examples, the second antigen is PD1 or PD-L1. In some examples, the second antigen is other immune checkpoint molecules including CTLA-4, OX40, OX40L, 4-1BB (CD137), CD40, CD40L, ICOS, CD70, CD27, GITR, GITRL, TL1A, TNFRSF25, VISTA, TIM-3, LAG-3, TIGIT, CD112, CD112R, CD226, CD96, B7-H3, B7-H4, CD48, CD244, CD200R, CD200, HVEM, BTLA, CD160, LIGHT, HHLA2, TMIGD2, BTNL2, CD39, CD73, NKG2A, NKG2D, MICA/B, KIR2DL-1, KIR2DL-2, KIR2DL-3, and KIR3DL2. In some examples, the second antigen is EGFR. In some examples, the second antigen is CD19, CD20, CD22, CD33, CD44, CD52, CD79b, CD96, CD97, CD99, CD123, CD138, CD155, CD171, PTHR2, HAVCR2, or other known cancer cell marker. Additional examples of suitable second antigens include, though are not limited to, FcγRI, CD 15, p185 HER2, HERS, FcγRIII (CD16), CD3, malignant B-cell (1D10), p97, claudin18.2, OVCAR-3, glypican-3, mesothelin, L-D1 (colon carcinoma), Trop2, melanocyte stimulating hormone analog, ErbB2, CAMA1, MoV18, CAIX (carboxy-anhydrase-IX), DCC, UNC5A, MET, TrkC, TrkA, RET, ALK, neural cell adhesion molecule (NCAM), folate binding protein (FBP), GD2, GD3, EpCAM, EGP-40, VEGFR2, MUC-1, MUC-16, STEAP1 (six-transmembrane epithelial antigen of the prostate), PSMA, PSCA (prostate stem cell antigen), GPC-3, LMP-1, DNAM-1 (DNAX accessory molecule-1), pan carcinoma associated antigen (AMOC-31), saporin, Id-1, CD7, CD38, CD30, CD44v7/8, CEA, ricin A chain, interferon-α (IFN-α), hybridoma idiotype, vinca alkaloid, alkaline phosphatase, fibrin, tissue plasminogen activator (tPA), urokinase-type plasminogen activator (uPA), low density lipoprotein (LDL), Fc receptor (e.g. FcγRI, FcγRII or FcγRIII), herpes simplex virus (HSV), T-cell receptor, influenza, FcγR, HIV, EOTUBE, DPTA, hapten, rabbit IgG, ferritin, horse radish peroxidase (HRP), hormone, somatostatin, substance P, FITC, and beta-galactosidase. Other suitable second antigens include, though are not limited to, a tumor cell antigen, a cytotoxic trigger molecule, a toxin a fibrinolytic agent, a cell surface receptor, infectious disease target, a vaccine adjuvants, a diagnostic agent, a detection molecule, and a reporter molecule.

Polynucleotides and Vectors of the Present Invention

In some embodiments, the present disclosure provides isolated nucleic acids encoding any of the antigen binding units disclosed herein. In another embodiment, the present disclosure provides vectors comprising a nucleic acid sequence encoding any antigen binding unit disclosed herein. In some embodiments, this invention provides isolated nucleic acids that encode a light-chain CDR and a heavy-chain CDR of an antigen binding unit disclosed herein.

The subject antigen binding units can be prepared by recombinant DNA technology, synthetic chemistry techniques, or a combination thereof. For instance, sequences encoding the desired components of the antigen binding units, including light chain CDRs and heavy chain CDRs are typically assembled cloned into an expression vector using standard molecular techniques know in the art. These sequences may be assembled from other vectors encoding the desired protein sequence, from PCR-generated fragments using respective template nucleic acids, or by assembly of synthetic oligonucleotides encoding the desired sequences. Expression systems can be created by transfecting a suitable cell with an expressing vector comprising the antigen binding unit of interest.

Nucleotide sequences corresponding to various regions of light or heavy chains of an existing antibody can be readily obtained and sequenced using convention techniques including but not limited to hybridization, PCR, and DNA sequencing. Hybridoma cells that produce monoclonal antibodies serve as a preferred source of antibody nucleotide sequences. A vast number of hybridoma cells producing an array of monoclonal antibodies may be obtained from public or private repositories. The largest depository agent is American Type Culture Collection (atcc.org), which offers a diverse collection of well-characterized hybridoma cell lines. Alternatively, antibody nucleotides can be obtained from immunized or non-immunized rodents or humans, and form organs such as spleen and peripheral blood lymphocytes. Specific techniques applicable for extracting and synthesizing antibody nucleotides are described in Orlandi et al. (1989) *Proc. Natl. Acad. Sci. U.S.A* 86: 3833-3837; Larrick et al. (1989) *Biochem. Biophys. Res. Commun.* 160:1250-1255; Sastry et al. (1989) *Proc. Natl. Acad. Sci., U.S.A.* 86: 5728-5732; and U.S. Pat. No. 5,969,108.

Polynucleotides encoding antigen binding units can also be modified, for example, by substituting the coding sequence for human heavy and light chain constant regions in place of the homologous non-human sequences. In that manner, chimeric antibodies are prepared that retain the binding specificity of the original antigen binding unit.

It is also understood that the polynucleotides embodied in the invention include those coding for functional equivalents and fragments thereof of the exemplified polypeptides. Functionally equivalent polypeptides include those that enhance, decrease or not significantly affect properties of the polypeptides encoded thereby. Functional equivalents may be polypeptides having conservative amino acid substitutions, analogs including fusions, and mutants.

Due to the degeneracy of the genetic code, there can be considerable variation in nucleotides of an antigen binding unit coding sequence, as well as sequences suitable for construction of the polynucleotide and vectors of the present invention. Sequence variants may have modified DNA or amino acid sequences, one or more substitutions, deletions, or additions, the net effect of which is to retain the desired antigen-binding activity. For instance, various substitutions can be made in the coding region that either do not alter the amino acids encoded or result in conservative changes. These substitutions are encompassed by the present invention. Conservative amino acid substitutions include substitutions within the following groups: glycine, alanine; valine, isoleucine, leucine; aspartic acid, glutamic acid; asparagine, glutamine; serine, threonine; lysine, arginine; and phenylalanine, tyrosine. While conservative substitutions do effectively change one or more amino acid residues contained in the polypeptide to be produced, the substitutions are not expected to interfere with the antigen-binding activity of the resulting antigen binding units to be produced. Nucleotide substitutions that do not alter the amino acid residues encoded are useful for optimizing gene expression in different systems. Suitable substitutions are known to those of skill in the art and are made, for instance, to reflect preferred codon usage in the expression systems.

Where desired, the recombinant polynucleotides may comprise heterologous sequences that facilitate detection of the expression and purification of the gene product. Examples of such sequences are known in the art and include those encoding reporter proteins such as β-galactosidase, β-lactamase, chloramphenicol acetyltransferase (CAT), luciferase, green fluorescent protein (GFP) and their derivatives. Other heterologous sequences that facilitate purification may code for epitopes such as Myc, HA (derived from influenza virus hemagglutinin), His-6 (SEQ ID NO: 313), FLAG, or the Fc portion of immunoglobulin, glutathione S-transferase (GST), and maltose-binding protein (MBP).

Polynucleotides disclosed herein can be conjugated to a variety of chemically functional moieties described above. Commonly employed moieties include labels capable of producing a detectable signal, signal peptides, agents that enhance immunologic reactivity, agents that facilitate coupling to a solid support, vaccine carriers, bioresponse modifiers, paramagnetic labels and drugs. The moieties can be covalently linked polynucleotide recombinantly or by other means known in the art.

Polynucleotides of the invention can comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention.

Polynucleotides embodied in this invention can be obtained using chemical synthesis, recombinant cloning methods, PCR, or any combination thereof. Methods of chemical polynucleotide synthesis are well known in the art and need not be described in detail herein. One of skill in the art can use the sequence data provided herein to obtain a desired polynucleotide by employing a DNA synthesizer or ordering from a commercial service.

Polynucleotides comprising a desired sequence can be inserted into a suitable vector which in turn can be introduced into a suitable host cell for replication and amplification. Accordingly, the invention encompasses a variety of vectors comprising one or more of the polynucleotides of the present invention. Also provided are selectable libraries of expression vectors comprising at least one vector encoding an antigen binding units disclosed herein.

Vectors of the present invention generally comprises a transcriptional or translational control sequences required for expressing the antigen binding units. Suitable transcription or translational control sequences include but are not limited to replication origin, promoter, enhancer, repressor binding regions, transcription initiation sites, ribosome binding sites, translation initiation sites, and termination sites for transcription and translation.

The choice of promoters will largely depend on the host cells in which the vector is introduced. It is also possible, to utilize promoters normally associated with a desired light or heavy chain gene, provided that such control sequences are compatible with the host cell system. Cell-specific or tissue-specific promoters may also be used. A vast diversity of tissue specific promoters have been described and employed by artisans in the field. Exemplary promoters operative in selective animal cells include hepatocyte-specific promoters and cardiac muscle specific promoters. Depending on the choice of the recipient cell types, those skilled in the art will know of other suitable cell-specific or tissue-specific promoters applicable for the construction of the expression vectors of the present invention.

Using known molecular cloning or gene engineering techniques, appropriate transcriptional control sequences, enhancers, terminators, or any other genetic element known in the art can integrated in operative relationship, optionally additionally with intact selectable fusion genes to be expressed in accordance with the present invention. In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell.

The polynucleotides and vectors of this invention have several specific uses. They are useful, for example, in expression systems for the production of antigen binding units. Such polynucleotides are useful as primers to effect amplification of desired polynucleotides. Furthermore, polynucleotides of this invention are also useful in pharmaceutical compositions including vaccines, diagnostics, and drugs.

The host cells of this invention can be used, inter alia, as repositories of the subject polynucleotides, vectors, or as vehicles for producing and screening desired antigen binding units based on their antigen binding specificities.

Accordingly, the invention provides a method of identifying an antigen binding unit that is immunoreactive with a desired antigen. Such a method can involve the following steps: (a) preparing a genetically diverse library of antigen binding units, wherein the library comprises at least one subject antigen binding unit; (b) contacting the library of antigen binding units with the desired antigen; (c) detecting a specific binding between antigen binding units and the antigen, thereby identifying the antigen binding unit that is immunoreactive with the desired antigen.

The ability of an antigen binding unit to specifically bind to a desired antigen can be tested by a variety of procedures well established in the art. See Harlow and Lane (1988) Antibodies: A Laboratory Manual, Cold Spring Harbor Laboratory, New York; Gherardi et al. (1990) *J. Immunol. Meth.* 126:61-68. Typically, antigen binding units exhibiting desired binding specificities can be detected directly by immunoassays, for example, by reacting labeled antigen binding units with the antigens that are immobilized on a solid support or substrate. In general, the substrate to which the antigen is adhered is fabricated with material exhibiting a low level of non-specific binding during immunoassay. An example solid support is made from one or more of the following types of materials: plastic polymers, glass, cellulose, nitrocellulose, semi-conducting material, and metal. In some examples, the substrate is petri dish, chromatography beads, magnetic beads, and the like.

For such solid-phase assays, the unreacted antigen binding units are removed by washing. In a liquid-phase assay, however, the unreacted antigen binding units are removed by some other separation technique, such as filtration or chromatography. After binding the antigen to the labeled antigen binding units, the amount of bound label is determined. A variation of this technique is a competitive assay, in which the antigen is bound to saturation with an original binding molecule. When a population of the subject antigen binding unit is introduced to the complex, only those that exhibit higher binding affinity will be able to compete, and thus remain bound to the antigen.

Alternatively, specific binding to a given antigen can be assessed by cell sorting, which involves presenting the desired antigen on the cells to be sorted, then labeling the target cells with antigen binding units that are coupled to detectable agents, followed by separating the labeled cells from the unlabeled ones in a cell sorter. A sophisticated cell separation method is fluorescence-activated cell sorting (FACS). Cells traveling in single file in a fine stream are passed through a laser beam, and the fluorescence of each cell bound by the fluorescently labeled antigen binding unit is then measured.

Subsequent analysis of the eluted antigen binding units may involve protein sequencing for delineating the amino acid sequences of the light chains and heavy chains. Based on the deduced amino acid sequences, the cDNA encoding the antibody polypeptides can then be obtained by recombinant cloning methods including PCR, library screening, homology searches in existing nucleic acid databases, or any combination thereof. Commonly employed databases include but are not limited to GenBank, EMBL, DDBJ, PDB, SWISS-PROT, EST, STS, GSS, and HTGS.

When a library of antigen binding unit is displayed on phage or bacterial particles, selection is preferably performed using affinity chromatography. The method typically proceeds with binding a library of phage antigen binding units to an antigen coated plates, column matrices, cells or to biotinylated antigen in solution followed by capture. The phages or bacteria bound to the solid phase are washed and then eluted by soluble hapten, acid or alkali. Alternatively, increasing concentrations of antigen can be used to dissociate the antigen binding units from the affinity matrix. For certain antigen binding units with extremely high affinity or avidity to the antigen, efficient elution may require high pH or mild reducing solution as described in WO 92/01047.

The efficiency of selection is likely to depend on a combination of several factors, including the kinetics of dissociation during washing, and whether multiple antigen binding units on a single phage or bacterium can simultaneously bind to antigens on a solid support. For example, antibodies with fast dissociation kinetics (and weak binding affinities) can be retained by use of short washes, multivalent display and a high coating density of antigen at the solid support. Conversely, the selection of antigen binding units with slow dissociation kinetics (and good binding affinities) can be favored by use of long washes, monovalent phages, and a low coating density of antigen.

Where desired, the library of antigen binding units can be pre-selected against an unrelated antigen to counter-select the undesired antigen binding units. The library may also be pre-selected against a related antigen in order to isolate, for example, anti-idiotypic antigen binding units.

Host Cells of the Present Invention

In some embodiments, the present disclosure provides host cells expressing any one of the antigen binding units disclosed herein. A subject host cell typically comprises a nucleic acid encoding any one of the antigen binding units disclosed herein.

The invention provides host cells transfected with the polynucleotides, vectors, or a library of the vectors described above. The vectors can be introduced into a suitable prokaryotic or eukaryotic cell by any of a number of appropriate means, including electroporation, microprojectile bombardment; lipofection, infection (where the vector is coupled to an infectious agent), transfection employing calcium chloride, rubidium chloride, calcium phosphate, DEAE-dextran, or other substances. The choice of the means for introducing vectors will often depend on features of the host cell.

For most animal cells, any of the above-mentioned methods is suitable for vector delivery. Preferred animal cells are vertebrate cells, preferably mammalian cells, capable of expressing exogenously introduced gene products in large quantity, e.g. at the milligram level. Non-limiting examples of preferred cells are NIH3T3 cells, COS, HeLa, and CHO cells.

Once introduced into a suitable host cell, expression of the antigen binding units can be determined using any nucleic acid or protein assay known in the art. For example, the presence of transcribed mRNA of light chain CDRs or heavy chain CDRs, or the antigen binding unit can be detected and/or quantified by conventional hybridization assays (e.g. Northern blot analysis), amplification procedures (e.g. RT-PCR), SAGE (U.S. Pat. No. 5,695,937), and array-based technologies (see e.g. U.S. Pat. Nos. 5,405,783, 5,412,087 and 5,445,934), using probes complementary to any region of antigen binding unit polynucleotide.

Expression of the vector can also be determined by examining the antigen binding unit expressed. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and SDS-PAGE.

Preparation of Antigen-Binding Units

In some embodiments, the present disclosure provides methods of producing any antigen binding unit disclosed herein, wherein the method comprises culturing host cells expressing the antigen binding unit under conditions suitable for expressing the antigen binding unit, and isolating the antigen binding unit expressed by the host cell.

The expressed antigen binding units can be isolated using a variety of protein purification techniques known in the art. Generally, the antigen binding unit is isolated from culture media as secreted polypeptides, although they can be recovered from host cell lysates or bacterial periplasm, when directly produced without signal peptides. If the antigen binding units are membrane-bound, they can be solubilized by suitable detergent solutions commonly employed by artisans in the field. The recovered antigen binding units may be further purified by salt precipitation (e.g., with ammonium sulfate), ion exchange chromatography (e.g. on a cationic or anionic exchange column run at neutral pH and eluted with step gradients of increasing ionic strength), gel filtration chromatography (including gel filtration HPLC), and chromatography on tag-affinity column, or on affinity resins such as protein A, protein G, hydroxyapatite, and anti-immunoglobulin.

In addition, derivatized immunoglobulins with added chemical linkers, detectable moieties such as fluorescent dyes, enzymes, substrates, chemiluminescent moieties, specific binding moieties such as streptavidin, avidin, or biotin, or drug conjugates can be utilized in the methods and compositions of the present invention.

Additionally disclosed herein are antigen binding unites conjugated to a chemically functional moiety. Typically, the moiety is a label capable of producing a detectable signal. These conjugated antigen binding units are useful, for example, in detection systems such as quantitation of tumor burden, and imaging of metastatic foci and tumor imaging. Such labels are known in the art and include, but are not limited to, radioisotopes, enzymes, fluorescent compounds, chemiluminescent compounds, bioluminescent compounds substrate cofactors and inhibitors. See, for examples of patents teaching the use of such labels, U.S. Pat. Nos. 3,817,837; 3,850,752; 3,939,350; 3,996,345; 4,277,437; 4,275,149; and 4,366,241. The moieties can be covalently linked to antigen binding units, recombinantly linked, or conjugated to antigen binding units through a secondary reagent, such as a second antibody, protein A, or a biotin-avidin complex.

Other functional moieties include signal peptides, agents that enhance immunologic reactivity, agents that facilitate coupling to a solid support, vaccine carriers, bioresponse modifiers, paramagnetic labels and drugs. Signal peptides is a short amino acid sequence that directs a newly synthesized protein through a cellular membrane, usually the endoplasmic reticulum in eukaryotic cells, and either the inner membrane or both inner and outer membranes of bacteria. Signal peptides can be at the N-terminal portion of a polypeptide or the C-terminal portion of a polypeptide, and can be removed enzymatically between biosynthesis and secretion of the polypeptide from the cell. Such a peptide can be incorporated into an antigen binding units to allow secretion of the synthesized molecules.

Agents that enhance immunologic reactivity include, but are not limited to, bacterial superantigens. Agents that facilitate coupling to a solid support include, but are not limited to, biotin or avidin. Immunogen carriers include, but are not limited to, any physiologically acceptable buffers. Bioresponse modifiers include cytokines, particularly tumor necrosis factor (TNF), interleukin-2, interleukin-4, granulocyte macrophage colony stimulating factor and γ-interferons.

Suitable drug moieties include antineoplastic agents. Non-limiting examples include radioisotopes, vinca alkaloids such as the vinblastine, vincristine and vindesine sulfates, adriamycin, bleomycin sulfate, carboplatin, cisplatin, cyclophosphamide, cytarabine, dacarbazine, dactinomycin, duanorubicin hydrochloride, doxorubicin hydrochloride, etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, taxol, thioguanine, and uracil mustard.

Immunotoxins, including antigen binding units, can be produced by recombinant means. Production of various immunotoxins is well-known in the art, and methods can be found, for example, in "Monoclonal Antibody-toxin Conjugates: Aiming the Magic Bullet," Thorpe et al. (1982) *Monoclonal Antibodies in Clinical Medicine*, Academic Press, pp. 168-190; Vitatta (1987) *Science* 238:1098-1104; and Winter and Milstein (1991) *Nature* 349:293-299. Suitable toxins include, but are not limited to, ricin, radionuclides, pokeweed antiviral protein, *Pseudomonas* exotoxin A, diphtheria toxin, ricin A chain, fungal toxins such as restrictocin and phospholipase enzymes. See, generally, "Chimeric Toxins," Olsnes and Pihl, *Pharmac. Ther.* 15:355-381 (1981); and "Monoclonal Antibodies for Cancer Detection and Therapy," eds. Baldwin and Byers, pp. 159-179, 224-266, Academic Press (1985).

Chemically functional moieties can be made recombinantly for instance by creating a fusion gene encoding the antigen binding unit and the functional moiety. Alternatively, the antigen binding unit can be chemically bonded to the moiety by any of a variety of well-established chemical procedures. For example, when the moiety is a protein, the linkage can be by way of heterobifunctional cross linkers, e.g., SPDP, carbodiimide glutaraldehyde, or the like. The moieties can be covalently linked, or conjugated, through a secondary reagent, such as a second antibody, protein A, or a biotin-avidin complex. Paramagnetic moieties and the conjugation thereof to antibodies are well-known in the art. See, e.g., Miltenyi et al. (1990) *Cytometry* 11:231-238.

Methods of Use and Treatment

CD47-specific antigen binding units and pharmaceutical compositions comprising the same can find a wide variety of applications, including, but not limited to, treatment and diagnosis.

In one embodiment, the present disclosure provides pharmaceutical compositions comprising a pharmaceutically acceptable excipient and any of the antigen binding units disclosed herein.

In another embodiment, the present disclosure provides methods of inducing phagocytosis of cells expressing CD47, said method comprising contacting the cell expressing CD47 with any antigen binding unit disclosed herein. In some aspects, the cell is a cancer cell. In some aspects, the cell is a non-lymphoma cancer cell. In some aspects, the cell is a non-leukemia cancer cell. In some aspects, the cell is a non-lymphoma and non-leukemia cancer cell. In some aspects, the cell is a hematological cancer cell. Hematological cancers include, but are not limited to, leukemia, lymphoma and myeloma. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. Certain forms of lymphoma include, by way of non-limiting example, Hodgkin's lymphoma, both indolent and aggressive non-Hodgkin's lymphoma, Burkitt's lymphoma, and follicular lymphoma (small cell and large cell). Certain forms of myeloma include, by way of non-limiting example, multiple myeloma (MM), giant cell myeloma, heavy-chain myeloma, and light chain or Bence-Jones myeloma. Solid tumors include, e.g., breast tumors, ovarian tumors, lung tumors, pancreatic tumors, prostate tumors, melanoma tumors, colorectal tumors, lung tumors, head and neck tumors, bladder tumors, leiomyosarcoma, glioma, glioblastoma, brain tumors, esophageal tumors, gastric tumors, liver tumors, and kidney tumors.

In yet another embodiment, the present disclosure provides methods of inducing phagocytosis of cells expressing CD47 in a human subject, said method comprising administering to the human subject a pharmaceutical composition comprising a pharmaceutically acceptable excipient and any antigen binding unit disclosed herein. In some aspects, the cell is a cancer cell. In some aspects, the cell is a non-lymphoma cancer cell. In some aspects, the cell is a non-leukemia cancer cell. In some aspects, the cell is a non-lymphoma and non-leukemia cancer cell. In some aspects, the cell is a hematological cancer cell. Hematological cancers include, but are not limited to, leukemia, lymphoma and myeloma. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. Certain forms of lymphoma include, by way of non-limiting example, Hodgkin's lymphoma, both indolent and aggressive non-Hodgkin's lymphoma, Burkitt's lymphoma, and follicular lymphoma (small cell and large cell). Certain forms of myeloma include, by way of non-limiting example, multiple myeloma (MM), giant cell myeloma, heavy-chain myeloma, and light chain or Bence-Jones myeloma. Solid tumors include, e.g., breast tumors, ovarian tumors, lung tumors, pancreatic tumors, prostate tumors, melanoma tumors, colorectal tumors, lung tumors, head and neck tumors, bladder tumors, leiomyosarcoma, glioma, glioblastoma, brain tumors, esophageal tumors, gastric tumors, liver tumors, and kidney tumors.

In some aspects of methods of inducing phagocytosis as disclosed herein, phagocytosis of cells expressing CD47 occurs with an efficiency within the range of 1% to 100%. In some examples, phagocytosis occurs with about 1%, 5%, 10%, 15%, 20%, 25%, 30%, 35%, 40%, 45%, 50%, 55%, 60%, 65%, 70%, 75%, 80%, 85%, 90%, 95%, or 100% efficiency. In some examples, phagocytosis occurs with at least about 1%, 5%, 10%, 15%, 20%, 25%, 30%, 35%, 40%, 45%, 50%, 55%, 60%, 65%, 70%, 75%, 80%, 85%, 90%, 95%, or 100% efficiency. In some aspects of any of the embodiments disclosed herein, an antigen binding unit induces phagocytosis of cells expressing CD47 to a greater extent than that of a reference antigen binding unit. Such a reference antigen binding unit can have the amino acid sequences shown in 1) SEQ ID NO: 240-241, 2) SEQ ID NO:242-243, or 3) SEQ ID NO:244-245, or any other known anti-CD47 antigen binding unit. Phagocytosis extent can be determined by any method known in the art. In some cases, the extend of phagocytosis is determined the number of macrophages that have performed phagocytosis (referred to as phagocytes) among a population of macrophages. For example, the number of phagocytes per 100 macrophages can be determined and thereby the extend of phagocytosis can be expressed as a percentage or phagocytic index.

In some aspects of methods of inducing phagocytosis as disclosed herein, the antigen binding unit used in said method does not cause significant hemagglutination. In some cases, hemagglutination induced in said method using any of the antigen binding units disclosed herein is at least 1 fold less as compared to that induced by an reference antigen binding unit having the amino acid sequences shown in 1) SEQ ID NO: 240-241, 2) SEQ ID NO:242-243, or 3) SEQ ID NO:244-245. In some cases, hemagglutination induced upon contacting the red blood cells with a subject antigen binding unit is at least 1 fold less, at least 2 fold less, at least 3 fold less, at least 4 fold less, at least 5 fold less, at least 6 fold less, at least 7 fold less, at least 8 fold less, at least 9 fold less, or at least 10 fold less as compared to that induced by a reference antigen binding unit having the amino acid sequences shown in 1) SEQ ID NO: 240-241, 2) SEQ ID NO:242-243, or 3) SEQ ID NO:244-245. In some cases, hemagglutination induced upon contacting the red blood cells with a subject antigen binding unit is greater than at least 10 fold less as compared to that induced by a reference antigen binding unit having the amino acid sequences shown in 1) SEQ ID NO: 240-241, 2) SEQ ID NO:242-243, or 3) SEQ ID NO:244-245.

In some embodiments, the present disclosure provides methods of treating cancer in a subject in need thereof. In some aspects, the method comprises administering to the subject in need thereof, an effective amount of any of the antigen binding units disclosed herein. In some aspects, the cancer is a non-lymphoma cancer. In some aspects, the cancer is a non-leukemia cancer. In some aspects, the cancer is a non-lymphoma and non-leukemia cancer. In some aspects, the cell is a hematological cancer cell. Hematological cancers include, but are not limited to, leukemia, lymphoma and myeloma. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. Certain forms of lymphoma include, by way of non-limiting example, Hodgkin's lymphoma, both indolent and aggressive non-Hodgkin's lymphoma, Burkitt's lymphoma, and follicular lymphoma (small cell and large cell). Certain forms of myeloma include, by way of non-limiting example, multiple myeloma (MM), giant cell myeloma, heavy-chain myeloma, and light chain or Bence-Jones myeloma. Solid tumors include, e.g., breast tumors, ovarian tumors, lung tumors, pancreatic tumors, prostate tumors, melanoma tumors, colorectal tumors, lung tumors, head and neck tumors, bladder tumors, leiomyosarcoma, glioma, glioblastoma, brain tumors, esophageal tumors, gastric tumors, liver tumors, and kidney tumors. In most cases, the effective amount is determined empirically via testing methods well known in the art.

In some embodiments, the present disclosure provides methods of treating cancer in a subject in need thereof. In some aspects, the method comprises administering to the subject in need thereof, an effective amount of a pharmaceutical comprising a pharmaceutically acceptable excipient and any of the antigen binding units disclosed herein. In some aspects, the cancer is a non-lymphoma cancer. In some aspects, the cancer is a non-leukemia cancer. In some aspects, the cancer is a non-lymphoma and non-leukemia cancer. In some aspects, the cell is a hematological cancer cell. Hematological cancers include, but are not limited to, leukemia, lymphoma and myeloma. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. Certain forms of lymphoma include, by way of non-limiting example, Hodgkin's lymphoma, both indolent and aggressive non-Hodgkin's lymphoma, Burkitt's lymphoma, and follicular lymphoma (small cell and large cell). Certain forms of myeloma include, by way of non-limiting example, multiple myeloma (MM), giant cell myeloma, heavy-chain myeloma, and light chain or Bence-Jones myeloma. Solid tumors include, e.g., breast tumors, ovarian tumors, lung tumors, pancreatic tumors, prostate tumors, melanoma tumors, colorectal tumors, lung tumors, head and neck tumors, bladder tumors, leiomyosarcoma, glioma, glioblastoma, brain tumors, esophageal tumors, gastric tumors, liver tumors, and kidney tumors. In most cases, the effective amount is determined empirically via testing methods well known in the art.

Cancers of interest for treatment by the methods of the invention include, but are not limited to, leukemias; acute leukemias such as T-ALL, B-ALL, AML, etc.; lymphomas (Hodgkin's and non-Hodgkin's); sarcomas; melanomas; adenomas; carcinomas of solid tissue including ovarian carcinoma, breast carcinoma, pancreatic carcinoma, colon carcinoma, squamous cell carcinoma, transitional cell carcinoma, etc., hypoxic tumors, squamous cell carcinomas of the mouth, throat, larynx, and lung, genitourinary cancers such as cervical and bladder cancer, hematopoietic cancers, head and neck cancers, and nervous system cancers, such as gliomas, astrocytomas, meningiomas, etc., benign lesions such as papillomas, and the like.

Treatment of cancer can be evidenced by reducing growth of cancer cells including, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with AML, etc. Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

In some aspects, treatment of cancer can be evidenced by reduced tumor volume. Tumor volume can be determined using any known method in the field. For example, tumor volume can be determined by measuring the tumor using a caliper. In such cases, two dimensions of the tumor can be measured and tumor volume can be determined using the formula $V=0.5\ a \times b^2$, where a and b are a first and second diameter. In some cases, the first diameter is the long diameter or the larger of the two diameters. In some cases, the second diameter is the short diameter or the smaller of the two diameters.

In some aspects, treatment of cancer can be evidenced by reduced tumor volume. In some cases, tumor volume is reduced by a percentage within the range of 1% to 100%. In some examples, tumor volume is reduced by about 1%, 5%, 10%, 15%, 20%, 25%, 30%, 35%, 40%, 45%, 50%, 55%, 60%, 65%, 70%, 75%, 80%, 85%, 90%, 95%, or 100%. In some examples, tumor volume is reduced by at least about 1%, 5%, 10%, 15%, 20%, 25%, 30%, 35%, 40%, 45%, 50%, 55%, 60%, 65%, 70%, 75%, 80%, 85%, 90%, 95%, or 100%. In some aspects of any of the embodiments disclosed herein, an antigen binding unit can reduce the tumor volume to a greater extent than that of a reference antigen binding unit. Such a reference antigen binding unit can have the amino acid sequences shown in 1) SEQ ID NO: 240-241, 2) SEQ ID NO:242-243, or 3) SEQ ID NO:244-245, or any other known anti-CD47 antigen binding unit.

In some aspects, comparison of the effect of a subject antigen binding unit compared to a reference antigen binding unit can be determined by calculating anti-tumor effectiveness. In such cases, tumor volume can be measure such as described above. Alternatively, a different parameter of tumor size or other appropriate characteristic of the tumor can be determined or measured. When working with quantifiable characteristics such as tumor volume, the anti-tumor effectiveness can be determined by using the formula: T/C, where T is the selected measurement (e.g., tumor volume) for the treatment group and C is the selected measurement (e.g., tumor volume) for the control group. Anti-tumor effectiveness can be determined over any desired period of time and can be determined using average value from any desired number of samples. Anti-tumor effectiveness can be expressed as a number or a percent. In some examples, anti-tumor effectiveness can be about 1%, 5%, 10%, 15%, 20%, 25%, 30%, 35%, 40%, 45%, 50%, 55%, 60%, 65%, 70%, 75%, 80%, 85%, 90%, 95%, or 100%. In some examples, anti-tumor effectiveness can be at most 1%, 5%, 10%, 15%, 20%, 25%, 30%, 35%, 40%, 45%, 50%, 55%, 60%, 65%, 70%, 75%, 80%, 85%, 90%, 95%, or 100%. In some examples, anti-tumor effectiveness can be at least 1%, 5%, 10%, 15%, 20%, 25%, 30%, 35%, 40%, 45%, 50%, 55%, 60%, 65%, 70%, 75%, 80%, 85%, 90%, 95%, or 100%.

Compositions, e.g. antigen binding units and pharmaceutical compositions, disclosed herein can be administered using any medically appropriate procedure, e.g., intravascular (intravenous, intra-arterial, intra-capillary) administration, injection into the lymph nodes, etc. Intravascular injection may be by intravenous or intraarterial injection. An effective amount of a composition to be given to a particular patient will depend on a variety of factors, several of which will be different from patient to patient and can be determined empirically. Dosage of the composition will depend on the determined treatment regime, route of administration, the nature of the therapeutics, sensitivity of the tumor to the therapeutics, etc. Utilizing $LD_{50}$ animal data, and other information available for an antigen binding unit disclosed herein, a clinician can determine the maximum safe dose for an individual, depending on the route of administration. For instance, an intravenously administered dose may be more than an locally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular composition.

In some aspects, a method for treatment of cancer is provided, the method comprising administering an effective amount of any of the foregoing pharmaceutical compositions comprising a subject antigen binding unit to a subject in need thereof. In some embodiments, the cancer is leukemia, breast cancer, prostate cancer, pancreatic cancer, lung cancer, including non-small cell lung cancer or carcinoma, liver cancer, ovarian cancer, bladder cancer, head and neck cancer, colorectal cancer, skin cancer, a brain tumor, or hepatocellular carcinoma (HCC). In certain aspects, the cancer is leukemia. The cancer can be a solid tumor. The cancer can be Mixed Lineage Leukemia (MLL), Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AML), hairy cell leukemia, and/or other leukemias; myeloproliferative disorder/neoplasm (MPDS), giant cell myeloma, heavy-chain myeloma, light chain or Bence-Jones Myeloma, myelodysplasia syndrome, multiple myeloma. The cancer can be lymphomas such as all subtypes of Hodgkin's lymphoma or non-Hodgkin's lymphoma.

The present disclosure also provides methods for combination therapies in which an agent known to modulate other pathways, or other components of the same pathway, or even overlapping sets of target enzymes are used in combination with a subject antigen binding unit or pharmaceutical composition comprising a subject antigen binding unit. In one aspect, such therapy includes but is not limited to the combination of one or more antigen binding units of the disclosure with chemotherapeutic agents, therapeutic antibodies, and radiation treatment, to provide a synergistic or additive therapeutic effect.

Where desired, a subject antigen binding unit can be used in combination with Notch inhibitors and/or c-Myb inhibitors. Where desired, an antigen binding unit or pharmaceutical composition of the present disclosure can be used in combination with MLL-WDR5 inhibitors and/or Dot11 inhibitors.

Many chemotherapeutics are presently known in the art and can be used in combination with a subject antigen binding unit. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; ellipitinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the antigen binding units or pharmaceutical composition of the present disclosure can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

This disclosure further relates to a method for using a subject antigen binding unit or a pharmaceutical composition provided herein, in combination with radiation therapy for inhibiting abnormal cell growth or treating the hyperproliferative disorder in the mammal. Techniques for administering radiation therapy are known in the art, and these techniques can be used in the combination therapy described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The antigen binding units or pharmaceutical compositions of the disclosure can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with an antigen binding unit of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-11, MMP-12, and MMP-13). Some specific examples of MMP inhibitors useful in the disclosure are AG-3340, RO 32-3555, and RS 13-0830.

Autophagy inhibitors include, but are not limited to chloroquine, 3-methyladenine, hydroxychloroquine (Plaquenil™), bafilomycin A1,5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, the antigen binding units and pharmaceutical compositions described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the subject antigen binding units include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with an antigen binding unit of the disclosure include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine an antigen binding unit of the present disclosure with sorafenib and/or Avastin. For treating an endometrial disorder, one may combine an antigen binding unit of the present disclosure with doxorubincin, taxotere (taxol), and/or cisplatin (carboplatin). For treating ovarian cancer, one may combine an antigen binding unit of the present disclosure with cisplatin (carboplatin), taxotere, doxorubincin, topotecan, and/or tamoxifen. For treating breast cancer, one may combine an antigen binding unit of the present disclosure with taxotere (taxol), gemcitabine (capecitabine), tamoxifen, letrozole, tarceva, lapatinib, PD0325901, avastin, herceptin, OSI-906, and/or OSI-930. For treating lung cancer, one may combine an antigen binding unit of the present disclosure with taxotere (taxol), gemcitabine, cisplatin, pemetrexed, Tarceva, PD0325901, and/or avastin.

Further therapeutic agents that can be combined with an antigen binding unit of the disclosure are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The antigen binding units described herein can be used in combination with the agents disclosed herein or other suitable agents, depending on the condition being treated. Hence, in some embodiments the one or more antigen binding units of the disclosure will be co-administered with other agents as described above. When used in combination therapy, the antigen binding units described herein are administered with the second agent simultaneously or separately. This administration in combination can include simultaneous administration of the two agents in the same dosage form, simultaneous administration in separate dosage forms, and separate administration. That is, an antigen binding unit described herein and any of the agents described above can be formulated together in the same dosage form and administered simultaneously. Alternatively, an antigen binding unit of the disclosure and any of the agents described above can be simultaneously administered, wherein both the agents are present in separate formulations. In another alternative, an antigen binding unit of the present disclosure can be administered just followed by and any of the agents described above, or vice versa. In some embodiments of the separate administration protocol, an antigen binding unit of the disclosure and any of the agents described above are administered a few minutes apart, or a few hours apart, or a few days apart.

Further illustration of the development and use of antigen binding units, polynucleotides, vectors and host cells according to this invention are provided in the Example section below. The examples are provided as a guide to a practitioner of ordinary skill in the art, and are not meant to be limiting in any way.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Antigen Binding Unit Generation and Screening

Two different mouse strains (Balb/c and C57/BL6) were used for immunization to generate anti-CD47 monoclonal antibodies. Recombinant fragment of CD47, SEQ ID NO: 161, was expressed in 293F cells and used for immunization. Serum from serial or terminal blood samples was analyzed for the presence of specific antibodies. Serum titer data was used to select mice for hybridoma fusions.

Single cell suspensions were prepared from the best responder animals' spleens and electro-fused with myeloma cells before seeding and culture in 96 well plates. The hybridomas were then cultured in selection media for seven days prior to screening of supernatants.

Produced antigen binding units were characterized by a combination of binding of hybridoma supernatants to CD47 protein by ELISA, Raji cell expressed human CD47 using flow cytometry, and neutralizing ELISA. The antigen binding units were further characterization by their blocking efficacy in CD47-SIRPα interaction assays. A commercialized anti-CD47 mAb, referred to as "Positive 1", was used as a positive control and diluted pre-immune sera was used as negative reference.

Subcloning to obtain monoclonal hybridoma cell lines was performed.

Example 2. Macrophage Phagocytosis Assay

Select antibody hits were assessed in a macrophage phagocytosis assay to confirm the functional activity in vitro. Human monocyte derived macrophage (MDM) were co-cultured with target tumor cells HL-60 which were labelled with fluorescent dye CSFE. Phagocytosis was analyzed by Cellomics after two hours incubation. The percentage of macrophages that contain tumor cells were calculated and expressed as phagocytosis index. Results from one representative experiment are shown in FIG. 1. In FIG. 1, the antibodies are present at a concentration of 3 micrograms per mL; the white arrows point to examples of phagocytosed AML cells; human promyelocytic leukemia HL-60 cells are labeled in green; and human macrophages are labeled in red.

For this assay, human monocytes were purified from human PBMC with CD14 Miltenyi cell isolation beads. Purified CD14+ monocytes were cultured in T75 flask in the presence of M-CSF (100 ng/ml) for 7-10 days. Monocytes derived macrophages were harvested by incubation in dissociation buffer for 5 minutes, followed by gentle scraping. Then, M2 cells were labeled with PKH26 (red), $1\times10^4$ macrophages were plated in a flat-bottom 96-well tissue culture plate in IMDM containing 10% FBS for 24 hours, media was replaced with serum-free media for another 2-hour incubation. $5\times10^4$ CFSE-labeled HL-60 cells were added in to the well in the presence of indicated antibodies for 2 hours. Wells were washed 3 times with IMDM and cells were fixed with 2% PFA. Then the fluorescence-labeled cells were analyzed on Cellomics machine.

Figure 2A:
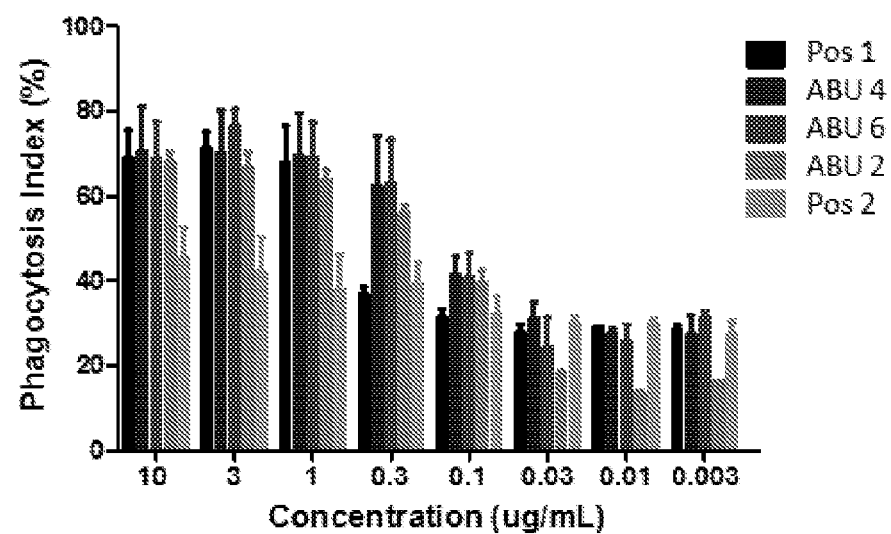
FIGS. 2A-2B depict data from an example phagocytosis experiment.
Figure 2B:
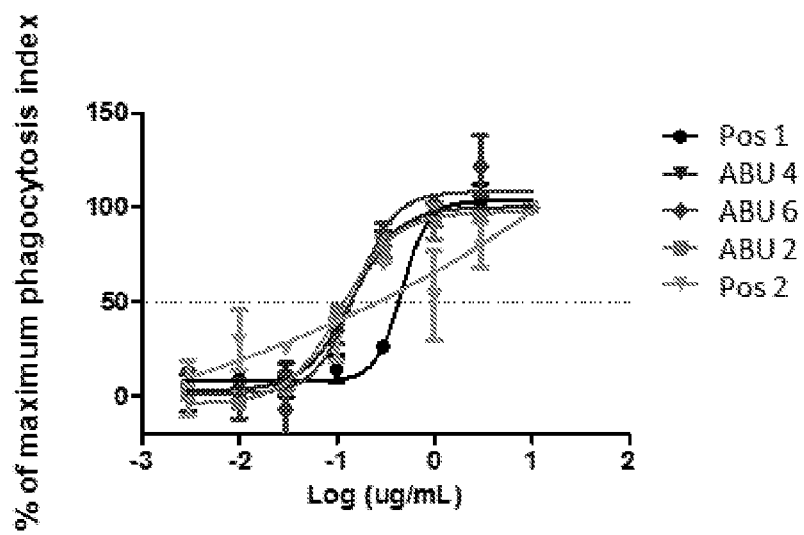

Phagocytosis index was determined by calculating the number of phagocytes per 100 macrophages, the data was calculated in Office Excel and graphed in Prism5, as shown in FIGS. 2A-2B. The EC50 was calculated based on percent of maximum of phagocytosis index, as shown in Table 4.

TABLE 4

| ABU | EC50 (nM) |
|---|---|
| ABU1 | +++ |
| ABU2 | +++ |
| ABU3 | ++ |
| ABU4 | +++ |
| ABU5 | ++ |

TABLE 4-continued

| ABU | EC50 (nM) |
|---|---|
| ABU6 | +++ |
| ABU7 | + |
| Positive 1 | ++ |
| Positive 2 | ++ |

+++: <1 nM;
++: >1 nM and <5 nM;
+: >5 nM

Example 3. CD47 Binding Assay

Binding affinity of antibodies for select antibodies (ABU-#) and chimeric antibodies (C-ABU-#) were measured by using both CD47 expressing CHO cells and Jurkat cells using either ELISA or flow cytometry. The protein binding kinetics of the antigen binding units were studied by SPR using Biacore T100 (GE Healthcare). Commercially available reference antibody was used as a control.

For ELISA-based binding analysis, human SIRPA (Novoprotein, Cat #C385) at a concentration of 1 µg/mL was coated in the bottom of a 96-half-well plate overnight at 4° C. Blocking was done with 3% skim milk in PBS (DOUBLE HELIX, Cat #P10033) for 1 hour at room temperature after 3 times wash by PBST (PBS with 0.05% tween-20 (Sangon, Cat #9005-64-5)). Serial diluted human CD47 protein (Novoprotein, Cat #CG18) were added into the wells and incubate at room temperature for 1 hour; after PBST wash 3 times, the bound CD47 protein were detected by HRP-conjugated goat polyclonal secondary antibody to human IgG-Fc (Abcam, Cat #ab98624) and then developed by TMB substrate (Biopanda, Cat #TMB-S-003) after 3 times PBST wash, followed by measurement of OD450. The binding curve (OD450 versus CD47 Concentration) were analyzed by GraphPad Prism and EC90 calculated for CD47 neutralizing study. Binding results are depicted below in Table 5.

TABLE 5

| Clone ID | Binding on CHO-CD47 Cells (EC50, nM) | Binding on Jurkat Cells (EC50, nM) | SIRPα blocking on cells (IC50, nM) | Affinity by SPR (nM) |
|---|---|---|---|---|
| ABU 1 | +++ | +++ | ++ | − |
| ABU 2 | +++ | +++ | ++ | + |
| ABU 3 | ++++ | ++++ | ++ | + |
| ABU 4 | ++++ | +++ | +++ | + |
| ABU 5 | +++ | +++ | ++ | + |
| ABU 6 | ++++ | ++++ | +++ | + |
| C-ABU 1 | ++++ | ++ | ++ | ND |
| positive 1 | +++ | +++ | ++ | + |
| positive 2 | ++++ | ++ | ++ | + |

Figure 3A:
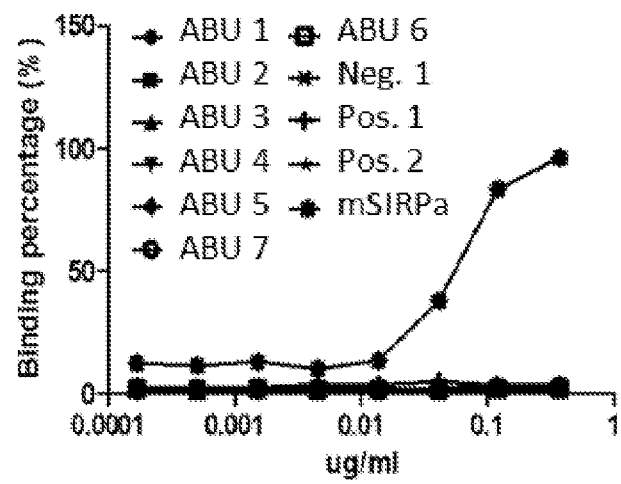
FIGS. 3A-3B depict data from an example antibody binding experiment.
Figure 3B:
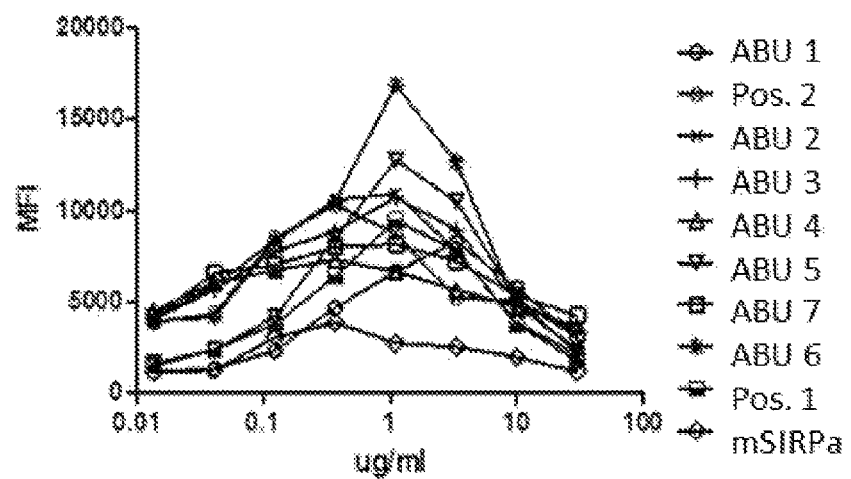

++++: <0.05 nM;
+++: >0.05 nM and <1 nM;
++: >1 nM and <10 nM;
+: >10 nM and <40 nM;
−: >40 nM;
ND: Note determined Antibody cross-reactivity was studied by flow cytometry using cells expressing CD47 from different species. Cynomolgus monkey red blood cells was used for monkey cross reactivity. CHO cell expressing mouse CD47 was used for mouse cross reactivity study. For flow cytometry-based binding analysis, human SIRPa expressing CHO cell line were generated and SIRPa expression were evaluated by binding of CD47-Fc protein (Novoprotein, Cat #CG18) or biotin labelled polyhistidine tagged CD47 protein (Novoprotein, Cat #321). Briefly, Human SIRPα expressing CHO cells were dissociated by Trypsin-EDTA dissociation buffer and washed 3 times with FACS buffer (PBS buffer with 2% FBS). The cells were plated into 96 wells plate and spin the cells done. Serially diluted CD47 protein (Fc tagged protein for murine antibody and biotin labelled polyhistindine tagged CD47 protein for chimeric/humanized antibody) were used to re-suspend the cells and incubate at 4° C. for one hours and then stained with APC labelled anti-human Fc antibody after washing out those non-bound proteins. After one hour incubation at 4 degree and 3 times wash, the cells were analyzed on Guava HL6T machine and data were analyzed using FlowJo software. at a concentration of 1 μg/mL was coated in the bottom of a 96-half-well plate overnight at 4° C. The binding curve (mean fluorescence intensity verse CD47 Concentration) were analyzed by GraphPad Prism and EC90 calculated for CD47 neutralizing study. Data from an example experiment is depicted in FIGS. 3A and 3B.

Example 4. Neutralizing ELISA

The neutralizing effect of select antibodies was analyzed by ELISA using SIRPα coated plates. Briefly, the SIRPα protein was coated on microtiter plates and CD47-hFc protein was added in serial dilution to establish a corresponding EC90. Select antibodies were serial diluted and mixed with hCD47-hFc fusion protein at its EC90 concentration, and their dose dependent blocking effect was detected with HRP labelled anti-hIgG antibodies against CD47-hFc.

Briefly, human SIRPA (Novoprotein, Cat #C385) at a concentration of 1 μg/mL was coated in the bottom of a 96-half-well plate overnight at 4° C. Blocking was done with 3% skim milk in PBS (DOUBLE HELIX, Cat #P10033) for 1 hour at room temperature. At the same time, pre-incubate 12.5 μL human CD47 (Novoprotein, Cat #CG18) at 2.5 μg/mL with hybridoma supernatant or anti-CD47 antibody gradients ("Positive 1" (eBioscience, Cat #14-0479) as positive control and "Negative 1" (eBioscience, Cat #14-0478) as negative control) for 1 hour at room temperature, which were then applied to each blocked well for 1 hour at room temperature. The blocking effect were detected by HRP-conjugated goat polyclonal secondary antibody to human IgG-Fc (Abcam, Cat #ab98624) and then developed by TMB substrate (Biopanda, Cat #TMB-S-003) after 3 times PBST wash, followed by measurement of OD450. The neutralizing activity (OD450 verse antibody Concentration) were analyzed by GraphPad Prism and IC50 calculated for evaluation.

The neutralizing effect of select antibodies was also analyzed by flow cytometry. Human SIRPa expressing CHO cell line were generated and SIRPa expression were evaluated by CD47 protein binding. Briefly, Human SIRPa expressing CHO cells were dissociated by Trypsin-EDTA dissociation buffer and washed 3 times with FACS buffer (PBS buffer with 2% FBS). The cells were plated into 96 wells plate and spin the cells done. Pre-incubate 25 μL human CD47-Fc at 2.5 μg/mL or biotinylated CD47 protein with hybridoma supernatant or anti-CD47 antibody gradients (B6H12 (eBioscience, Cat #14-0479) as positive control and 2D3 (eBioscience, Cat #14-0478) as negative control) for 1 hour at room temperature, and then re-suspend the cell pellet and incubate one hour at 4 degree. then stained with APC labelled anti-human Fc antibody or APC-Streptavidin after washing out those non-bound proteins. After one hour incubation at 4 degree and 3 times wash, the cells were analyzed on Guava HL6T machine and data were analyzed using Flowjo software. The neutralizing activity (mean fluorescence intensity verse antibody Concentration) were analyzed by GraphPad Prism and IC50 calculated for evaluation. Results from an example neutralizing ELISA experiment are summarized in Table 6.

TABLE 6

| Antibody | ABU 2 | ABU 3 | ABU 4 | ABU 5 | Abu 6 | Pos. 1 |
|---|---|---|---|---|---|---|
| IC50 (nM) | ++++ | ++ | +++ | ++++ | + | ++++ |

++++: <8 nM;
+++: >8 nM and <15 nM;
++: >15 nM and <20 nM;
+: >20 nM

Example 5. Anti-CD47 Antibody-Dependent Phagocytosis

The dose dependent effect of select antibodies on in vitro phagocytosis were performed to obtain EC50.

Human monocytes were purified from human PBMC with CD14 Miltenyi cell isolation beads. Purified CD14+ monocytes were cultured in T75 flask in the presence of M-CSF (100 ng/ml) for 7-10 days. Monocytes derived macrophages were harvested by incubation in dissociation buffer for 5 minutes, followed by gentle scraping. Then, M2 cells were labeled with PKH26 (red), 1×10$^4$ macrophages were plated in a flat-bottom 96-well tissue culture plate in IMDM containing 10% FBS for 24 hours, media was replaced with serum-free media for another 2-hour incubation. 5×10$^4$ CFSE-labeled HL-60 cells were added in to the well in the presence of indicated antibodies for 2 hours. Wells were washed 3 times with IMDM and cells were fixed with 2% PFA. Then the fluorescence-labeled cells were analyzed on Cellomics machine.

The phagocytosis index were determined by calculating the number of phagocytes per 100 macrophages, the data was calculated in Office Excel and graphed in Prism5. The EC50 was calculated based on percent of maximum of phagocytosis index.

Figure 4:
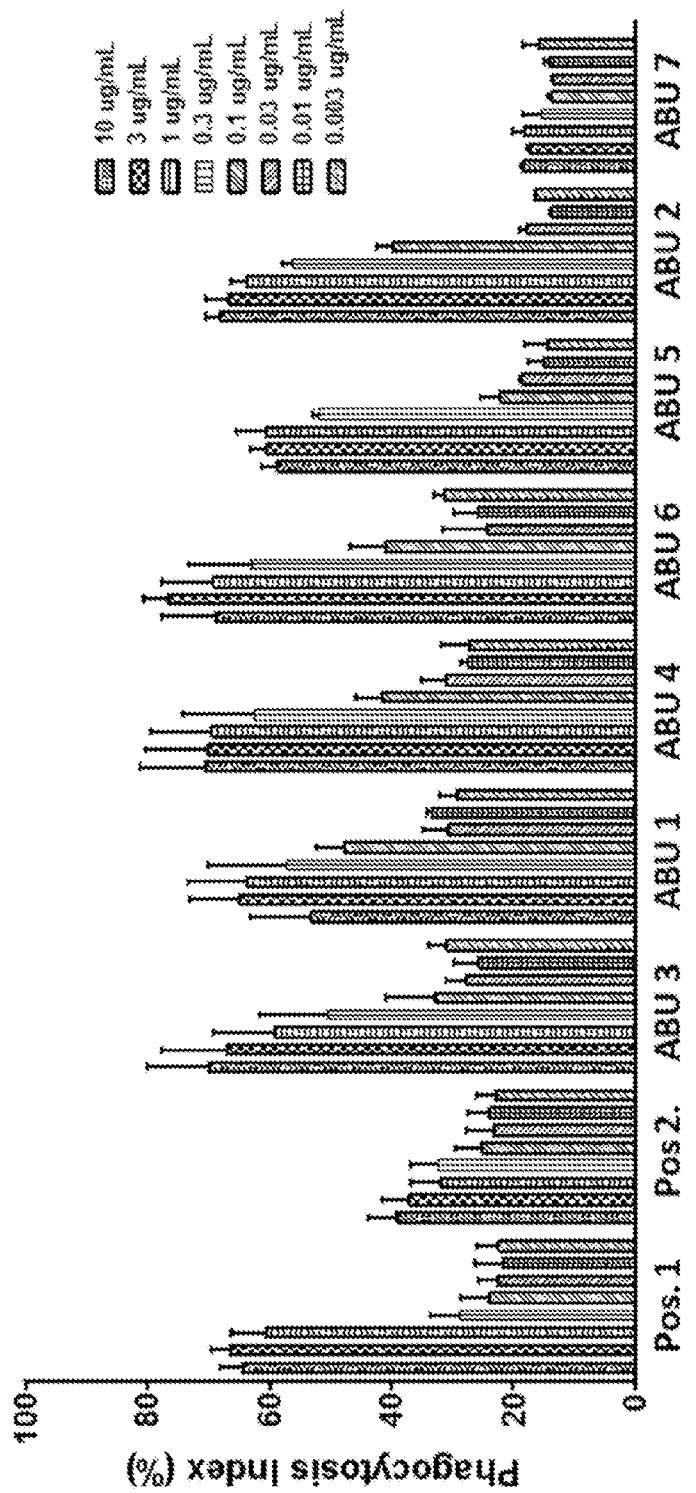
FIG. 4 depicts data from an example phagocytosis experiment.
Figure 5:
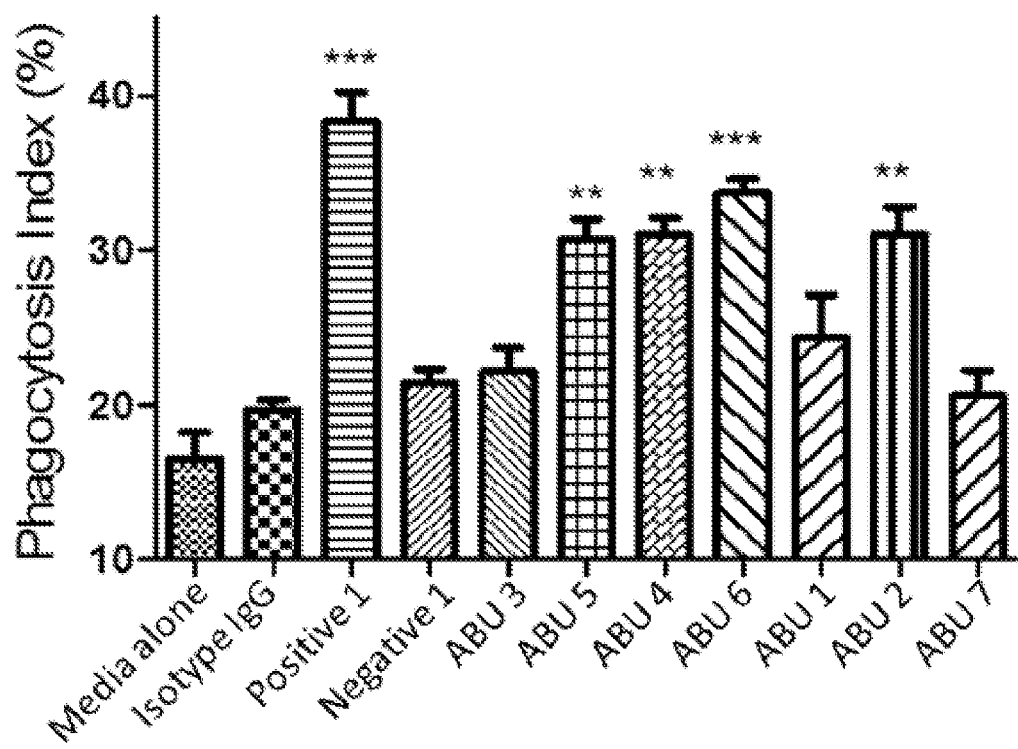
FIG. 5 depicts data from an example phagocytosis experiment.

Data from example phagocytosis experiments using HL60 cell line cells are depicted in FIG. 4. The EC50 were calculated and summarized in Table 7. Data from example phagocytosis experiments using DLD-1 human colon cancer cell line are depicted in FIG. 5.

TABLE 7

| Ab ID | ABU 1 | ABU 2 | ABU 3 | ABU 4 | ABU 5 | ABU 6 | Pos. 1 | Pos. 2 |
|---|---|---|---|---|---|---|---|---|
| IC50 (nM) | +++ | ++ | + | ++ | + | ++ | + | + |

+++: <0.6 nM;
++: >0.6 nM and <1 nM;
+: >1 nM

Example 6. Epitope Binning of CD47 Hit Antibodies

Epitope binning of these hits were conducted using CD47-expressing CHO cells with a commercial anti-CD47 blocking antibody Positive 1 comprising SEQ ID NO: 240 and SEQ ID NO: 241, a benchmark analogue antibody Positive 2 comprising SEQ ID NO: 242 and SEQ ID NO:

243, as well as an analogue antibody Positive 3 comprising SEQ ID NO: 244 and SEQ ID NO: 245. Positive 1 also comprised SEQ ID NO: 149-154. Positive 2 also comprised SEQ ID NO: 155-160. Briefly, seven neutralizing CD47 antibodies and 3 reference antibodies were analyzed and grouped according to their competitive binding to CHO cell expressing CD47 using flow cytometry. A biotinylated antibody was first used to calculate the concentration for 90% binding, then the CD47 antibodies were serially diluted and mixed with one of the biotinylated antibodies at the predetermined 90% binding concentration. SA-APC was used to detect the binding of biotinylated antibody binding. As the experiment designed, the binding of labeled antibodies should be affected by the Abs of the same bin and classified as one group. If the binding of labeled antibodies is not affected, then those testing antibodies are not in the same bin and characterized as a separate group. Three binding profiles on the CHO expressing CD47 were identified and the six hits subjected to two groups shown below in Table 8. ABU4 and ABU5 belong to one epitope binding group while the other, including positive 3, belong to a different one. Positive 1 interfered the two groups binding on the cells.

TABLE 8

| ABU | Epitope group |
|---|---|
| ABU4 | A |
| ABU5 | A |
| ABU1 | B |
| ABU2 | B |
| ABU3 | B |
| ABU6 | B |
| Positive 2 | B |
| Positive 3 | B |
| Positive 1 | A/B |

Example 7. Red Blood Cell Binding and Hemagglutination Assay

Figure 6:
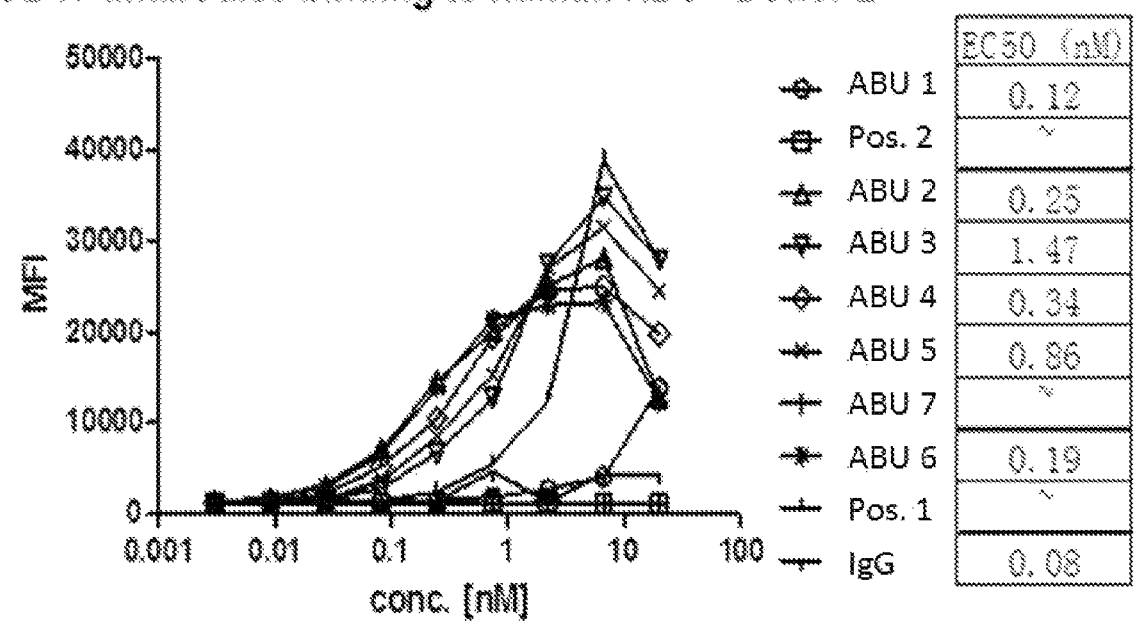
FIG. 6 depicts data form an example red blood cell binding experiment.

CD47 is ubiquitously expressed with particular high expression on red blood cells. To evaluate the binding affinity on human red blood cells, the RBC binding assay were performed using RBCs from several donors. The binding curve and EC50 from an example experiment is depicted in FIG. 6.

Select antibodies were also tested in a hemagglutination assay to identify antibodies showing strong hemagglutination effect. The antibodies to be tested were diluted as indicated concentration in PBS and 90 ul of antibodies with series dilution were added in the V-bottom culture plate for incubation of 37° C. for 1 hour. Then 10 uL of human red blood cells (RBCs) were added with 10% final concentration in PBS. The RBCs were incubated with antibodies in 37° C. and the hemagglutinin will be observed in 2-4 hours. Evidence of hemagglutinin is demonstrated by the presence of non-settlement RBCs, appearing as haze compared to punctuate red dots of non-hemagglutinated RBCs.

Figure 7A:
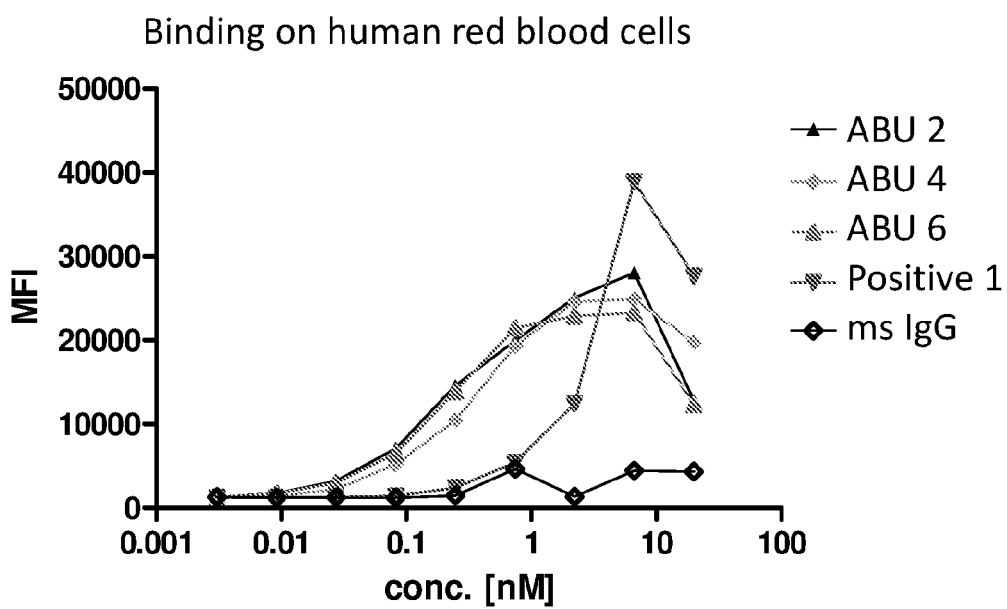
FIGS. 7A-7B depict data from an example hemagglutination experiment.
Figure 7B:
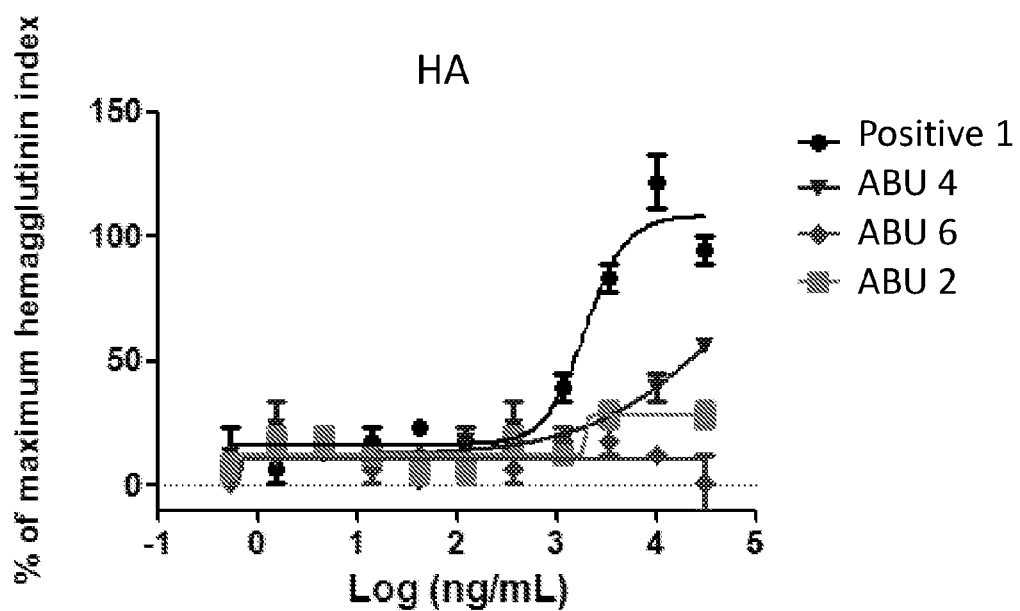

Hemagglutination index was quantified by the area of RBC pellets in presence or absence of mAbs, the diameter of RBC pellets were determined by ImageJ software in pixel, then the area was calculated in excel. The calculated data was normalized to the isotype IgG. The log concentration v.s index was plotted in Prism 5 and is depicted in FIGS. 7A-7B.

Figure 8:
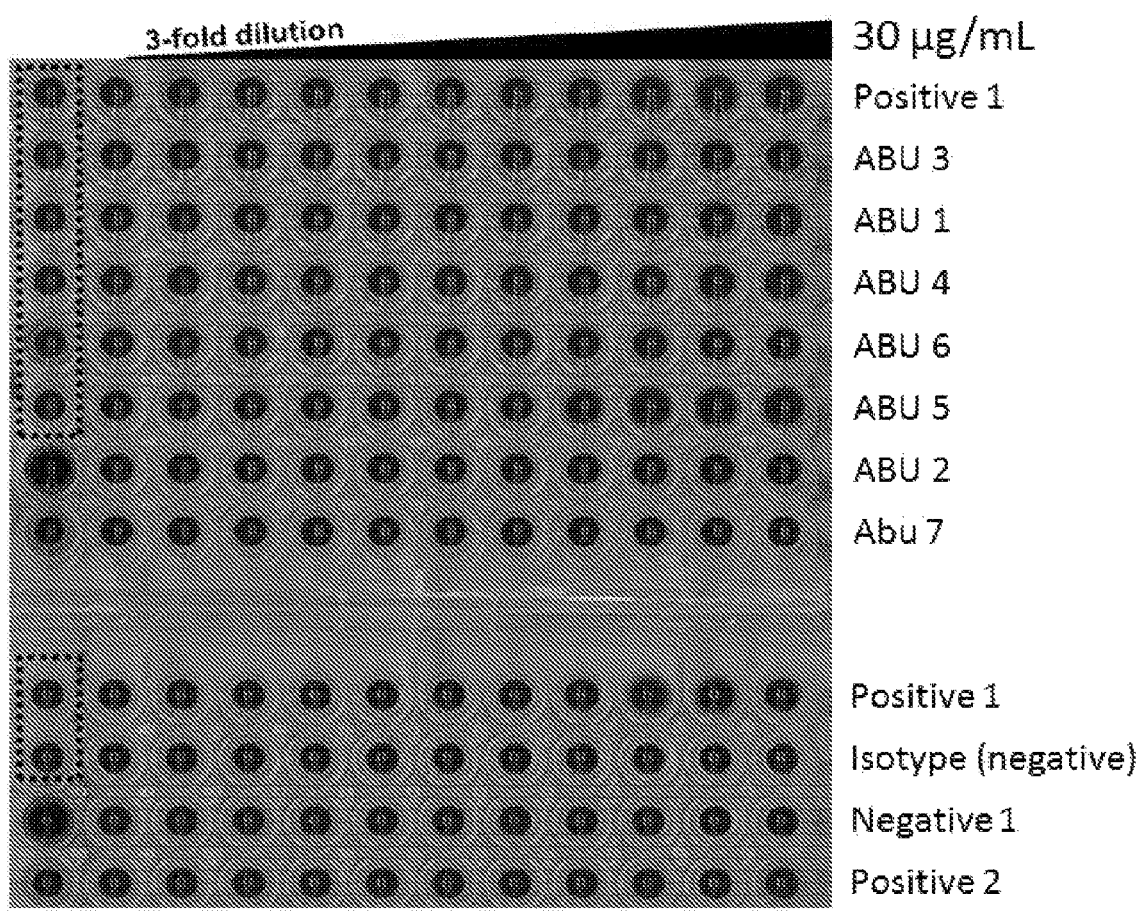
FIG. 8 depicts data from an example hemagglutination experiment.

Images from an example experiment is depicted in FIG. 8. Induction of significant hemagglutination of human red blood cell would be evidenced by a haze appearance in the wells. In FIG. 8, Isotype muIgG1 serves as a negative control; the dotted line marks blank controls; a positive hemagglutination control is circles in blue; and a negative hemagglutination control is circles in yellow.

Example 8. Characterization of Chimeric Anti-CD47 Antibodies

To generate chimeric antibodies, selected antigen binding units were picked and expanded and the V-region sequences were recovered. The V regions were synthesized and subcloned in vectors to obtain human IgG4 (S228P) chimera. S228P refers to the amino acid position where IgG4 is split as described in Aalberse R C and Schuurman J (2002) IgG4 breaking the rules. Immunology 105:9-19 (incorporated herein in its entirety). The human IgG4 sequence was cloned onto the C-terminus of the light chain variable region sequence and heavy chain variable region sequence of the selected antibodies. The chimeric hIgG4 antibodies were expressed in 293F cells and purified as human IgG4 format for functional validation. Chimeric antibodies were also generated with IgG1 constant region in place of the IgG4 region.

Figure 9:
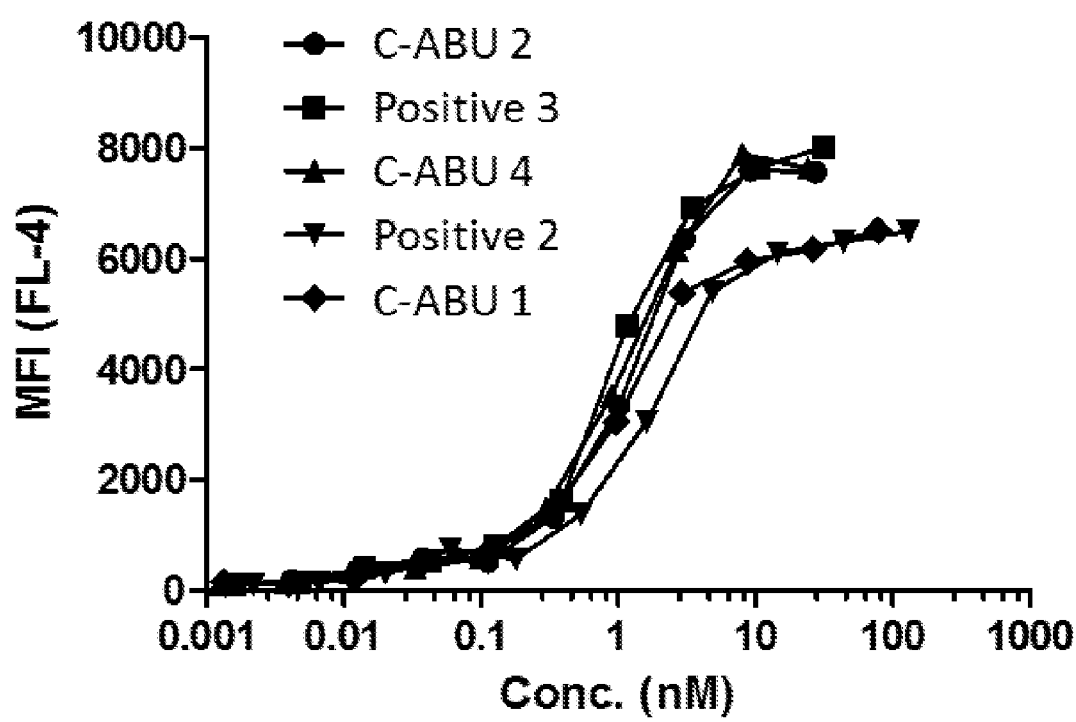
FIG. 9 depicts data from an example antibody binding experiment.

Binding affinities of the chimeric antibodies were measured by flow cytometry with CD47-expressing cell lines. Results from an example experiment are depicted in FIG. 9.

Figure 10:
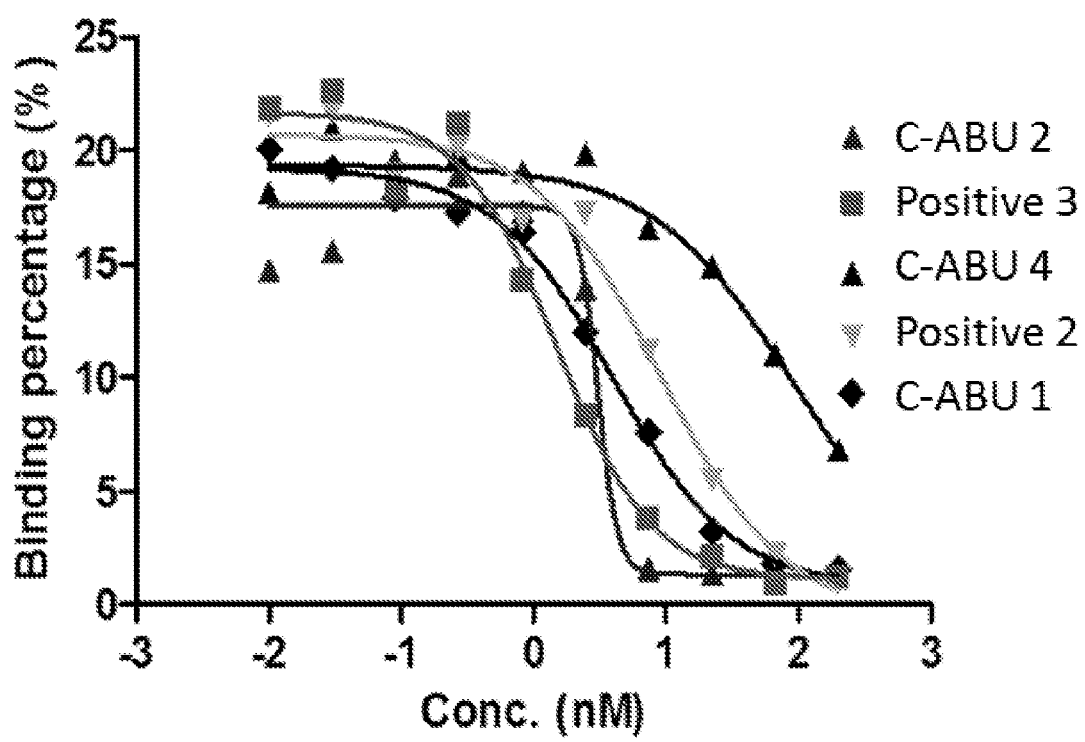
FIG. 10 depicts data from an example antibody neutralization experiment.

The neutralizing effect of select chimeric antibodies was analyzed using cells expressing CD47. Briefly, human chimeric IgG4 antibody was diluted and mixed with biotinylated human CD47 protein. The dose-dependent SIRPα binding-blocking effects was then detected for C-ABU1, C-ABU2, and C-ABU 4. Results from example experiments are depicted in FIG. 10.

Figure 11:
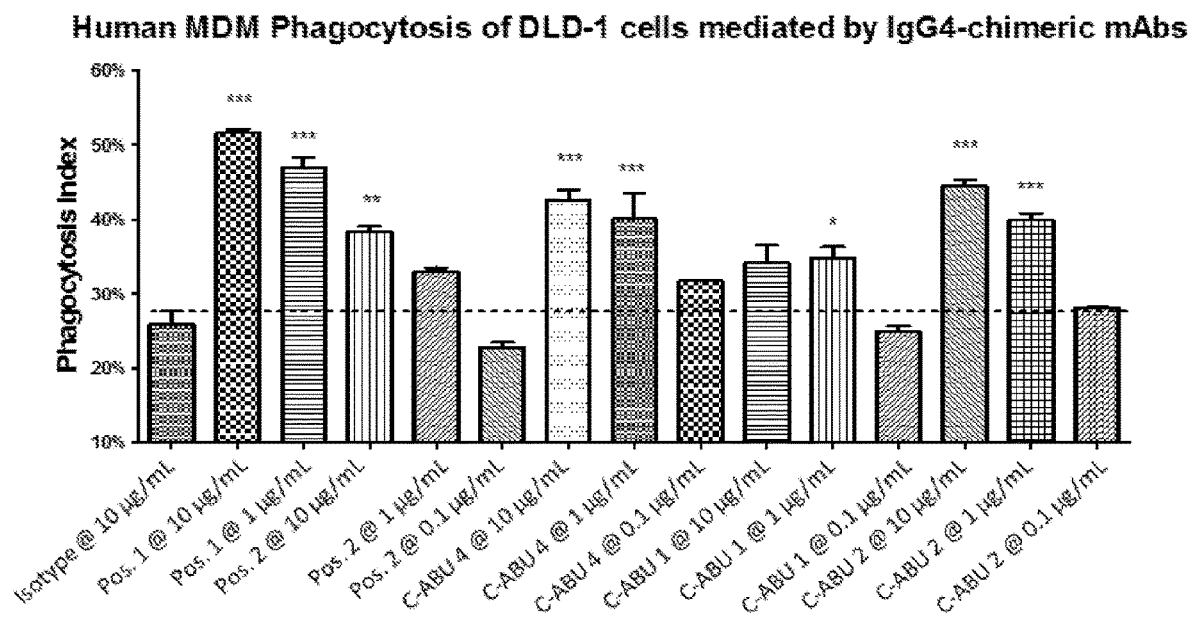
FIG. 11 depicts data from an example phagocytosis experiment.

Select chimeric antibodies were further characterized in a DLD-1 cell phagocytosis assay performed as described above. Results from example experiments are depicted in FIG. 11, and the asterisks denote statistical significance based on a p value calculated by one-way ANOVA post Dunnett's test.

Example 9. Phage Selection of Additional Anti-CD47 Fabs

Anti-CD47 Fabs were generated using the following phage-based method. Total RNA from spleens of immunized mice was prepared. After oligo(dT) primed reverse transcription, the antibody variable regions VL and VH were amplified by PCR. The murine VL and VH regions were then fused to human constant regions CL and CH1 of light chain and heavy chain respectively. The combination of the chimeric light chains and heavy chain fragments was cloned into the phagemid vector pComb3X and resulted in a murine/human Fab library displayed on phage.

The generated phage library was then screened for anti-CD47 specific Fabs. Dynabeads conjugated with Streptavidin were first blocked by incubating for 1 hour at room temperature with PBS containing 3% BSA. Approximately 1 µL blocked Dynabeads were incubated for 30 minutes with decreasing amount of biotinylated CD47-Fc (100 nM, 50 nM and 25 nM for rounds 1, 2 and 3, respectively) to capture antigen. Phage libraries were pre-adsorbed on another approximately 1 µL blocked Dynabeads in PBS containing 3% BSA for 30 minutes, followed by depletion with approximately 1 µg/mL human Fc fragment in PBS containing 3% BSA. Depleted phage library then were mixed with antigen coated Dynabeads for 1 hour at room temperature with gentle rotating head-over-head. The Dynabeads were then washed with 1 mL PBS containing 0.05% Tween-20 (5, 10 and 15 times for rounds 1, 2 and 3, respectively) using magnetic separator. Bound phage were eluted by incubation at room temperature for 10 minutes with 500 μL elution buffer followed by neutralization with 50 μL neutralization buffer. Eluted phage were rescued by infection of E. coli TG1 cells and a phage library was prepared for the next round of screening.

Select Fabs were characterized by various ELISA assays. Soluble Fab fragments were induced and periplasmic fractions were prepared by the following method. Individual clones from third round of screening were picked from an agar plate and cultured overnight in a microtiter plate containing 2YT. 5 μL of each overnight culture was transferred to a microtiter plate containing 150 μL of 2YT, 2% glucose, 50 μg/mL carbenicillin, and grown at 37° C. for 3 hours. Isoproplythiogalactoside (IPTG) was added to each well to a final concentration of 1 mM. After overnight grown with shaking at 25° C., plates were spun down, and supernatant was used directly in binding ELISA. For preparation of periplasmic fractions, cell pellets were resuspended and incubate on ice for 20 minutes. These periplasmic fractions, were then used for testing specificity by flow cytometry and blocking ELISA assays.

Large scale induction of soluble Fab fragments from individual clones was performed on a 50 ml scale in 2YT containing 50 μg/ml carbenicillin and 2% glucose. After growth at 37° C. to an OD600 of 0.9, IPTG was added to the final concentration of 1 mM. After growing overnight at 25° C., cell pellets were harvested and periplasmic fractions were prepared as described above.

The pooled large scale of periplasmic fraction descried above were passed over a 1 mL Ni— resin according to the manufacturer's instructions. The column was washed with buffer and the protein was eluted by applying buffer. The eluted protein was filtered to change the buffer to PBS. Purified Fabs then were analyzed by SDS-PAGE under non-reducing as well as reducing conditions and the concentration determined spectrophotometrically.

Select Fabs were screened by ELISA. Microtiter plate was coated with human CD47-Fc at a concentration of 1 μg/ml in PBS overnight at 4 degrees Celsius, washed three times with PBS/0.05% Tween 20, blocked with PBS/3% skim milk for 1 hour at room temperature, and then incubated with 50 μL of supernatant from individual clone for 1 hour at room temperature. After 3 washes with PBS/0.05% Tween 20, 50 μL of a 1:5000 dilution of HRP conjugated anti-human IgG F(ab)2 specific was added and incubate for 1 hour at room temperature. Following 3 washes with PBS/0.05% Tween 20, 50 μL of TMB substrate was added for color development. Reactions were stopped by addition of 50 μL of HCl, and OD450 was measured in a microtiter plate reader.

Activity of blocking CD47's interaction with SIRPa of each clone was carried out by inhibition ELISAs. Microtiter plate was coated with Human SIRPa at a concentration of 1 μg/ml in PBS overnight at 4° C., washed three times with PBS/0.05% Tween 20, blocked with PBS/3% skim milk for 1 hour at room temperature. 50 μL of periplasmic fraction of each clone was mixed with approximately 1 μL of human CD47 and incubated for 1 hour at room temperature, followed by adding 50 μL of the mixture into blocked wells of microtiter plate. Incubated for 1 hour at room temperature and the following steps were exactly same as above.

Figure 12A:
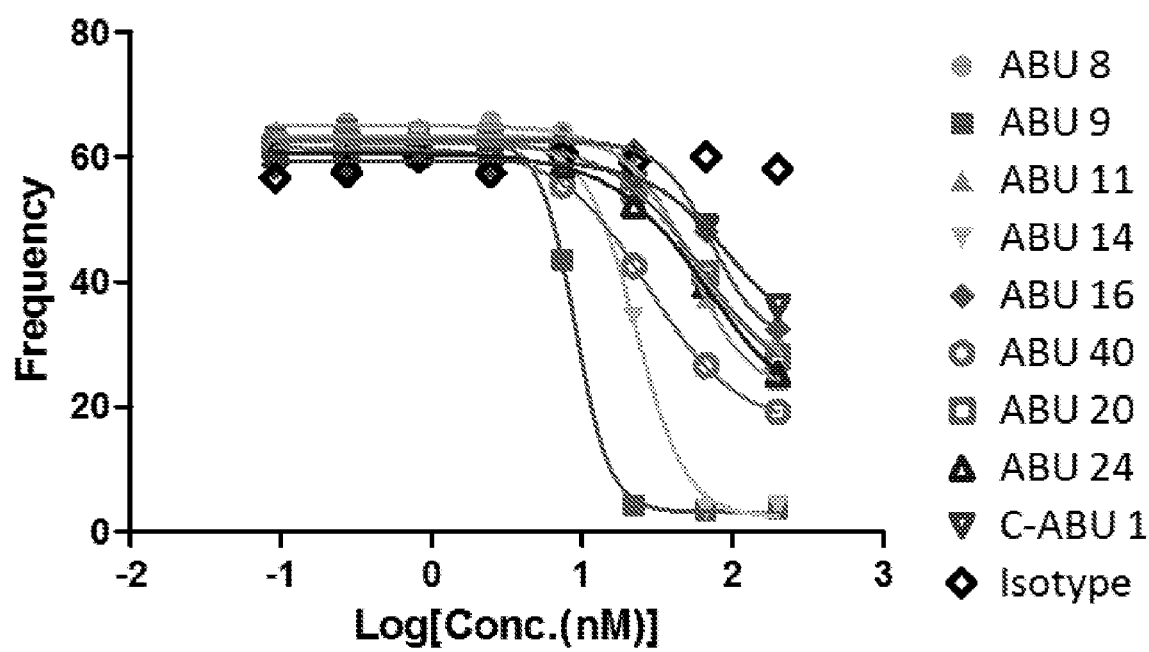
FIGS. 12A, 12B, and 12C depict data form an example antibody binding experiment.

CHO cells that had been stably transfected with human SIRPa were detached using cell dissociation buffer. Aliquots of 200 μL containing 10^5 cells were distributed into wells of U-bottom 96-well plate. After washing three times with FACS buffer (2% FBS in PBS), 0.07 μg/mL of biotinylated CD47 was added in the presence of serial diluted concentrations of Fab in FACS buffer to resuspend cells, and incubated at 4° C. for 30 minutes. Then, the cells were washed with FACS buffer three times, followed by incubation with 1:1000 diluted APC-labeled SA (Invitrogen) at 4° C. for 30 minutes. After three times of washing, binding was measured on Guava HL6T machine. Data from an example experiments are shown in FIG. 12A and Table 9.

Figure 12B:
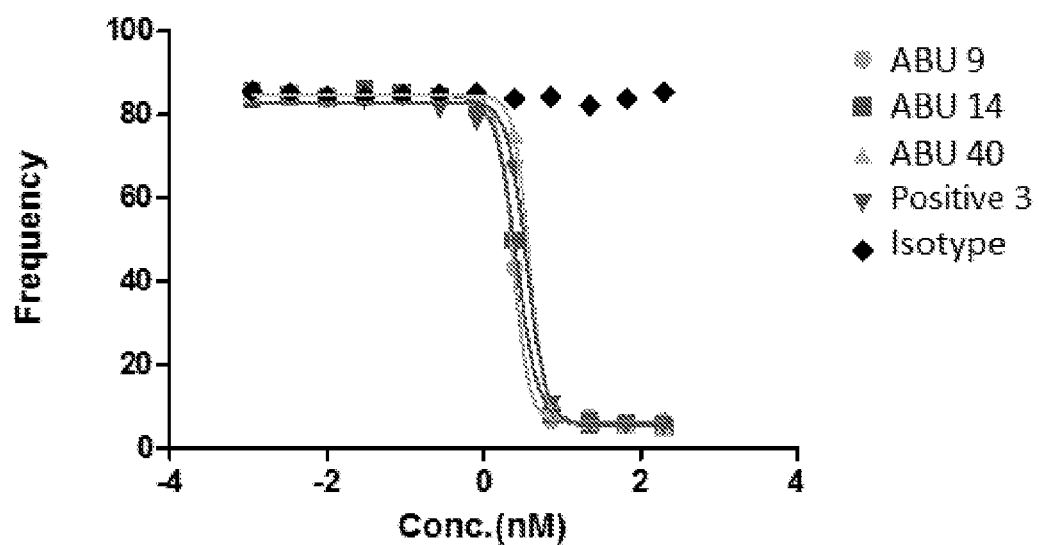
Figure 12C:
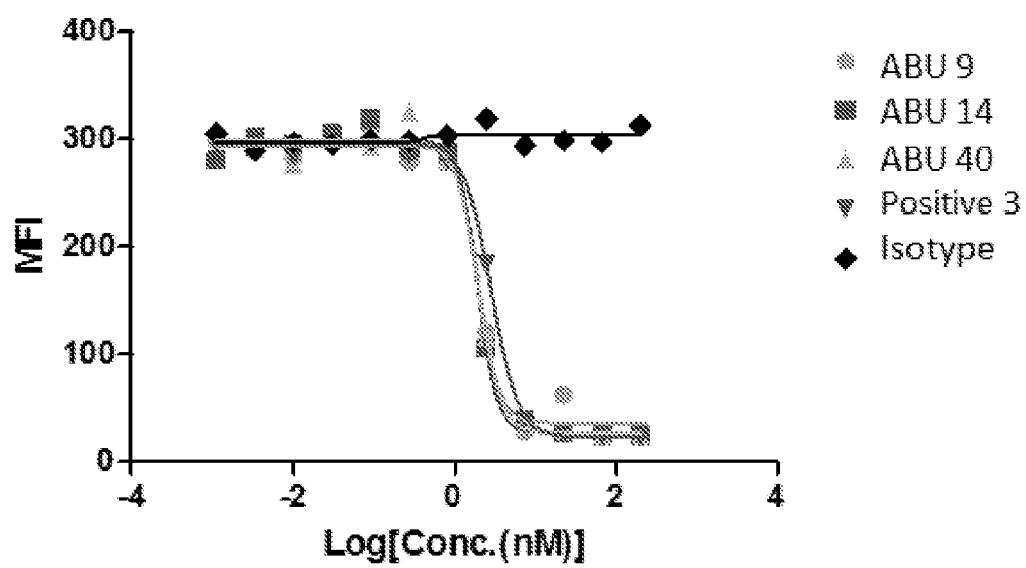

CHO cells that had been stably transfected with human SIRPα were detached using cell dissociation buffer. Aliquots of 200 μL containing 10^4 cells were distributed into wells of U-bottom 96-well plate. After washing three times with FACS buffer (2% FBS in PBS), 0.07 μg/mL of His-tagged CD47 was added in the presence of serial diluted concentrations of Fab in FACS buffer to resuspend cells, and incubated at 4° C. for 30 minutes. Then, the cells were washed with FACS buffer three times, followed by incubation with 1:1000 diluted anti-His-APC (GenScript #A01802) at 4° C. for 30 minutes. After three times of washing, binding was measured on Guava HL6T machine. Data from an example experiment are shown in FIGS. 12B-12C and Table 10.

TABLE 9

| | ABU8 | ABU9 | ABU11 | ABU14 | ABU16 | ABU40 | ABU20 | ABU24 | C-ABU1 |
|---|---|---|---|---|---|---|---|---|---|
| IC50(nM) | ++ | +++ | ++ | ++ | + | ++ | ++ | + | + |

+++: <10 nM;
++: >10 nM and <65 nM;
+: >65 nM

TABLE 10

| | ABU9 | ABU14 | ABU40 | Positive 3 |
|---|---|---|---|---|
| IC50(nM) Frequency | ++ | ++ | + | + |
| IC50(nM) MFI | +++ | +++ | +++ | + |

+++: <2 nM;
++: >2 nM and <2.7 nM;
+: >2.7 nM

Figure 13A:
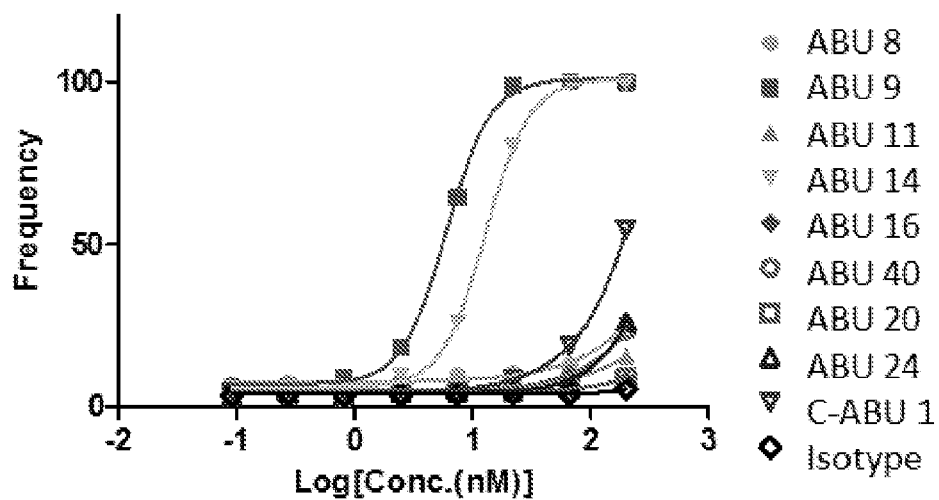
FIGS. 13A, 13B, 13C, and 13D depict data form an example antibody binding experiment.
Figure 13B:
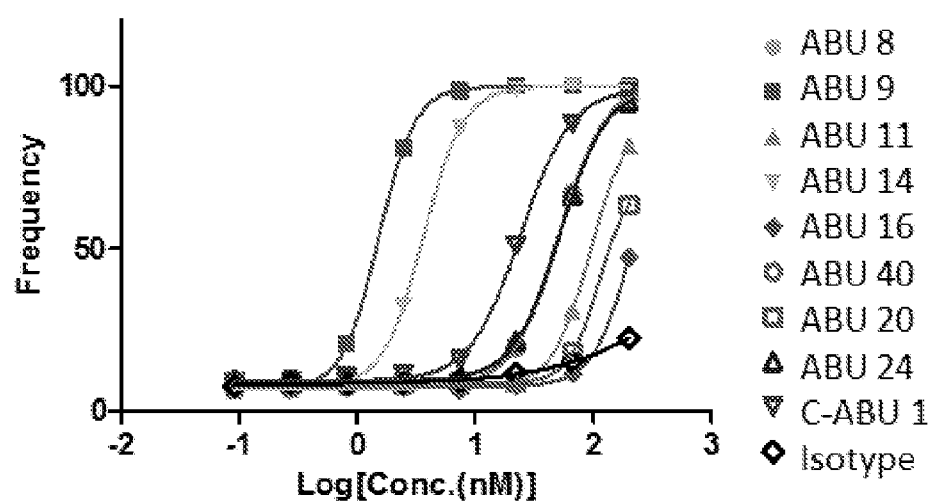
Figure 13C:
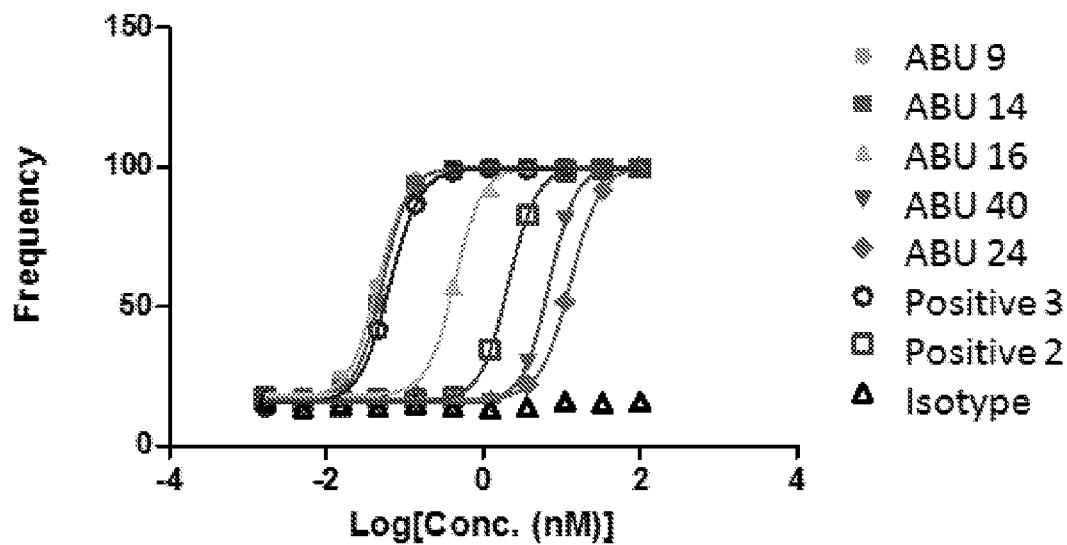
Figure 13D:
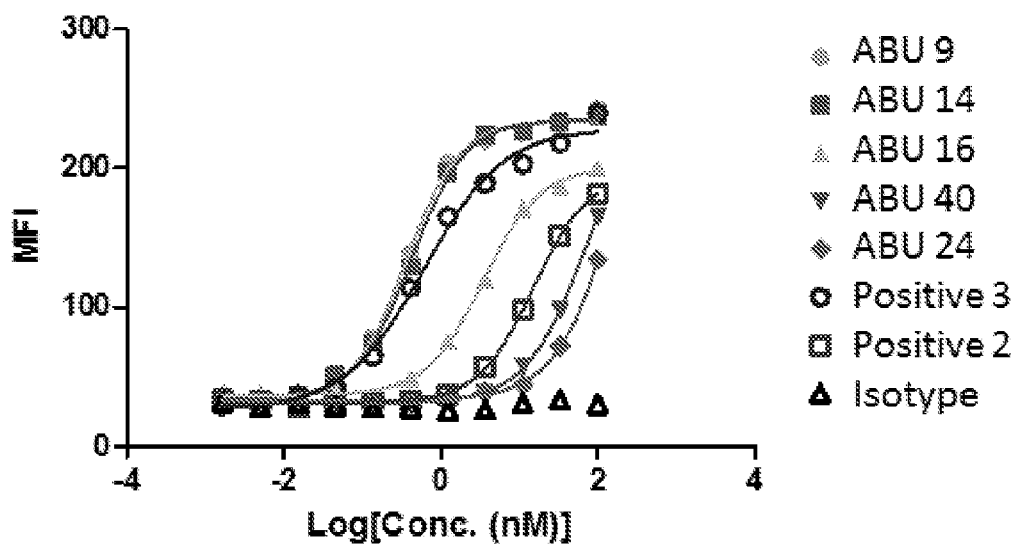

Select Fabs were also characterized by cell-binding assays. Aliquots of 200 μL containing 10^5 HL60 cells or DLD1 cells were distributed into wells of U-bottom 96-well plate. After washing three times with FACS buffer (2% FBS in PBS), cells were resuspended in serial diluted concentrations of Fab or IgG in FACS buffer and incubated at 4° C. for 30 minutes. Then, the cells were washed with FACS buffer three times, followed by incubation with approximately three fold diluted APC-labeled anti-human (Fab)2 specific antibody or APC-labeled goat anti-human IgG, respectively, at 4° C. for 30 minutes. After three times of washing, binding was measured on Guava HL6T machine. Data from an example experiment using HL60 cells and Fabs are shown in FIG. 13A and Table 11. Data from an example experiment using DLD1 cells and Fabs are shown in FIG. 13B and Table 12. Additional experiments using DLD1 cells and IgGs are shown in FIGS. 13C and 13D and Table 13.

TABLE 11

| | ABU8 | ABU9 | ABU11 | ABU14 | ABU16 | ABU40 | ABU20 | ABU24 | C-ABU1 |
|---|---|---|---|---|---|---|---|---|---|
| EC50(nM) | +++ | ++ | +++ | + | +++ | +++ | +++ | +++ | +++ |

+++: <1 nM;
++: >1 nM and <7 nM;
+: >7 nM

TABLE 12

| | ABU8 | ABU9 | ABU11 | ABU14 | ABU16 | ABU40 | ABU20 | ABU24 | C-ABU1 |
|---|---|---|---|---|---|---|---|---|---|
| EC50(nM) | ++ | +++ | + | +++ | +++ | ++ | + | ++ | ++ |

+++: <5 nM;
++: >5 nM and <60 nM;
+: >60 nM

TABLE 13

| | ABU9 | ABU14 | ABU16 | ABU40 | ABU24 | Positive 3 | Positive 2 |
|---|---|---|---|---|---|---|---|
| IC50(nM) Frequency | +++ | +++ | +++ | ++ | ++ | +++ | ++ |
| IC50(nM) MFI | +++ | +++ | ++ | + | +++ | +++ | ++ |

+++: <2 nM;
++: >2 nM and <20 nM;
+: >20 nM

TABLE 14

| | ABU9 | ABU14 | ABU40 | ABU24 | Positive 3 |
|---|---|---|---|---|---|
| IC50(nM) Frequency | +++ | +++ | +++ | +++ | ++ |
| IC50(nM) MFI | +++ | +++ | + | + | +++ |

+++: <1 nM;
++: >1 nM and <20 nM;
+: >20 nM

Figure 14A:
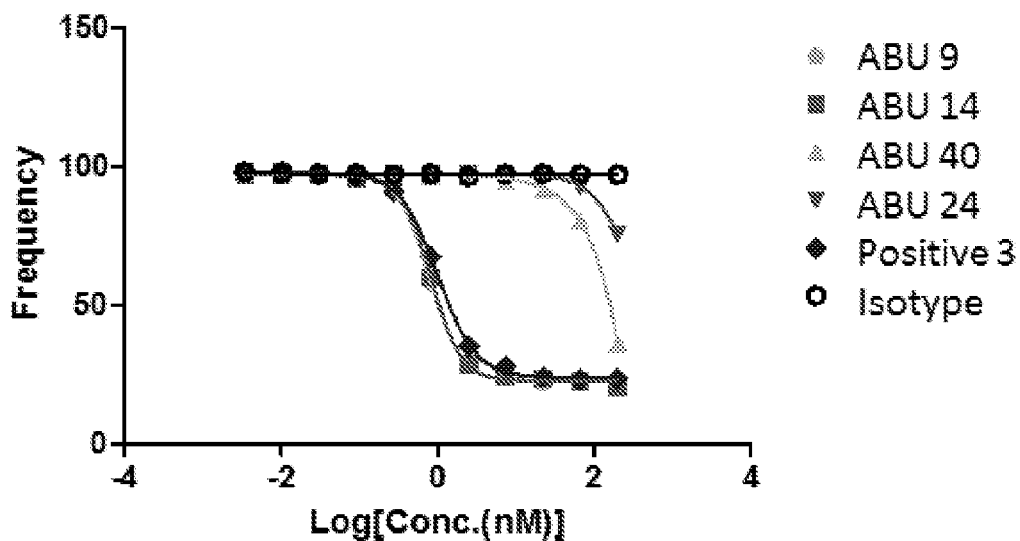
FIGS. 14A-14B depict data from an example antibody binding experiment.
Figure 14B:
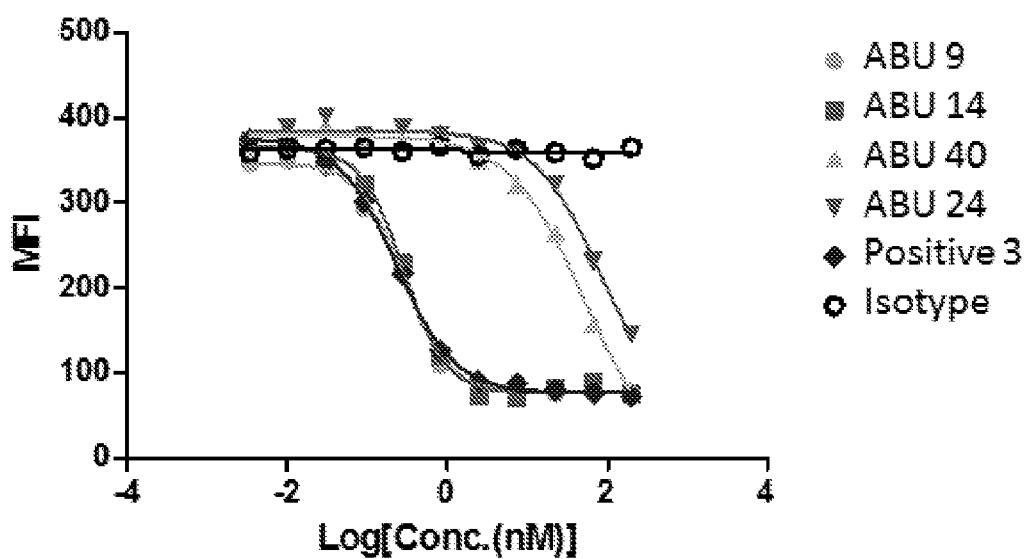

Chimeric versions of select Fabs were generated and subjected to an ELISA assay. FcRn blocked DLD1 cells expressing CD47 were aliquoted so approximately 10^4 cells were distributed into wells of U-bottom 96-well plate. After washing three times with FACS buffer (2% FBS in PBS), 100 nM of biotinylated SIRPα-Fc was added in the presence of serial diluted concentrations of Fab in FACS buffer to resuspend cells, and incubated at 4° C. for 30 minutes. Then, the cells were washed with FACS buffer three times, followed by incubation with diluted APC-labeled SA (Invitrogen) at 4° C. for 30 minutes. After three times of washing, binding was measured on Guava HL6T machine. Data from an example experiment are shown in FIGS. 14A and 14B and Table 14.

Example 10. Humanization of Anti-CD47 Antibodies

Figure 15A:
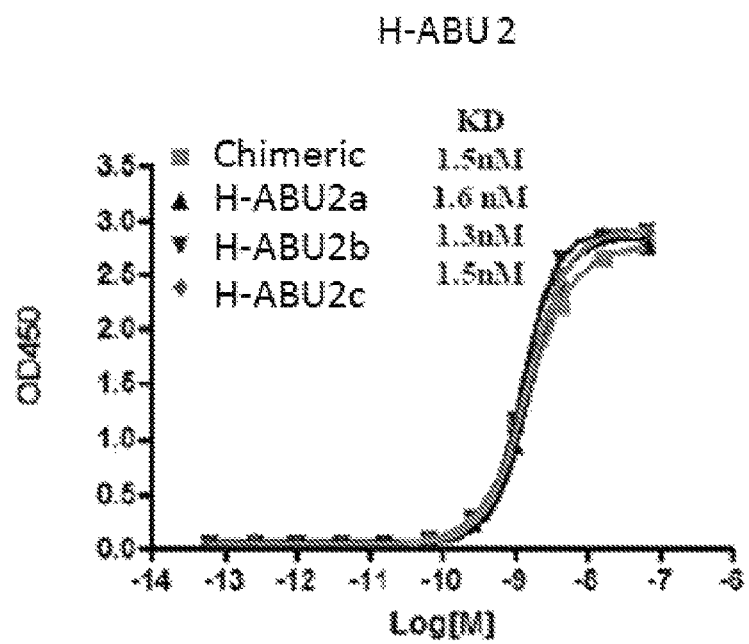
FIG. 15A-depicts data from an example antibody binding experiment.

Antibody sequences were subjected to profiling using structure modeling, to identify best matched germline and back mutation sites. The optimized mutants were synthesized and recombinant antibodies were produced for binding affinity determined by ELISA. After grafting and back mutation, the affinity of the humanized antibodies was either retained or improved (FIG. 15A), H-ABU2 was further affinity-matured by FACS screening of mutagenesis library to select clones that could bind the antigen better, in some cases up to 10 fold, compared with the corresponding chimeric parental antibody.

Figure 15B:
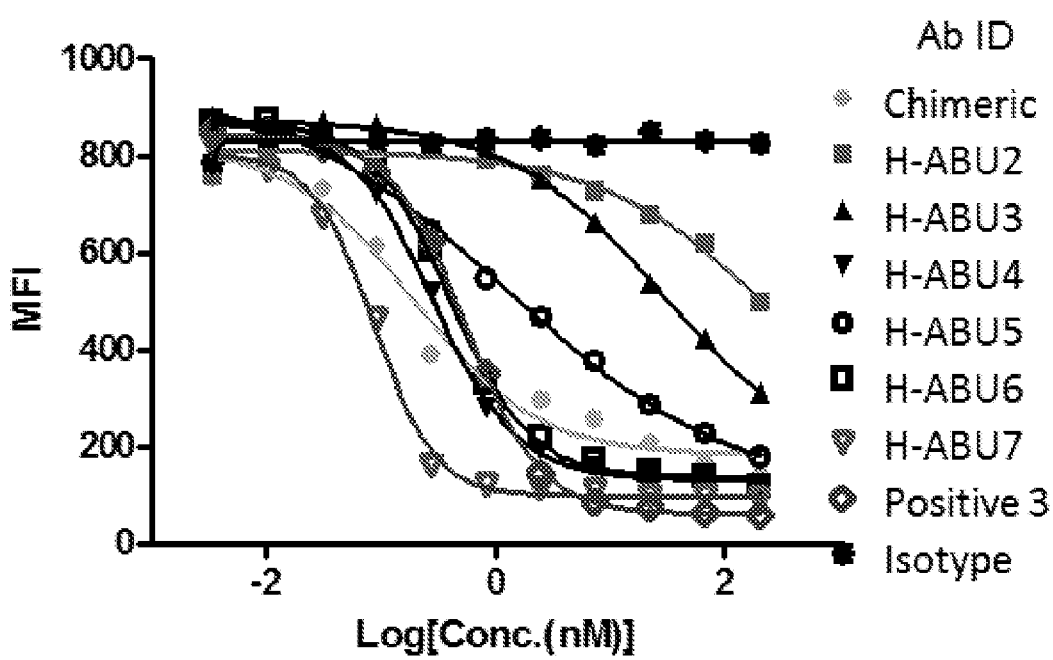
FIGS. 15B and 15C depict data from an example blocking experiment.
Figure 15C:
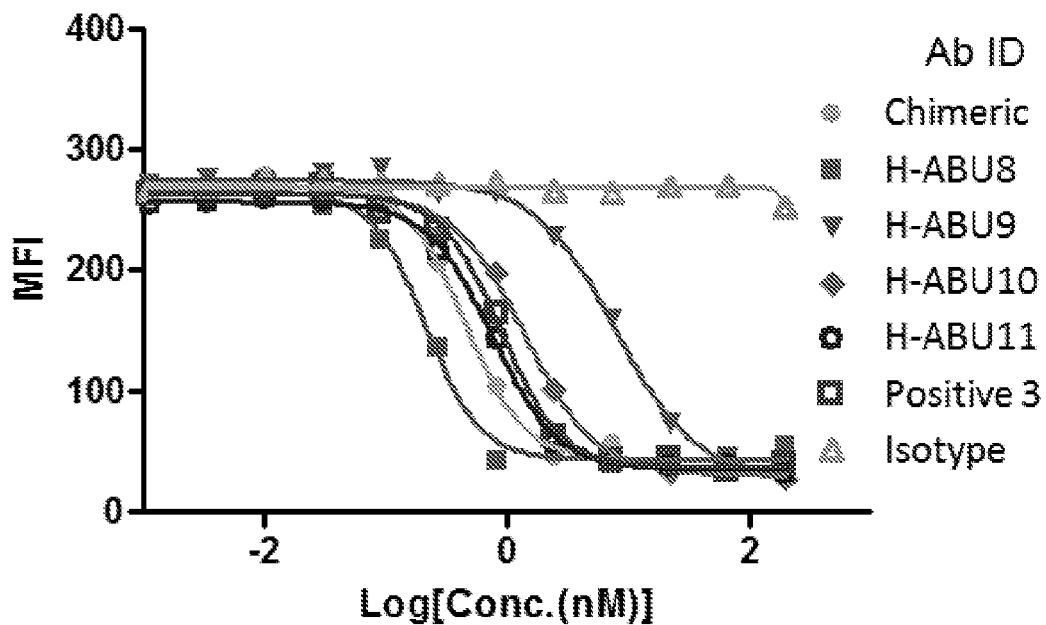

Select affinity matured humanized antibodies were further characterized in a blocking experiment as described previously. Data from example experiments using Raji cells are depicted in FIGS. 15B-15C and Table 15.

TABLE 15

| | Chimeric | H-ABU2 | H-ABU3 | H-ABU4 | H-ABU5 | H-ABU6 | H-ABU7 | Positive 3 |
|---|---|---|---|---|---|---|---|---|
| IC50 | +++ | + | + | +++ | ++ | +++ | +++ | +++ |

| | Chimeric | H-ABU8 | H-ABU9 | H-ABU10 | H-ABU11 | Positive 3 |
|---|---|---|---|---|---|---|
| IC50 | +++ | +++ | ++ | ++ | +++ | +++ |

+++: <1 nM;
++: >1 nM and <20 nM;
+: >20 nM

Figure 16A:
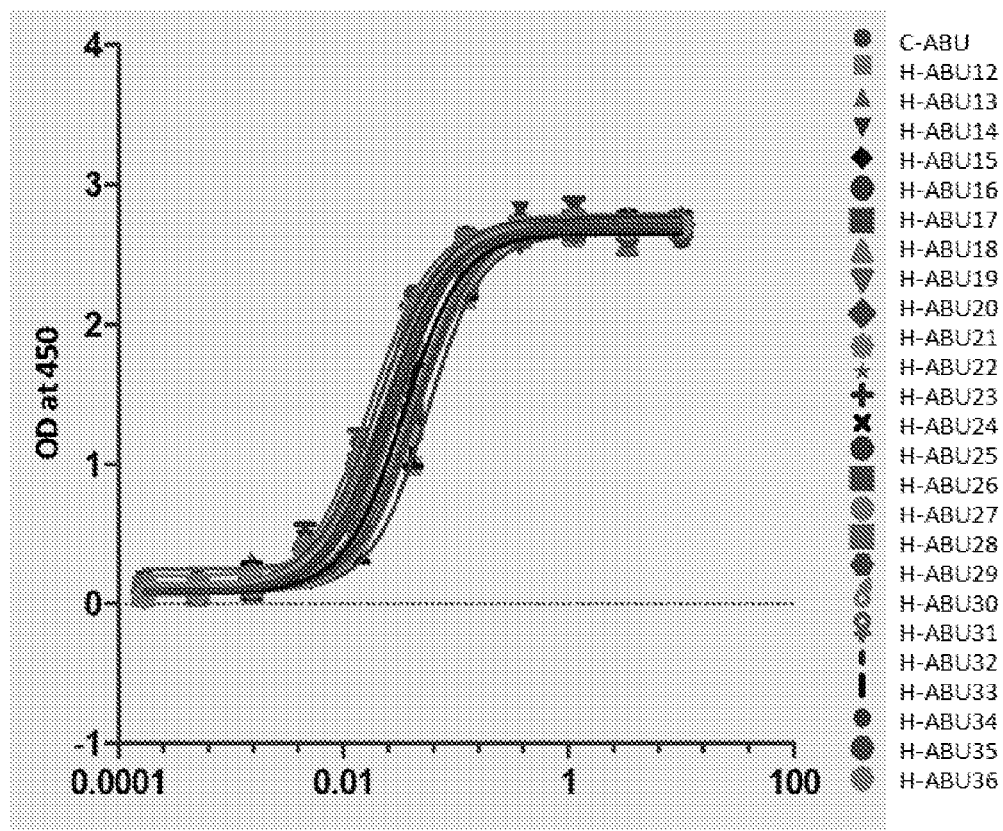
FIG. 16A depicts data from an example binding assay.
Figure 16B:
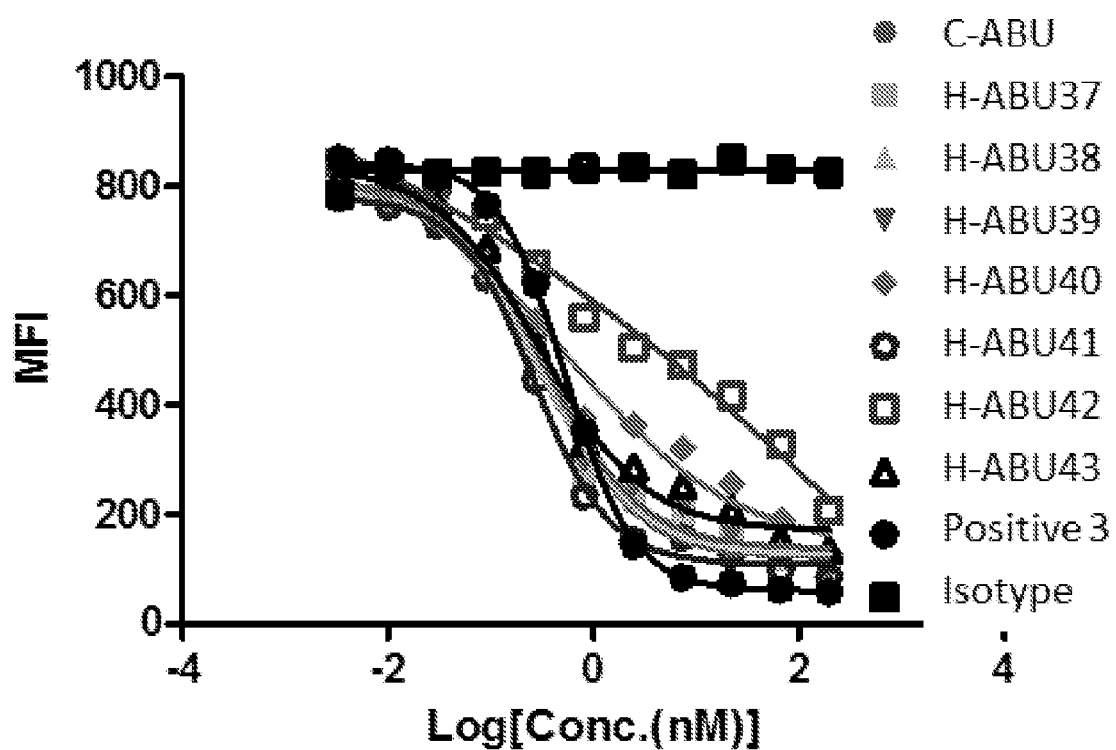
FIG. 16B depicts data from an example blocking assay.

Another set of humanized antibodies were analyzed in a binding assay as described previously. The binding assays performed were ELISA binding EC50 studies similar to those described in Example 3 using CD47 coated plates. Data from an example experiment are depicted in FIG. 16A and Table 16. A group of these antibodies were further characterized in a SIRP-alpha blocking experiment using Raji cells as described previously. Blocking assays were performed similarly to those described in Example 4. Data from an example experiment is depicted in FIG. 16B and Table 17.

TABLE 16

| | C-ABU | H-ABU12 | H-ABU13 | H-ABU14 | H-ABU15 | H-ABU16 | H-ABU17 | H-ABU18 | H-ABU19 |
|---|---|---|---|---|---|---|---|---|---|
| EC50 | + | + | + | + | + | + | + | + | + |

| | H-ABU20 | H-ABU21 | H-ABU22 | H-ABU23 | H-ABU24 | H-ABU25 | H-ABU26 | H-ABU27 | H-ABU28 |
|---|---|---|---|---|---|---|---|---|---|
| EC50 | + | + | + | + | + | + | + | + | + |

| | H-ABU29 | H-ABU30 | H-ABU31 | H-ABU32 | H-ABU33 | H-ABU34 | H-ABU35 | H-ABU36 |
|---|---|---|---|---|---|---|---|---|
| EC50 | + | + | + | + | + | + | + | + |

+: <0.06 μg/mL

TABLE 17

| | C-ABU | H-ABU37 | H-ABU38 | H-ABU39 | H-ABU40 | H-ABU41 | H-ABU42 | H-ABU43 | Positive 3 |
|---|---|---|---|---|---|---|---|---|---|
| IC50 (nM) | + | + | + | + | + | + | N.A. | + | + |

+: <0.6 nM

Select murine, chimeric, and humanized antibodies were subjected to a hemagglutination assay as described previously. Briefly, monoclonal antibodies were serially diluted and incubated for 1 hour before adding whole blood for a final blood concentration of 10%. After 2-4 hours of incubation, hemagglutination effect was examined by scanner.

Select murine, chimeric, and humanized antibodies were also subjected to a red blood cell and platelet binding assay. Among the humanized antibodies were H-ABU 2-G1, which comprises a human IgG1 constant region, and H-ABU 2-G4, which comprises a human IgG4 constant region. Blood was diluted 1:100 with DPBS. Monoclonal antibodies starting at 10 μg/mL were serially diluted and added to the diluted blood with a volume ration of 1:2 (20 μl of antibodies and 40 μl of diluted blood). The mixture was incubated for 30 minutes at 40 degrees Celsius and then washed twice with DPBS. Secondary antibodies were then added, namely APC-anti-human or APB-anti-mouse monoclonal antibodies (Jackson Immuno Research 315-606-046 or 109-605-088 respectively), and FITC labeled anti-human CD61 (BD, 555753) for platelet binding. After the secondary antibodies were added, the mixture was incubated for 30 minutes at 4 degrees Celsius. Cells were washed twice with DPBS and binding affinity was assessed using a flow cytometer.

Figure 17:
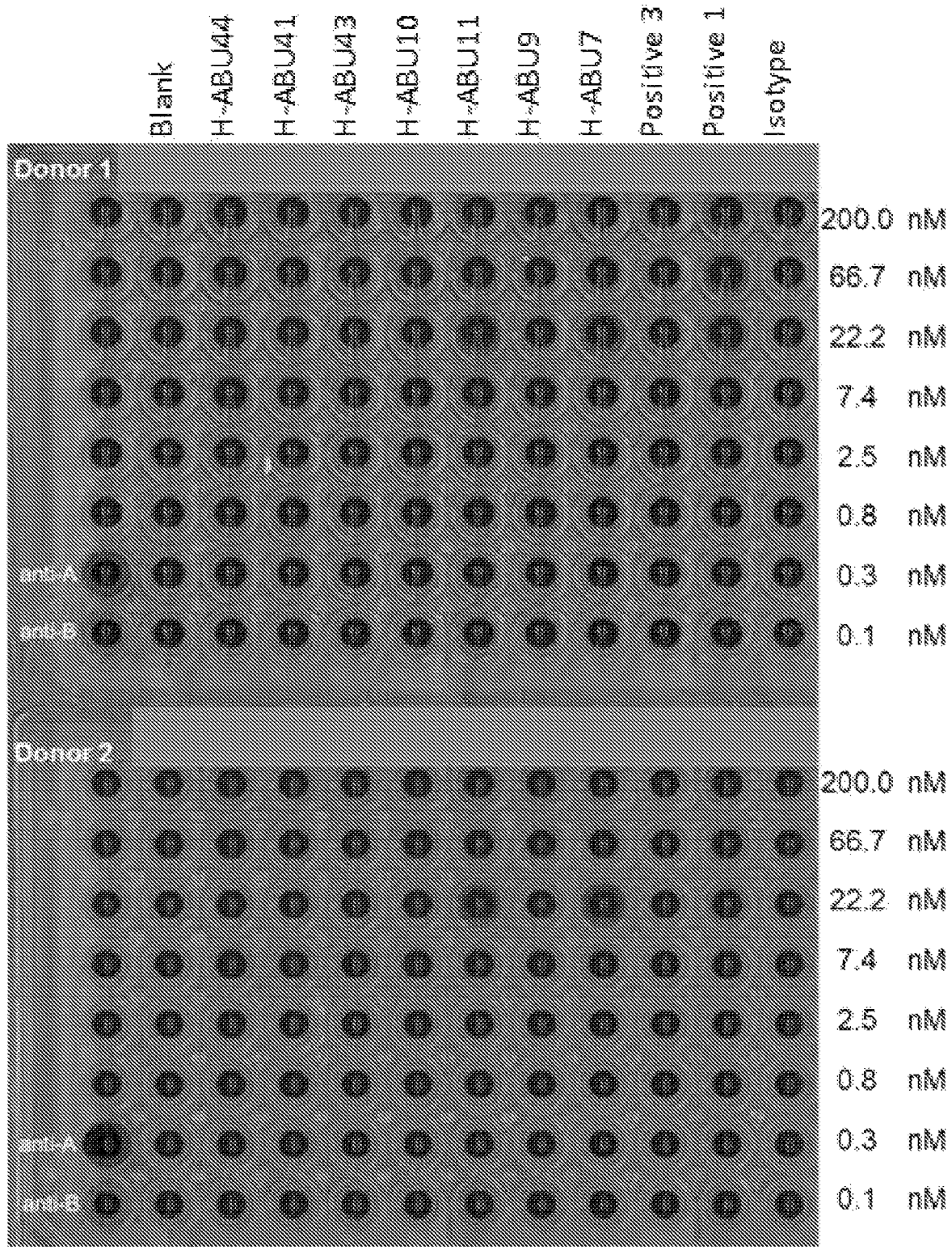
FIG. 17 depicts data from an example hemagglutination assay.

Select humanized antibodies were analyzed using a hemagglutination assay as described previously. Data from an example experiment using samples from two different donors and the indicated antibodies or controls at the listed concentration are depicted in FIG. 17. Hemagglutination assays were performed similarly to those described in Example 7. As described above, a distinct puncta of blood cells that lack of a hazy halo appearance indicates that no significant hemagglutination has occurred. Many of the humanized antibodies showed no significant hemagglutination effect.

Figure 18:
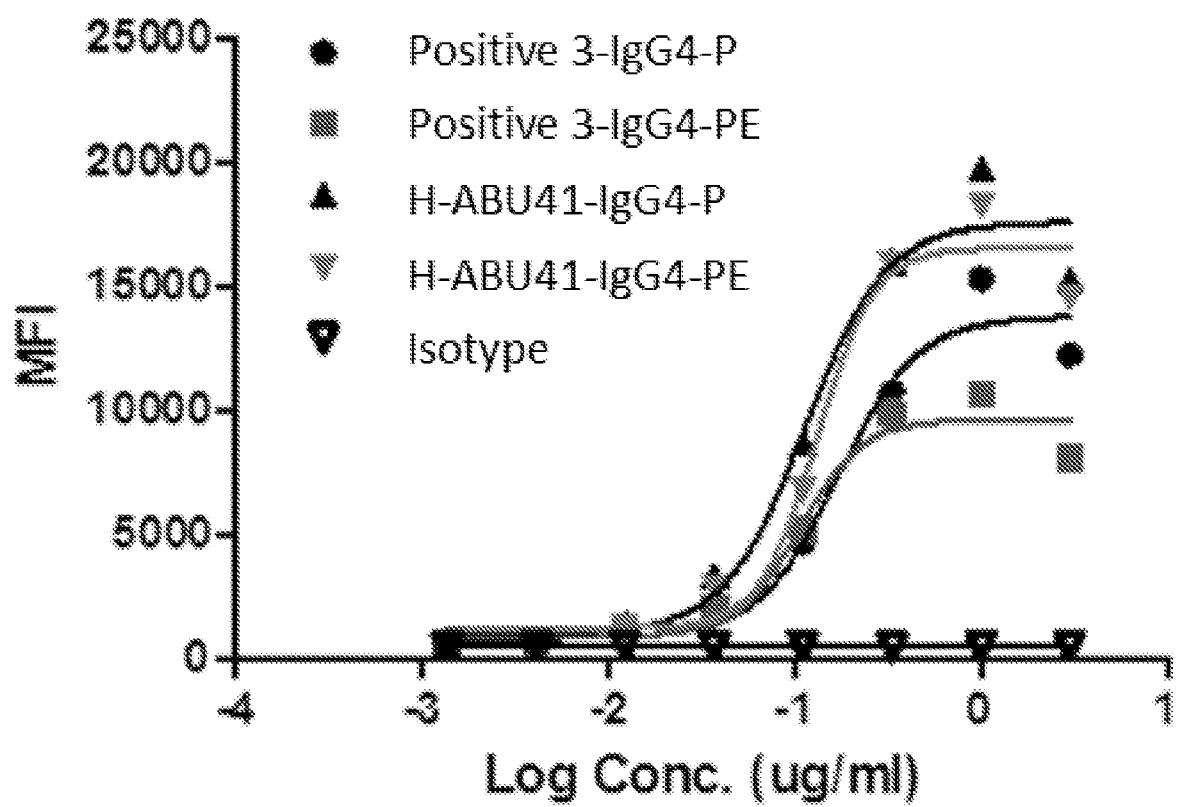
FIG. 18 depicts data from an example binding assay.

Select antibodies were next tested using a binding assay using cynomolgus monkey red blood cells expressing CD47 to test for monkey cross-reactivity. The assay was performed similarly to that described in Example 3. Data from an example experiment are depicted in FIG. 18. In this example, antibodies with two variations of IgG were tested. Namely, the IgG4 used were one of two different Fc gamma receptor variants: either IgG4 with a S228P mutation (SEQ ID NO: 37), or an IgG with both a S228P and L235E mutations (SEQ ID NO:18). The Positive-3-IgG4-PE antibody comprises SEQ ID NO: 305 and SEQ ID NO: 306. The Positive-3-IgG4-P antibody comprises SEQ ID NO: 307 and SEQ ID NO: 308.

Figure 19A:
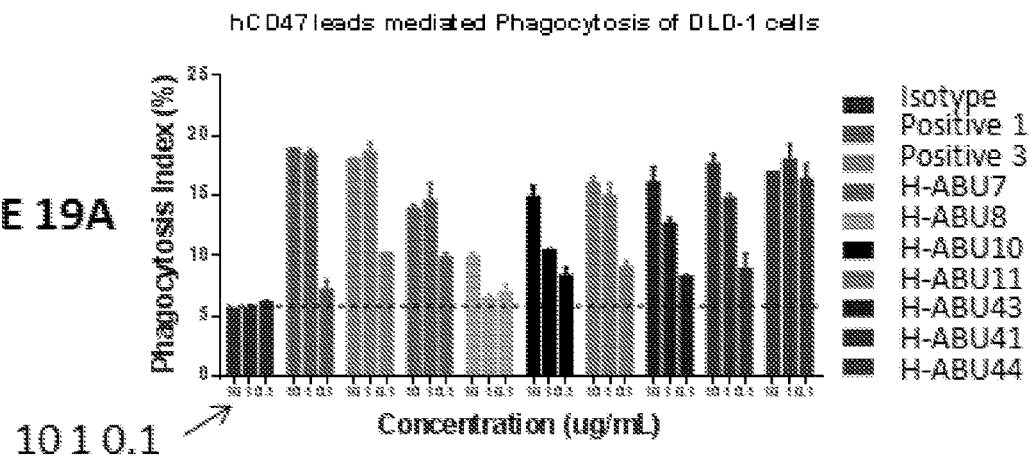
FIGS. 19A, 19B, and 19C depict data from example phagocytosis assays.
Figure 19B:
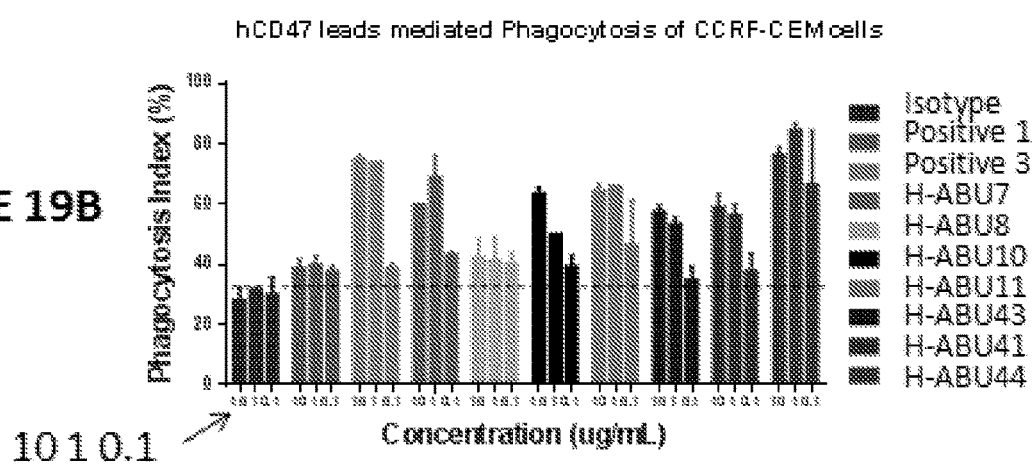
Figure 19C:
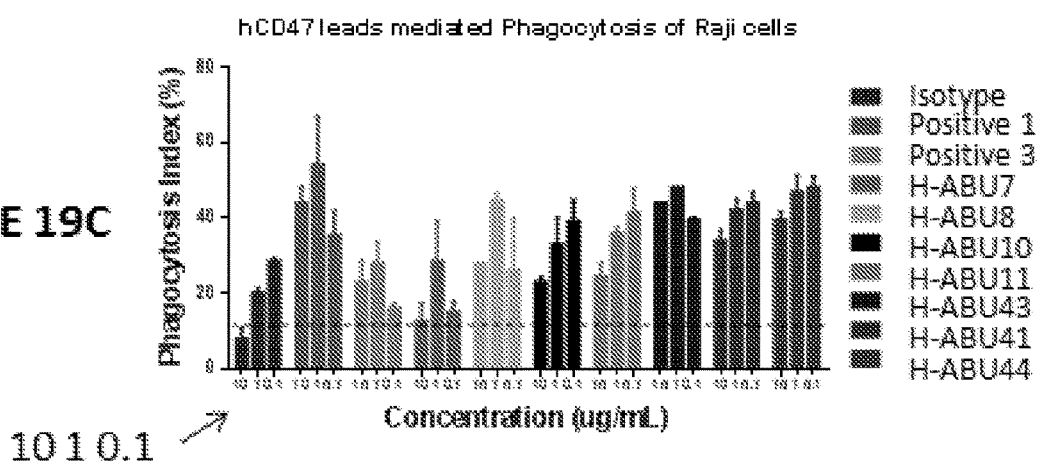

Select antibodies were tested using a phagocytosis assay as described previously. These assays were performed similarly to those described in Example 5. Either DLD-1 cells, CCRF-CEM cells, or Raji cells were used in these experiments. Data from example experiments are depicted in FIGS. 19A-19C.

Figure 20A:
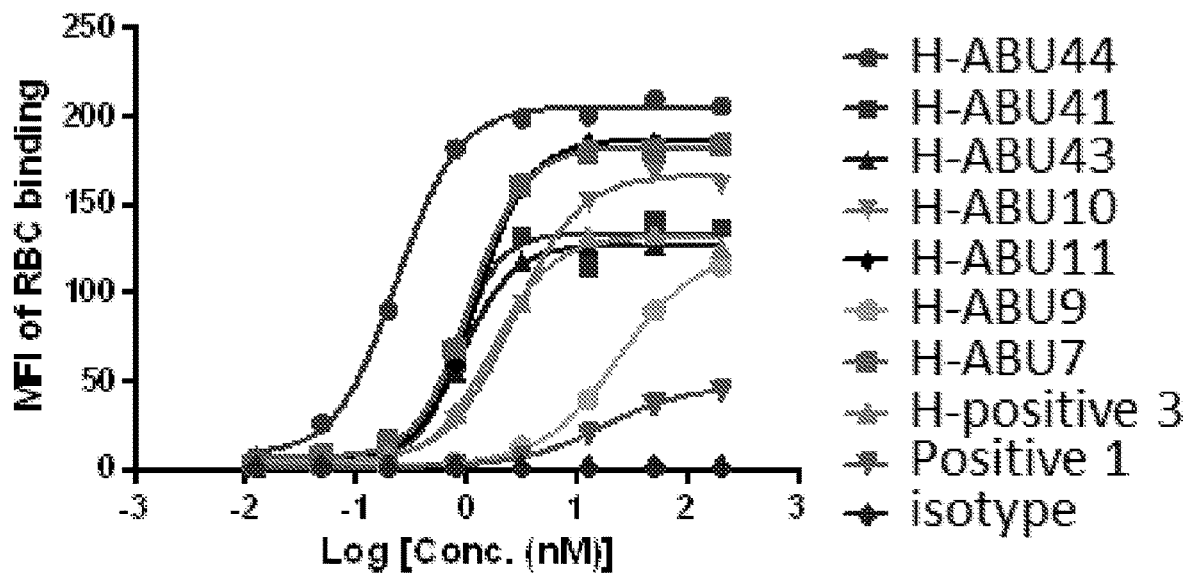
FIGS. 20A, 20B, 20C, and 20D depict data from example red blood cell and platelet binding assays.
Figure 20B:
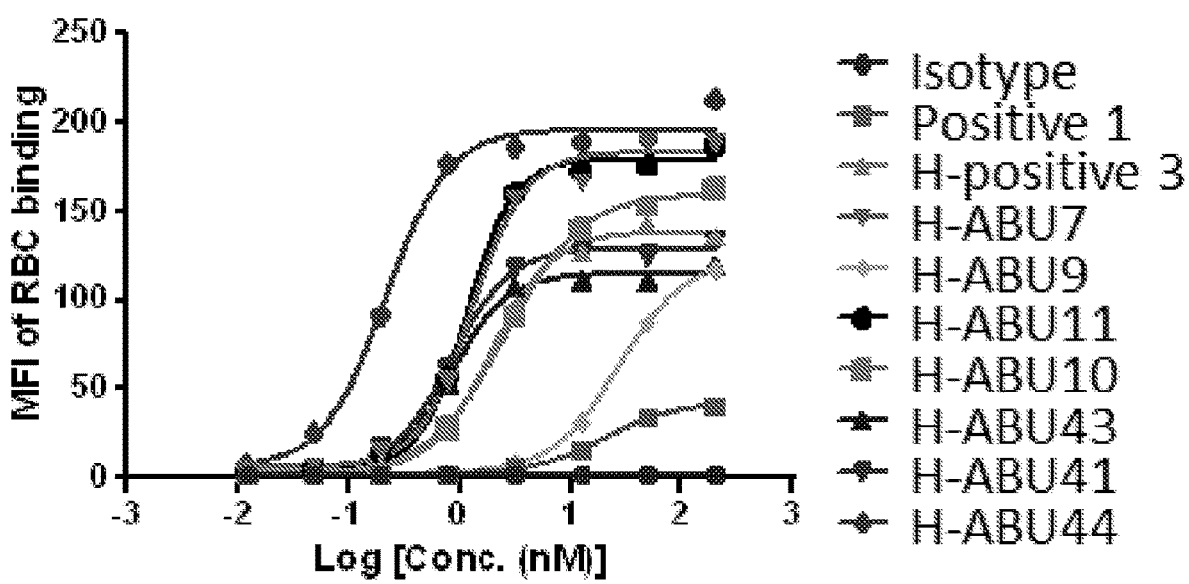
Figure 20C:
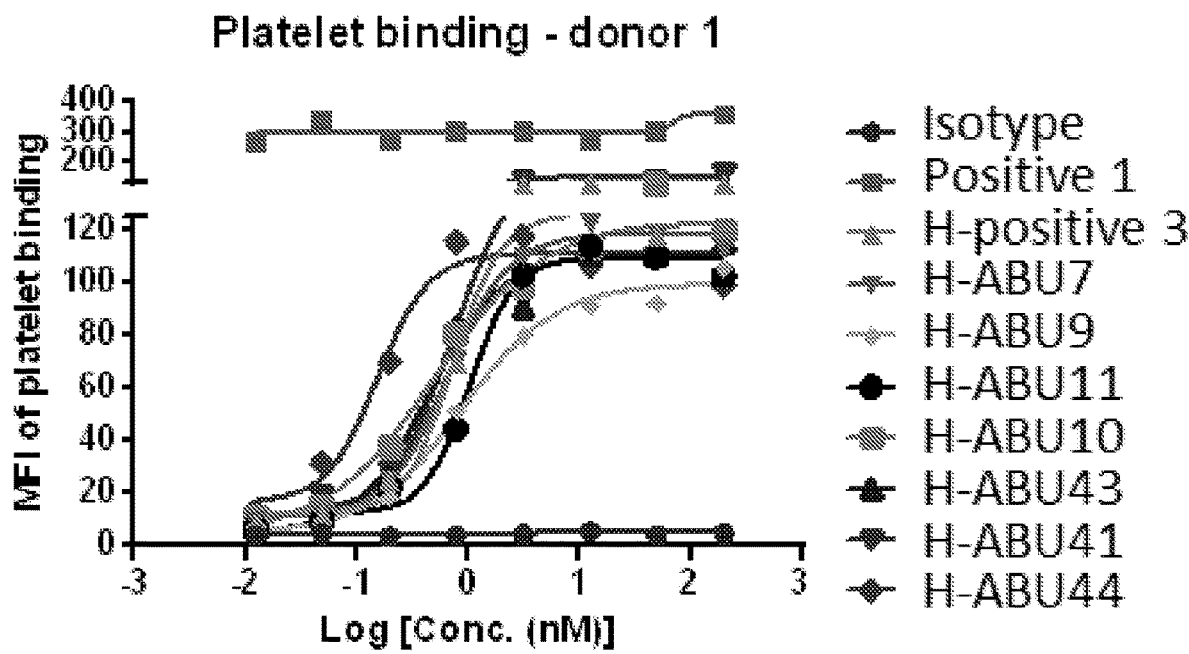
Figure 20D:
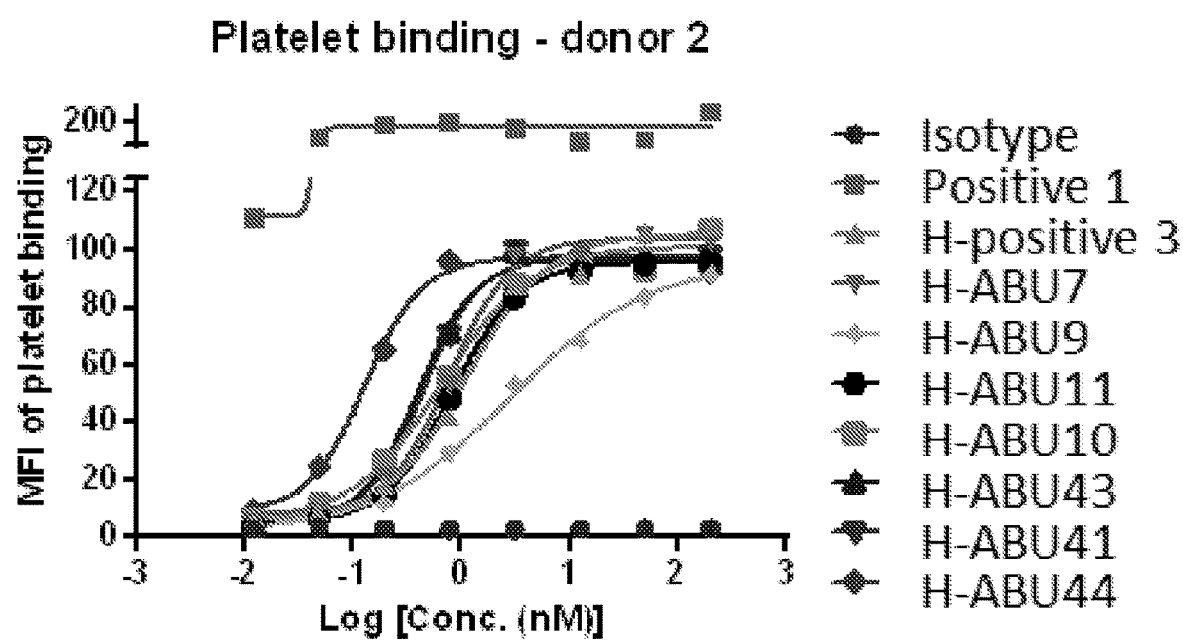

Select antibodies were further tested using a binding assay as described previously. Antibodies were tested for their binding level to either RBC (FIGS. 20A and 20B) or platelets (FIG. 20C or 20D). In this example, antibodies with two variations of IgG were tested. Namely, the IgG4 used were one of two different Fc gamma receptor variants: either IgG4 with a S228P mutation (SEQ ID NO: 37), or an IgG with both a S228P and L235E mutations (SEQ ID NO:18).

Example 11. In Vivo CDX Model and In Vivo Anti-Tumor Activity of Humanized Antibodies Raji cells were maintained in vitro as a culture in RPMI-1640 medium supplemented with 10% heat inactivated fetal bovine serum, 100 U/ml penicillin and 100 μg/ml streptomycin at 37° C. in an atmosphere of 5% CO2 in air. The tumor cells were routinely sub-cultured twice weekly. The cells growing in an exponential growth phase were harvested and counted for tumor inoculation. Each mouse was inoculated subcutaneously at the right flank with Raji tumor cells (3×10⁶) in 0.1 ml of PBS for tumor development. The treatments were started on day 8 after tumor inoculation when the average tumor size reached approximately 113 mm³. Each group consisted of 7 or 8 tumor-bearing mice.

At the time of routine monitoring, the animals were daily checked for any effects of tumor growth and treatments on normal behavior such as mobility, food and water consumption (by looking only), body weight gain/loss (body weights were measured twice weekly), eye/hair matting and any other abnormal effect as stated in the protocol. Death and observed clinical signs were recorded on the basis of the numbers of animals within each subset.

Tumor size was measured twice weekly in two dimensions using a caliper, and the volume was expressed in mm³ using the formula: V=0.5 a×b² where a and b are the long and short diameters of the tumor, respectively. The tumor size was then used for calculation of T/C value. The T/C value (in percent) is an indication of antitumor effectiveness; T and C are the mean volumes of the treated and control groups, respectively, on a given day.

A one-way ANOVA was performed to compare tumor volume among groups, and when a significant F-statistics (a ratio of treatment variance to the error variance) was obtained, comparisons between groups were carried out with Games-Howell test. All data were analyzed using Graphpad5.0. $P<0.05$ was considered to be statistically significant.

Figure 21:
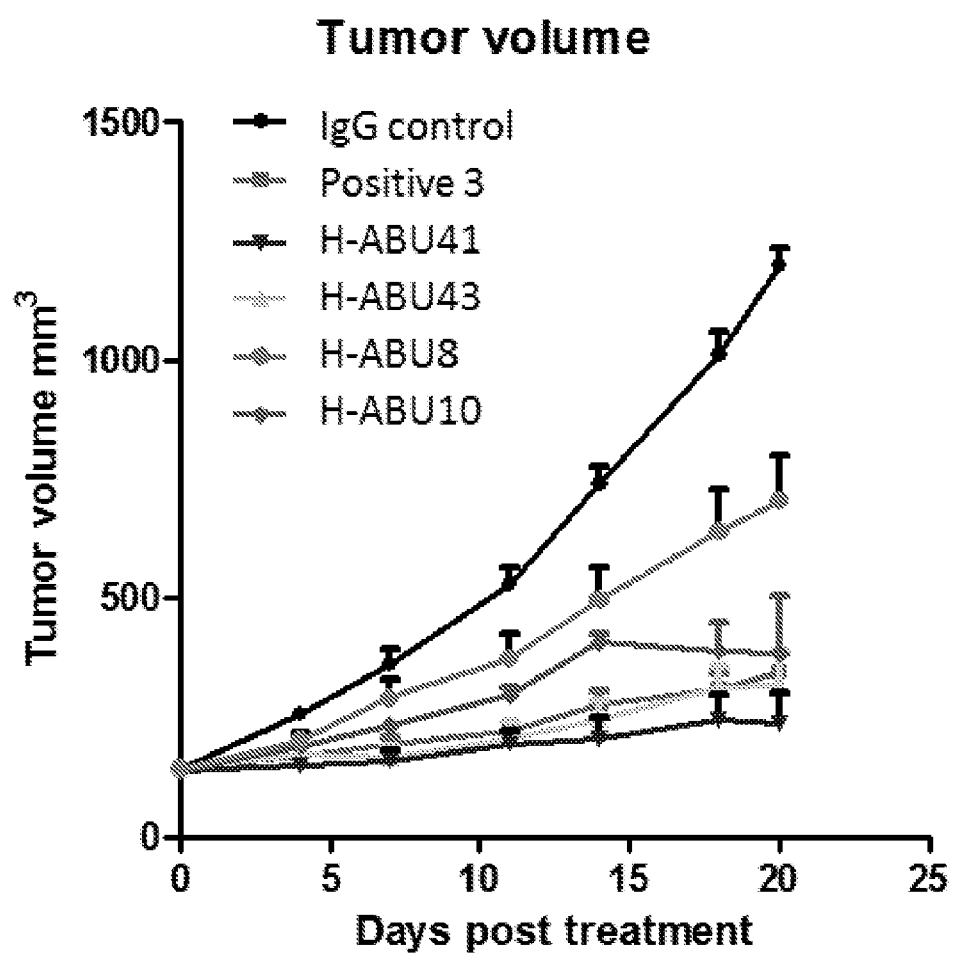
FIG. 21 depicts data from an example xenografting experiment.

Select humanized antibodies were tested in vivo as described above to determine their effect on tumor size. Briefly, approximately 3 million Raji cells were subcutaneously transplanted into NOD/SCID mice. The dosage of anti-CD47 antibodies were 10 mpk, i.p., 3 times per week. The dosing of antibody started when the tumor volume reached 100 mm³. Data for an example experiments is depicted in FIG. 21.

Example 12: Comparison of IgG4P and IgG4PE Form

Figure 22A:
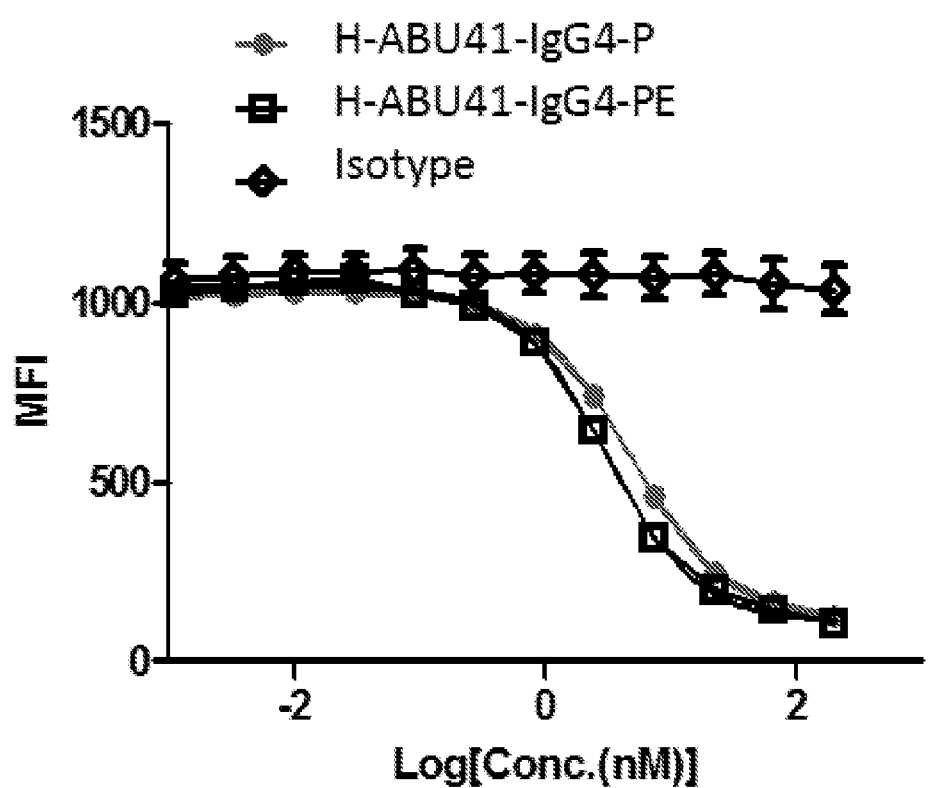
FIG. 22A depicts data from an example blocking assay.
Figure 22B:
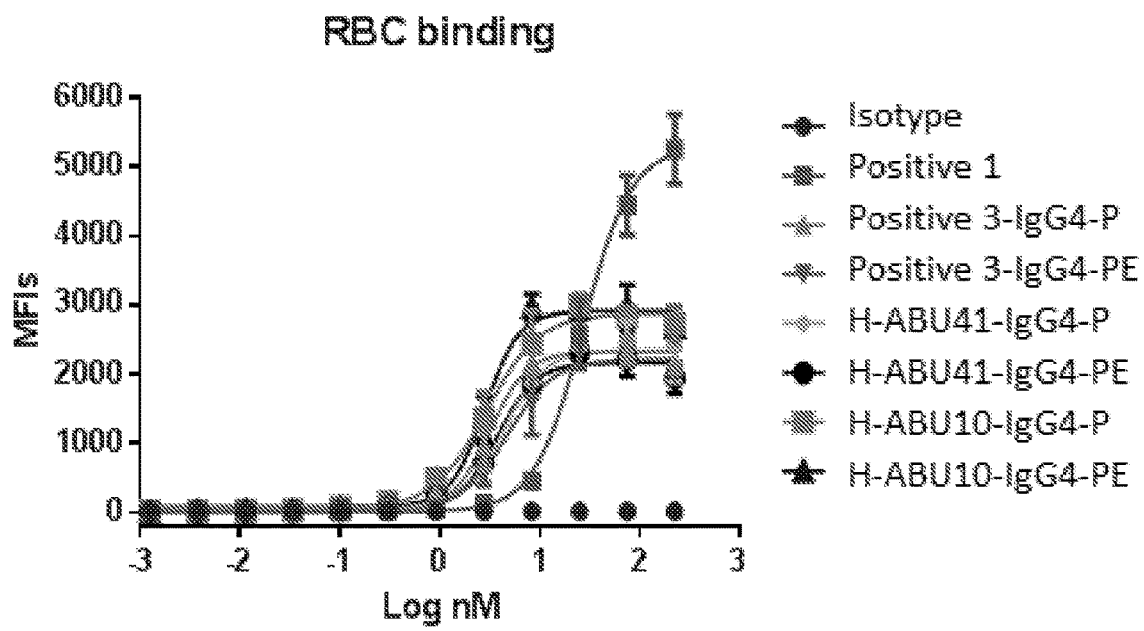
FIG. 22B depicts data from an example RBC binding assay.
Figure 22C:
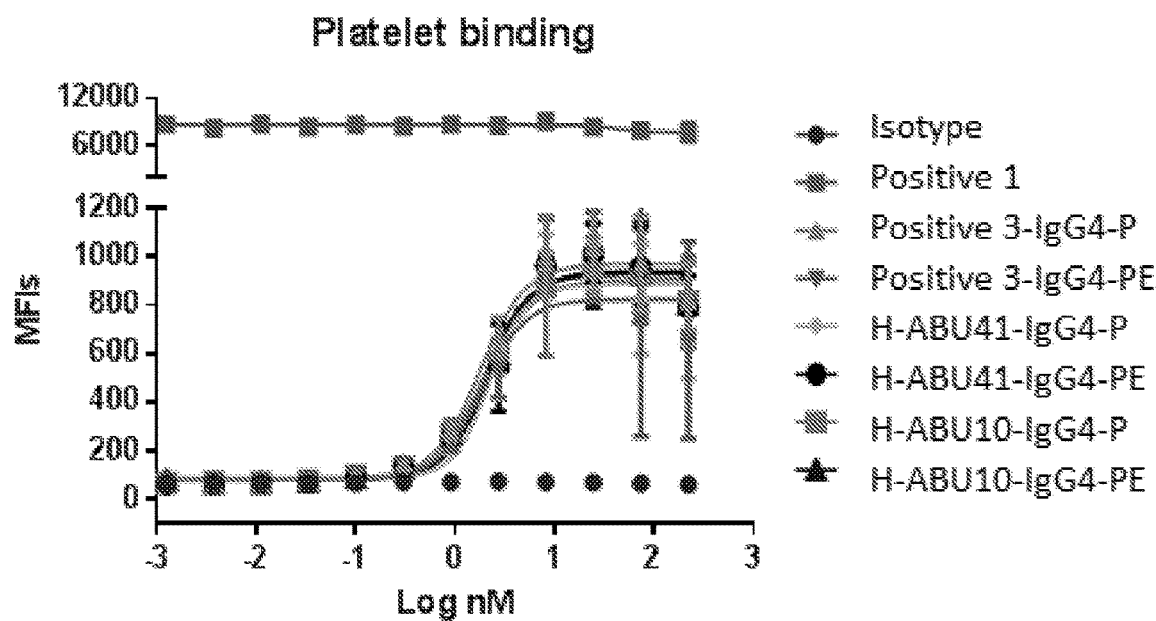
FIG. 22C depicts data from an example platelet binding assay.
Figure 22D:
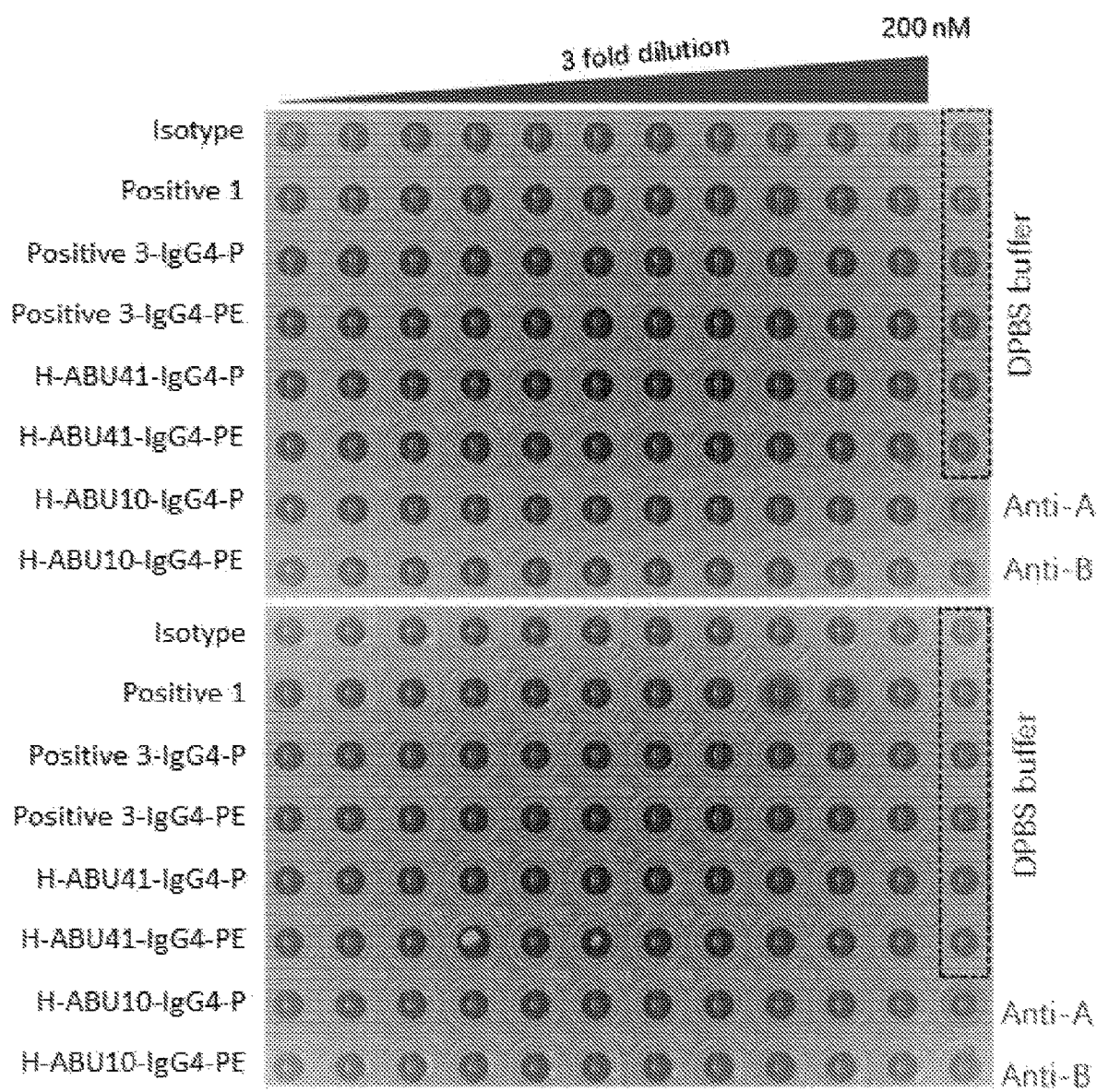
FIG. 22D depicts data from an example hemagglutination assay.

Select humanized antibodies were further characterized by testing variants comprising either of two variations of IgG. Namely, the IgG4 used were one of two different Fc gamma receptor variants: either IgG4 with a S228P mutation (SEQ ID NO: 37, P variant), or an IgG with both a S228P and L235E mutations (SEQ ID NO:18, PE variant). FIG. 22A depicts data from an example blocking assay using Raji cells which was generally performed as described previously. FIGS. 22B and 23C depict data from an example RBC and platelet binding assays respective, which were generally performed as previously described. FIG. 22D depicts data from an example hemagglutination assay, which was generally performed as described previously. As described above, a distinct puncta of blood cells that lack of a hazy halo appearance indicates that no significant hemagglutination has occurred.

Figure 23:
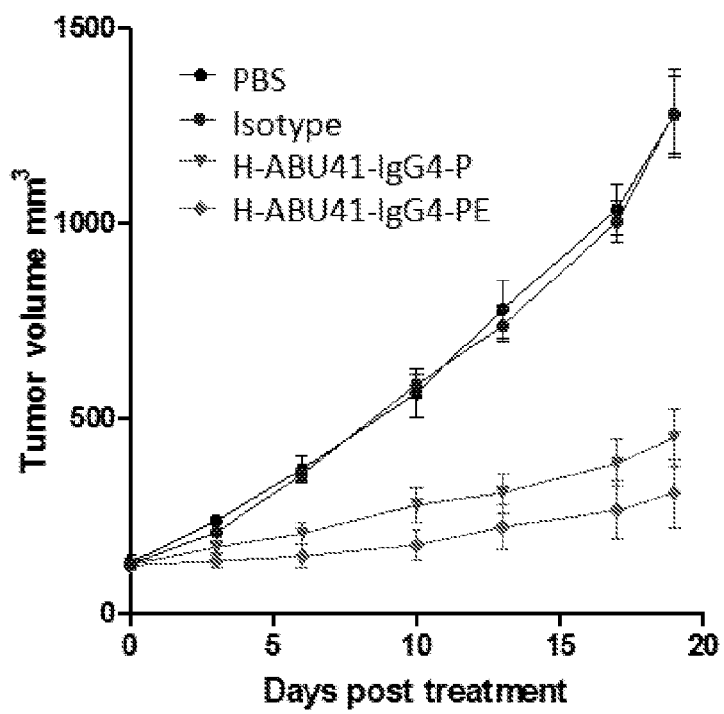
FIG. 23 depicts data from an example xenografting experiment.

Example 13. Characterization and Anti-Tumor Activity of Humanized Antibodies and Combination Therapy Select humanized antibodies were tested in vivo as described above to determine their affect on tumor size. Data form example experiments is depicted in FIG. 23. Xenograft experiments were performed generally as described in Example 10. Briefly, approximately 3 million Raji cells were subcutaneously transplanted into NOD/SCID mice. The dosage of anti-CD47 antibodies were 10 mpk, i.p., 3 times per week. The assay was started when the tumor volume reached 100 mm³. In this example, antibodies with two variations anti-CD47 antibodies with different IgG were tested. Namely, the IgG4 used were one of two different Fc gamma receptor variants: either IgG4 with a S228P mutation (SEQ ID NO: 37), or an IgG with both a S228P and L235E mutations (SEQ ID NO:18).

Figure 24:
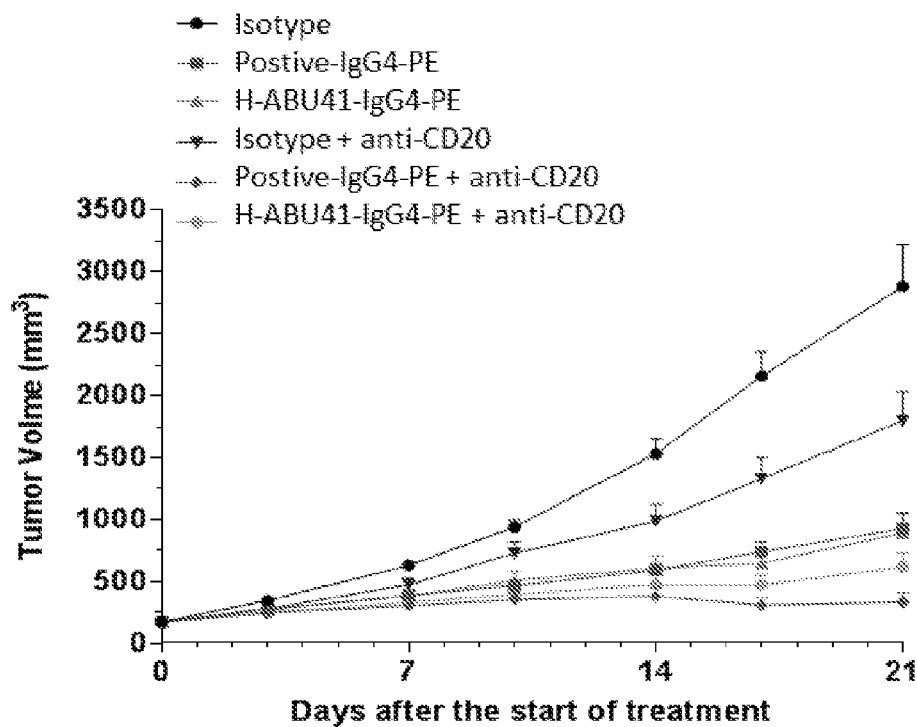
FIG. 24 depicts data from an example xenografting experiment.

Select antibodies were used in xenografting experiments in combination with anti-CD20 antibodies to determine their effect on tumor size as described previously above. Three million of Raji cells were subcutaneously transplanted into the NOD/SCID mice. When the tumor volume reached 100 mm³, C-ABU 1 antibody, anti-CD20 or a combination of both were injected by intraperitoneal at 10 mg/kg, every other day and the tumor sizes were recorded. Combination with C-ABU 1 and anti-CD20 significantly prevented the progress of the tumor. Data from example experiments is summarized in FIG. 24. Each antibody or control was administered as summarized in Table 18. The dosage of anti-CD20 and anti-CD47 antibodies were 10 mpk, i.p., 3 times per week. The assay was started when the tumor volume reached 100 mm³. In this example, antibodies with two variations anti-CD47 antibodies with different IgG were tested. Namely, the IgG4 used were one of two different Fc gamma receptor variants: either IgG4 with a S228P mutation (SEQ ID NO: 37), or an IgG with both a S228P and L235E mutations (SEQ ID NO:18). Anti-CD20 used in this assay was in a human IgG1 format.

TABLE 18

| Group | n[a] | Treatment | Dose (mg/kg) | Dosing Route | Schedule[c] |
|---|---|---|---|---|---|
| 1 | 8 | Isotype Control | 10 | i.p. | TIW X 3 wks |
| 2 | 8 | Positive IgG4-PE | 10 | i.p. | TIW X 3 wks |
| 3 | 8 | H-ABU41-IgG4-PE | 10 | i.p. | TIW X 3 wks |
| 4 | 8 | Isotype Control + anti-CD20 | 10 | i.p. | TIW X 3 wks |
| 5 | 8 | Positive IgG4-PE + anti-CD20 | 10 | i.p. | TIW X 3 wks |
| 6 | 8 | H-ABU41-IgG4-PE + anti-CD20 | 10 | i.p. | TIW X 3 wks |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

| SEQUENCE LISTING |
| --- |

SEQ ID NO: 1 KSSQSLLYSSNQKNYLA

SEQ ID NO: 2 RASKNIGKYLA

SEQ ID NO: 3 KASQDIKSYLS

SEQ ID NO: 4 SASSSVSYMN

SEQ ID NO: 5 RSSQSIVYSNGNTYLE

SEQ ID NO: 6 KASENVGTYVS

SEQ ID NO: 7 RSSQSIVHSNGNTYLE

SEQ ID NO: 8 DTSKLAS

SEQ ID NO: 9 GASNRYT

SEQ ID NO: 10 KVSNRFS

SEQ ID NO: 11 RVANRFS

SEQ ID NO: 12 SGSTLQS

SEQ ID NO: 13 WASTRDS

SEQ ID NO: 14 YATSLAD

SEQ ID NO: 15 FQGSHVPWT

SEQ ID NO: 16 FQGSHVPYT

SEQ ID NO: 17 GQSYSYPLT

SEQ ID NO: 18
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFEGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLGK

SEQ ID NO: 19 LQHGESPFT

SEQ ID NO: 20 QQHNEYPYT

SEQ ID NO: 21 QQWNSNPPT

SEQ ID NO: 22 QQYYSYPLT

SEQ ID NO: 23 DFYIN

SEQ ID NO: 24 DTYMH

SEQ ID NO: 25 DYGMA

SEQ ID NO: 26 GYYMN

SEQ ID NO: 27 NYWIA

SEQ ID NO: 28 NYWMN

SEQ ID NO: 29 NYWMQ

SEQ ID NO: 30 DFYPGNTSTNYNEKFKT

SEQ ID NO: 31 EINPSTGGTTYNQKFKA

SEQ ID NO: 32 FISNLAKRIYYVDTVTG

SEQ ID NO: 33 MIDPSDSESRLNQKFKD

SEQ ID NO: 34 RIDPAKDNTKYDPKFQG

SEQ ID NO: 35 RIDPYDSETLYNQKFKD

SEQ ID NO: 36 WIYLGSGNTKYNEKFKG

SEQ ID NO: 37

SEQUENCE LISTING

ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAKTKPREEQFNST
YRVVSVLTVLHQDWLNGKEYKCKVSNKGLPSSIEKTISKAKGQPREPQVYTLPPSQEEM
TKNQVSLTCLVKGFYPSDIAVEWESNGQPENNYKTTPPVLDSDGSFFLYSRLTVDKSRW
QEGNVFSCSVMHEALHNHYTQKSLSLSLGK

SEQ ID NO: 38 AYRYALDY

SEQ ID NO: 39 GGKGGFGY

SEQ ID NO: 40 GHYGSSYVVY

SEQ ID NO: 41 REERGFAY

SEQ ID NO: 42 RGRGGSSY

SEQ ID NO: 43 RGSPMITSFAY

SEQ ID NO: 44 YDGYEGFAY

SEQ ID NO: 45
DIKMTQSPSSMYASLGERVTITCKASQDIKSYLSWYQQKPWKSPKTLIYYATSLADGVP
RFSGSGSGQHYSLTISSLESDDTATYYCLQHGESPFTFGSGTKLEIK

SEQ ID NO: 46
DIQMTQSPSSLSASVGDRVTITCRASKNIGKYLAWYQQKPGKAPKLLIYSGSTLQSGVPS
RFSGSGSGTDFTLTISSLQPEDFATYYCQQHNEYPYTFGQGTKVEIK

SEQ ID NO: 47
DIVMSQSPSSLAVSVGEKVTMSCKSSQSLLYSSNQKNYLAWYQQKPGQSPKLLIYWAS
TRDSGVPDRFTGSGSGTDFTLTISSVKAEDLAVYYCQQYYSYPLTFGAGTKLELK

SEQ ID NO: 48
DIVMTQSPDSLAVSLGERATINCKSSQSLLYSSNQKNYLAWYQQKPGQPPKLLIYWAST
RDSGVPDRFSGSGSGTDFTLTISSLQAEDVAVYYCQQYYSYPLTFGQGTKVEIK

SEQ ID NO: 49
DVLMTQTPLSLPVSLGDQASISCRSSQSIVYSNGNTYLEWYLQKPGQSPKLLIYKVSNRF
SGVPDRFSGSGSGTDFTLKISRVEAEDLGVYYCFQGSHVPYTFGGGTKLEIK

SEQ ID NO: 50
DVQITQSPSFLAASPGETITINCRASKNIGKYLAWFQEKPGKTNKLLIYSGSTLQSGIPSRF
SGSGSGTDFTLTISSLEPEDFAIYYCQQHNEYPYTFGGGTKLEIK

SEQ ID NO: 51
EVKLVESGGGLVQPGGSRKLSCAASGFTFSDYGMAWVRQAPGKGPECVAFISNLAKRI
YYVDTVTGRFTISRENAKNTLYLEMSSLRSEDTAMYYCTRAYRYALDYWGQGTTLTVS
S

SEQ ID NO: 52
EVQLQQSGAELVKPGASVKLSCTASGFTIKDTYMHWVKQRPEQGLEWIGRIDPAKDNT
KYDPKFQGKATITLDTSSNIAYLQLSSLTSEDTAVYFCARGHYGSSYVVYWGQGTLVTV
SA

SEQ ID NO: 53
EVQLQQSGPELVKPGASVKISCKASGYSFTGYYMNWVKQSPEKSLEWIGEINPSTGGTT
YNQKFKAKATLTVDKSSSTAYMQLKSLTFEDSAVYYCAIYDGYEGFAYWGQGTLVTVS
A

SEQ ID NO: 54
QIVLTQSPAIMSASPGEKVTMTCSASSSVSYMNWYQQKSGTSPKRWIYDTSKLASGVPA
RFSGSGSGTSYSLTISSMEAEDAATYYCQQWNSNPPTFGTGTKLELK

SEQ ID NO: 55
EVKLVESGGGLVQPGGSRKLSCAASGFTFSDYGMAWVRQAPGKGPECVAFISNLAKRI
YYVDTVTGRFTISRENAKNTLYLEMSSLRSEDTAMYYCTRAYRYALDYWGQGTTLTVS
S

SEQ ID NO: 56
DIKMTQSPSSMYASLGERVTITCKASQDIKSYLSWYQQKPWKSPKTLIYYATSLADGVP
SRFSGSGSGQHYSLTISSLESDDTATYYCLQHGESPFTFGSGTKLEIK

SEQ ID NO: 57
DIVMSQSPSSLAVSVGEKVTMSCKSSQSLLYSSNQKNYLAWYQQKPGQSPKLLIYWAS
TRDSGVPDRFTGSGSGTDFTLTISSVKAEDLAVYYCQQYYSYPLTFGAGTKLELK

SEQUENCE LISTING

```
SEQ ID NO: 58
NILMTQSPKSMSMSVGERVTLSCKASENVGTYVSWYQQKPDQSPKLLIYGASNRYTGV
PDRFTGSGSATDFTLTISSVQAEDLADYHCGQSYSYPLTFGAGTKLELK

SEQ ID NO: 59
EVQLQQSGPELVKPGASVKISCKASGYSFTGYYMNWVKQSPEKSLEWIGEINPSTGGTT
YNQKFKAKATLTVDKSSSTAYMQLKSLTFEDSAVYYCAIYDGYEGFAYWGQGTLVTVS
A

SEQ ID NO: 60
QVQLQQSGPQLVRPGASVKISCKTSGYSFTNYWMQWVKQRPGQGLEWIGMIDPSDSES
RLNQKFKDKATLTVDKSSSTAYMQLSSPTFEDSAVYYCARRGSPMITSFAYWGQGTLVT
VSA

SEQ ID NO: 61
QVQLQQPGAELVKPGASVKMSCKASGYTFTNYWIAWVKRRPGQGLEWIGDFYPGNTS
TNYNEKFKTKATLTIDTSSSTAYMQLSSLTSEDSAVYYCARRGRGGSSYWGQGTTLTVS
S

SEQ ID NO: 62
QIQLQQSGPELVKPGASVKISCKVSGYIFTDFYINWVKQRPGQGLEWIGWIYLGSGNTK
YNEKFKGKATLTVDTSSSTAYMQLSSLTSEDSAVYFCARREERGFAYWGQGTLVTVSA

SEQ ID NO: 63
QVQLQQPGAELVRPGASVKLSCKASGYTFTNYWMNWFKQRPEQGLEWIGRIDPYDSE
TLYNQKFKDKAILTVDKSSSTAYMQLSSLTSEDSAVYYCAGGGKGGFGYWGQGTLVTV
SA

SEQ ID NO: 64
EVQLQQSGAELVKPGASVKLSCTASGFTIKDTYMHWVKQRPEQGLEWIGRIDPAKDNT
KYDPKFQGKATITLDTSSNIAYLQLSSLTSEDTAVYFCARGHYGSSYVVYWGQGTLVTV
SA

SEQ ID NO: 65
DVLMTQTPLSLPVSLGDQASISCRSSQSIVYSNGNTYLEWYLQKPGQSPKLLIYKVSNRF
SGVPDRFSGSGSGTDFTLKISRVEAEDLGVYYCFQGSHVPYTFGGGTKLEIK

SEQ ID NO: 66
DVLMTQTPLSLPVSLGEQASISCRSSQSIVHSNGNTYLEWYLQKPGQSPKLLIYRVANRF
SGVPDRFSGSGSGTDFTLKISRVEAEDLGVYYCFQGSHVPWTFGGGTKLEIK

SEQ ID NO: 67
DVLMTQTPLSLPVSLGEQASISCRSSQSIVHSNGNTYLEWYLQKPGQSPKLLIYRVANRF
SGVPDRFSGSGSGTDFTLKISRVEAEDLGVYYCFQGSHVPWTFGGGTKLEIK

SEQ ID NO: 68
DVQITQSPSFLAASPGETITINCRASKNIGKYLAWFQEKPGKTNKLLIYSGSTLQSGIPSRF
SGSGSGTDFTLTISSLEPEDFAIYYCQQHNEYPYTFGGGTKLEIK

SEQ ID NO: 69
NILMTQSPKSMSMSVGERVTLSCKASENVGTYVSWYQQKPDQSPKLLIYGASNRYTGV
PDRFTGSGSATDFTLTISSVQAEDLADYHCGQSYSYPLTFGAGTKLELK

SEQ ID NO: 70
QIQLQQSGPELVKPGASVKISCKVSGYIFTDFYINWVKQRPGQGLEWIGWIYLGSGNTK
YNEKFKGKATLTVDTSSSTAYMQLSSLTSEDSAVYFCARREERGFAYWGQGTLVTVSA

SEQ ID NO: 71
QIVLTQSPAIMSASPGEKVTMTCSASSSVSYMNWYQQKSGTSPKRWIYDTSKLASGVPA
RFSGSGSGTSYSLTISSMEAEDAATYYCQQWNSNPPTFGTGTKLELK

SEQ ID NO: 72
QVQLQQPGAELVKPGASVKMSCKASGYTFTNYWIAWVKRRPGQGLEWIGDFYPGNTS
TNYNEKFKTKATLTIDTSSSTAYMQLSSLTSEDSAVYYCARRGRGGSSYWGQGTTLTVS
S

SEQ ID NO: 73
QVQLQQPGAELVRPGASVKLSCKASGYTFTNYWMNWFKQRPEQGLEWIGRIDPYDSE
TLYNQKFKDKAILTVDKSSSTAYMQLSSLTSEDSAVYYCAGGGKGGFGYWGQGTLVTV
SA

SEQ ID NO: 74
QVQLQQSGPQLVRPGASVKISCKTSGYSFTNYWMQWVKQRPGQGLEWIGMIDPSDSES
RLNQKFKDKATLTVDKSSSTAYMQLSSPTFEDSAVYYCARRGSPMITSFAYWGQGTLVT
VSA
```

SEQUENCE LISTING

SEQ ID NO: 75
QVQLVQSGAEVKKPGASVKVSCKASGYTFTDFYINWVRQAPGQRLEWMGWIYLGSG
NTKYNEKFKGRVTITRDTSASTAYMELSSLRSEDTAVYYCARREERGFAYWGQGTLVT
VSS

SEQ ID NO: 76
QVQLVQSGAEVKKPGASVKVSCKASGYTFTDFYINWVRQAPGQRLEWMGWIYLGSG
NTKYNEKFKGRVTITVDTSASTAYMELSSLRSEDTAVYYCARREERGFAYWGQGTLVT
VSS

SEQ ID NO: 77
QVQLVQSGAEVKKPGASVKVSCKASGYTFTNYWMQWVRQAPGQGLEWMGMIDPSD
SESRLNQKFKDRVTMTRDTSTSTVYMELSSLRSEDTAVYYCARRGSPMTTSFAYWGQGT
LVTVSS

SEQ ID NO: 78
QVQLVQSGAEVKKPGASVKVSCKASGYTFTNYWMQWVRQAPGQGLEWMGMIDPSD
SESRLNQKFKDRVTMTVDTSTSTVYMELSSLRSEDTAVYYCARRGSPMITSFAYWGQGT
LVTVSS

SEQ ID NO: 79
QVQLVQSGAEVKKPGASVKVSCKTSGYTFTNYWMQWVRQAPGQGLEWMGMIDPSDS
ESRLNQKFKDRVTMTVDTSTSTVYMELSSLRSEDTAVYYCARRGSPMITSFAYVVGQGTL
VTVSS

SEQ ID NO: 80
QVQLVQSGAEVKKPGASVKVSCKVSGYTFTDFYINWVRQAPGQRLEWMGWIYLGSG
NTKYNEKFKGRVTITVDTSASTAYMELSSLRSEDTAVYYCARREERGFAYWGQGTLVT
VSS

SEQ ID NO: 81
MWPLVAALLLGSACCGSAQLLFNKTKSVEFTFCNDTVVIPCFVTNMEAQNTTEVYVK
WKFKGRDIYTFDGALNKSTVPTDFSSAKIEVSQLLKGDASLKMDKSDAVSHTGNYTCEV
TELTREGETIIELKYRVVSWFSPNENILIVIFPIFAILLFWGQFGIKTLKYRSGGMDEKTIAL
LVAGLVITVIVIVGAILFVPGEYSLKNATGLGLIVTSTGILILLHYYVFSTAIGLTSFVIAILV
IQVIAYILAVVGLSLCIAACIPMHGPLLISGLS1LALAQLLGLVYMKFVE

SEQ ID NO: 82
MWPLAAALLLGSCCCGSAQLLFSNVNSIEFTSCNETVVIPCIVRNVEAQSTEEMFVKWK
LNKSYIFIYDGNKNSTTTDQNFTSAKISVSDLINGIASLKMDKRDAMVGNYTCEVTELSR
EGKTVIELKNRTAFNTDQGSACSYEEEKGGCKLVSWFSPNEKILIVIFPILAILLFWGKFGI
LTLKYKSSHTNKRIILLLVAGLVLTVIVVVGAILLIPGEKPVKNASGLGLIVISTGILILLQY
NVFMTAFGMTSFTIAILITQVLGYVLALVGLCLCIMACEPVHGPLLISGLGIIALAELLGLV
YMKFVASNQRTIQPPRNR

SEQ ID NO: 83
MWPLVAALLLGSACCGSAQLLFNKTKSVEFTFCNDTVVIPCFVTNMEAQNTTEVYVK
WKFKGRDIYTFDGALNKSTVPTDFSSAKIEVSQLLKGDASLKMDKSDAVSHTGNYTCEV
TELTREGETIIELKYRVVSWFSPNENILIVIFPIFAILLFWGQFGIKTLKYRSGGMDEKTIAL
LVAGLVITVIVIVGAILFVPGEYSLKNATGLGLIVTSTGILILLHYYVFSTAIGLTSFVIAILV
IQVIAYILAVVGLSLCIAACIPMHGPLLISGLSILALAQLLGLVYMKEVASNQKTIQPPRNN

SEQ ID NO: 84
MWPLAAALLLGSCCCGSAQLLFSNVNSIEFTSCNETVVIPCIVRNVEAQSTEEMFVKWK
LNKSYIFIYDGNKNSTTTDQNFTSAKISVSDLINGIASLKMDKRDAMVGNYTCEVTELSR
EGKTVIELKNRTVSWFSPNEKILIVIFPILAILLFWGKFGILTLKYKSSHTNKRIILLLVAGL
VLTVIVVVGAILLIPGEKPVKNASGLGLIVVSTGILILLQYNVFMTAFGMTSFTIAILITQVL
GYVLALVGLCLCIMACEPVHGPLLISGLGIIALAELLGLVYMKFVASNQRTIQPPRNR

SEQ ID NO: 85
DIQMTQSPASLSASVGETVTITCRASENIYSYLAWYQQKQGKSPQLLVYNAKTLAEGVP
SRFSGSGSGTQFSLKIKSLQPEDEGSYYCQHHYGTPLTEGGGTKLELK

SEQ ID NO: 86
EVQLQQSGTELVKPGASVKLSCKASGYTFISYWMHWVKQRPGQGLEWIGNINPSSGNT
NYNEKFKTKATLTVDKSSSTAYMQLSSLTSEDSAVYYCVRDYYGNYWGQGTTVTVSS

SEQ ID NO: 87
DIKMNQSPSSLSASLGDTITITCHASQNINVWLSWYQQKPGNIPKLLIYKASNLHTGVPS
RFSGSGSGTGFTLTISSLQPEDIATYYCQQGQSYPLTFGAGTKLELK

SEQ ID NO: 88
EVQLQQSGPELVKPGASVKLSCKASGFTFTNYYIHWVKQRPGQGPEWIGWIYLGSGNT
KYNEKFKGKATLTADTSSSTAYLQLSTLISEDSAVYYCARYDYDLYLDSWGQGTTVTVS
S

SEQUENCE LISTING

SEQ ID NO: 89
DIQMMQSPASLSASVGETVTITCRASENIYSYLAWYQQKGKSPQLLVYNAKTLAEGV
PSRFSGSGSGTQFSLKINSLQPEDFGNYYCQHHYGTPLAFGAGTKLEIK

SEQ ID NO: 90
EVQLQQPGAELVKPGTSVKLSCKASGYSFTAYWMHWVKQRPGQGLEWIGNINPSSGD
SHYNEKFKSKATLTVDKSSTAYTQLNSLTSEDSAVYYCARDYYGAYWGHGTLVTVSA

SEQ ID NO: 91
DIQMTQSPASLSASVGETVTITCRASENVYSYLAWYQQKQGKSPQLLVYKANTLAEGV
PSRFSGSGSGTQFSLKINSLQPEDFGTYYCQHHYGTPLTFGSGTKLEIK

SEQ ID NO: 92
EVQLQQPGAELVRPGSSVKLSCKASGYSFTTYWMHWVKQRPGQGLEWIGNINPSSGDS
HYNEKFKSKATLTVD KSSSTAYLQLNSLTSEDSAVYYCARDYYGAYWGHGTLVTVSA

SEQ ID NO: 93
DIQMIQSPASLSASVGETVTITCRASENIYSYLAWYQQKQGKSPQLLVYNAKTLAEGVP
SRFSGSGSGTQFSLRINTLQPEDLGTYYCQHHYGAPLSFGGGTKLEIKR

SEQ ID NO: 94
EVQLQQPGAELVRPGTSVKLSCKASGYTFTSYWMHWVKQRPGQGLEWIGNINPSSGDS
HYNEKFKSKATLTVDKSSSTAYMQLNSLTSEDSAVYYCARDYYGAYWGHGTLVTVSA

SEQ ID NO: 95
DIQMTQSPASLSASVGETVTITCRASENIYSYLAWYQQKQGKSPQLLVYNAKTLAEGVP
SRFSGSGSGTQFSLKINSLQPEDFGSYYCQHHYGTPLTFGAGTKLEIK

SEQ ID NO: 96
EVQLQQPGTELVKPGASVKLSCKASGYTFTSYWMHWVKQRPGQGLEWIGNINPSSGD
AHYSEEFKSKATLTVDKSSSTAYMQLSSLTSEDSAVYYCARDYYGAYWGHGTLVTVSA

SEQ ID NO: 97
DIQINQSPSSLSASLGDTITITCHASQNINVWLSWYQQKPGNIPKLLIYKASNLHTGVPSR
FSGSGSGTGFTLTISSLQPEDIATYYCQQGQSYPLTFGAGTKLEIK

SEQ ID NO: 98
EVQLQQSGPELVKPGASVKISCKASGYSFTNYHIHWVKQRPGQGLEWIGWIYPGSGNT
KYNEKFKGMAILTADTSSSTAYMQLSSLTSEDSAVYYCARYDYDLYLHSWGQGTTVTV
SS

SEQ ID NO: 99
DIQMTQSPASLSASVGETVTITCRASENIYSYLAWYQQKQGKSPQLLVYNAKTLAEGVP
SRFSGSGSGTQFSLKINSLQPEDFGSYYCQHHYGTPLTFGAGTKLEIK

SEQ ID NO: 100
EVQLQQPGTEVVKPGASVKLSCKASGYSFTTYWMHWVKQRPGQGLEWIGNINPSSGD
SHYNEKFKSKATLTVDKSSSTAYMQLNSLTSEDSAVYYCARDYYGAYWGHGTLVTVS
A

SEQ ID NO: 101
RHCFNQSPAIIVISASPGEKVTMTCSASSSVSYMHVVYQQKSGTSPKRWIYDTSNLASGVP
VRFSGSGSGTSYSLTISRMEAEDAATYYCQQWSNYPFTFGSGTKLELK

SEQ ID NO: 102
RVQLQQSGAELVRPGTSVKVSCKASAYAFTNYLIEWVKKRPGQGLEWIGVINPGSGGT
NYNEKFKGKATLTADKSSSTAYMQLSSLTSEDSAVYFCARGDGYGSLFAYWGQGTLVT
VSA

SEQ ID NO: 103
DIQMIQSPASLSASVGETVTITCRASENIYSYLAWYQQKQGKSPQLLVYGAKTLAEGVP
SRFSGSGSGTQFSLKINSLQPEDFGSYYCQHHYGIPLTFGAGTKLEIK

SEQ ID NO: 104
EVQLQQPGTELVKPGASVKLSCKASGYTFISYWMHWVKQRPGQGLEWIGNINPSSGNT
NYNEKFKTKATLTVDKSSSTAYMQLSSLTSEDSAVYYCVRDYYGNYWGQGTSVTVSS

SEQ ID NO: 105
DIQMIQSPASLSASVGETVTITCRASENIYSYLAWYQQKLGKSPQLLVYNAKTLAEGVP
SRFSGSGSGTHFSLKINSLQPEDFGTYYCQHHYGNSLTFGAGTKLELK

SEQ ID NO: 106
EVQLQQSGTELVKPGASVKLSCKASGYPFTSYWMHWVKQRPGQGLEWIGNINPSSGGT
NYNEKFKTKATLTVDKSSSTAYMQLSSLTSEDSAVYYCARDYYGNYWGQGTTVTVSS

SEQUENCE LISTING

SEQ ID NO: 107
DIQMTQSPASLSASVGETVTITCRASENIYSYLAWYQQKQGKSPQLLVYNAKTLAEGVP
SRFSGSGSGTQFSLKINSLQPEDFGSYYCQHHYGTPLTFGAGTKLEIK

SEQ ID NO: 108
EVQLQQPGTELVKPGASVKLSCKTSGYSFVTYWMHWVKQRPGQGLEWIGNINPSSGDS
HYSEKFKSKATLTVDKSSTAYMQLKSLTSEDSAVYYCVRDYYGAYWGQGTLVTVSA

SEQ ID NO: 109
DAVVTQESALTTSPGETVTLTCRSSTGAVTTNNYANVVVQEKPDHLFTGLIGGTNNRAP
GVPARFSGSLIGDKAALTITGAQTEDEAIYFCALWYSNHLVFGGGTKLTVL

SEQ ID NO: 110
PRGKVQESGPGLVKPSQSLSLTCSVTGYSITSGYYWNWIRQFPGNKLEWMGYINYDGS
NNYNPSLKNRISITRDTSKNQFFLKLNSVTTEDTATYYCARGYYYGSSYGYWYFDVWG
TGTTVTVSS

SEQ ID NO: 111
DIQMTQSPASLSASVGETVTITCRASENIYSYLAWYQQKQGKSPQLLVYAATNLADGVP
SRFSGSRSGTQFSLKINSLQPEDFGSYYCQHHYGTPLTFGAGTKLEIK

SEQ ID NO: 112
EVQLQQPGTELAKPGASVKLSCKASGYTFISYWMHWVKQRPGQGLEWIGNINPSSGGT
NYNEKFKSKATLTVDKSSTAYMQLSSLTSEDSAVYYCVRDYYGSYWGQGTTVTVSS

SEQ ID NO: 113
DIQMTQSPASLSASVGETVTITCRASENIYSYLAWYQQKQGKSPQLLVYKAKTLVEGVP
SRFSGSGSGTQFSLKINSLQPEDFGSYYCQHHYGTPLTFGAGTKLEIK

SEQ ID NO: 114
RGPTAATWTELVKPGTSVKLSCKASGYTFISYWMHWVKQRPGQGLEWIGNINPSSGDT
SYNEKFKSKATLTVDKSSTAYMQLSSLTSEDSAVYYCARDYYGAYWGQGTSVTVSA

SEQ ID NO: 115
DIQMMQSPASLSASVGETVTITCRASENIYSYLAWYQQKQGKSPQLLVYNAKTLAEGV
PSRFSGSGSGTQFSLKINSLQPEDFGNYYCQHHYGTPLTFGSGTKLELK

SEQ ID NO: 116
EVQLQQPGTELVKPGASVKVSCKASGYTFTSYWMHWVKQRPGQGLEWIGNINPSSGD
SHYSEKFRSKATLTVDKSSSTAYMQLNSLTSEDSAVYYCARDYYGAYWGHGTLVTVSA

SEQ ID NO: 117
DAVVTQESALTTSPGETVTLTCRSSTGAVSTSNYANWVQEKPDHLFTGLIGGTNNRAPG
VPARFSGSLIGDKAALTITGAQTEDEAIYFCALWYSNHWVFGGGTKLTVL

SEQ ID NO: 118
EVQLQQPGTELVKPGASVKLSCKASGYTFTSYWMHWVKQRPGQGLEWIGNVVPNND
GTNYNEKFRNKATLTVDKSSTAYMQLSSLTSEDSAVYYCAVTYFAYWGQGTLVTVSA

SEQ ID NO: 119
DIQMMQSPASLSASVGETVTITCRASENIYSYLAWYQQKQGKSPQLLVYNAKTLAEGV
PSRFSGSGSGTQFSLKINSLQPEDFGSYYCQHHYGTPLTFGAGTKLELK

SEQ ID NO: 120
EVQLQQSGAELVKPGASVKLSCKASGYSFTTYWMHWVKQRPGQGLEWIGNINPSSGS
AHYNEKFKSKATLTVDKSSNTAYMQLSSLTSEDSAVYYCARDYYGAYWGHGTLVTVS
A

SEQ ID NO: 121
DIQMTQSPASLSASVGETVTITCRASENIYSYLAWYQQKQGKSPQLLVYNAKTLAEGVP
SRFSGSGSGTHFSLKINSLQPEDEGSYYCQHHYGTPLTFGAGTKLELK

SEQ ID NO: 122
EVQLQQPGAELVRPGSSVKLSCKASGYTFISYWIHWVKQRPGQGLEWIGNINPSSGSSN
YNEKFKNKATLTVDKSSTAYMQLSSLTSEDSAVYYCARDYYGAYWGHGTLVTVSA

SEQ ID NO: 123
DIQMTQSPASLSASVGETVTITCRASENIYSYLAWYQQKQGKSPQLLVYNAKTLAEGVP
SRFSGSGSGTQFSLKINSLQPEDFGNYYCQHHYGTPLTFGAGTKLEIK

SEQ ID NO: 124
EVQLQQPGTELVKPGASVKLSCKASGYSFITYWMHWVKQRPGQGLEWIGNINPSSGDS
HYSEKFKSKATLTVDKSSTAYMQLNSLTSEDSAVYYCVRDYYGAYWGHGTLVTVSA

SEQUENCE LISTING

SEQ ID NO: 125
DIKINQSPASLSASVGETVTITCRASENIYSYLAWYQQKQGKSPQLLVYKAKTLVEGVPS
RFSGSGSGTQFSLKISSLQPEDEGSYYCQHHYGTPLTFGAGTKLELK

SEQ ID NO: 126
EVQLQQPGAELVKPGASVKLSCKASGYTFISYWMHWVRQRPGQGLEWIGNINPSSGNT
NYNEKFKTKATLTVDKSSSTAYMQLSSLTSEDSAVYYCVRDYYGNYWGQGTSVTVSS

SEQ ID NO: 127
GIQMTQSPASLSASVGETVTITCRASENIYSYLAWYQQKQGKSPQLLVYKAKTLVEGVP
SRFSGSGSGTQFSLKINSLQPEDEGSYYCQHHYGTPLTFGAGTKLELK

SEQ ID NO: 128
EVQLQQPGTELVKPGASVKLSCKASGYTFISYWIHWVKQRPGQGLEWIGNINPSSGGTN
YNEKFKSKATLTVDKSSSTAYMHLNSLTSEDSAVYYCARDYYGNYWGQGTTLTVSS

SEQ ID NO: 129
DIQMTQSPASLSASVGETVTITCRASDNIYSYLAWYQQKQGKSPQLLVYNAKTSAEGVP
SRFSGSGSGTQFSLKINSLQPEDEGSYYCQHHYGTPLTFGAGTKLELK

SEQ ID NO: 130
EVQLQQPGTELVKPGASVKLSCKASGYSFTTYWMHWVKQRPGQGLEWIGNINPSSGDS
HYNEKFKSKATLTVDKSSSTAYMQLNSLTSEDSAVYYCARDYYGAYWGHGTLVTVSA

SEQ ID NO: 131
DIQMTQSPASLSASVGETVTITCRASENIYSYLAWYQQKQGKSPQLLVYNAKTLAEGVP
SRFSGSGSGTQFSLKINNLQPEDFGSYYCQHHYGTPLTFGAGTKLEMK

SEQ ID NO: 132
EVQLQQSGAEHVRPGSSVKLSCKASGYSFITYWMHWVKQRPGQGLEWIGNINPSSGDS
HYNEKFKSKATLTVDKSSSTAYMQLSSLTSEDSAVYYCARDYYGAYVVGQGTLVTVSA

SEQ ID NO: 133
DIKMNQSPSSLSASLGDTITITCHASQNINVWLSWYQQKPGNIPKLLIYKASNLHTGVPS
RFSGSGSGTGFTLTISSLQPEDIATYYCQQGQSYPLTFGTGTKLEIK

SEQ ID NO: 134
EVQLQQSGPELVKPGASVKISCKASGDSFTSDHIHWVKQRPGQGLEWIGWIYPGSGNTK
YNEKFKGKATLTADTSSSTAYMQLSRLTSEDSAVYYCVTYDYDLYFDNWGQGTTLTVS
S

SEQ ID NO: 135
STLMTQSPASLAVSLGQRATISCRASESVDSYGNSFMHWYQQKPGQPPKLLIYLASNLE
SGVPARFSGSGSGTDFILNIHPVEEEDAATYYCLHSRELPFTFGSGTKLELK

SEQ ID NO: 136
EVKLMESGGGLVKPGGSLKLSCAASGFTFSDYGMHWVRQAPEKGLEWVAYISSGSSTI
YYADTVKGRFTISRDNAKNTLFLQMTSLRSEDTAMYYCARPDDGYYGFAYWGQGTLV
TVSA

SEQ ID NO: 137
DIQMTQSPASLSASVGETVTITCRASENVYSYLAWYQQKQGKSPQLLVYNAKTLAEGV
PSRFSGSGSGTQFSLKINSLQPEDFGSYYCQHHYGTPLTFGAGTKLELK

SEQ ID NO: 138
EVQLQQPGTELVKPGASVKLSCKASGYSFTTYWMHWVKQRPGQGLEWIGNINPSSGDS
HYNEKFKSKATLTVDKSSSTAYMHLSSLTSEDSAVYYCARDYYGAYVVGHGTLVTVSA

SEQ ID NO: 139
DIQMTQSPASLSASVGETVTITCRASENIYSYLAWYQQKQGKSPQLLVFNAKTLAEGVP
SRFSGSGSGTHFSLKINNLQPEDFGTYYCQHHYGTPLTFGAGTKLEIK

SEQ ID NO: 140
EVQLQQSGAELVKPGASVKLSCKASGYSFISYWIHWVKQRPGQGLEWIGNINPSSGGNT
YNEKFKNKATLTVDKSSSTAYMQLSRLTSEDSAVYYCTRDYYGAYWGQGTLVTVSA

SEQ ID NO: 141
DIQMTQSPASLSASVGETVTITCRASENIYSYLAWYQQKQGKSPQLLVYNAKTLAEGVP
SRFSGSGSGTQFSLKINSLQPEDFGSYYCQHHYGTPLAFGSGTKLELK

SEQ ID NO: 142
EVQLQQPGTELVKPGASVKLSCKASGYSFITYWMHWVKQRPGQGLEWIGNINPSGGDS
HYSEKFKSKATLTVDKSSSTAYMQLNSLTSEDSAVYYCVRDYYGAYWGHGTLVTVSA

SEQUENCE LISTING

SEQ ID NO: 143
DIQMIQSPASLSASVGETVTITCRASENIYSYLAWYQQKQGKSPQLLVFNAKTLAEGVPS
RFSGSGSGTQFSLKINSLQPEDFGSYYCQHHYGTPLTFGAGTKLEIK

SEQ ID NO: 144
EVQLQQSGAELVKPGASVKLSCKASGYSFISYWIHWVKQRPGQGLEWIGNINPSSGGSS
YNEKFKSKATLTVDKSSSTAYMQLSSLTSEDSAVYYCTRDYYGAYWGQGTLVTVSA

SEQ ID NO: 145
DIVLSQSPAIMSASPGEKVTMTCSASSSVSYMHWYQQKSGTSPKRWIYDTSKLASGVPA
RFSGSGSGTSYSLTLSSMAAEDAATYSCQQWSGNSPTFGAGTKLEIK

SEQ ID NO: 146
EVQLVESGGGLVQPKGSLKLSCAASGFTENTYAMHWVRQAPGKGLEWVARIRSKSSN
YATYYADSVKDRFTISRDDSQSIVYLQMNNLKTEDTAMYYCVRAWDYGSSWDYFDYW
GQGTSVTVSS

SEQ ID NO: 147
DIQMMQSPASLSASVGETVTITCRASENIYSYLAWYQQKQGKSPQLLVYNAQTLAEGV
PSRFSGSGSGTQFSLKINSLQSEDIGSYYCQHHYGTPLTFGAGTKLELK

SEQ ID NO: 148
RGPTQQPGTELVKPGASVKLSRKASGYTFTTYWMHWVKQRPGQGLEWIGN1NPSSGDS
HYNEKFKSKATLTVDKSSSTAYMQLNSLTSEDSAVYYCARDYYGAYWGHGTLVTVSA

SEQ ID NO: 149 GYGMS

SEQ ID NO: 150 TITSGGTYTYYPDSVKG

SEQ ID NO: 151 SLAGNAMDY

SEQ ID NO: 152 RASQTISDYLH

SEQ ID NO: 153 FASQSIS

SEQ ID NO: 154 QNGHGFPRT

SEQ ID NO: 155 NYNMH

SEQ ID NO: 156 TIYPGNDDTSYNQKFKD

SEQ ID NO: 157 GGYRAMDY

SEQ ID NO: 158 RSSQSIVYSNGNTYLG

SEQ ID NO: 159 KVSNRFS

SEQ ID NO: 160 FQGSHVPYT

SEQ ID NO: 161
MWPLVAALLLGSACCGSAQLLFNKTKSVEFTFCNDTVVIPCFVTNMEAQNTTEVYVK
WKFKGRDIYTFDGALNKSTVPTDFSSAKIEVSQLLKGDASLKMDKSDAVSHTGNYTCEV
TELTREGETIIELKYRVVSWFSP

SEQ ID NO: 162 DNIYSY

SEQ ID NO: 163 ENIYSY

SEQ ID NO: 164 ENVYSY

SEQ ID NO: 165 ESVDSYGNSF

SEQ ID NO: 166 QNINVW

SEQ ID NO: 167 SSVSY

SEQ ID NO: 168 TGAVSTSNY

SEQ ID NO: 169 TGAVTTNNY

SEQ ID NO: 170 AAT

SEQ ID NO: 171 DTS

SEQ ID NO: 172 GAK

-continued

| SEQUENCE LISTING |
|---|
| SEQ ID NO: 173 GTN |
| SEQ ID NO: 174 KAK |
| SEQ ID NO: 175 KAN |
| SEQ ID NO: 176 KAS |
| SEQ ID NO: 177 LAS |
| SEQ ID NO: 178 NAK |
| SEQ ID NO: 179 NAQ |
| SEQ ID NO: 180 ALWYSNHLV |
| SEQ ID NO: 181 ALWYSNHWV |
| SEQ ID NO: 182 LHSRELPFT |
| SEQ ID NO: 183 QHHYGAPLS |
| SEQ ID NO: 184 QHHYGIPLT |
| SEQ ID NO: 185 QHHYGNSLT |
| SEQ ID NO: 186 QHHYGTPLA |
| SEQ ID NO: 187 QHHYGTPLT |
| SEQ ID NO: 188 QQGQSYPLT |
| SEQ ID NO: 189 QQWSGNSPT |
| SEQ ID NO: 190 QQWSNYPFT |
| SEQ ID NO: 191 AYAFTNYL |
| SEQ ID NO: 192 GDSFTSDH |
| SEQ ID NO: 193 GFTFNTYA |
| SEQ ID NO: 194 GFTFSDYG |
| SEQ ID NO: 195 GFTFTNYY |
| SEQ ID NO: 196 GYPFTSYW |
| SEQ ID NO: 197 GYSFISYW |
| SEQ ID NO: 198 GYSFITYVV |
| SEQ ID NO: 199 GYSFTAYVV |
| SEQ ID NO: 200 GYSFTNYH |
| SEQ ID NO: 201 GYSFTTYW |
| SEQ ID NO: 202 GYSFVTYVV |
| SEQ ID NO: 203 GYSITSGYY |
| SEQ ID NO: 204 GYTFISYVV |
| SEQ ID NO: 205 GYTFTSYW |
| SEQ ID NO: 206 GYTFTTYW |
| SEQ ID NO: 207 INPGSGGT |
| SEQ ID NO: 208 INPSGGDS |
| SEQ ID NO: 209 INPSSGDA |
| SEQ ID NO: 210 INPSSGDS |
| SEQ ID NO: 211 INPSSGDT |

SEQUENCE LISTING

SEQ ID NO: 212 INPSSGGN

SEQ ID NO: 213 INPSSGGS

SEQ ID NO: 214 INPSSGGT

SEQ ID NO: 215 INPSSGNT

SEQ ID NO: 216 INPSSGSA

SEQ ID NO: 217 INPSSGSS

SEQ ID NO: 218 INYDGSN

SEQ ID NO: 219 IRSKSSNYAT

SEQ ID NO: 220 ISSGSSTI

SEQ ID NO: 221 IYLGSGNT

SEQ ID NO: 222 IYPGSGNT

SEQ ID NO: 223 VVPNNDGT

SEQ ID NO: 224 ARDYYGAY

SEQ ID NO: 225 ARDYYGNY

SEQ ID NO: 226 ARGDGYGSLFAY

SEQ ID NO: 227 ARGYYYGSSYGYWYFDV

SEQ ID NO: 228 ARPDDGYYGFAY

SEQ ID NO: 229 ARYDYDLYLDS

SEQ ID NO: 230 ARYDYDLYLHS

SEQ ID NO: 231 AVTYFAY

SEQ ID NO: 232 TRDYYGAY

SEQ ID NO: 233 VRAWDYGSSWDYFDY

SEQ ID NO: 234 VRDYYGAY

SEQ ID NO: 235 VRDYYGNY

SEQ ID NO: 236 VRDYYGSY

SEQ ID NO: 237 VTYDYDLYFDN

SEQ ID NO: 238
DIQMTQSPASLSASVGETVTITCRASENIYSYLAWYQQKQGKSPQLLVYNAKTLAEGVP
SRFSGSGSGTQFSLKINSLQPEDFGSYYCQHHYGTPLTFGAGTKLELK

SEQ ID NO: 239
EVQLQQPGTELVKPGASVKLSCKASGYSFTTYWMHWVKQRPGQGLEWIGN1NPSSGDS
HYNEKFKSKATLTVDKSSSTAYMQLNSLTSEDSAVYYCARDYYGAYWGHGTLVTVSA

SEQ ID NO: 240
EVQLVESGGDLVKPGGSLKLSCAASGFTFSGYGMSWVRQTPDKRLEWVATITSGGTYT
YYPDSVKGRFTISRDNAKNTLYLQIDSLKSEDTAIYFCARSLAGNAMDYWGQGTSVTVS
S

SEQ ID NO: 241
DIVMTQSPATLSVTPGDRVSLSCRASQTISDYLHWYQQKSHESPRLLIKFASQSISGIPSR
FSGSGSGSDFTLSINSVEPEDVGVYYCQNGHGFPRTFGGGTKLEIK

SEQ ID NO: 242
QVQLQQPGAELVKPGASVMMSCKASGYTFTNYNMHWVKQTPGQGLEWIGTIYPGND
DTSYNQKFKDKATLTADKSSSAAYMQLSSLTSEDSAVYYCARGGYRAMDYWGQTSVT
VSS

SEQUENCE LISTING

SEQ ID NO: 243
DVLMTQTPLSLPVSLGDQASISCRSSQSIVYSNGNTYLGWYLQKPGQSPKLLIYKVSNRF
SGVPDRFSGSGSGTDFTLKISRVEAEDLGVYHCFQGSHVPYTFGGGTKVEIK

SEQ ID NO: 244
QMQLVQSGAEVKKTGSSVKVSCKASGFNIKDYYLHWVRQAPGQALEWMGWIDPDQG
DTEYAQKFQDRVTITRDRSMSTAYMELSSLRSEDTAMYYCNAAYGSSSYPMDYWGQG
TTVTV

SEQ ID NO: 245
NIQMTQSPSAMSASVGDRVTITCKASQDIHRYLSWFQQKPGKVPKHLIYRANRLVSGVP
SRFSGSGSGTEFTLTISSLQPEDFATYYCLQYDEFPYTFGGGTKVEIK

SEQ ID NO: 246
QVQLVQSGAEVKKPGASVKVSCKASGYTFTDSYINWVRQAPGQRLEWMGWIYTGSG
NTKYNEKFKGRVTITRDTSASTAYMELSSLRSEDTAVYYCARREERGFAYWGQGTLVT
VSS

SEQ ID NO: 247
QVQLVQSGAEVKKPGASVKVSCKASGYTFTDIYINWVRQAPGQRLEWMGWIYLGSGN
VKYNEKFKGRVTITRDTSASTAYMELSSLRSEDTAVYYCARREDRGFAYWGQGTLVTV
SS

SEQ ID NO: 248
QVQLVQSGAEVKKPGASVKVSCKASGYTFTDNYINWVRQAPGQRLEWMGWIYLGSG
NTKYNEKFKGRVTITRDTSASTAYMELSSLRSEDTAVYYCARREERGFAVWGQGTLVT
VSS

SEQ ID NO: 249
QVQLVQSGAEVKKPGASVKVSCKASGYTFTDFYINWVRQAPGQRLEWMGWIYLGSG
NTKYNEKFKGRVTITRDTSASTAYMELSSLRSEDTAVYYCARREERGFAYWGQGTLVT
VSS

SEQ ID NO: 250
QVQLVQSGAEVKKPGASVKVSCKASGYTFTDHYINWVRQAPGQRLEWMGWIYLGSG
NTKYNEKFKGRVTITRDTSASTAYMELSSLRSEDTAVYYCARREDRGFAYWGQGTLVT
VSS

SEQ ID NO: 251
QVQLVQSGAEVKKPGASVKVSCKASGYTFTDNYINWVRQAPGQRLEWMGWVYLGSG
NTKYNEKFKGRVTITRDTSASTAYMELSSLRSEDTAVYYCARREERGFAYWGQGTLVT
VSS

SEQ ID NO: 252
QVQLVQSGAEVKKPGASVKVSCKASGYTFTDLYINWVRQAPGQRLEWMGWIYLGSG
NTKYNEKFKGRVTITRDTSASTAYMELSSLRSEDTAVYYCARREERGFAYWGQGTLVT
VSS

SEQ ID NO: 253
QVQLVQSGAEVKKPGASVKVSCKASGYTFTDNYINWVRQAPGQRLEWMGWIYLGSG
NTKYNEKFKGRVTITRDTSASTAYMELSSLRSEDTAVYYCARREERGFAPWGQGTLVTV
SS

SEQ ID NO: 254
QVQLVQSGAEVKKPGASVKVSCKASGYTFTDSYINWVRQAPGQRLEWMGWIYPGSGN
TKYNEKFKGRVTITRDTSASTAYMELSSLRSEDTAVYYCARREERGFAYWGQGTLVTVS
S

SEQ ID NO: 255
QVQLVQSGAEVKKPGASVKVSCKASGYTFTDFYIHWVRQAPGQRLEWMGWIYLGSG
NTKYNEKFKGRVTITRDTSASTAYMELSSLRSEDTAVYYCARREEDGFAHWGQGTLVT
VSS

SEQ ID NO: 256
QVQLVQSGAEVKKPGASVKVSCKASGYTFTDNYINWVRQAPGQRLEWMGWIYLGSG
NTKYNEKFKGRVTITRDTSASTAYMELSSLRSEDTAVYYCARRKERGFAYWGQGTLVT
VSS

SEQ ID NO: 257
QVQLVQSGAEVKKPGASVKVSCKASGYTFTDTYINWVRQAPGQRLEWMGWIYLGSG
NIKYNEKFKGRVTITRDTSASTAYMELSSLRSEDTAVYYCARREERGFAYWGQGTLVTV
SS

SEQUENCE LISTING

SEQ ID NO: 258
QVQLVQSGAEVKKPGASVKVSCKASGYTFTDYYINWVRQAPGQRLEWMGWIYLGSG
NTKYNEKFKGRVTITRDTSASTAYMELSSLRSEDTAVYYCARREDRGFAYWGQGTLVT
VSS

SEQ ID NO: 259
QVQLVQSGAEVKKPGASVKVSCKASGYTFTDTYINWVRQAPGQRLEWMGWIYLGSG
NVKYNEKFKGRVTITRDTSASTAYMELSSLRSEDTAVYYCARREERGFAHWGQGTLVT
VSS

SEQ ID NO: 260
QVQLVQSGAEVKKPGASVKVSCKASGYTFTDLYINWVRQAPGQRLEWMGWIYLGSG
NVKYNEKFKGRVTITRDTSASTAYMELSSLRSEDTAVYYCARREERGFAYWGQGTLVT
VSS

SEQ ID NO: 261
QVQLVQSGAEVKKPGASVKVSCKASGYTFTDSYINWVRQAPGQRLEWMGWIYGGSG
NTKYNEKFKGRVTITRDTSASTTYMELSSLRSEDTAVYYCARREEDGFAYWGQGTLVT
VSS

SEQ ID NO: 262
QVQLVQSGAEVKKPGASVKVSCKASGYTFTDSYINVVRQAPGQRLEWMGWIYGGSG
NTKYNEKFKGRVTITRDTSASTAYMELSSLRSEDTAVYYCARREERGFAYWGQGTLVT
VSS

SEQ ID NO: 263
QVQLVQSGAEVKKPGASVKVSCKASGYTFTDSYINWVRQAPGQRLEWMGWIYLGSG
NVKYNEKFKGRVTITRDTSASTAYMELSSLRSEDTAVYYCARRIERGFAYWGQGTLVTV
SS

SEQ ID NO: 264
QVQLVQSGAEVKKPGASVKVSCKASGYTFTDSYINWVRQAPGQRLEWMGWVYLGSG
NTKYNEKFKGRVTITRDTSASTAYMELSSLRSEDTAVYYCARREERGFAVWGQGTLVT
VSS

SEQ ID NO: 265
DIVMTQSPDSLAYSLGERATINCKSSQSILYSSNQKNYLAWYQQKPGQPPKLLIYWASV
RDSGVPDRFSGSGSGTDFTLTISSLQAEDVAVYYCQQYYHYPLTFGQGTKVEIK

SEQ ID NO: 266
DIVMTQSPDSLAVSLGERATINCKSSQSLLSSNQKYYLAWYQQKPGQPPKLLIYWASTR
DSGVPDRFSGSGSGTDFTLTISSLQAEDVAVYYCQQFYSYPLTFGQGTKVEIK

SEQ ID NO: 267
DIVMTQSPDSLAYSLGERATINCKSSQSLYSSNKKNYLAWYQQKPGQPPKLLIYWASSR
DSGVPDRFSGSGSGTDFTLTISSLQAEDVAVYYCQQYYSYPLTFGQGTKVEIK

SEQ ID NO: 268
DIVMTQSPDSLAVSLGERATINCKSSQSLLSSNQKNYLAWYQQKPGQPPKLLIYWASVR
DSGVPDRFSGSGSGTDFTLTISSLQAEDVAVYYCQQFYSYPLTFGQGTKVEIK

SEQ ID NO: 269
DIVMTQSPDSLAVSLGERATINCKSSQSLLSSSQKNYLAWYQQKPGQPPKLLIYWASVR
DSGVPDRFSGSGSGTDFTLTISSLQAEDVAVYYCQQYYSYPLTFGQGTKVEIK

SEQ ID NO: 270
DIVMTQSPDSLAVSLGERATINCKSSQSLLYSSNKKNYLAWYQQKPGQPPKLLIYWASV
RDSGVPDRFSGSGSGTDFTLTISSLQAEDVAVYYCQQYYHYPLTFGQGTKVEIK

SEQ ID NO: 271
DIVMTQSPDSLAVSLGERATINCKSSQSLVSSSQKNYLAWYQQKPGQPPKLLIYWASVR
DSGVPDRFSGSGSGTDFTLTISSLQAEDVAVYYCQQYYSYPLTFGQGTKVEIK

SEQ ID NO: 272
DIVMTQSPDSLAVSLGERATINCKSSQSLLSSSQKNYLAWYQQKPGQPPKLLIYWASTR
DSGVPDRFSGSGSGTDFTLTISSLQAEDVAVYYCQQFYSYPLTFGQGTKVEIK

SEQ ID NO: 273
DIVMTQSPDSLAVSLGERATINCKSSQSLLYSSNQKNYLAWYQQKPGQPPKWYWASV
RDSGVPDRFSGSGSGTDFTLTISSLQAEDVAVYYCQQFYSYPLTFGQGTKVEIK

SEQ ID NO: 274
DIVMTQSPDSLAVSLGERATINCKSSQSLLYKSNQKNYLAWYQQKPGQPPKLLIYWAS
VRDSGVPDRFSGSGSGTDFTLTISSLQAEDVAVYYCQQLYSYPLTFGQGTKVEIK

SEQUENCE LISTING

SEQ ID NO: 275
DIVMTQSPDSLAVSLGERATINCKSSQSVLYSSNQKNYLAWYQQKPGQPPKLLIYWAS
VRDSGVPDRFSGSGSGTDFTLTISSLQAEDVAVYYCQQYYHYPLTFGQGTKVEIK

SEQ ID NO: 276
DIVMTQSPDSLAVSLGERATINCKSSQSLLSSSQKNYLAWYQQKPGQPPKLLIYWASGR
DSGVPDRFSGSGSGTDFTLTISSLQAEDVAVYYCQQYYSYPLTFGQGTKVEIK

SEQ ID NO: 277
DIVMTQSPDSLAVSLGERATINCKSSQSLLTSNQKNYLAWYQQKPGQPPKWYWASIR
DSGVPDRFSGSGSGTDFTLTISSLQAEDVAVYYCQQYYSYPLTFGQGTKVEIK

SEQ ID NO: 278
DIVMTQSPDSLAVSLGERATINCKSSQSLLYSSNRKNYLAWYQQKPGQPPKLLIYWASS
RDSGVPDRFSGSGSGTDFTLTISSLQAEDVAVYYCQQYYHYPLTFGQGTKVEIK

SEQ ID NO: 279
DIVMTQSPDSLAVSLGERATINCKSSQSLLYSSNNKNYLAWYQQKPGQPPKLLIYWASS
RDSGVPDRFSGSGSGTDFTLTISSLQAEDVAVYYCQQFYSYPLTFGQGTKVEIK

SEQ ID NO: 280
DIVMTQSPDSLAVSLGERATINCKSSQSLLSSNNKNYLAWYQQKPGQPPKLLIYWASVR
DSGVPDRFSGSGSGTDFTLTISSLQAEDVAVYYCQQYYSYPLTFGQGTKVEIK

SEQ ID NO: 281
DIVMTQSPDSLAVSLGERATINCKSSQSLYTSNQKNYLAWYQQKPGQPPKLLIYWASTR
DSGVPDRFSGSGSGTDFTLTISSLQAEDVAVYYCQQYYSYPLTFGQGTKVEIK

SEQ ID NO: 282
DIVMTQSPDSLAVSLGERATINCKSSQSLLYNSNQKNYLAWYQQKPGQPPKLLIYWAST
RDSGVPDRFSGSGSGTDFTLTISSLQAEDVAVYYCQQYYHYPLTFGQGTKVEIK

SEQ ID NO: 283
DIVMTQSPDSLAVSLGERATINCKSSQSLLYKSNQKNYLAWYQQKPGQPPKWYWAS
VRDSGVPDRFSGSGSGTDFTLTISSLQAEDVAVYYCQQFYSYPLTFGQGTKVEIK

SEQ ID NO: 284
DIVMTQSPDSLAVSLGERATINCKSSQSLYSSSQKNYLAWYQQKPGQPPKWYWASVR
DSGVPDRFSGSGSGTDFTLTISSLQAEDVAVYYCQQYYSYPLTFGQGTKVEIK

SEQ ID NO: 285
DIVMTQSPDSLAVSLGERATINCKSSQSLLYNSNQKNYLAWYQQKPGQPPKWYWAS
VRDSGVPDRFSGSGSGTDFTLTISSLQAEDVAVYYCQQYYHYPLTFGQGTKVEIK

SEQ ID NO: 286
DIVMTQSPDSLAVSLGERATINCKSSQSLLYSSNQKNYLAWYQQKPGQPPKWYWASV
RDSGVPDRFSGSGSGTDFTLTISSLQAEDVAVYYCQQYYHYPLTFGQGTKVEIK

SEQ ID NO: 287
DIQMTQSPSSLSASVGDRVTITCRASKNIGKYLAWFQQKPGKAPKSLIYSGSTLQSGVPS
RFSGSGSGTDFTLTISSLQPEDFATYYCQQHNEYPYTFGGGTKVEIK

SEQ ID NO: 288
DVQITQSPSSLSASVGDRVTITCRASKNIGKYLAWFQQKPGKAPKSLIYSGSTLQSGYPS
RFSGSGSGTDFTLTISSLQPEDFATYYCQQHNEYPYTFGGGTKVEIK

SEQ ID NO: 289
DIQMTQSPSSLSASVGDRVTITCRASKNIGKYLAWFQQKPGKAPKSLIYSGSTLQSGIPSR
FSGSGSGTDFTLTISSLQPEDFATYYCQQHNEYPYTFGGGTKVEIK

SEQ ID NO: 290
DVQITQSPSSLSASVGDRVTITCRASKNIGKYLAWFQQKPGKAPKSLIYSGSTLQSGIPSR
FSGSGSGTDFTLTISSLQPEDFATYYCQQHNEYPYTFGGGTKVEIK

SEQ ID NO: 291
DVQITQSPSSLSASVGDRVTITCRASKNIGKYLAWFQQKPGKTNKLLIYSGSTLQSGIPSR
FSGSGSGTDFTLTISSLQPEDFATYYCQQHNEYPYTFGGGTKVEIK

SEQ ID NO: 292
QVQLVQSGAEVKKPGASVKVSCKASGYTFTNYWMQWVRQAPGQGLEWMGMIDPSD
SESRLNQKFKDRVTMTRDTSTSTVYMELSSLRSEDTAVYYCARRGSPMITSFAYWGQGT
LVTVSS

SEQUENCE LISTING

SEQ ID NO: 293
QVQLVQSGAEVKKPGASVKVSCKTSGYSFTNYWMQWVRQAPGQGLEWMGMIDPSDS
ESRLNQKFKDRVTMTRDTSTSTAYMELSSLRSEDTAVYYCARRGSPMITSFAYWGQGTL
VTVSS

SEQ ID NO: 294
QVQLVQSGAEVKKPGASVKVSCKASGYTFTNYWMQWVRQAPGQGLEWIGM1DPSDS
ESRLNQKFKDRATLTVDTSTSTVYMELSSLRSEDTAVYYCARRGSPMITSFAYWGQGTL
VTVSS

SEQ ID NO: 295
QVQLVQSGAEVKKPGASVKVSCKTSGYSFTNYWMQWVRQAPGQGLEWIGMIDPSDSE
SRLNQKFKDRATLTVDTSTSTAYMELSSLRSEDTAVYYCARRGSPMITSFAYWGQGTLV
TVSS

SEQ ID NO: 296
QVQLQQSGAEVKKPGASVKVSCKTSGYSFTNYWMQWVRQAPGQGLEWIGMIDPSDSE
SRLNQKFKDKATLTVDKSTSTAYMELSSLRSEDTAVYYCARRGSPMITSFAYWGQGTLV
TVSS

SEQ ID NO: 297
DIQMTQSPSSVSASVGDRVTITCHASQNINVWLSWYQQKPGKAPKLLIYKASNLHTGVP
SRFSGSGSGTDFTLTISSLQPEDFATYYCQQGQSYPLTFGQGTKLEIK

SEQ ID NO: 298
DIQITQSPSSVSASVGDRVTITCHASQNINVWLSWYQQKPGKAPKWYKASNLHTGVPS
RFSGSGSGTGFTLTISSLQPEDFATYYCQQGQSYPLTFGQGTKLEIK

SEQ ID NO: 299
DIQITQSPSSVSASVGDRVTITCHASQNINVWLSWYQQKPGKIPKWYKASNLHTGVPS
RFSGSGSGTGFTLTISSLQPEDFATYYCQQGQSYPLTFGQGTKLEIK

SEQ ID NO: 300
QVQLVQSGAEVKKPGASVKVSCKASGYTFTNYHIHWVRQAPGQRLEWMGWIYPGSG
NTKYNEKFKGRVTITRDTSASTAYMELSSLRSEDTAVYYCARYDYDLYLHSWGQGTLV
TVSS

SEQ ID NO: 301
QVQLVQSGAEVKKPGASVKVSCKASGYSFTNYHIHWVRQAPGQRLEWIGWIYPGSGN
TKYNEKFKGRVTITRDTSASTAYMELSSLRSEDTAVYYCARYDYDLYLHSWGQGTLVT
VSS

SEQ ID NO: 302
QVQLVQSGAEVKKPGASVKVSCKASGYSFTNYHIHWVRQAPGQRLEWIGWIYPGSGN
TKYNEKFKGRATLTADTSASTAYMELSSLRSEDTAVYYCARYDYDLYLHSWGQGTLVT
VSS

SEQ ID NO: 303
QVQLVQSGAEVKKPGASVKVSCKASGYSFTNYHIHWVRQAPGQRLEWIGWIYPGSGN
TKYNEKFKGMATLTADTSASTAYMELSSLRSEDTAVYYCARYDYDLYLHSWGQGTLV
TVSS

SEQ ID NO: 304
EVQLVQSGAEVKKPGASVKVSCKASGYSFTNYHIHWVKQAPGQRLEWIGWIYPGSGN
TKYNEKFKGMATLTADTSASTAYMELSSLRSEDTAVYYCARYDYDLYLHSWGQGTLV
TVSS

SEQ ID NO: 305
QMQLVQSGAEVKKTGSSVKVSCKASGFNIKDYYLHWVRQAPGQALEWMGWIDPDQG
DTEYAQKFQDRVTITRDRSMSTAYMELSSLRSEDTAMYYCNAAYGSSSYPMDYWGQG
TTVTVSSASTKGPSVFPLAPCSRSTSESTAALGCLVKDYFPEPVTVSWNSGALTSGVHTFP
AVLQSSGLYSLSSVVTVPSSSLGTKTYTCNVDHKPSNTKVDKRVESKYGPPCPPCPAPEF
EGGPSVFLFPPKPKDTLMISRTPEVTCVVVDVSQEDPEVQFNWYVDGVEVHNAKTKPRE
EQFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK

SEQ ID NO: 306
"QMTQSPSAMSASVGDRVTITCKASQDIHRYLSWFQQKPGKVPKHLIYRANRLVSGVPS
RFSGSGSGTEFTLTISSLQPEDFATYYCLQYDEFPYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC

SEQ ID NO: 307
QMQLVQSGAEVKKTGSSVKVSCKASGFNIKDYYLHWVRQAPGQALEWMGWIDPDQG
DTEYAQKFQDRVTITRDRSMSTAYMELSSLRSEDTAMYYCNAAYGSSSYPMDYWGQG

SEQUENCE LISTING

```
TTVTVSSASTKGPSVFPLAPCSRSTSESTAALGCLVKDYFPEPVTVSWNSGALTSGVHTFP
AVLQSSGLYSLSSVVTVPSSSLGTKTYTCNVDHKPSNTKVDKRVESKYGPPCPPCPAPEF
LGGPSVFLFPPKPKDTLMISRTPEVTCVVVDVSQEDPEVQFNWYVDGVEVHNAKTKPRE
EQFNSTYRVVSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDGSFFLYSRLTV
DKSRWQEGNVFSCSVMHEALHNHYTQKSLSLSLGK

SEQ ID NO: 308
"QMTQSPSAMSASVGDRVTITCKASQDIHRYLSWFQQKPGKVPKHLIYRANRLVSGYPS
RFSGSGSGTEFTLTISSLQPEDFATYYCLQYDEFPYTFGGGTKVEIKRTVAAPSVFIFPPSD
EQLKSGTASVVCLLNNFYPREAKVQWKVDNALQSGNSQESVTEQDSKDSTYSLSSTLTL
SKADYEKHKVYACEVTHQGLSSPVTKSFNRGEC

SEQ ID NO: 309
DVQITQSPSFLAASPGETITINCRASKNIGKYLAWFQEKPGKTNKLLIYSGSTLQSGIPSRF
SGSGSGTDFTLTISSLEPEDFAIYYCQQHNEYPYTFGGGTKLEIKRTVAAPSVFIFPPSDEQ
LKSGTASVVCLLNNFYPREAKVQWKVDNALQSGNSQESVTEQDSKDSTYSLSSTLTLSK
ADYEKHKVYACEVTHQGLSSPVTKSFNRGEC

SEQ ID NO: 310
QVQLQQSGPQLVRPGASVKISCKTSGYSFTNYWMQWVKQRPGQGLEWIGMIDPSDSES
RLNQKFKDKATLTVDKSSSTAYMQLSSPTFEDSAVYYCARRGSPMITSFAYWGQGTLVT
VSAASTKGPSVFPLAPCSRSTSESTAALGCLVKDYFPEPVTVSWNSGALTSGVHTFPAVL
QSSGLYSLSSVVTVPSSSLGTKTYTCNVDHKPSNTKVDKRVESKYGPPCPPCPAPEFLGG
PSVFLFPPKPKDTLMISRTPEVTCVVVDVSQEDPEVQFNWYVDGVEVHNAKTKPREEQF
NSTYRVVSVLTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFFLYSRLTVDK
SRWQEGNVFSCSVMHEALHNHYTQKSLSLSLGK

SEQ ID NO: 311
DIQINQSPSSLSASLGDTITITCHASQNINVWLSWYQQKPGNIPKLLIYKASNLHTGVPSR
FSGSGSGTGFTLTISSLQPEDIATYYCQQGQSYPLTFGAGTKLEIKRTVAAPSVFIFPPSDE
QLKSGTASVVCLLNNFYPREAKVQWKVDNALQSGNSQESVTEQDSKDSTYSLSSTLTLS
KADYEKHKVYACEVTHQGLSSPVTKSFNRGEC

SEQ ID NO: 312
EVQLQQSGPELVKPGASVKISCKASGYSFTNYHIHWVKQRPGQGLEWIGWIYPGSGNT
KYNEKFKGMAILTADTSSSTAYMQLSSLTSEDSAVYYCARYDYDLYLHSWGQGTTVTV
SSASTKGPSVFPLAPCSRSTSESTAALGCLVKDYFPEPVTVSWNSGALTSGVHTFPAVLQ
SSGLYSLSSVVTVPSSSLGTKTYTCNVDHKPSNTKVDKRVESKYGPPCPPCPAPEFLGGPS
VFLFPPKPKDTLMISRTPEVTCVVVDVSQEDPEVQFNWYVDGVEVHNAKTKPREEQFNS
TYRVVSVLTVLHQDWLNGKEYKCKVSNKGLPSSIEKTISKAKGQPREPQVYTLPPSQEE
MTKNQVSLTCLVKGFYPSDIAVEWESNGQPENNYKTTPPVLDSDGSFFLYSRLTVDKSR
WQEGNVFSCSVMHEALHNHYTQKSLSLSLGK
```

What is claimed is:

1. An antigen binding unit comprising a variable light chain region and a variable heavy chain region, wherein the antigen binding unit binds to CD47
wherein the variable light chain region comprises light chain complementarity-determining regions LC-CDR1, LC-CDR2, and LC-CDR3, and the variable heavy chain region comprises complementarity-determining regions HC-CDR1, HC-CDR2, and HC-CDR3;
wherein the LC-CDR1 has the sequence of SEQ ID NO: 2, LC-CDR2 has the sequence of SEQ ID NO: 12, and LC-CDR3 has the sequence of SEQ ID NO: 20; and wherein the HC-CDR1 has the sequence of SEQ ID NO: 29, HC-CDR2 has the sequence of SEQ ID NO: 33, and HC-CDR3 has the sequence of SEQ ID NO: 43.

2. The antigen binding unit of claim 1, wherein binding of the antigen binding unit to CD47 prevents binding of CD47 to SIRPa that is expressed on a macrophage cell.

3. The antigen binding unit of claim 1, wherein the antigen binding unit induces phagocytosis of cells expressing CD47 to a greater extent as compared to an antigen binding unit having the amino acid sequences of SEQ ID NOs: 240 and 241, or SEQ ID NOs: 242 and 243, or SEQ ID NOs: 244 and 245.

4. The antigen binding unit of claim 1, wherein the antigen binding unit exhibits a higher binding affinity to CD47 as compared to an antigen binding unit having the amino acid sequences of SEQ ID NOs: 240 and 241, or SEQ ID NOs: 242 and 243, or SEQ ID NOs: 244 and 245, when assayed in an in vitro binding assay utilizing cells expressing CD47.

5. The antigen binding unit of claim 1, wherein hemagglutination induced upon contacting the red blood cells with the antigen binding unit is at least 1 fold less as compared to that induced by an antigen binding unit having the amino acid sequences of SEQ ID NOs: 240 and 241, or SEQ ID NOs: 242 and 243, or SEQ ID NOs: 244 and 245.

6. The antigen binding unit of claim 1, wherein the antigen binding unit is a monoclonal antibody, a humanized antibody, or a chimeric antibody.

7. The antigen binding unit of claim 1, wherein the antigen binding unit is a scFv, a Fv, a Fab, or a (Fab)2.

8. The antigen binding unit of claim 1, wherein the antigen binding unit competes for binding to an epitope of CD47 recognized by an antigen binding unit having the amino acid sequences of (i) SEQ ID NOs: 240 and 241; (ii) SEQ ID NOs: 242 and 243; or (iii) SEQ ID NOs: 244 and 245.

9. A pharmaceutical composition comprising the antigen binding unit of claim 1, and a pharmaceutically acceptable excipient.

10. The antigen binding unit of claim 1, wherein the antigen binding unit specifically binds to CD47.

11. The antigen binding unit of claim 1, wherein the antigen binding unit induces phagocytosis of cells expressing CD47 upon binding to CD47.

12. The antigen binding unit of claim 1, wherein the antigen binding unit lacks the ability to induce substantial hemagglutination when mixed with red blood cells at a concentration range of 1.5 ng/ml to 30 μg/ml of the antigen binding unit.

13. An isolated nucleic acid encoding the antigen binding unit of claim 1.

14. A host cell comprising a nucleic acid encoding the antigen binding unit of claim 1.

15. A method of treating a cancer in a subject in need thereof, the method comprising administering to the subject an effective amount of the antigen binding unit of claim 1.

16. The method of claim 15, wherein the cancer is a hematological cancer or a solid tumor.

17. The method of claim 16, wherein treating the cancer comprises reducing tumor volume.

18. The method of claim 16, further comprising administering a therapeutic antibody.

19. The method of claim 18, wherein the therapeutic antibody is an anti-CD20 antibody.

20. The method of claim 17, wherein the tumor volume is reduced to a greater extent as compared to an antigen binding unit having the amino acid sequences of SEQ ID NOs: 240 and 241, or SEQ ID NOs: 242 and 243, or SEQ ID NOs: 244 and 245.

21. The antigen binding unit of claim 1, wherein the antigen binding unit comprises the amino acid sequences of SEQ ID NOs: 291 and 296, or SEQ ID NOs: 291 and 293.

\* \* \* \* \*

SEQUENCE LISTING

<160> NUMBER OF SEQ ID NOS: 313

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ser Ser Gln Ser Leu Leu Tyr Ser Ser Asn Gln Lys Asn Tyr Leu
1               5                   10                  15

Ala

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 2

Arg Ala Ser Lys Asn Ile Gly Lys Tyr Leu Ala
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ala Ser Gln Asp Ile Lys Ser Tyr Leu Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala Ser Ser Ser Val Ser Tyr Met Asn
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Ser Gln Ser Ile Val Tyr Ser Asn Gly Asn Thr Tyr Leu Glu
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Glu Asn Val Gly Thr Tyr Val Ser
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Ser Gln Ser Ile Val His Ser Asn Gly Asn Thr Tyr Leu Glu
1               5                   10                  15

<210> SEQ ID NO 8
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 8

Asp Thr Ser Lys Leu Ala Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Ser Asn Arg Tyr Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Val Ser Asn Arg Phe Ser
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Val Ala Asn Arg Phe Ser
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Gly Ser Thr Leu Gln Ser
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Ala Ser Thr Arg Asp Ser
1               5
```

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Ala Thr Ser Leu Ala Asp
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Phe Gln Gly Ser His Val Pro Trp Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Gln Gly Ser His Val Pro Tyr Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gln Ser Tyr Ser Tyr Pro Leu Thr
1               5

<210> SEQ ID NO 18
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Gln His Gly Glu Ser Pro Phe Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln His Asn Glu Tyr Pro Tyr Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Trp Asn Ser Asn Pro Pro Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Tyr Tyr Ser Tyr Pro Leu Thr
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Phe Tyr Ile Asn
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Thr Tyr Met His
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Tyr Gly Met Ala
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 26

Gly Tyr Tyr Met Asn
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asn Tyr Trp Ile Ala
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Tyr Trp Met Asn
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Tyr Trp Met Gln
1               5

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Phe Tyr Pro Gly Asn Thr Ser Thr Asn Tyr Asn Glu Lys Phe Lys
1               5                   10                  15

Thr

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Ile Asn Pro Ser Thr Gly Gly Thr Thr Tyr Asn Gln Lys Phe Lys
1               5                   10                  15

Ala
```

```
<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Ile Ser Asn Leu Ala Lys Arg Ile Tyr Tyr Val Asp Thr Val Thr
1               5                   10                  15

Gly

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Ile Asp Pro Ser Asp Ser Glu Ser Arg Leu Asn Gln Lys Phe Lys
1               5                   10                  15

Asp

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ile Asp Pro Ala Lys Asp Asn Thr Lys Tyr Asp Pro Lys Phe Gln
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ile Asp Pro Tyr Asp Ser Glu Thr Leu Tyr Asn Gln Lys Phe Lys
1               5                   10                  15

Asp

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Ile Tyr Leu Gly Ser Gly Asn Thr Lys Tyr Asn Glu Lys Phe Lys
1               5                   10                  15
```

Gly

<210> SEQ ID NO 37
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gly Gly Lys Gly Gly Phe Gly Tyr
1               5

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly His Tyr Gly Ser Ser Tyr Val Val Tyr
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Arg Glu Glu Arg Gly Phe Ala Tyr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Gly Arg Gly Gly Ser Ser Tyr
1               5

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Arg Gly Ser Pro Met Ile Thr Ser Phe Ala Tyr
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Tyr Asp Gly Tyr Glu Gly Phe Ala Tyr
1               5

<210> SEQ ID NO 45
<211> LENGTH: 107
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 45

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Tyr Gln Gln Lys Pro Trp Lys Ser Pro Lys Thr Leu Ile
        35                  40                  45

Tyr Tyr Ala Thr Ser Leu Ala Asp Gly Val Pro Ser Arg Phe Ser Gly
    50                  55                  60

Ser Gly Ser Gly Gln His Tyr Ser Leu Thr Ile Ser Ser Leu Glu Ser
65                  70                  75                  80

Asp Asp Thr Ala Thr Tyr Tyr Cys Leu Gln His Gly Glu Ser Pro Phe
                85                  90                  95

Thr Phe Gly Ser Gly Thr Lys Leu Glu Ile Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asn Ile Gly Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gln Gly Thr Lys Val Glu Ile Lys
            100                 105

<210> SEQ ID NO 47
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Asp Ser Gly Val

```
                 50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                     85                  90                  95

Tyr Tyr Ser Tyr Pro Leu Thr Phe Gly Ala Gly Thr Lys Leu Glu Leu
                100                 105                 110

Lys

<210> SEQ ID NO 48
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Tyr Ser
                 20                  25                  30

Ser Asn Gln Lys Asn Tyr Leu Ala Trp Tyr Gln Gln Lys Pro Gly Gln
             35                  40                  45

Pro Pro Lys Leu Leu Ile Tyr Trp Ala Ser Thr Arg Asp Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                     85                  90                  95

Tyr Tyr Ser Tyr Pro Leu Thr Phe Gly Gln Gly Thr Lys Val Glu Ile
                100                 105                 110

Lys

<210> SEQ ID NO 49
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Asp Val Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val Tyr Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                     85                  90                  95

Ser His Val Pro Tyr Thr Phe Gly Gly Gly Thr Lys Leu Glu Ile Lys
                100                 105                 110
```

```
<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Val Gln Ile Thr Gln Ser Pro Ser Phe Leu Ala Ala Ser Pro Gly
1               5                   10                  15

Glu Thr Ile Thr Ile Asn Cys Arg Ala Ser Lys Asn Ile Gly Lys Tyr
            20                  25                  30

Leu Ala Trp Phe Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Ile Tyr Tyr Cys Gln Gln His Asn Glu Tyr Pro Tyr
                85                  90                  95

Thr Phe Gly Gly Gly Thr Lys Leu Glu Ile Lys
            100                 105

<210> SEQ ID NO 51
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Asp Tyr
            20                  25                  30

Gly Met Ala Trp Val Arg Gln Ala Pro Gly Lys Gly Pro Glu Cys Val
        35                  40                  45

Ala Phe Ile Ser Asn Leu Ala Lys Arg Ile Tyr Tyr Val Asp Thr Val
50                  55                  60

Thr Gly Arg Phe Thr Ile Ser Arg Glu Asn Ala Lys Asn Thr Leu Tyr
65                  70                  75                  80

Leu Glu Met Ser Ser Leu Arg Ser Glu Asp Thr Ala Met Tyr Tyr Cys
                85                  90                  95

Thr Arg Ala Tyr Arg Tyr Ala Leu Asp Tyr Trp Gly Gln Gly Thr Thr
            100                 105                 110

Leu Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Gln Gln Ser Gly Ala Glu Leu Val Lys Pro Gly Ala
```

-continued

```
                1               5                  10                 15
Ser Val Lys Leu Ser Cys Thr Ala Ser Gly Phe Thr Ile Lys Asp Thr
                    20                 25                 30

Tyr Met His Trp Val Lys Gln Arg Pro Glu Gln Gly Leu Glu Trp Ile
                    35                 40                 45

Gly Arg Ile Asp Pro Ala Lys Asp Asn Thr Lys Tyr Asp Pro Lys Phe
         50                 55                 60

Gln Gly Lys Ala Thr Ile Thr Leu Asp Thr Ser Ser Asn Ile Ala Tyr
 65                 70                 75                 80

Leu Gln Leu Ser Ser Leu Thr Ser Glu Asp Thr Ala Val Tyr Phe Cys
                    85                 90                 95

Ala Arg Gly His Tyr Gly Ser Ser Tyr Val Val Tyr Trp Gly Gln Gly
                   100                105                110

Thr Leu Val Thr Val Ser Ala
                   115
```

<210> SEQ ID NO 53
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Glu Val Gln Leu Gln Gln Ser Gly Pro Glu Leu Val Lys Pro Gly Ala
 1               5                  10                 15

Ser Val Lys Ile Ser Cys Lys Ala Ser Gly Tyr Ser Phe Thr Gly Tyr
                    20                 25                 30

Tyr Met Asn Trp Val Lys Gln Ser Pro Glu Lys Ser Leu Glu Trp Ile
                    35                 40                 45

Gly Glu Ile Asn Pro Ser Thr Gly Gly Thr Thr Tyr Asn Gln Lys Phe
         50                 55                 60

Lys Ala Lys Ala Thr Leu Thr Val Asp Lys Ser Ser Ser Thr Ala Tyr
 65                 70                 75                 80

Met Gln Leu Lys Ser Leu Thr Phe Glu Asp Ser Ala Val Tyr Tyr Cys
                    85                 90                 95

Ala Ile Tyr Asp Gly Tyr Glu Gly Phe Ala Tyr Trp Gly Gln Gly Thr
                   100                105                110

Leu Val Thr Val Ser Ala
         115
```

<210> SEQ ID NO 54
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Gln Ile Val Leu Thr Gln Ser Pro Ala Ile Met Ser Ala Ser Pro Gly
 1               5                  10                 15

Glu Lys Val Thr Met Thr Cys Ser Ala Ser Ser Ser Val Ser Tyr Met
                    20                 25                 30

Asn Trp Tyr Gln Gln Lys Ser Gly Thr Ser Pro Lys Arg Trp Ile Tyr
                    35                 40                 45

Asp Thr Ser Lys Leu Ala Ser Gly Val Pro Ala Arg Phe Ser Gly Ser
```

```
            50                  55                  60
Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Asn Ser Asn Pro Pro Thr
                 85                  90                  95

Phe Gly Thr Gly Thr Lys Leu Glu Leu Lys
            100                 105

<210> SEQ ID NO 55
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Val Lys Leu Val Glu Ser Gly Gly Gly Leu Val Gln Pro Gly Gly
 1               5                   10                  15

Ser Arg Lys Leu Ser Cys Ala Ala Ser Gly Phe Thr Phe Ser Asp Tyr
                 20                  25                  30

Gly Met Ala Trp Val Arg Gln Ala Pro Gly Lys Gly Pro Glu Cys Val
             35                  40                  45

Ala Phe Ile Ser Asn Leu Ala Lys Arg Ile Tyr Tyr Val Asp Thr Val
         50                  55                  60

Thr Gly Arg Phe Thr Ile Ser Arg Glu Asn Ala Lys Asn Thr Leu Tyr
 65                  70                  75                  80

Leu Glu Met Ser Ser Leu Arg Ser Glu Asp Thr Ala Met Tyr Tyr Cys
                 85                  90                  95

Thr Arg Ala Tyr Arg Tyr Ala Leu Asp Tyr Trp Gly Gln Gly Thr Thr
            100                 105                 110

Leu Thr Val Ser Ser
        115

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Lys Met Thr Gln Ser Pro Ser Ser Met Tyr Ala Ser Leu Gly
 1               5                   10                  15

Glu Arg Val Thr Ile Thr Cys Lys Ala Ser Gln Asp Ile Lys Ser Tyr
                 20                  25                  30

Leu Ser Trp Tyr Gln Gln Lys Pro Trp Lys Ser Pro Lys Thr Leu Ile
            35                  40                  45

Tyr Tyr Ala Thr Ser Leu Ala Asp Gly Val Pro Ser Arg Phe Ser Gly
        50                  55                  60

Ser Gly Ser Gly Gln His Tyr Ser Leu Thr Ile Ser Ser Leu Glu Ser
 65                  70                  75                  80

Asp Asp Thr Ala Thr Tyr Tyr Cys Leu Gln His Gly Glu Ser Pro Phe
                 85                  90                  95

Thr Phe Gly Ser Gly Thr Lys Leu Glu Ile Lys
            100                 105
```

-continued

```
<210> SEQ ID NO 57
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Val Met Ser Gln Ser Pro Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Asp Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asn Ile Leu Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
                20                  25                  30

Val Ser Trp Tyr Gln Gln Lys Pro Asp Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Leu
                85                  90                  95

Thr Phe Gly Ala Gly Thr Lys Leu Glu Leu Lys
            100                 105

<210> SEQ ID NO 59
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Gln Gln Ser Gly Pro Glu Leu Val Lys Pro Gly Ala
1               5                   10                  15
```

Ser Val Lys Ile Ser Cys Lys Ala Ser Gly Tyr Ser Phe Thr Gly Tyr
            20                  25                  30

Tyr Met Asn Trp Val Lys Gln Ser Pro Glu Lys Ser Leu Glu Trp Ile
        35                  40                  45

Gly Glu Ile Asn Pro Ser Thr Gly Gly Thr Thr Tyr Asn Gln Lys Phe
    50                  55                  60

Lys Ala Lys Ala Thr Leu Thr Val Asp Lys Ser Ser Thr Ala Tyr
65                  70                  75                  80

Met Gln Leu Lys Ser Leu Thr Phe Glu Asp Ser Ala Val Tyr Tyr Cys
                85                  90                  95

Ala Ile Tyr Asp Gly Tyr Glu Gly Phe Ala Tyr Trp Gly Gln Gly Thr
            100                 105                 110

Leu Val Thr Val Ser Ala
        115

<210> SEQ ID NO 60
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Gln Gln Ser Gly Pro Gln Leu Val Arg Pro Gly Ala
1               5                   10                  15

Ser Val Lys Ile Ser Cys Lys Thr Ser Gly Tyr Ser Phe Thr Asn Tyr
            20                  25                  30

Trp Met Gln Trp Val Lys Gln Arg Pro Gly Gln Gly Leu Glu Trp Ile
        35                  40                  45

Gly Met Ile Asp Pro Ser Asp Ser Glu Ser Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Phe Glu Asp Ser Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ala
        115                 120

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Trp Ile Ala Trp Val Lys Arg Arg Pro Gly Gln Gly Leu Glu Trp Ile
        35                  40                  45

Gly Asp Phe Tyr Pro Gly Asn Thr Ser Thr Asn Tyr Asn Glu Lys Phe
    50                  55                  60

```
Lys Thr Lys Ala Thr Leu Thr Ile Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Arg Gly Arg Gly Gly Ser Ser Tyr Trp Gly Gln Gly Thr Thr
            100                 105                 110

Leu Thr Val Ser Ser
        115
```

<210> SEQ ID NO 62
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Gln Ile Gln Leu Gln Gln Ser Gly Pro Glu Leu Val Lys Pro Gly Ala
 1               5                  10                  15

Ser Val Lys Ile Ser Cys Lys Val Ser Gly Tyr Ile Phe Thr Asp Phe
                20                  25                  30

Tyr Ile Asn Trp Val Lys Gln Arg Pro Gly Gln Gly Leu Glu Trp Ile
            35                  40                  45

Gly Trp Ile Tyr Leu Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Arg Glu Glu Arg Gly Phe Ala Tyr Trp Gly Gln Gly Thr Leu
            100                 105                 110

Val Thr Val Ser Ala
        115
```

<210> SEQ ID NO 63
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Gln Val Gln Leu Gln Gln Pro Gly Ala Glu Leu Val Arg Pro Gly Ala
 1               5                  10                  15

Ser Val Lys Leu Ser Cys Lys Ala Ser Gly Tyr Thr Phe Thr Asn Tyr
                20                  25                  30

Trp Met Asn Trp Phe Lys Gln Arg Pro Glu Gln Gly Leu Glu Trp Ile
            35                  40                  45

Gly Arg Ile Asp Pro Tyr Asp Ser Glu Thr Leu Tyr Asn Gln Lys Phe
    50                  55                  60

Lys Asp Lys Ala Ile Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Gly Gly Gly Lys Gly Gly Phe Gly Tyr Trp Gly Gln Gly Thr Leu
            100                 105                 110
```

Val Thr Val Ser Ala
        115

<210> SEQ ID NO 64
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Thr Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Lys Asp Asn Thr Lys Tyr Asp Pro Lys Phe
    50                  55                  60

Gln Gly Lys Ala Thr Ile Thr Leu Asp Thr Ser Ser Asn Ile Ala Tyr
65                  70                  75                  80

Leu Gln Leu Ser Ser Leu Thr Ser Glu Asp Thr Ala Val Tyr Phe Cys
                85                  90                  95

Ala Arg Gly His Tyr Gly Ser Ser Tyr Val Val Tyr Trp Gly Gln Gly
            100                 105                 110

Thr Leu Val Thr Val Ser Ala
        115

<210> SEQ ID NO 65
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 66
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Val Leu Met Thr Gln Thr Pro Leu Ser Leu Pro Val Ser Leu Gly
1               5                   10                  15

Glu Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ala Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 67
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Val Leu Met Thr Gln Thr Pro Leu Ser Leu Pro Val Ser Leu Gly
1               5                   10                  15

Glu Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Arg Val Ala Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 68
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Val Gln Ile Thr Gln Ser Pro Ser Phe Leu Ala Ala Ser Pro Gly
1               5                   10                  15

Glu Thr Ile Thr Ile Asn Cys Arg Ala Ser Lys Asn Ile Gly Lys Tyr
            20                  25                  30

Leu Ala Trp Phe Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro

```
                65                  70                  75                  80
Glu Asp Phe Ala Ile Tyr Tyr Cys Gln Gln His Asn Glu Tyr Pro Tyr
                    85                  90                  95

Thr Phe Gly Gly Gly Thr Lys Leu Glu Ile Lys
                100                 105

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asn Ile Leu Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Leu
                85                  90                  95

Thr Phe Gly Ala Gly Thr Lys Leu Glu Leu Lys
                100                 105

<210> SEQ ID NO 70
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Ile Gln Leu Gln Gln Ser Gly Pro Glu Leu Val Lys Pro Gly Ala
1               5                   10                  15

Ser Val Lys Ile Ser Cys Lys Val Ser Gly Tyr Ile Phe Thr Asp Phe
            20                  25                  30

Tyr Ile Asn Trp Val Lys Gln Arg Pro Gly Gln Gly Leu Glu Trp Ile
        35                  40                  45

Gly Trp Ile Tyr Leu Gly Ser Gly Asn Thr Lys Tyr Asn Glu Lys Phe
    50                  55                  60

Lys Gly Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Glu Glu Arg Gly Phe Ala Tyr Trp Gly Gln Gly Thr Leu
                100                 105                 110

Val Thr Val Ser Ala
            115

<210> SEQ ID NO 71
<211> LENGTH: 106
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 71

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Pro Thr
                85                  90                  95

Phe Gly Thr Gly Thr Lys Leu Glu Leu Lys
            100                 105

<210> SEQ ID NO 72
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Trp Ile Ala Trp Val Lys Arg Arg Pro Gly Gln Gly Leu Glu Trp Ile
        35                  40                  45

Gly Asp Phe Tyr Pro Gly Asn Thr Ser Thr Asn Tyr Asn Glu Lys Phe
    50                  55                  60

Lys Thr Lys Ala Thr Leu Thr Ile Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Gly Arg Gly Gly Ser Ser Tyr Trp Gly Gln Gly Thr Thr
            100                 105                 110

Leu Thr Val Ser Ser
        115

<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Asn Tyr
            20                  25                  30

```
Trp Met Asn Trp Phe Lys Gln Arg Pro Glu Gln Gly Leu Glu Trp Ile
            35                  40                  45

Gly Arg Ile Asp Pro Tyr Asp Ser Glu Thr Leu Tyr Asn Gln Lys Phe
 50                  55                  60

Lys Asp Lys Ala Ile Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Gly Gly Gly Lys Gly Gly Phe Gly Tyr Trp Gly Gln Gly Thr Leu
                100                 105                 110

Val Thr Val Ser Ala
        115
```

```
<210> SEQ ID NO 74
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Gln Gln Ser Gly Pro Gln Leu Val Arg Pro Gly Ala
1               5                   10                  15

Ser Val Lys Ile Ser Cys Lys Thr Ser Gly Tyr Ser Phe Thr Asn Tyr
                20                  25                  30

Trp Met Gln Trp Val Lys Gln Arg Pro Gly Gln Gly Leu Glu Trp Ile
            35                  40                  45

Gly Met Ile Asp Pro Ser Asp Ser Glu Ser Arg Leu Asn Gln Lys Phe
 50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Phe Glu Asp Ser Ala Val Tyr Tyr Cys
                85                  90                  95

Ala Arg Arg Gly Ser Pro Met Ile Thr Ser Phe Ala Tyr Trp Gly Gln
                100                 105                 110

Gly Thr Leu Val Thr Val Ser Ala
        115                 120
```

```
<210> SEQ ID NO 75
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Arg Leu Glu Trp Met
            35                  40                  45

Gly Trp Ile Tyr Leu Gly Ser Gly Asn Thr Lys Tyr Asn Glu Lys Phe
 50                  55                  60

Lys Gly Arg Val Thr Ile Thr Arg Asp Thr Ser Ala Ser Thr Ala Tyr
 65                  70                  75                  80
```

Met Glu Leu Ser Ser Leu Arg Ser Glu Asp Thr Ala Val Tyr Tyr Cys
                85                  90                  95

Ala Arg Arg Glu Glu Arg Gly Phe Ala Tyr Trp Gly Gln Gly Thr Leu
            100                 105                 110

Val Thr Val Ser Ser
        115

<210> SEQ ID NO 76
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Thr Lys Tyr Asn Glu Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Tyr Trp Gly Gln Gly Thr Leu
            100                 105                 110

Val Thr Val Ser Ser
        115

<210> SEQ ID NO 77
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Met Ile Asp Pro Ser Asp Ser Glu Ser Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ser
        115                 120

<210> SEQ ID NO 78
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Met Ile Asp Pro Ser Asp Ser Glu Ser Arg Leu Asn Gln Lys Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ser
        115                 120
```

<210> SEQ ID NO 79
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Met Ile Asp Pro Ser Asp Ser Glu Ser Arg Leu Asn Gln Lys Phe
    50                  55                  60

Lys Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ser
        115                 120
```

<210> SEQ ID NO 80
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 80

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Phe
                20                  25                  30

Tyr Ile Asn Trp Val Arg Gln Ala Pro Gly Gln Arg Leu Glu Trp Met
            35                  40                  45

Gly Trp Ile Tyr Leu Gly Ser Gly Asn Thr Lys Tyr Asn Glu Lys Phe
        50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Tyr Trp Gly Gln Gly Thr Leu
            100                 105                 110

Val Thr Val Ser Ser
        115
```

<210> SEQ ID NO 81
<211> LENGTH: 293
<212> TYPE: PRT
<213> ORGANISM: Homo sapiens

<400> SEQUENCE: 81

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
        130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240
```

```
Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Glu
    290

<210> SEQ ID NO 82
<211> LENGTH: 324
<212> TYPE: PRT
<213> ORGANISM: Mus musculus

<400> SEQUENCE: 82

Met Trp Pro Leu Ala Ala Leu Leu Leu Gly Ser Cys Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Ala Phe Asn Thr Asp Gln Gly Ser Ala Cys Ser Tyr Glu
    130                 135                 140

Glu Glu Lys Gly Gly Cys Lys Leu Val Ser Trp Phe Ser Pro Asn Glu
145                 150                 155                 160

Lys Ile Leu Ile Val Ile Phe Pro Ile Leu Ala Ile Leu Leu Phe Trp
                165                 170                 175

Gly Lys Phe Gly Ile Leu Thr Leu Lys Tyr Lys Ser Ser His Thr Asn
            180                 185                 190

Lys Arg Ile Ile Leu Leu Val Ala Gly Leu Val Leu Thr Val Ile
        195                 200                 205

Val Val Val Gly Ala Ile Leu Leu Ile Pro Gly Glu Lys Pro Val Lys
    210                 215                 220

Asn Ala Ser Gly Leu Gly Leu Ile Val Ile Ser Thr Gly Ile Leu Ile
225                 230                 235                 240

Leu Leu Gln Tyr Asn Val Phe Met Thr Ala Phe Gly Met Thr Ser Phe
                245                 250                 255

Thr Ile Ala Ile Leu Ile Thr Gln Val Leu Gly Tyr Val Leu Ala Leu
            260                 265                 270

Val Gly Leu Cys Leu Cys Ile Met Ala Cys Glu Pro Val His Gly Pro
        275                 280                 285

Leu Leu Ile Ser Gly Leu Gly Ile Ile Ala Leu Ala Glu Leu Leu Gly
    290                 295                 300

Leu Val Tyr Met Lys Phe Val Ala Ser Asn Gln Arg Thr Ile Gln Pro
```

```
305              310              315              320
Pro Arg Asn Arg

<210> SEQ ID NO 83
<211> LENGTH: 305
<212> TYPE: PRT
<213> ORGANISM: Homo sapiens

<400> SEQUENCE: 83

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Asn
    290                 295                 300

Asn
305

<210> SEQ ID NO 84
<211> LENGTH: 303
<212> TYPE: PRT
<213> ORGANISM: Mus musculus

<400> SEQUENCE: 84
```

```
Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Gly Ala
            180                 185                 190

Ile Leu Leu Ile Pro Gly Glu Lys Pro Val Lys Asn Ala Ser Gly Leu
        195                 200                 205

Gly Leu Ile Val Val Ser Thr Gly Ile Leu Ile Leu Leu Gln Tyr Asn
210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Phe Val Ala Ser Asn Gln Arg Thr Ile Gln Pro Pro Arg Asn Arg
    290                 295                 300
```

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
```

```
                   50                  55                  60
Ser Gly Ser Gly Thr Gln Phe Ser Leu Lys Ile Lys Ser Leu Gln Pro
 65                  70                  75                  80

Glu Asp Phe Gly Ser Tyr Tyr Cys Gln His His Tyr Gly Thr Pro Leu
                     85                  90                  95

Thr Phe Gly Gly Gly Thr Lys Leu Glu Leu Lys
                100                 105
```

<210> SEQ ID NO 86
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Glu Val Gln Leu Gln Gln Ser Gly Thr Glu Leu Val Lys Pro Gly Ala
  1               5                  10                  15

Ser Val Lys Leu Ser Cys Lys Ala Ser Gly Tyr Thr Phe Ile Ser Tyr
                 20                  25                  30

Trp Met His Trp Val Lys Gln Arg Pro Gly Gln Gly Leu Glu Trp Ile
             35                  40                  45

Gly Asn Ile Asn Pro Ser Ser Gly Asn Thr Asn Tyr Asn Glu Lys Phe
         50                  55                  60

Lys Thr Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Val Arg Asp Tyr Tyr Gly Asn Tyr Trp Gly Gln Gly Thr Thr Val Thr
                100                 105                 110

Val Ser Ser
        115
```

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Asp Ile Lys Met Asn Gln Ser Pro Ser Ser Leu Ser Ala Ser Leu Gly
  1               5                  10                  15

Asp Thr Ile Thr Ile Thr Cys His Ala Ser Gln Asn Ile Asn Val Trp
                 20                  25                  30

Leu Ser Trp Tyr Gln Gln Lys Pro Gly Asn Ile Pro Lys Leu Leu Ile
             35                  40                  45

Tyr Lys Ala Ser Asn Leu His Thr Gly Val Pro Ser Arg Phe Ser Gly
         50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Leu
                 85                  90                  95

Thr Phe Gly Ala Gly Thr Lys Leu Glu Leu Lys
                100                 105
```

-continued

```
<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Gln Gln Ser Gly Pro Glu Leu Val Lys Pro Gly Ala
1               5                   10                  15

Ser Val Lys Leu Ser Cys Lys Ala Ser Gly Phe Thr Phe Thr Asn Tyr
            20                  25                  30

Tyr Ile His Trp Val Lys Gln Arg Pro Gly Gln Gly Pro Glu Trp Ile
        35                  40                  45

Gly Trp Ile Tyr Leu Gly Ser Gly Asn Thr Lys Tyr Asn Glu Lys Phe
    50                  55                  60

Lys Gly Lys Ala Thr Leu Thr Ala Asp Thr Ser Ser Thr Ala Tyr
65                  70                  75                  80

Leu Gln Leu Ser Thr Leu Ile Ser Glu Asp Ser Ala Val Tyr Tyr Cys
                85                  90                  95

Ala Arg Tyr Asp Tyr Asp Leu Tyr Leu Asp Ser Trp Gly Gln Gly Thr
            100                 105                 110

Thr Val Thr Val Ser Ser
        115

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Gln Met Met Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Gly Thr Pro Leu
                85                  90                  95

Ala Phe Gly Ala Gly Thr Lys Leu Glu Ile Lys
            100                 105

<210> SEQ ID NO 90
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Gln Gln Pro Gly Ala Glu Leu Val Lys Pro Gly Thr
1               5                   10                  15
```

Ser Val Lys Leu Ser Cys Lys Ala Ser Gly Tyr Ser Phe Thr Ala Tyr
            20                  25                  30

Trp Met His Trp Val Lys Gln Arg Pro Gly Gln Gly Leu Glu Trp Ile
            35                  40                  45

Gly Asn Ile Asn Pro Ser Ser Gly Asp Ser His Tyr Asn Glu Lys Phe
50                      55                  60

Lys Ser Lys Ala Thr Leu Thr Val Asp Lys Ser Ser Ser Thr Ala Tyr
65                  70                  75                  80

Thr Gln Leu Asn Ser Leu Thr Ser Glu Asp Ser Ala Val Tyr Tyr Cys
                85                  90                  95

Ala Arg Asp Tyr Tyr Gly Ala Tyr Trp Gly His Gly Thr Leu Val Thr
            100                 105                 110

Val Ser Ala
        115

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Val Tyr Ser Tyr
            20                  25                  30

Leu Ala Trp Tyr Gln Gln Lys Gln Gly Lys Ser Pro Gln Leu Leu Val
            35                  40                  45

Tyr Lys Ala Asn Thr Leu Ala Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Thr Tyr Tyr Cys Gln His His Tyr Gly Thr Pro Leu
                85                  90                  95

Thr Phe Gly Ser Gly Thr Lys Leu Glu Ile Lys
            100                 105

<210> SEQ ID NO 92
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Gln Gln Pro Gly Ala Glu Leu Val Arg Pro Gly Ser
1               5                   10                  15

Ser Val Lys Leu Ser Cys Lys Ala Ser Gly Tyr Ser Phe Thr Thr Tyr
            20                  25                  30

Trp Met His Trp Val Lys Gln Arg Pro Gly Gln Gly Leu Glu Trp Ile
            35                  40                  45

Gly Asn Ile Asn Pro Ser Ser Gly Asp Ser His Tyr Asn Glu Lys Phe
        50                  55                  60

Lys Ser Lys Ala Thr Leu Thr Val Asp Lys Ser Ser Ser Thr Ala Tyr
65                  70                  75                  80

```
Leu Gln Leu Asn Ser Leu Thr Ser Glu Asp Ser Ala Val Tyr Tyr Cys
                85                  90                  95

Ala Arg Asp Tyr Tyr Gly Ala Tyr Trp Gly His Gly Thr Leu Val Thr
            100                 105                 110

Val Ser Ala
        115

<210> SEQ ID NO 93
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Met Ile Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Arg Ile Asn Thr Leu Gln Pro
65                  70                  75                  80

Glu Asp Leu Gly Thr Tyr Tyr Cys Gln His His Tyr Gly Ala Pro Leu
                85                  90                  95

Ser Phe Gly Gly Gly Thr Lys Leu Glu Ile Lys Arg
            100                 105

<210> SEQ ID NO 94
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Gln Gln Pro Gly Ala Glu Leu Val Arg Pro Gly Thr
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Gly Asp Ser His Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Tyr Tyr Gly Ala Tyr Trp Gly His Gly Thr Leu Val Thr
            100                 105                 110

Val Ser Ala
        115

<210> SEQ ID NO 95
```

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Ile Lys
            100                 105

<210> SEQ ID NO 96
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Ser Gly Asp Ala His Tyr Ser Glu Glu Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Tyr Gly Ala Tyr Trp Gly His Gly Thr Leu Val Thr
            100                 105                 110

Val Ser Ala
        115

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Gln Ile Asn Gln Ser Pro Ser Ser Leu Ser Ala Ser Leu Gly
1               5                   10                  15

```
Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Ile Lys
            100                 105
```

<210> SEQ ID NO 98
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asn Tyr
            20                  25                  30

His Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Met Ala Ile Leu Thr Ala Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Asp Leu Tyr Leu His Ser Trp Gly Gln Gly Thr
            100                 105                 110

Thr Val Thr Val Ser Ser
        115
```

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80
```

Glu Asp Phe Gly Ser Tyr Tyr Cys Gln His Tyr Gly Thr Pro Leu
            85                  90                  95

Thr Phe Gly Ala Gly Thr Lys Leu Glu Ile Lys
            100                 105

<210> SEQ ID NO 100
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Gln Gln Pro Gly Thr Glu Val Val Lys Pro Gly Ala
1               5                   10                  15

Ser Val Lys Leu Ser Cys Lys Ala Ser Gly Tyr Ser Phe Thr Thr Tyr
            20                  25                  30

Trp Met His Trp Val Lys Gln Arg Pro Gly Gln Gly Leu Glu Trp Ile
        35                  40                  45

Gly Asn Ile Asn Pro Ser Ser Gly Asp Ser His Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Tyr Tyr Gly Ala Tyr Trp Gly His Gly Thr Leu Val Thr
            100                 105                 110

Val Ser Ala
        115

<210> SEQ ID NO 101
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Arg His Cys Phe Asn Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Asn Tyr Pro Phe Thr
                85                  90                  95

Phe Gly Ser Gly Thr Lys Leu Glu Leu Lys
            100                 105

<210> SEQ ID NO 102
<211> LENGTH: 119
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 102

Arg Val Gln Leu Gln Gln Ser Gly Ala Glu Leu Val Arg Pro Gly Thr
1               5                   10                  15

Ser Val Lys Val Ser Cys Lys Ala Ser Ala Tyr Ala Phe Thr Asn Tyr
            20                  25                  30

Leu Ile Glu Trp Val Lys Lys Arg Pro Gly Gln Gly Leu Glu Trp Ile
        35                  40                  45

Gly Val Ile Asn Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Asp Gly Tyr Gly Ser Leu Phe Ala Tyr Trp Gly Gln Gly
            100                 105                 110

Thr Leu Val Thr Val Ser Ala
        115

<210> SEQ ID NO 103
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Ile Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Gly Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Tyr Gly Ile Pro Leu
                85                  90                  95

Thr Phe Gly Ala Gly Thr Lys Leu Glu Ile Lys
            100                 105

<210> SEQ ID NO 104
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Trp Met His Trp Val Lys Gln Arg Pro Gly Gln Gly Leu Glu Trp Ile

```
                35                  40                  45
Gly Asn Ile Asn Pro Ser Ser Gly Asn Thr Asn Tyr Asn Glu Lys Phe
         50                  55                  60

Lys Thr Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Val Arg Asp Tyr Tyr Gly Asn Tyr Trp Gly Gln Gly Thr Ser Val Thr
                100                 105                 110

Val Ser Ser
        115

<210> SEQ ID NO 105
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Asp Ile Gln Met Ile Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
                20                  25                  30

Leu Ala Trp Tyr Gln Gln Lys Leu Gly Lys Ser Pro Gln Leu Leu Val
             35                  40                  45

Tyr Asn Ala Lys Thr Leu Ala Glu Gly Val Pro Ser Arg Phe Ser Gly
         50                  55                  60

Ser Gly Ser Gly Thr His Phe Ser Leu Lys Ile Asn Ser Leu Gln Pro
 65                  70                  75                  80

Glu Asp Phe Gly Thr Tyr Tyr Cys Gln His His Tyr Gly Asn Ser Leu
                 85                  90                  95

Thr Phe Gly Ala Gly Thr Lys Leu Glu Leu Lys
                100                 105

<210> SEQ ID NO 106
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Val Gln Leu Gln Gln Ser Gly Thr Glu Leu Val Lys Pro Gly Ala
 1               5                  10                  15

Ser Val Lys Leu Ser Cys Lys Ala Ser Gly Tyr Pro Phe Thr Ser Tyr
                20                  25                  30

Trp Met His Trp Val Lys Gln Arg Pro Gly Gln Gly Leu Glu Trp Ile
             35                  40                  45

Gly Asn Ile Asn Pro Ser Ser Gly Gly Thr Asn Tyr Asn Glu Lys Phe
         50                  55                  60

Lys Thr Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Tyr Tyr Gly Asn Tyr Trp Gly Gln Gly Thr Thr Val Thr
```

-continued

```
                100                 105                 110

Val Ser Ser
        115

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Ile Lys
            100                 105

<210> SEQ ID NO 108
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Gln Gln Pro Gly Thr Glu Leu Val Lys Pro Gly Ala
1               5                   10                  15

Ser Val Lys Leu Ser Cys Lys Thr Ser Gly Tyr Ser Phe Val Thr Tyr
            20                  25                  30

Trp Met His Trp Val Lys Gln Arg Pro Gly Gln Gly Leu Glu Trp Ile
        35                  40                  45

Gly Asn Ile Asn Pro Ser Ser Gly Asp Ser His Tyr Ser Glu Lys Phe
    50                  55                  60

Lys Ser Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Val Arg Asp Tyr Tyr Gly Ala Tyr Trp Gly Gln Gly Thr Leu Val Thr
            100                 105                 110

Val Ser Ala
        115

<210> SEQ ID NO 109
<211> LENGTH: 109
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 109

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Asn
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Leu Val Phe Gly Gly Gly Thr Lys Leu Thr Val Leu
            100                 105

<210> SEQ ID NO 110
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Pro Arg Gly Lys Val Gln Glu Ser Gly Pro Gly Leu Val Lys Pro Ser
1               5                   10                  15

Gln Ser Leu Ser Leu Thr Cys Ser Val Thr Gly Tyr Ser Ile Thr Ser
            20                  25                  30

Gly Tyr Tyr Trp Asn Trp Ile Arg Gln Phe Pro Gly Asn Lys Leu Glu
        35                  40                  45

Trp Met Gly Tyr Ile Asn Tyr Asp Gly Ser Asn Asn Tyr Asn Pro Ser
    50                  55                  60

Leu Lys Asn Arg Ile Ser Ile Thr Arg Asp Thr Ser Lys Asn Gln Phe
65                  70                  75                  80

Phe Leu Lys Leu Asn Ser Val Thr Thr Glu Asp Thr Ala Thr Tyr Tyr
                85                  90                  95

Cys Ala Arg Gly Tyr Tyr Gly Ser Ser Tyr Gly Tyr Trp Tyr Phe
            100                 105                 110

Asp Val Trp Gly Thr Gly Thr Thr Val Thr Val Ser Ser
        115                 120                 125

<210> SEQ ID NO 111
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

```
Tyr Ala Ala Thr Asn Leu Ala Asp Gly Val Pro Ser Arg Phe Ser Gly
        50                  55                  60

Ser Arg Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Leu
                 85                  90                  95

Thr Phe Gly Ala Gly Thr Lys Leu Glu Ile Lys
            100                 105
```

<210> SEQ ID NO 112
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Glu Val Gln Leu Gln Gln Pro Gly Thr Glu Leu Ala Lys Pro Gly Ala
 1               5                  10                  15

Ser Val Lys Leu Ser Cys Lys Ala Ser Gly Tyr Thr Phe Ile Ser Tyr
             20                  25                  30

Trp Met His Trp Val Lys Gln Arg Pro Gly Gln Gly Leu Glu Trp Ile
         35                  40                  45

Gly Asn Ile Asn Pro Ser Ser Gly Gly Thr Asn Tyr Asn Glu Lys Phe
     50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Val Arg Asp Tyr Tyr Gly Ser Tyr Trp Gly Gln Gly Thr Thr Val Thr
            100                 105                 110

Val Ser Ser
        115
```

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Asp Ile Gln Met Thr Gln Ser Pro Ala Ser Leu Ser Ala Ser Val Gly
 1               5                  10                  15

Glu Thr Val Thr Ile Thr Cys Arg Ala Ser Glu Asn Ile Tyr Ser Tyr
             20                  25                  30

Leu Ala Trp Tyr Gln Gln Lys Gln Gly Lys Ser Pro Gln Leu Leu Val
         35                  40                  45

Tyr Lys Ala Lys Thr Leu Val Glu Gly Val Pro Ser Arg Phe Ser Gly
     50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Leu
                 85                  90                  95

Thr Phe Gly Ala Gly Thr Lys Leu Glu Ile Lys
            100                 105
```

<210> SEQ ID NO 114
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Arg Gly Pro Thr Ala Ala Thr Trp Thr Glu Leu Val Lys Pro Gly Thr
1               5                   10                  15
Ser Val Lys Leu Ser Cys Lys Ala Ser Gly Tyr Thr Phe Ile Ser Tyr
            20                  25                  30
Trp Met His Trp Val Lys Gln Arg Pro Gly Gln Gly Leu Glu Trp Ile
        35                  40                  45
Gly Asn Ile Asn Pro Ser Ser Gly Asp Thr Ser Tyr Asn Glu Lys Phe
    50                  55                  60
Lys Ser Lys Ala Thr Leu Thr Val Asp Lys Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Asp Tyr Tyr Gly Ala Tyr Trp Gly Gln Gly Thr Ser Val Thr
            100                 105                 110
Val Ser Ala
        115
```

<210> SEQ ID NO 115
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

```
Asp Ile Gln Met Met Gln Ser Pro Ala Ser Leu Ser Ala Ser Val Gly
1               5                   10                  15
Glu Thr Val Thr Ile Thr Cys Arg Ala Ser Glu Asn Ile Tyr Ser Tyr
            20                  25                  30
Leu Ala Trp Tyr Gln Gln Lys Gln Gly Lys Ser Pro Gln Leu Leu Val
        35                  40                  45
Tyr Asn Ala Lys Thr Leu Ala Glu Gly Val Pro Ser Arg Phe Ser Gly
    50                  55                  60
Ser Gly Ser Gly Thr Gln Phe Ser Leu Lys Ile Asn Ser Leu Gln Pro
65                  70                  75                  80
Glu Asp Phe Gly Asn Tyr Tyr Cys Gln His His Tyr Gly Thr Pro Leu
                85                  90                  95
Thr Phe Gly Ser Gly Thr Lys Leu Glu Leu Lys
            100                 105
```

<210> SEQ ID NO 116
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Val Gln Leu Gln Gln Pro Gly Thr Glu Leu Val Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Ile Asn Pro Ser Ser Gly Asp Ser His Tyr Ser Glu Lys Phe
    50                  55                  60

Arg Ser Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
            85                  90                  95

Ala Arg Asp Tyr Tyr Gly Ala Tyr Trp Gly His Gly Thr Leu Val Thr
                100                 105                 110

Val Ser Ala
        115

<210> SEQ ID NO 117
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Ser Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
            85                  90                  95

His Trp Val Phe Gly Gly Gly Thr Lys Leu Thr Val Leu
                100                 105

<210> SEQ ID NO 118
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Asn Val Val Pro Asn Asn Asp Gly Thr Asn Tyr Asn Glu Lys Phe
    50                  55                  60

```
Arg Asn Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Val Thr Tyr Phe Ala Tyr Trp Gly Gln Gly Thr Leu Val Thr Val
                100                 105                 110

Ser Ala

<210> SEQ ID NO 119
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Asp Ile Gln Met Met Gln Ser Pro Ala Ser Leu Ser Ala Ser Val Gly
  1               5                  10                  15

Glu Thr Val Thr Ile Thr Cys Arg Ala Ser Glu Asn Ile Tyr Ser Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Leu
                 85                  90                  95

Thr Phe Gly Ala Gly Thr Lys Leu Glu Leu Lys
                100                 105

<210> SEQ ID NO 120
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Gln Gln Ser Gly Ala Glu Leu Val Lys Pro Gly Ala
  1               5                  10                  15

Ser Val Lys Leu Ser Cys Lys Ala Ser Gly Tyr Ser Phe Thr Thr Tyr
                 20                  25                  30

Trp Met His Trp Val Lys Gln Arg Pro Gly Gln Gly Leu Glu Trp Ile
             35                  40                  45

Gly Asn Ile Asn Pro Ser Ser Gly Ser Ala His Tyr Asn Glu Lys Phe
 50                  55                  60

Lys Ser Lys Ala Thr Leu Thr Val Asp Lys Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Asp Tyr Tyr Gly Ala Tyr Trp Gly His Gly Thr Leu Val Thr
                100                 105                 110

Val Ser Ala
        115
```

```
<210> SEQ ID NO 121
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
50                  55                  60

Ser Gly Ser Gly Thr His Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Leu Lys
            100                 105

<210> SEQ ID NO 122
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Ile Ser Tyr
            20                  25                  30

Trp Ile His Trp Val Lys Gln Arg Pro Gly Gln Gly Leu Glu Trp Ile
        35                  40                  45

Gly Asn Ile Asn Pro Ser Ser Gly Ser Ser Asn Tyr Asn Glu Lys Phe
50                  55                  60

Lys Asn Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Tyr Gly Ala Tyr Trp Gly His Gly Thr Leu Val Thr
            100                 105                 110

Val Ser Ala
        115

<210> SEQ ID NO 123
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Asp Ile Gln Met Thr Gln Ser Pro Ala Ser Leu Ser Ala Ser Val Gly
1               5                   10                  15
```

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Ser Leu Gln Pro
65                  70                  75                  80

Glu Asp Phe Gly Asn Tyr Tyr Cys Gln His His Tyr Gly Thr Pro Leu
                85                  90                  95

Thr Phe Gly Ala Gly Thr Lys Leu Glu Ile Lys
                100                 105

<210> SEQ ID NO 124
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Gln Gln Pro Gly Thr Glu Leu Val Lys Pro Gly Ala
1               5                   10                  15

Ser Val Lys Leu Ser Cys Lys Ala Ser Gly Tyr Ser Phe Ile Thr Tyr
                20                  25                  30

Trp Met His Trp Val Lys Gln Arg Pro Gly Gln Gly Leu Glu Trp Ile
            35                  40                  45

Gly Asn Ile Asn Pro Ser Ser Gly Asp Ser His Tyr Ser Glu Lys Phe
 50                  55                  60

Lys Ser Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Val Arg Asp Tyr Tyr Gly Ala Tyr Trp Gly His Gly Thr Leu Val Thr
                100                 105                 110

Val Ser Ala
        115

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asp Ile Lys Ile Asn Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
                20                  25                  30

Leu Ala Trp Tyr Gln Gln Lys Gln Gly Lys Ser Pro Gln Leu Leu Val
            35                  40                  45

Tyr Lys Ala Lys Thr Leu Val Glu Gly Val Pro Ser Arg Phe Ser Gly
 50                  55                  60

Ser Gly Ser Gly Thr Gln Phe Ser Leu Lys Ile Ser Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Leu Lys
            100                 105

<210> SEQ ID NO 126
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Trp Met His Trp Val Arg Gln Arg Pro Gly Gln Gly Leu Glu Trp Ile
        35                  40                  45

Gly Asn Ile Asn Pro Ser Ser Gly Asn Thr Asn Tyr Asn Glu Lys Phe
50                  55                  60

Lys Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Val Arg Asp Tyr Tyr Gly Asn Tyr Trp Gly Gln Gly Thr Ser Val Thr
            100                 105                 110

Val Ser Ser
        115

<210> SEQ ID NO 127
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Lys Ala Lys Thr Leu Val Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Leu Lys
            100                 105

<210> SEQ ID NO 128
<211> LENGTH: 115
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 128

Glu Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Ile Ser Tyr
            20                  25                  30

Trp Ile His Trp Val Lys Gln Arg Pro Gly Gln Gly Leu Glu Trp Ile
        35                  40                  45

Gly Asn Ile Asn Pro Ser Ser Gly Gly Thr Asn Tyr Asn Glu Lys Phe
50                  55                  60

Lys Ser Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Asp Tyr Tyr Gly Asn Tyr Trp Gly Gln Gly Thr Thr Leu Thr
                100                 105                 110

Val Ser Ser
        115

<210> SEQ ID NO 129
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Asp Ile Gln Met Thr Gln Ser Pro Ala Ser Leu Ser Ala Ser Val Gly
1               5                   10                  15

Glu Thr Val Thr Ile Thr Cys Arg Ala Ser Asp Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Ser Ala Glu Gly Val Pro Ser Arg Phe Ser Gly
50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Leu Lys
                100                 105

<210> SEQ ID NO 130
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Gln Gln Pro Gly Thr Glu Leu Val Lys Pro Gly Ala
1               5                   10                  15

Ser Val Lys Leu Ser Cys Lys Ala Ser Gly Tyr Ser Phe Thr Thr Tyr
            20                  25                  30
```

```
Trp Met His Trp Val Lys Gln Arg Pro Gly Gln Gly Leu Glu Trp Ile
            35                  40                  45

Gly Asn Ile Asn Pro Ser Ser Gly Asp Ser His Tyr Asn Glu Lys Phe
 50                      55                  60

Lys Ser Lys Ala Thr Leu Thr Val Asp Lys Ser Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Asp Tyr Tyr Gly Ala Tyr Trp Gly His Gly Thr Leu Val Thr
                100                 105                 110

Val Ser Ala
        115
```

<210> SEQ ID NO 131
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Asp Ile Gln Met Thr Gln Ser Pro Ala Ser Leu Ser Ala Ser Val Gly
  1               5                  10                  15

Glu Thr Val Thr Ile Thr Cys Arg Ala Ser Glu Asn Ile Tyr Ser Tyr
                 20                  25                  30

Leu Ala Trp Tyr Gln Gln Lys Gln Gly Lys Ser Pro Gln Leu Leu Val
             35                  40                  45

Tyr Asn Ala Lys Thr Leu Ala Glu Gly Val Pro Ser Arg Phe Ser Gly
 50                  55                  60

Ser Gly Ser Gly Thr Gln Phe Ser Leu Lys Ile Asn Asn Leu Gln Pro
 65                  70                  75                  80

Glu Asp Phe Gly Ser Tyr Tyr Cys Gln His His Tyr Gly Thr Pro Leu
                 85                  90                  95

Thr Phe Gly Ala Gly Thr Lys Leu Glu Met Lys
                100                 105
```

<210> SEQ ID NO 132
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Glu Val Gln Leu Gln Gln Ser Gly Ala Glu His Val Arg Pro Gly Ser
  1               5                  10                  15

Ser Val Lys Leu Ser Cys Lys Ala Ser Gly Tyr Ser Phe Ile Thr Tyr
                 20                  25                  30

Trp Met His Trp Val Lys Gln Arg Pro Gly Gln Gly Leu Glu Trp Ile
             35                  40                  45

Gly Asn Ile Asn Pro Ser Ser Gly Asp Ser His Tyr Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95
```

Ala Arg Asp Tyr Tyr Gly Ala Tyr Trp Gly Gln Gly Thr Leu Val Thr
            100                 105                 110

Val Ser Ala
        115

<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Lys Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Thr Gly Thr Lys Leu Glu Ile Lys
            100                 105

<210> SEQ ID NO 134
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Gln Gln Ser Gly Pro Glu Leu Val Lys Pro Gly Ala
1               5                   10                  15

Ser Val Lys Ile Ser Cys Lys Ala Ser Gly Asp Ser Phe Thr Ser Asp
            20                  25                  30

His Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Arg Leu Thr Ser Glu Asp Ser Ala Val Tyr Tyr Cys
                85                  90                  95

Val Thr Tyr Asp Tyr Asp Leu Tyr Phe Asp Asn Trp Gly Gln Gly Thr
            100                 105                 110

Thr Leu Thr Val Ser Ser
        115

<210> SEQ ID NO 135
<211> LENGTH: 111
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 135

Ser Thr Leu Met Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Ile Leu Asn Ile His
65                  70                  75                  80

Pro Val Glu Glu Glu Asp Ala Ala Thr Tyr Tyr Cys Leu His Ser Arg
                85                  90                  95

Glu Leu Pro Phe Thr Phe Gly Ser Gly Thr Lys Leu Glu Leu Lys
            100                 105                 110

<210> SEQ ID NO 136
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Lys Leu Met Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Pro Asp Asp Gly Tyr Tyr Gly Phe Ala Tyr Trp Gly Gln Gly
            100                 105                 110

Thr Leu Val Thr Val Ser Ala
        115

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Val Tyr Ser Tyr
            20                  25                  30

Leu Ala Trp Tyr Gln Gln Lys Gln Gly Lys Ser Pro Gln Leu Leu Val

```
                35                  40                  45
Tyr Asn Ala Lys Thr Leu Ala Glu Gly Val Pro Ser Arg Phe Ser Gly
 50                  55                  60
Ser Gly Ser Gly Thr Gln Phe Ser Leu Lys Ile Asn Ser Leu Gln Pro
65                  70                  75                  80
Glu Asp Phe Gly Ser Tyr Tyr Cys Gln His Tyr Gly Thr Pro Leu
                85                  90                  95
Thr Phe Gly Ala Gly Thr Lys Leu Glu Leu Lys
            100                 105
```

<210> SEQ ID NO 138
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Glu Val Gln Leu Gln Gln Pro Gly Thr Glu Leu Val Lys Pro Gly Ala
1               5                   10                  15
Ser Val Lys Leu Ser Cys Lys Ala Ser Gly Tyr Ser Phe Thr Thr Tyr
            20                  25                  30
Trp Met His Trp Val Lys Gln Arg Pro Gly Gln Gly Leu Glu Trp Ile
        35                  40                  45
Gly Asn Ile Asn Pro Ser Ser Gly Asp Ser His Tyr Asn Glu Lys Phe
    50                  55                  60
Lys Ser Lys Ala Thr Leu Thr Val Asp Lys Ser Ser Thr Ala Tyr
65                  70                  75                  80
Met His Leu Ser Ser Leu Thr Ser Glu Asp Ser Ala Val Tyr Tyr Cys
                85                  90                  95
Ala Arg Asp Tyr Tyr Gly Ala Tyr Trp Gly His Gly Thr Leu Val Thr
            100                 105                 110
Val Ser Ala
        115
```

<210> SEQ ID NO 139
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Asp Ile Gln Met Thr Gln Ser Pro Ala Ser Leu Ser Ala Ser Val Gly
1               5                   10                  15
Glu Thr Val Thr Ile Thr Cys Arg Ala Ser Glu Asn Ile Tyr Ser Tyr
            20                  25                  30
Leu Ala Trp Tyr Gln Gln Lys Gln Gly Lys Ser Pro Gln Leu Leu Val
        35                  40                  45
Phe Asn Ala Lys Thr Leu Ala Glu Gly Val Pro Ser Arg Phe Ser Gly
    50                  55                  60
Ser Gly Ser Gly Thr His Phe Ser Leu Lys Ile Asn Asn Leu Gln Pro
65                  70                  75                  80
Glu Asp Phe Gly Thr Tyr Tyr Cys Gln His His Tyr Gly Thr Pro Leu
                85                  90                  95
Thr Phe Gly Ala Gly Thr Lys Leu Glu Ile Lys
```

<210> SEQ ID NO 140
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Ser Phe Ile Ser Tyr
            20                  25                  30

Trp Ile His Trp Val Lys Gln Arg Pro Gly Gln Gly Leu Glu Trp Ile
        35                  40                  45

Gly Asn Ile Asn Pro Ser Ser Gly Gly Asn Thr Tyr Asn Glu Lys Phe
    50                  55                  60

Lys Asn Lys Ala Thr Leu Thr Val Asp Lys Ser Ser Ser Thr Ala Tyr
65                  70                  75                  80

Met Gln Leu Ser Arg Leu Thr Ser Glu Asp Ser Ala Val Tyr Tyr Cys
                85                  90                  95

Thr Arg Asp Tyr Tyr Gly Ala Tyr Trp Gly Gln Gly Thr Leu Val Thr
            100                 105                 110

Val Ser Ala
        115

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Ala Phe Gly Ser Gly Thr Lys Leu Glu Leu Lys
            100                 105

<210> SEQ ID NO 142
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Glu Val Gln Leu Gln Gln Pro Gly Thr Glu Leu Val Lys Pro Gly Ala
1               5                   10                  15

Ser Val Lys Leu Ser Cys Lys Ala Ser Gly Tyr Ser Phe Ile Thr Tyr
            20                  25                  30

Trp Met His Trp Val Lys Gln Arg Pro Gly Gln Gly Leu Glu Trp Ile
        35                  40                  45

Gly Asn Ile Asn Pro Ser Gly Gly Asp Ser His Tyr Ser Glu Lys Phe
    50                  55                  60

Lys Ser Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Val Arg Asp Tyr Tyr Gly Ala Tyr Trp Gly His Gly Thr Leu Val Thr
                100                 105                 110

Val Ser Ala
        115
```

<210> SEQ ID NO 143
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

```
Asp Ile Gln Met Ile Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Phe Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Ile Lys
                100                 105
```

<210> SEQ ID NO 144
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 144

```
Glu Val Gln Leu Gln Gln Ser Gly Ala Glu Leu Val Lys Pro Gly Ala
1               5                   10                  15

Ser Val Lys Leu Ser Cys Lys Ala Ser Gly Tyr Ser Phe Ile Ser Tyr
            20                  25                  30

Trp Ile His Trp Val Lys Gln Arg Pro Gly Gln Gly Leu Glu Trp Ile
        35                  40                  45

Gly Asn Ile Asn Pro Ser Ser Gly Gly Ser Ser Tyr Asn Glu Lys Phe
    50                  55                  60
```

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asp Tyr Tyr Gly Ala Tyr Trp Gly Gln Gly Thr Leu Val Thr
                100                 105                 110

Val Ser Ala
        115

<210> SEQ ID NO 145
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Val Leu Ser Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Leu Ser Ser Met Ala Ala Glu
65                  70                  75                  80

Asp Ala Ala Thr Tyr Ser Cys Gln Gln Trp Ser Gly Asn Ser Pro Thr
                85                  90                  95

Phe Gly Ala Gly Thr Lys Leu Glu Ile Lys
                100                 105

<210> SEQ ID NO 146
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met His Trp Val Arg Gln Ala Pro Gly Lys Gly Leu Glu Trp Val
            35                  40                  45

Ala Arg Ile Arg Ser Lys Ser Ser Asn Tyr Ala Thr Tyr Tyr Ala Asp
        50                  55                  60

Ser Val Lys Asp Arg Phe Thr Ile Ser Arg Asp Asp Ser Gln Ser Ile
65                  70                  75                  80

Val Tyr Leu Gln Met Asn Asn Leu Lys Thr Glu Asp Thr Ala Met Tyr
                85                  90                  95

Tyr Cys Val Arg Ala Trp Asp Tyr Gly Ser Ser Trp Asp Tyr Phe Asp
                100                 105                 110

Tyr Trp Gly Gln Gly Thr Ser Val Thr Val Ser Ser
            115                 120

<210> SEQ ID NO 147
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Met Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Gln Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Ser
65                  70                  75                  80

Glu Asp Ile Gly Ser Tyr Tyr Cys Gln His His Tyr Gly Thr Pro Leu
                85                  90                  95

Thr Phe Gly Ala Gly Thr Lys Leu Glu Leu Lys
            100                 105

<210> SEQ ID NO 148
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Arg Gly Pro Thr Gln Gln Pro Gly Thr Glu Leu Val Lys Pro Gly Ala
1               5                   10                  15

Ser Val Lys Leu Ser Arg Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Asn Ile Asn Pro Ser Ser Gly Asp Ser His Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Tyr Tyr Gly Ala Tyr Trp Gly His Gly Thr Leu Val Thr
            100                 105                 110

Val Ser Ala
        115

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Gly Tyr Gly Met Ser
1               5

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Thr Ile Thr Ser Gly Gly Thr Tyr Thr Tyr Tyr Pro Asp Ser Val Lys
1               5                   10                  15

Gly

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ser Leu Ala Gly Asn Ala Met Asp Tyr
1               5

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Arg Ala Ser Gln Thr Ile Ser Asp Tyr Leu His
1               5                   10

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Phe Ala Ser Gln Ser Ile Ser
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Asn Gly His Gly Phe Pro Arg Thr
1               5

<210> SEQ ID NO 155
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 155

Asn Tyr Asn Met His
1               5

<210> SEQ ID NO 156
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Thr Ile Tyr Pro Gly Asn Asp Asp Thr Ser Tyr Asn Gln Lys Phe Lys
1               5                   10                  15

Asp

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Gly Tyr Arg Ala Met Asp Tyr
1               5

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Arg Ser Ser Gln Ser Ile Val Tyr Ser Asn Gly Asn Thr Tyr Leu Gly
1               5                   10                  15

<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Lys Val Ser Asn Arg Phe Ser
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160
```

Phe Gln Gly Ser His Val Pro Tyr Thr
1               5

<210> SEQ ID NO 161
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro
        130                 135

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Asp Asn Ile Tyr Ser Tyr
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Asn Ile Tyr Ser Tyr
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

```
Glu Asn Val Tyr Ser Tyr
1               5

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Glu Ser Val Asp Ser Tyr Gly Asn Ser Phe
1               5                   10

<210> SEQ ID NO 166
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gln Asn Ile Asn Val Trp
1               5

<210> SEQ ID NO 167
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Ser Val Ser Tyr
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Thr Gly Ala Val Ser Thr Ser Asn Tyr
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Thr Gly Ala Val Thr Thr Asn Asn Tyr
1               5

<210> SEQ ID NO 170
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 170

Ala Ala Thr
1

<210> SEQ ID NO 171
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asp Thr Ser
1

<210> SEQ ID NO 172
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Ala Lys
1

<210> SEQ ID NO 173
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Thr Asn
1

<210> SEQ ID NO 174
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Ala Lys
1

<210> SEQ ID NO 175
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Lys Ala Asn
1
```

```
<210> SEQ ID NO 176
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Lys Ala Ser
1

<210> SEQ ID NO 177
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Ala Ser
1

<210> SEQ ID NO 178
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asn Ala Lys
1

<210> SEQ ID NO 179
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asn Ala Gln
1

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Leu Trp Tyr Ser Asn His Leu Val
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 181

Ala Leu Trp Tyr Ser Asn His Trp Val
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Leu His Ser Arg Glu Leu Pro Phe Thr
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gln His His Tyr Gly Ala Pro Leu Ser
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln His His Tyr Gly Ile Pro Leu Thr
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gln His His Tyr Gly Asn Ser Leu Thr
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gln His His Tyr Gly Thr Pro Leu Ala
1               5

<210> SEQ ID NO 187
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 187

Gln His His Tyr Gly Thr Pro Leu Thr
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Gln Gly Gln Ser Tyr Pro Leu Thr
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln Gln Trp Ser Gly Asn Ser Pro Thr
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Gln Trp Ser Asn Tyr Pro Phe Thr
1               5

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ala Tyr Ala Phe Thr Asn Tyr Leu
1               5

<210> SEQ ID NO 192
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Asp Ser Phe Thr Ser Asp His
1               5
```

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Phe Thr Phe Asn Thr Tyr Ala
1               5

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gly Phe Thr Phe Ser Asp Tyr Gly
1               5

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Phe Thr Phe Thr Asn Tyr Tyr
1               5

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Tyr Pro Phe Thr Ser Tyr Trp
1               5

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gly Tyr Ser Phe Ile Ser Tyr Trp
1               5

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Gly Tyr Ser Phe Ile Thr Tyr Trp
1               5

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Tyr Ser Phe Thr Ala Tyr Trp
1               5

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Tyr Ser Phe Thr Asn Tyr His
1               5

<210> SEQ ID NO 201
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Tyr Ser Phe Thr Thr Tyr Trp
1               5

<210> SEQ ID NO 202
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Gly Tyr Ser Phe Val Thr Tyr Trp
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Tyr Ser Ile Thr Ser Gly Tyr Tyr
1               5

<210> SEQ ID NO 204
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Tyr Thr Phe Ile Ser Tyr Trp
1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Tyr Thr Phe Thr Ser Tyr Trp
1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Tyr Thr Phe Thr Thr Tyr Trp
1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile Asn Pro Gly Ser Gly Gly Thr
1               5

<210> SEQ ID NO 208
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ile Asn Pro Ser Gly Gly Asp Ser
1               5

<210> SEQ ID NO 209
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ile Asn Pro Ser Ser Gly Asp Ala
```

```
1               5
```

<210> SEQ ID NO 210
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

```
Ile Asn Pro Ser Ser Gly Asp Ser
1               5
```

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

```
Ile Asn Pro Ser Ser Gly Asp Thr
1               5
```

<210> SEQ ID NO 212
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

```
Ile Asn Pro Ser Ser Gly Gly Asn
1               5
```

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

```
Ile Asn Pro Ser Ser Gly Gly Ser
1               5
```

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Ile Asn Pro Ser Ser Gly Gly Thr
1               5
```

<210> SEQ ID NO 215
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

Ile Asn Pro Ser Ser Gly Asn Thr
1               5

<210> SEQ ID NO 216
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ile Asn Pro Ser Ser Gly Ser Ala
1               5

<210> SEQ ID NO 217
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ile Asn Pro Ser Ser Gly Ser Ser
1               5

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ile Asn Tyr Asp Gly Ser Asn
1               5

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ile Arg Ser Lys Ser Ser Asn Tyr Ala Thr
1               5                   10

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ile Ser Ser Gly Ser Ser Thr Ile
1               5

<210> SEQ ID NO 221

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ile Tyr Leu Gly Ser Gly Asn Thr
1               5

<210> SEQ ID NO 222
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ile Tyr Pro Gly Ser Gly Asn Thr
1               5

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Val Val Pro Asn Asn Asp Gly Thr
1               5

<210> SEQ ID NO 224
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ala Arg Asp Tyr Tyr Gly Ala Tyr
1               5

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Arg Asp Tyr Tyr Gly Asn Tyr
1               5

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226
```

```
Ala Arg Gly Asp Gly Tyr Gly Ser Leu Phe Ala Tyr
1               5                   10
```

<210> SEQ ID NO 227
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

```
Ala Arg Gly Tyr Tyr Tyr Gly Ser Ser Tyr Gly Tyr Trp Tyr Phe Asp
1               5                   10                  15

Val
```

<210> SEQ ID NO 228
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

```
Ala Arg Pro Asp Asp Gly Tyr Tyr Gly Phe Ala Tyr
1               5                   10
```

<210> SEQ ID NO 229
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

```
Ala Arg Tyr Asp Tyr Asp Leu Tyr Leu Asp Ser
1               5                   10
```

<210> SEQ ID NO 230
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

```
Ala Arg Tyr Asp Tyr Asp Leu Tyr Leu His Ser
1               5                   10
```

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

```
Ala Val Thr Tyr Phe Ala Tyr
1               5
```

<210> SEQ ID NO 232
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 232

Thr Arg Asp Tyr Tyr Gly Ala Tyr
1               5

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Val Arg Ala Trp Asp Tyr Gly Ser Ser Trp Asp Tyr Phe Asp Tyr
1               5                   10                  15

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Val Arg Asp Tyr Tyr Gly Ala Tyr
1               5

<210> SEQ ID NO 235
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Val Arg Asp Tyr Tyr Gly Asn Tyr
1               5

<210> SEQ ID NO 236
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Val Arg Asp Tyr Tyr Gly Ser Tyr
1               5

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Val Thr Tyr Asp Tyr Asp Leu Tyr Phe Asp Asn
1               5                   10
```

<210> SEQ ID NO 238
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Thr Pro Leu
                85                  90                  95

Thr Phe Gly Ala Gly Thr Lys Leu Glu Leu Lys
            100                 105

<210> SEQ ID NO 239
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Val Gln Leu Gln Gln Pro Gly Thr Glu Leu Val Lys Pro Gly Ala
1               5                   10                  15

Ser Val Lys Leu Ser Cys Lys Ala Ser Gly Tyr Ser Phe Thr Thr Tyr
            20                  25                  30

Trp Met His Trp Val Lys Gln Arg Pro Gly Gln Gly Leu Glu Trp Ile
        35                  40                  45

Gly Asn Ile Asn Pro Ser Ser Gly Asp Ser His Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Asp Tyr Tyr Gly Ala Tyr Trp Gly His Gly Thr Leu Val Thr
            100                 105                 110

Val Ser Ala
        115

<210> SEQ ID NO 240
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser
            115

<210> SEQ ID NO 241
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys
            100                 105

<210> SEQ ID NO 242
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Gln Val Gln Leu Gln Gln Pro Gly Ala Glu Leu Val Lys Pro Gly Ala
1               5                   10                  15

Ser Val Met Met Ser Cys Lys Ala Ser Gly Tyr Thr Phe Thr Asn Tyr
            20                  25                  30

Asn Met His Trp Val Lys Gln Thr Pro Gly Gln Gly Leu Glu Trp Ile
        35                  40                  45

Gly Thr Ile Tyr Pro Gly Asn Asp Asp Thr Ser Tyr Asn Gln Lys Phe
    50                  55                  60

```
Lys Asp Lys Ala Thr Leu Thr Ala Asp Lys Ser Ser Ser Ala Ala Tyr
 65                  70                  75                  80

Met Gln Leu Ser Ser Leu Thr Ser Glu Asp Ser Ala Val Tyr Tyr Cys
                 85                  90                  95

Ala Arg Gly Gly Tyr Arg Ala Met Asp Tyr Trp Gly Gln Thr Ser Val
            100                 105                 110

Thr Val Ser Ser
        115

<210> SEQ ID NO 243
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Asp Val Leu Met Thr Gln Thr Pro Leu Ser Leu Pro Val Ser Leu Gly
  1               5                  10                  15

Asp Gln Ala Ser Ile Ser Cys Arg Ser Gln Ser Ile Val Tyr Ser
             20                  25                  30

Asn Gly Asn Thr Tyr Leu Gly Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr His Cys Phe Gln Gly
                 85                  90                  95

Ser His Val Pro Tyr Thr Phe Gly Gly Gly Thr Lys Val Glu Ile Lys
            100                 105                 110

<210> SEQ ID NO 244
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gln Met Gln Leu Val Gln Ser Gly Ala Glu Val Lys Lys Thr Gly Ser
  1               5                  10                  15

Ser Val Lys Val Ser Cys Lys Ala Ser Gly Phe Asn Ile Lys Asp Tyr
             20                  25                  30

Tyr Leu His Trp Val Arg Gln Ala Pro Gly Gln Ala Leu Glu Trp Met
             35                  40                  45

Gly Trp Ile Asp Pro Asp Gln Gly Asp Thr Glu Tyr Ala Gln Lys Phe
 50                  55                  60

Gln Asp Arg Val Thr Ile Thr Arg Asp Arg Ser Met Ser Thr Ala Tyr
 65                  70                  75                  80

Met Glu Leu Ser Ser Leu Arg Ser Glu Asp Thr Ala Met Tyr Tyr Cys
                 85                  90                  95

Asn Ala Ala Tyr Gly Ser Ser Tyr Pro Met Asp Tyr Trp Gly Gln
            100                 105                 110

Gly Thr Thr Val Thr Val
        115
```

```
<210> SEQ ID NO 245
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Asn Ile Gln Met Thr Gln Ser Pro Ser Ala Met Ser Ala Ser Val Gly
1               5                   10                  15

Asp Arg Val Thr Ile Thr Cys Lys Ala Ser Gln Asp Ile His Arg Tyr
            20                  25                  30

Leu Ser Trp Phe Gln Gln Lys Pro Gly Lys Val Pro Lys His Leu Ile
        35                  40                  45

Tyr Arg Ala Asn Arg Leu Val Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Tyr
                85                  90                  95

Thr Phe Gly Gly Gly Thr Lys Val Glu Ile Lys
            100                 105

<210> SEQ ID NO 246
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Ile Asn Trp Val Arg Gln Ala Pro Gly Gln Arg Leu Glu Trp Met
        35                  40                  45

Gly Trp Ile Tyr Thr Gly Ser Gly Asn Thr Lys Tyr Asn Glu Lys Phe
50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Tyr Trp Gly Gln Gly Thr Leu
            100                 105                 110

Val Thr Val Ser Ser
        115

<210> SEQ ID NO 247
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gln Val Gln Leu Val Gln Ser Gly Ala Glu Val Lys Lys Pro Gly Ala
```

```
                1               5                   10                  15
Ser Val Lys Val Ser Cys Lys Ala Ser Gly Tyr Thr Phe Thr Asp Ile
                20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Val Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Asp Arg Gly Phe Ala Tyr Trp Gly Gln Gly Thr Leu
                100                 105                 110

Val Thr Val Ser Ser
            115

<210> SEQ ID NO 248
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asn
                20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Val Trp Gly Gln Gly Thr Leu
                100                 105                 110

Val Thr Val Ser Ser
            115

<210> SEQ ID NO 249
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Thr Lys Tyr Asn Glu Lys Phe
```

```
            50                  55                  60
Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Glu Arg Gly Phe Ala Tyr Trp Gly Gln Gly Thr Leu
            100                 105                 110

Val Thr Val Ser Ser
        115

<210> SEQ ID NO 250
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp His
                20                  25                  30

Tyr Ile Asn Trp Val Arg Gln Ala Pro Gly Gln Arg Leu Glu Trp Met
            35                  40                  45

Gly Trp Ile Tyr Leu Gly Ser Gly Asn Thr Lys Tyr Asn Glu Lys Phe
        50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Glu Asp Arg Gly Phe Ala Tyr Trp Gly Gln Gly Thr Leu
            100                 105                 110

Val Thr Val Ser Ser
        115

<210> SEQ ID NO 251
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Asn
                20                  25                  30

Tyr Ile Asn Trp Val Arg Gln Ala Pro Gly Gln Arg Leu Glu Trp Met
            35                  40                  45

Gly Trp Val Tyr Leu Gly Ser Gly Asn Thr Lys Tyr Asn Glu Lys Phe
        50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Glu Glu Arg Gly Phe Ala Tyr Trp Gly Gln Gly Thr Leu
```

-continued

Val Thr Val Ser Ser
        115

<210> SEQ ID NO 252
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Leu
            20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Tyr Trp Gly Gln Gly Thr Leu
            100                 105                 110

Val Thr Val Ser Ser
        115

<210> SEQ ID NO 253
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asn
            20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Pro Trp Gly Gln Gly Thr Leu
            100                 105                 110

Val Thr Val Ser Ser
        115

<210> SEQ ID NO 254
<211> LENGTH: 117
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Ile Asn Trp Val Arg Gln Ala Pro Gly Gln Arg Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Tyr Trp Gly Gln Gly Thr Leu
            100                 105                 110

Val Thr Val Ser Ser
        115

<210> SEQ ID NO 255
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Tyr Ile His Trp Val Arg Gln Ala Pro Gly Gln Arg Leu Glu Trp Met
        35                  40                  45

Gly Trp Ile Tyr Leu Gly Ser Gly Asn Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Asp Gly Phe Ala His Trp Gly Gln Gly Thr Leu
            100                 105                 110

Val Thr Val Ser Ser
        115

<210> SEQ ID NO 256
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Thr Asp Asn
            20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Thr Lys Tyr Asn Glu Lys Phe
50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Lys Glu Arg Gly Phe Ala Tyr Trp Gly Gln Gly Thr Leu
            100                 105                 110

Val Thr Val Ser Ser
            115

<210> SEQ ID NO 257
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Thr
            20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Ile Lys Tyr Asn Glu Lys Phe
50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Tyr Trp Gly Gln Gly Thr Leu
            100                 105                 110

Val Thr Val Ser Ser
            115

<210> SEQ ID NO 258
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile Asn Trp Val Arg Gln Ala Pro Gly Gln Arg Leu Glu Trp Met
        35                  40                  45

Gly Trp Ile Tyr Leu Gly Ser Gly Asn Thr Lys Tyr Asn Glu Lys Phe
50                  55                  60

```
Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Glu Asp Arg Gly Phe Ala Tyr Trp Gly Gln Gly Thr Leu
            100                 105                 110

Val Thr Val Ser Ser
        115

<210> SEQ ID NO 259
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Thr
                 20                  25                  30

Tyr Ile Asn Trp Val Arg Gln Ala Pro Gly Gln Arg Leu Glu Trp Met
             35                  40                  45

Gly Trp Ile Tyr Leu Gly Ser Gly Asn Val Lys Tyr Asn Glu Lys Phe
         50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Glu Glu Arg Gly Phe Ala His Trp Gly Gln Gly Thr Leu
            100                 105                 110

Val Thr Val Ser Ser
        115

<210> SEQ ID NO 260
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Leu
                 20                  25                  30

Tyr Ile Asn Trp Val Arg Gln Ala Pro Gly Gln Arg Leu Glu Trp Met
             35                  40                  45

Gly Trp Ile Tyr Leu Gly Ser Gly Asn Val Lys Tyr Asn Glu Lys Phe
         50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Glu Glu Arg Gly Phe Ala Tyr Trp Gly Gln Gly Thr Leu
            100                 105                 110
```

Val Thr Val Ser Ser
        115

<210> SEQ ID NO 261
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Ile Asn Trp Val Arg Gln Ala Pro Gly Gln Arg Leu Glu Trp Met
        35                  40                  45

Gly Trp Ile Tyr Gly Gly Ser Gly Asn Thr Lys Tyr Asn Glu Lys Phe
    50                  55                  60

Lys Gly Arg Val Thr Ile Thr Arg Asp Thr Ser Ala Ser Thr Thr Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Asp Gly Phe Ala Tyr Trp Gly Gln Gly Thr Leu
            100                 105                 110

Val Thr Val Ser Ser
        115

<210> SEQ ID NO 262
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Ile Asn Trp Val Arg Gln Ala Pro Gly Gln Arg Leu Glu Trp Met
        35                  40                  45

Gly Trp Ile Tyr Gly Gly Ser Gly Asn Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Tyr Trp Gly Gln Gly Thr Leu
            100                 105                 110

Val Thr Val Ser Ser
        115

<210> SEQ ID NO 263
<211> LENGTH: 117
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 263

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Ile Asn Trp Val Arg Gln Ala Pro Gly Gln Arg Leu Glu Trp Met
            35                  40                  45

Gly Trp Ile Tyr Leu Gly Ser Gly Asn Val Lys Tyr Asn Glu Lys Phe
50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Ile Glu Arg Gly Phe Ala Tyr Trp Gly Gln Gly Thr Leu
            100                 105                 110

Val Thr Val Ser Ser
        115

<210> SEQ ID NO 264
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Ile Asn Trp Val Arg Gln Ala Pro Gly Gln Arg Leu Glu Trp Met
            35                  40                  45

Gly Trp Val Tyr Leu Gly Ser Gly Asn Thr Lys Tyr Asn Glu Lys Phe
50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Glu Arg Gly Phe Ala Val Trp Gly Gln Gly Thr Leu
            100                 105                 110

Val Thr Val Ser Ser
        115

<210> SEQ ID NO 265
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser Gln Ser Ile Leu Tyr Ser
             20                  25                  30

Ser Asn Gln Lys Asn Tyr Leu Ala Trp Tyr Gln Gln Lys Pro Gly Gln
         35                  40                  45

Pro Pro Lys Leu Leu Ile Tyr Trp Ala Ser Val Arg Asp Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                 85                  90                  95

Tyr Tyr His Tyr Pro Leu Thr Phe Gly Gln Gly Thr Lys Val Glu Ile
            100                 105                 110

Lys
```

```
<210> SEQ ID NO 266
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
             20                  25                  30

Asn Gln Lys Tyr Tyr Leu Ala Trp Tyr Gln Gln Lys Pro Gly Gln Pro
         35                  40                  45

Pro Lys Leu Leu Ile Tyr Trp Ala Ser Thr Arg Asp Ser Gly Val Pro
 50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Phe
                 85                  90                  95

Tyr Ser Tyr Pro Leu Thr Phe Gly Gln Gly Thr Lys Val Glu Ile Lys
            100                 105                 110
```

```
<210> SEQ ID NO 267
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Tyr Ser Ser
             20                  25                  30

Asn Lys Lys Asn Tyr Leu Ala Trp Tyr Gln Gln Lys Pro Gly Gln Pro
         35                  40                  45

Pro Lys Leu Leu Ile Tyr Trp Ala Ser Ser Arg Asp Ser Gly Val Pro
 50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
```

```
                        85                  90                  95

Tyr Ser Tyr Pro Leu Thr Phe Gly Gln Gly Thr Lys Val Glu Ile Lys
            100                 105                 110

<210> SEQ ID NO 268
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Asn Gln Lys Asn Tyr Leu Ala Trp Tyr Gln Gln Lys Pro Gly Gln Pro
        35                  40                  45

Pro Lys Leu Leu Ile Tyr Trp Ala Ser Val Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Phe
                85                  90                  95

Tyr Ser Tyr Pro Leu Thr Phe Gly Gln Gly Thr Lys Val Glu Ile Lys
            100                 105                 110

<210> SEQ ID NO 269
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Ser Gln Lys Asn Tyr Leu Ala Trp Tyr Gln Gln Lys Pro Gly Gln Pro
        35                  40                  45

Pro Lys Leu Leu Ile Tyr Trp Ala Ser Val Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Tyr Pro Leu Thr Phe Gly Gln Gly Thr Lys Val Glu Ile Lys
            100                 105                 110

<210> SEQ ID NO 270
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Lys Lys Asn Tyr Leu Ala Trp Tyr Gln Gln Lys Pro Gly Gln
            35                  40                  45

Pro Pro Lys Leu Leu Ile Tyr Trp Ala Ser Val Arg Asp Ser Gly Val
65              70                  75                  80

Pro Asp Arg Phe Ser Gly Ser Gly Ser Gly Thr Asp Phe Thr Leu Thr
65              70                  75                  80

Ile Ser Ser Leu Gln Ala Glu Asp Val Ala Val Tyr Tyr Cys Gln Gln
                85                  90                  95

Tyr Tyr His Tyr Pro Leu Thr Phe Gly Gln Gly Thr Lys Val Glu Ile
            100                 105                 110

Lys

<210> SEQ ID NO 271
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Val Ser Ser
                20                  25                  30

Ser Gln Lys Asn Tyr Leu Ala Trp Tyr Gln Gln Lys Pro Gly Gln Pro
            35                  40                  45

Pro Lys Leu Leu Ile Tyr Trp Ala Ser Val Arg Asp Ser Gly Val Pro
50                  55                  60

Asp Arg Phe Ser Gly Ser Gly Ser Gly Thr Asp Phe Thr Leu Thr Ile
65              70                  75                  80

Ser Ser Leu Gln Ala Glu Asp Val Ala Val Tyr Tyr Cys Gln Gln Tyr
                85                  90                  95

Tyr Ser Tyr Pro Leu Thr Phe Gly Gln Gly Thr Lys Val Glu Ile Lys
            100                 105                 110

<210> SEQ ID NO 272
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
                20                  25                  30

Ser Gln Lys Asn Tyr Leu Ala Trp Tyr Gln Gln Lys Pro Gly Gln Pro
            35                  40                  45

Pro Lys Leu Leu Ile Tyr Trp Ala Ser Thr Arg Asp Ser Gly Val Pro
50                  55                  60

```
Asp Arg Phe Ser Gly Ser Gly Ser Gly Thr Asp Phe Thr Leu Thr Ile
 65                  70                  75                  80

Ser Ser Leu Gln Ala Glu Asp Val Ala Val Tyr Tyr Cys Gln Gln Phe
                 85                  90                  95

Tyr Ser Tyr Pro Leu Thr Phe Gly Gln Gly Thr Lys Val Glu Ile Lys
            100                 105                 110

<210> SEQ ID NO 273
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Val Arg Asp Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Phe Tyr Ser Tyr Pro Leu Thr Phe Gly Gln Gly Thr Lys Val Glu Ile
            100                 105                 110

Lys

<210> SEQ ID NO 274
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Lys
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Val Arg Asp Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Leu Tyr Ser Tyr Pro Leu Thr Phe Gly Gln Gly Thr Lys Val Glu Ile
            100                 105                 110

Lys

<210> SEQ ID NO 275
```

<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Val Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr His Tyr Pro Leu Thr Phe Gly Gln Gly Thr Lys Val Glu Ile
            100                 105                 110

Lys

<210> SEQ ID NO 276
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Ser Gln Lys Asn Tyr Leu Ala Trp Tyr Gln Gln Lys Pro Gly Gln Pro
        35                  40                  45

Pro Lys Leu Leu Ile Tyr Trp Ala Ser Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Tyr Pro Leu Thr Phe Gly Gln Gly Thr Lys Val Glu Ile Lys
            100                 105                 110

<210> SEQ ID NO 277
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Thr Ser

```
            20                  25                  30

Asn Gln Lys Asn Tyr Leu Ala Trp Tyr Gln Gln Lys Pro Gly Gln Pro
            35                  40                  45

Pro Lys Leu Leu Ile Tyr Trp Ala Ser Ile Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Tyr Pro Leu Thr Phe Gly Gln Gly Thr Lys Val Glu Ile Lys
                100                 105                 110

<210> SEQ ID NO 278
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Arg Lys Asn Tyr Leu Ala Trp Tyr Gln Gln Lys Pro Gly Gln
            35                  40                  45

Pro Pro Lys Leu Leu Ile Tyr Trp Ala Ser Ser Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr His Tyr Pro Leu Thr Phe Gly Gln Gly Thr Lys Val Glu Ile
                100                 105                 110

Lys

<210> SEQ ID NO 279
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Ser Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

```
Phe Tyr Ser Tyr Pro Leu Thr Phe Gly Gln Gly Thr Lys Val Glu Ile
                100                 105                 110
Lys

<210> SEQ ID NO 280
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ser Ser
            20                  25                  30

Asn Asn Lys Asn Tyr Leu Ala Trp Tyr Gln Gln Lys Pro Gly Gln Pro
        35                  40                  45

Pro Lys Leu Leu Ile Tyr Trp Ala Ser Val Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Tyr Pro Leu Thr Phe Gly Gln Gly Thr Lys Val Glu Ile Lys
                100                 105                 110

<210> SEQ ID NO 281
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Tyr Thr Ser
            20                  25                  30

Asn Gln Lys Asn Tyr Leu Ala Trp Tyr Gln Gln Lys Pro Gly Gln Pro
        35                  40                  45

Pro Lys Leu Leu Ile Tyr Trp Ala Ser Thr Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Tyr Pro Leu Thr Phe Gly Gln Gly Thr Lys Val Glu Ile Lys
                100                 105                 110

<210> SEQ ID NO 282
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 282

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Asn
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Asp Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr His Tyr Pro Leu Thr Phe Gly Gln Gly Thr Lys Val Glu Ile
            100                 105                 110

Lys

<210> SEQ ID NO 283
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Lys
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Val Arg Asp Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Tyr Ser Tyr Pro Leu Thr Phe Gly Gln Gly Thr Lys Val Glu Ile
            100                 105                 110

Lys

<210> SEQ ID NO 284
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Tyr Ser Ser
            20                  25                  30

Ser Gln Lys Asn Tyr Leu Ala Trp Tyr Gln Gln Lys Pro Gly Gln Pro
        35                  40                  45

-continued

```
Pro Lys Leu Leu Ile Tyr Trp Ala Ser Val Arg Asp Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ser Tyr Pro Leu Thr Phe Gly Gln Gly Thr Lys Val Glu Ile Lys
            100                 105                 110
```

<210> SEQ ID NO 285
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Asn
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Val Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr His Tyr Pro Leu Thr Phe Gly Gln Gly Thr Lys Val Glu Ile
            100                 105                 110

Lys
```

<210> SEQ ID NO 286
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Pro Pro Lys Leu Leu Ile Tyr Trp Ala Ser Val Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr His Tyr Pro Leu Thr Phe Gly Gln Gly Thr Lys Val Glu Ile
            100                 105                 110

Lys
```

<210> SEQ ID NO 287
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asn Ile Gly Lys Tyr
            20                  25                  30

Leu Ala Trp Phe Gln Gln Lys Pro Gly Lys Ala Pro Lys Ser Leu Ile
        35                  40                  45

Tyr Ser Gly Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 288
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Asp Val Gln Ile Thr Gln Ser Pro Ser Ser Leu Ser Ala Ser Val Gly
1               5                   10                  15

Asp Arg Val Thr Ile Thr Cys Arg Ala Ser Lys Asn Ile Gly Lys Tyr
            20                  25                  30

Leu Ala Trp Phe Gln Gln Lys Pro Gly Lys Ala Pro Lys Ser Leu Ile
        35                  40                  45

Tyr Ser Gly Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
                85                  90                  95

Thr Phe Gly Gly Gly Thr Lys Val Glu Ile Lys
            100                 105

<210> SEQ ID NO 289
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Lys Asn Ile Gly Lys Tyr
             20                  25                  30

Leu Ala Trp Phe Gln Gln Lys Pro Gly Lys Ala Pro Lys Ser Leu Ile
         35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
             85                  90                  95

Thr Phe Gly Gly Gly Thr Lys Val Glu Ile Lys
            100                 105

<210> SEQ ID NO 290
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Asp Val Gln Ile Thr Gln Ser Pro Ser Ser Leu Ser Ala Ser Val Gly
1               5                   10                  15

Asp Arg Val Thr Ile Thr Cys Arg Ala Ser Lys Asn Ile Gly Lys Tyr
             20                  25                  30

Leu Ala Trp Phe Gln Gln Lys Pro Gly Lys Ala Pro Lys Ser Leu Ile
         35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
             85                  90                  95

Thr Phe Gly Gly Gly Thr Lys Val Glu Ile Lys
            100                 105

<210> SEQ ID NO 291
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Asp Val Gln Ile Thr Gln Ser Pro Ser Ser Leu Ser Ala Ser Val Gly
1               5                   10                  15

Asp Arg Val Thr Ile Thr Cys Arg Ala Ser Lys Asn Ile Gly Lys Tyr
             20                  25                  30

Leu Ala Trp Phe Gln Gln Lys Pro Gly Lys Thr Asn Lys Leu Leu Ile
         35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Tyr
             85                  90                  95
```

```
Thr Phe Gly Gly Gly Thr Lys Val Glu Ile Lys
            100                 105

<210> SEQ ID NO 292
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Met
        35                  40                  45

Gly Met Ile Asp Pro Ser Asp Ser Glu Ser Arg Leu Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ser
        115                 120

<210> SEQ ID NO 293
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Thr Asn Tyr
            20                  25                  30

Trp Met Gln Trp Val Arg Gln Ala Pro Gly Gln Gly Leu Glu Trp Met
        35                  40                  45

Gly Met Ile Asp Pro Ser Asp Ser Glu Ser Arg Leu Asn Gln Lys Phe
    50                  55                  60

Lys Asp Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ser
        115                 120

<210> SEQ ID NO 294
<211> LENGTH: 120
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 294

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met Gln Trp Val Arg Gln Ala Pro Gly Gln Gly Leu Glu Trp Ile
        35                  40                  45

Gly Met Ile Asp Pro Ser Asp Ser Glu Ser Arg Leu Asn Gln Lys Phe
    50                  55                  60

Lys Asp Arg Ala Thr Leu Thr Val Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ser
        115                 120

<210> SEQ ID NO 295
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Ser Phe Thr Asn Tyr
            20                  25                  30

Trp Met Gln Trp Val Arg Gln Ala Pro Gly Gln Gly Leu Glu Trp Ile
        35                  40                  45

Gly Met Ile Asp Pro Ser Asp Ser Glu Ser Arg Leu Asn Gln Lys Phe
    50                  55                  60

Lys Asp Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ser
        115                 120

<210> SEQ ID NO 296
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Gln Val Gln Leu Gln Gln Ser Gly Ala Glu Val Lys Lys Pro Gly Ala
1               5                   10                  15

Ser Val Lys Val Ser Cys Lys Thr Ser Gly Tyr Ser Phe Thr Asn Tyr

```
            20                  25                  30
Trp Met Gln Trp Val Arg Gln Ala Pro Gly Gln Gly Leu Glu Trp Ile
            35                  40                  45

Gly Met Ile Asp Pro Ser Asp Ser Glu Ser Arg Leu Asn Gln Lys Phe
    50                  55                  60

Lys Asp Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ser
            115                 120

<210> SEQ ID NO 297
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Asp Ile Gln Met Thr Gln Ser Pro Ser Ser Val Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Leu
                85                  90                  95

Thr Phe Gly Gln Gly Thr Lys Leu Glu Ile Lys
            100                 105

<210> SEQ ID NO 298
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Asp Ile Gln Ile Thr Gln Ser Pro Ser Ser Val Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Gln Lys Pro Gly Lys Ala Pro Lys Leu Leu Ile
            35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Leu
```

85                  90                  95

Thr Phe Gly Gln Gly Thr Lys Leu Glu Ile Lys
                100                 105

<210> SEQ ID NO 299
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Asp Ile Gln Ile Thr Gln Ser Pro Ser Ser Val Ser Ala Ser Val Gly
1               5                   10                  15

Asp Arg Val Thr Ile Thr Cys His Ala Ser Gln Asn Ile Asn Val Trp
            20                  25                  30

Leu Ser Trp Tyr Gln Gln Lys Pro Gly Lys Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Leu
                85                  90                  95

Thr Phe Gly Gln Gly Thr Lys Leu Glu Ile Lys
                100                 105

<210> SEQ ID NO 300
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

His Ile His Trp Val Arg Gln Ala Pro Gly Gln Arg Leu Glu Trp Met
        35                  40                  45

Gly Trp Ile Tyr Pro Gly Ser Gly Asn Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Asp Leu Tyr Leu His Ser Trp Gly Gln Gly Thr
                100                 105                 110

Leu Val Thr Val Ser Ser
        115

<210> SEQ ID NO 301
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 301

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

His Ile His Trp Val Arg Gln Ala Pro Gly Gln Arg Leu Glu Trp Ile
        35                  40                  45

Gly Trp Ile Tyr Pro Gly Ser Gly Asn Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Asp Leu Tyr Leu His Ser Trp Gly Gln Gly Thr
            100                 105                 110

Leu Val Thr Val Ser Ser
        115

<210> SEQ ID NO 302
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

His Ile His Trp Val Arg Gln Ala Pro Gly Gln Arg Leu Glu Trp Ile
        35                  40                  45

Gly Trp Ile Tyr Pro Gly Ser Gly Asn Thr Lys Tyr Asn Glu Lys Phe
    50                  55                  60

Lys Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Asp Leu Tyr Leu His Ser Trp Gly Gln Gly Thr
            100                 105                 110

Leu Val Thr Val Ser Ser
        115

<210> SEQ ID NO 303
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asn Tyr
            20                  25                  30

His Ile His Trp Val Arg Gln Ala Pro Gly Gln Arg Leu Glu Trp Ile
            35                  40                  45

Gly Trp Ile Tyr Pro Gly Ser Gly Asn Thr Lys Tyr Asn Glu Lys Phe
 50                  55                  60

Lys Gly Met Ala Thr Leu Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Asp Leu Tyr Leu His Ser Trp Gly Gln Gly Thr
            100                 105                 110

Leu Val Thr Val Ser Ser
        115

<210> SEQ ID NO 304
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Asn Tyr
            20                  25                  30

His Ile His Trp Val Lys Gln Ala Pro Gly Gln Arg Leu Glu Trp Ile
            35                  40                  45

Gly Trp Ile Tyr Pro Gly Ser Gly Asn Thr Lys Tyr Asn Glu Lys Phe
 50                  55                  60

Lys Gly Met Ala Thr Leu Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Asp Leu Tyr Leu His Ser Trp Gly Gln Gly Thr
            100                 105                 110

Leu Val Thr Val Ser Ser
        115

<210> SEQ ID NO 305
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Gln Met Gln Leu Val Gln Ser Gly Ala Glu Val Lys Lys Thr Gly Ser
 1               5                  10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
            35                  40                  45

Gly Trp Ile Asp Pro Asp Gln Gly Asp Thr Glu Tyr Ala Gln Lys Phe
 50                  55                  60

Gln Asp Arg Val Thr Ile Thr Arg Asp Arg Ser Met Ser Thr Ala Tyr
 65                  70                  75                  80

```
Met Glu Leu Ser Ser Leu Arg Ser Glu Asp Thr Ala Met Tyr Tyr Cys
                85                  90                  95

Asn Ala Ala Tyr Gly Ser Ser Tyr Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 306
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 306

Gln Met Thr Gln Ser Pro Ser Ala Met Ser Ala Ser Val Gly Asp Arg
1               5                   10                  15

Val Thr Ile Thr Cys Lys Ala Ser Gln Asp Ile His Arg Tyr Leu Ser
            20                  25                  30

Trp Phe Gln Gln Lys Pro Gly Lys Val Pro Lys His Leu Ile Tyr Arg
        35                  40                  45

Ala Asn Arg Leu Val Ser Gly Val Pro Ser Arg Phe Ser Gly Ser Gly
    50                  55                  60

Ser Gly Thr Glu Phe Thr Leu Thr Ile Ser Ser Leu Gln Pro Glu Asp
65                  70                  75                  80

Phe Ala Thr Tyr Tyr Cys Leu Gln Tyr Asp Glu Phe Pro Tyr Thr Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
        210

<210> SEQ ID NO 307
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Gln Met Gln Leu Val Gln Ser Gly Ala Glu Val Lys Lys Thr Gly Ser
1               5                   10                  15

Ser Val Lys Val Ser Cys Lys Ala Ser Gly Phe Asn Ile Lys Asp Tyr
            20                  25                  30

Tyr Leu His Trp Val Arg Gln Ala Pro Gly Gln Ala Leu Glu Trp Met
        35                  40                  45

Gly Trp Ile Asp Pro Asp Gln Gly Asp Thr Glu Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Asn Ala Ala Tyr Gly Ser Ser Ser Tyr Pro Met Asp Tyr Trp Gly Gln
            100                 105                 110

Gly Thr Thr Val Thr Val Ser Ser Ala Ser Thr Lys Gly Pro Ser Val
        115                 120                 125
```

```
Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 308
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Gln Met Thr Gln Ser Pro Ser Ala Met Ser Ala Ser Val Gly Asp Arg
1               5                   10                  15

Val Thr Ile Thr Cys Lys Ala Ser Gln Asp Ile His Arg Tyr Leu Ser
            20                  25                  30

Trp Phe Gln Gln Lys Pro Gly Lys Val Pro Lys His Leu Ile Tyr Arg
        35                  40                  45
```

Ala Asn Arg Leu Val Ser Gly Val Pro Ser Arg Phe Ser Gly Ser Gly
 50                  55                  60

Ser Gly Thr Glu Phe Thr Leu Thr Ile Ser Ser Leu Gln Pro Glu Asp
 65                  70                  75                  80

Phe Ala Thr Tyr Tyr Cys Leu Gln Tyr Asp Glu Phe Pro Tyr Thr Phe
                 85                  90                  95

Gly Gly Gly Thr Lys Val Glu Ile Lys Arg Thr Val Ala Ala Pro Ser
             100                 105                 110

Val Phe Ile Phe Pro Pro Ser Asp Glu Gln Leu Lys Ser Gly Thr Ala
         115                 120                 125

Ser Val Val Cys Leu Leu Asn Asn Phe Tyr Pro Arg Glu Ala Lys Val
 130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
             165                 170                 175

Leu Thr Leu Ser Lys Ala Asp Tyr Glu Lys His Lys Val Tyr Ala Cys
             180                 185                 190

Glu Val Thr His Gln Gly Leu Ser Ser Pro Val Thr Lys Ser Phe Asn
             195                 200                 205

Arg Gly Glu Cys
    210

<210> SEQ ID NO 309
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Asp Val Gln Ile Thr Gln Ser Pro Ser Phe Leu Ala Ala Ser Pro Gly
 1               5                  10                  15

Glu Thr Ile Thr Ile Asn Cys Arg Ala Ser Lys Asn Ile Gly Lys Tyr
             20                  25                  30

Leu Ala Trp Phe Gln Glu Lys Pro Gly Lys Thr Asn Lys Leu Leu Ile
         35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Ile Tyr Tyr Cys Gln Gln His Asn Glu Tyr Pro Tyr
                 85                  90                  95

Thr Phe Gly Gly Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
 130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
             165                 170                 175

Ser Thr Leu Thr Leu Ser Lys Ala Asp Tyr Glu Lys His Lys Val Tyr

```
            180                 185                 190
Ala Cys Glu Val Thr His Gln Gly Leu Ser Ser Pro Val Thr Lys Ser
        195                 200                 205

Phe Asn Arg Gly Glu Cys
    210

<210> SEQ ID NO 310
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Gln Val Gln Leu Gln Gln Ser Gly Pro Gln Leu Val Arg Pro Gly Ala
1               5                   10                  15

Ser Val Lys Ile Ser Cys Lys Thr Ser Gly Tyr Ser Phe Thr Asn Tyr
            20                  25                  30

Trp Met Gln Trp Val Lys Gln Arg Pro Gly Gln Gly Leu Glu Trp Ile
        35                  40                  45

Gly Met Ile Asp Pro Ser Asp Ser Glu Ser Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Phe Glu Asp Ser Ala Val Tyr Tyr Cys
                85                  90                  95

Ala Arg Arg Gly Ser Pro Met Ile Thr Ser Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 311
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Asp Ile Gln Ile Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 312
```

<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 312

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asn Tyr
            20                  25                  30

His Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Met Ala Ile Leu Thr Ala Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Asp Leu Tyr Leu His Ser Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln

```
                    370                 375                 380
Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 313
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 313

His His His His His His
1               5
```